US012662492B2

(12) United States Patent
Chung et al.

(10) Patent No.: US 12,662,492 B2
(45) Date of Patent: Jun. 23, 2026

(54) SITE-SPECIFIC ANTIBODY CONJUGATION AND ANTIBODY-DRUG CONJUGATE AS SPECIFIC EMBODIMENT THEREOF

(71) Applicant: ABTIS CO., LTD., Gyeonggi-do (KR)

(72) Inventors: Sang Jeon Chung, Seoul (KR); Ju Hwan Kim, Gyeonggi-do (KR); Young Geun Lee, Gyeonggi-do (KR); Tae Jin Lee, Gyeonggi-do (KR); Jin Woo Seo, Gyeonggi-do (KR)

(73) Assignee: ABTIS CO., LTD., Gyeonggi-do (KR)

( * ) Notice: Subject to any disclaimer, the term of this patent is extended or adjusted under 35 U.S.C. 154(b) by 1635 days.

(21) Appl. No.: 16/980,503

(22) PCT Filed: Mar. 9, 2020

(86) PCT No.: PCT/KR2020/003282

§ 371 (c)(1),
(2) Date: Sep. 14, 2020

(87) PCT Pub. No.: WO2020/184944

PCT Pub. Date: Sep. 17, 2020

(65) Prior Publication Data

US 2023/0158167 A1 May 25, 2023

Related U.S. Application Data

(60) Provisional application No. 62/815,557, filed on Mar. 8, 2019.

(51) Int. Cl.

| | |
|---|---|
| ***A61K 38/00*** | (2006.01) |
| ***A61K 47/68*** | (2017.01) |
| ***A61P 35/00*** | (2006.01) |
| ***C07D 207/46*** | (2006.01) |
| ***C07D 498/18*** | (2006.01) |
| ***C07K 16/32*** | (2006.01) |

(52) U.S. Cl.

CPC ...... *C07D 498/18* (2013.01); *A61K 47/68031* (2023.08); *A61K 47/68033* (2023.08); *A61K 47/68037* (2023.08); *A61K 47/6855* (2017.08); *A61K 47/6889* (2017.08); *A61P 35/00* (2018.01); *C07D 207/46* (2013.01); *C07K 16/32* (2013.01)

(58) Field of Classification Search

CPC ........ A61K 47/68031; A61K 47/68033; A61K 47/68037; A61K 47/6811; A61K 47/6855; A61K 47/6889; A61K 47/64; A61K 47/65; A61K 47/6801; A61K 47/6803; A61P 35/00; C07D 207/46; C07D 498/18; C07K 16/32; C07K 2317/24; C07K 7/08; C07K 16/42

See application file for complete search history.

(56) References Cited

U.S. PATENT DOCUMENTS

| | | | | |
|---|---|---|---|---|
| 10,329,321 | B2 | 6/2019 | Krantz et al. | |
| 2012/0172575 | A1 | 7/2012 | Boons et al. | |
| 2018/0141976 | A1* | 5/2018 | Ito | C07K 14/4748 |
| 2020/0190165 | A1* | 6/2020 | Yamada | A61K 47/68033 |
| 2021/0139541 | A1 | 5/2021 | Matsuda et al. | |

FOREIGN PATENT DOCUMENTS

| | | | | |
|---|---|---|---|---|
| CN | 107496978 A | 12/2017 | | |
| EP | 3299383 A1 | 3/2018 | | |
| EP | 3617235 A1 | 3/2020 | | |
| EP | 3915973 A1 * | 12/2021 | | A61K 31/537 |
| KR | 10-2018-0002734 A | 1/2018 | | |
| KR | 10-2020-0002858 A | 1/2020 | | |
| WO | 2013-001297 A1 | 1/2013 | | |
| WO | 2016-186206 | 11/2016 | | |
| WO | WO-2018199337 A1 * | 11/2018 | | A61K 47/68033 |
| WO | 2019-240287 A1 | 12/2019 | | |
| WO | WO-2020/184944 A1 | 9/2020 | | |

OTHER PUBLICATIONS

Kurosaki et al., Angewandte Chemie, International Edition (2005), 44(25), 3861-3864. (Year: 2005).*
Peng et al. (Mol Cell Proteomics. Sep. 9, 2011;10(12):M111. 012658) (Year: 2011).*
Translation of WO2018199337A1 provided by Espacenet (Year: 2018).*
Office Action from corresponding Australian Patent Application No. 2020234394 issued on Sep. 26, 2023.
Tamura, T., et al.; "Rapid labelling and covalent inhibition of intracellular native proteins using ligand-directed N-acyl-N-alkyl sulfonamide", Nature Communications, 2018, 9, 1870, pp. 1-12.
Extended European Search Report from corresponding European Patent Application No. 20770235.8, dated Oct. 10, 2022.
Kurosaki Hiromasa et al: "Irreversable Inhibition of Metallo-[beta]-lactamase (IMP-1) by 3-(30Mercaptopropionylsulfanyl)propionic Acid Pentafluorophenyl Ester", Angewandte Chemie International Edition, vol. 44, No. 25, Jun. 10, 2005, pp. 3861-3864.
Office Action from corresponding Japanese Patent Application No. 2021-553121, dated Oct. 21, 2022.

(Continued)

*Primary Examiner* — Lianko G Garyu
*Assistant Examiner* — Mercy H Sabila
(74) *Attorney, Agent, or Firm* — Harness, Dickey & Pierce, P.L.C.

(57) ABSTRACT

The present invention relates to technology capable of labeling a certain site of an antibody with a certain number of chemical functional groups or cargo moieties. The present invention may provide an antibody product having high uniformity. The present invention may provide an antibody product whose antibody functions are not degraded. That is, the present invention may provide an antibody product whose antibody binding affinity and half-life are not degraded. The present invention is of great significance as being the first technology allowing site-specific labeling of an antibody without any complicated processes.

12 Claims, 73 Drawing Sheets

Specification includes a Sequence Listing.

(56) References Cited

OTHER PUBLICATIONS

Yamaguchi, Y., et al.; "Structure-Function Analysis and Development of Inhibitors of Metallo-β-lactamases Conferring Drug Resistance in Bacteria", Yakugaku Zasshi, vol. 135, No. 11, 2015, pp. 1299-1305.
Van Geel, R. et al.; Chemoenzymatic Conjugation of Toxic Payloads to the Globally Conserved N Glycan of Native mAbs Provides Homogeneous and Highly Efficacious Antibody Drug Conjugates, Bioconjugate Chemistry, 2015, 26, pp. 2233-2242.
International Search Report from corresponding PCT Application No. PCT/KR2020/003282, dated Jun. 16, 2020.
Written Opinion from corresponding PCT Application No. PCT/KR2020/003282, dated Jun. 16, 2020.
Notice of Allowance from corresponding Korean Application No. 10-2020-0029224, dated Jul. 25, 2023.
Office Action from corresponding Korean Patent Application No. 10-2023-0099296 issued on Jan. 20, 2025.
Database Registry [Online], CAS Registry No. 862503-40-0 (Sep. 6, 2005).
Database Registry [Online], CAS Registry No. 2172798-01-3 (Feb. 2, 2018).
Office Action from corresponding Japanese Patent Application No. 2023-196070 issued on Dec. 2, 2024.
Razumienko, E.J. et al; "Small-Animal SPECT/CT of HER2 and HER3 Expression in Tumor Xenografts in Athymic Mice Using Trastuzumab Fab-Heregulin Bispecific Radioimmunoconjugates" J Nucl Med 2012. pp. 1943-1950.
Tamura, T. et al.; "Affinity-Guided Oxime Chemistry for Selective Protein Acylation in Live Tissue Systems" Journal of the American Society 2017, 139, 14181-14191.
Tsukiji, S. et al.; "Ligand-directed tosyl chemistry for protein labeling in vivo" Nature Chemical Biology 2009, vol. 5, No. 5, pp. 341-343.
Fujichima, S. H. et al.; "Ligand-Directed Acyl Imidazole Chemistry for Labeling of Membrane-Bound Proteins on Live Cells" Journal of the American Chemical Society 2012, 134, pp. 3961-3964.

* cited by examiner amino acid sequence :

Figure 1:
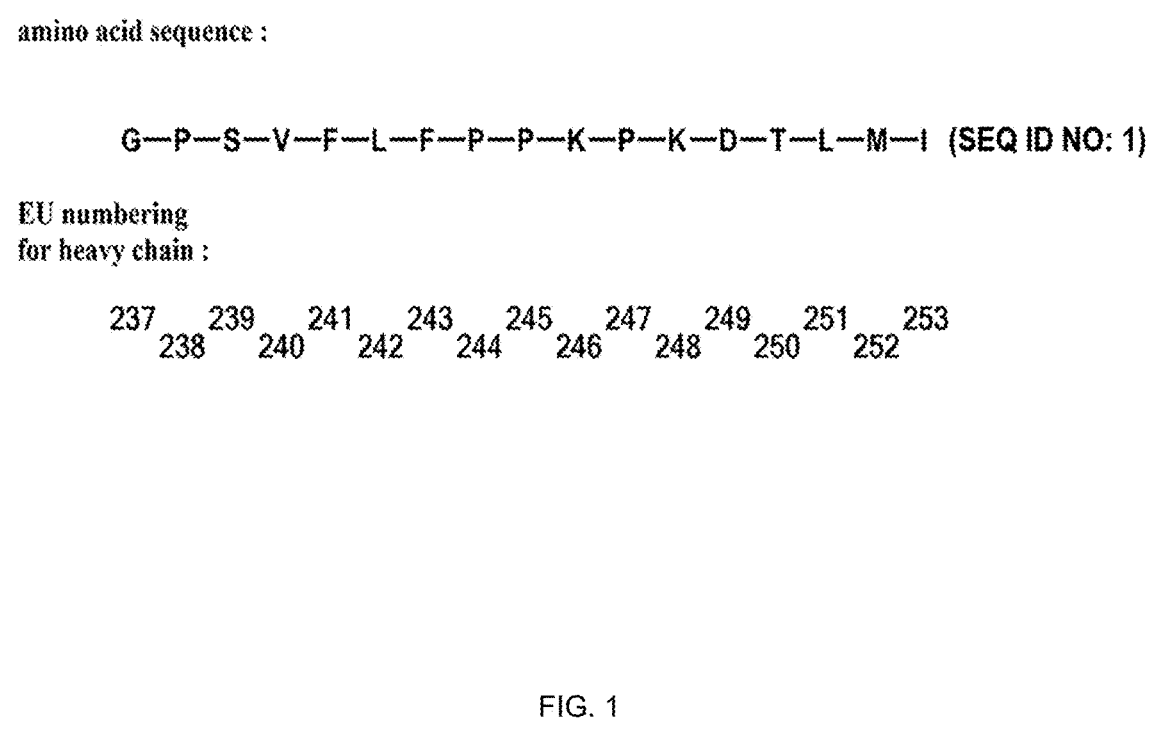

G—P—S—V—F—L—F—P—P—K—P—K—D—T—L—M—I (SEQ ID NO: 1)

EU numbering
for heavy chain :

$R_1$'-L2-SSAI

If $L_c$ is shorter than $D_{246,min}$

If $L_c$ is longer than $D_{248,max}$

If $L_c$ is between about $D_{246,min}$ and about $D_{248,max}$

1

2

I

3

II

4

5

III

6

7

(Continued)

8

9

10

IV (chemical structure of formula 16 pegylated)

Trastuzumab only (Fc/2)

Trastuzumab-norbornene conjugate (Fc/2)

Base peak

1. NC-DM1 : non-cleavable DM1 (tetrazine-PEG8-DM1)

2. VC-DM1 : cleavable DM1 (tetrazine-PEG8-valine-citrulline-DM1)

3. VC-MMAE : cleavable DM1 (tetrazine-PEG8-valine-citrulline-PAB-MMAE)

SEQUENCE LISTING

```
<160> NUMBER OF SEQ ID NOS: 25

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Gly Pro Ser Val Phe Leu Phe Pro Pro Lys Pro Lys Asp Thr Leu Met
1               5                   10                  15

Ile


<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Ala Trp His Leu Gly Glu Leu Val Trp
1               5


<210> SEQ ID NO 3
<211> LENGTH: 9
<212> TYPE: PRT
<213> ORGANISM: Artificial Sequence
<220> FEATURE:
```

```
<223> OTHER INFORMATION: Synthetic
<220> FEATURE:
<221> NAME/KEY: VARIANT
<222> LOCATION: (1)..(1)
<223> OTHER INFORMATION: not C
<220> FEATURE:
<221> NAME/KEY: VARIANT
<222> LOCATION: (2)..(2)
<223> OTHER INFORMATION: not C
<220> FEATURE:
<221> NAME/KEY: MOD_RES
<222> LOCATION: (4)..(4)
<223> OTHER INFORMATION: alanine variant comprising D3-X3 linked to the
      methyl sidechain, wherein D3 is bond or C1-3 alkylene and X3 is
      -NH2, -OH, or -SH
<220> FEATURE:
<221> NAME/KEY: VARIANT
<222> LOCATION: (6)..(6)
<223> OTHER INFORMATION: E or N
<220> FEATURE:
<221> NAME/KEY: VARIANT
<222> LOCATION: (9)..(9)
<223> OTHER INFORMATION: W, F or naphthylalanine

<400> SEQUENCE: 3

Xaa Xaa His Xaa Gly Xaa Leu Val Xaa
1               5


<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: alanine variant comprising D3-X3 linked to the
      methyl sidechain, wherein D3 is bond or C1-3 alkylene and X3 is
      -NH2, -OH, or -SH
<220> FEATURE:
<221> NAME/KEY: VARIANT
<222> LOCATION: (6)..(6)
<223> OTHER INFORMATION: E or N
<220> FEATURE:
<221> NAME/KEY: VARIANT
<222> LOCATION: (9)..(9)
<223> OTHER INFORMATION: W, F, or naphthylalanine

<400> SEQUENCE: 4

Ala Trp His Xaa Gly Xaa Leu Val Xaa
1               5


<210> SEQ ID NO 5
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: not C
<220> FEATURE:
<221> NAME/KEY: VARIANT
<222> LOCATION: (3)..(3)
<223> OTHER INFORMATION: not C
<220> FEATURE:
<221> NAME/KEY: MOD_RES
<222> LOCATION: (5)..(5)
<223> OTHER INFORMATION: alanine variant comprising D3-X3 linked to the
      methyl side chain, wherein D3 is bond or C1-3 alkylene and X3 is
      -NH2, -OH, or -SH
<220> FEATURE:
<221> NAME/KEY: VARIANT
```

<222> LOCATION: (7)..(7)
<223> OTHER INFORMATION: E or N
<220> FEATURE:
<221> NAME/KEY: VARIANT
<222> LOCATION: (10)..(10)
<223> OTHER INFORMATION: W, F or naphthylalanine

<400> SEQUENCE: 5

Pro Xaa Xaa His Xaa Gly Xaa Leu Val Xaa Pro
1 5 10

<210> SEQ ID NO 6
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: not C or absent
<220> FEATURE:
<221> NAME/KEY: VARIANT
<222> LOCATION: (2)..(2)
<223> OTHER INFORMATION: not C or absent
<220> FEATURE:
<221> NAME/KEY: VARIANT
<222> LOCATION: (3)..(3)
<223> OTHER INFORMATION: not C
<220> FEATURE:
<221> NAME/KEY: VARIANT
<222> LOCATION: (5)..(5)
<223> OTHER INFORMATION: not C
<220> FEATURE:
<221> NAME/KEY: VARIANT
<222> LOCATION: (6)..(6)
<223> OTHER INFORMATION: not C
<220> FEATURE:
<221> NAME/KEY: MOD_RES
<222> LOCATION: (8)..(8)
<223> OTHER INFORMATION: alanine variant comprising D3-X3 linked to the methyl side chain, wherein D3 is bond or C1-3 alkylene and X3 is -NH2, -OH, or -SH
<220> FEATURE:
<221> NAME/KEY: VARIANT
<222> LOCATION: (10)..(10)
<223> OTHER INFORMATION: E or N
<220> FEATURE:
<221> NAME/KEY: VARIANT
<222> LOCATION: (13)..(13)
<223> OTHER INFORMATION: W, F or naphthylalanine
<220> FEATURE:
<221> NAME/KEY: VARIANT
<222> LOCATION: (15)..(15)
<223> OTHER INFORMATION: not C
<220> FEATURE:
<221> NAME/KEY: VARIANT
<222> LOCATION: (16)..(16)
<223> OTHER INFORMATION: not C or absent
<220> FEATURE:
<221> NAME/KEY: VARIANT
<222> LOCATION: (17)..(17)
<223> OTHER INFORMATION: not C or absent

<400> SEQUENCE: 6

Xaa Xaa Xaa Cys Xaa Xaa His Xaa Gly Xaa Leu Val Xaa Cys Xaa Xaa
1 5 10 15

Xaa

<210> SEQ ID NO 7
<211> LENGTH: 15
<212> TYPE: PRT
<213> ORGANISM: Artificial Sequence
<220> FEATURE:

```
<223> OTHER INFORMATION: Synthetic
<220> FEATURE:
<221> NAME/KEY: VARIANT
<222> LOCATION: (4)..(4)
<223> OTHER INFORMATION: not C
<220> FEATURE:
<221> NAME/KEY: VARIANT
<222> LOCATION: (5)..(5)
<223> OTHER INFORMATION: not C
<220> FEATURE:
<221> NAME/KEY: MOD_RES
<222> LOCATION: (7)..(7)
<223> OTHER INFORMATION: alanine variant comprising D3-X3 linked to the
      methyl side chain, wherein D3 is bond or C1-3 alkylene and X3 is
      -NH2, -OH, or -SH
<220> FEATURE:
<221> NAME/KEY: VARIANT
<222> LOCATION: (9)..(9)
<223> OTHER INFORMATION: E or N
<220> FEATURE:
<221> NAME/KEY: VARIANT
<222> LOCATION: (12)..(12)
<223> OTHER INFORMATION: W, F or naphthylalanine
<220> FEATURE:
<221> NAME/KEY: SITE
<222> LOCATION: (15)..(15)
<223> OTHER INFORMATION: D-proline

<400> SEQUENCE: 7

Pro Asp Cys Xaa Xaa His Xaa Gly Xaa Leu Val Xaa Cys Thr Pro
1               5                   10                  15


<210> SEQ ID NO 8
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (4)..(4)
<223> OTHER INFORMATION: not C
<220> FEATURE:
<221> NAME/KEY: VARIANT
<222> LOCATION: (5)..(5)
<223> OTHER INFORMATION: not C
<220> FEATURE:
<221> NAME/KEY: MOD_RES
<222> LOCATION: (7)..(7)
<223> OTHER INFORMATION: alanine variant comprising D3-X3 linked to the
      methyl side chain, wherein D3 is bond or C1-3 alkylene and X3 is
      -NH2, -OH, or -SH
<220> FEATURE:
<221> NAME/KEY: VARIANT
<222> LOCATION: (9)..(9)
<223> OTHER INFORMATION: E or N
<220> FEATURE:
<221> NAME/KEY: VARIANT
<222> LOCATION: (12)..(12)
<223> OTHER INFORMATION: W, F or naphthylalanine

<400> SEQUENCE: 8

Cys Asp Cys Xaa Xaa His Xaa Gly Xaa Leu Val Xaa Cys Thr Cys
1               5                   10                  15


<210> SEQ ID NO 9
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: not C
```

```
<220> FEATURE:
<221> NAME/KEY: VARIANT
<222> LOCATION: (4)..(4)
<223> OTHER INFORMATION: not C
<220> FEATURE:
<221> NAME/KEY: MOD_RES
<222> LOCATION: (6)..(6)
<223> OTHER INFORMATION: alanine variant comprising D3-X3 linked to the
      methyl side chain, wherein D3 is bond or C1-3 alkylene and X3 is
      -NH2, -OH, or -SH
<220> FEATURE:
<221> NAME/KEY: VARIANT
<222> LOCATION: (8)..(8)
<223> OTHER INFORMATION: E or N
<220> FEATURE:
<221> NAME/KEY: VARIANT
<222> LOCATION: (11)..(11)
<223> OTHER INFORMATION: W, F or naphthylalanine

<400> SEQUENCE: 9

Asp Cys Xaa Xaa His Xaa Gly Xaa Leu Val Xaa Cys Thr
1               5                   10


<210> SEQ ID NO 10
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: alanine variant comprising D3-X3 linked to the
      methyl side chain, wherein D3 is bond or C1-3 alkylene and X3 is
      -NH2,-OH, or -SH

<400> SEQUENCE: 10

Asp Cys Ala Trp His Xaa Gly Glu Leu Val Trp Cys Thr
1               5                   10


<210> SEQ ID NO 11
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: not C
<220> FEATURE:
<221> NAME/KEY: VARIANT
<222> LOCATION: (2)..(2)
<223> OTHER INFORMATION: not C
<220> FEATURE:
<221> NAME/KEY: MOD_RES
<222> LOCATION: (4)..(4)
<223> OTHER INFORMATION: alanine variant comprising
      D3-X3-C(=O)-D2-X1-(C=O)-D1-R1' linked to the methyl side chain,
      wherein D3 is bond or C1-3 alkylene, X3 is -NH-, -O-, or -S-, D2
      is alkylene, alkenylene, or alkynylene,
<220> FEATURE:
<221> NAME/KEY: MOD_RES
<222> LOCATION: (4)..(4)
<223> OTHER INFORMATION: alanine variant (contd), wherein X1 is an
      element more electronegative than carbon, D1 is bond or alkylene,
      alkenylene, or alkynylene, and R1' is a first chemical functional
      group
<220> FEATURE:
<221> NAME/KEY: VARIANT
<222> LOCATION: (6)..(6)
<223> OTHER INFORMATION: E or N
<220> FEATURE:
<221> NAME/KEY: VARIANT
<222> LOCATION: (9)..(9)
```

```
<223> OTHER INFORMATION: W, F or naphthylalanine

<400> SEQUENCE: 11

Xaa Xaa His Xaa Gly Xaa Leu Val Xaa
1               5


<210> SEQ ID NO 12
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: not C or absent
<220> FEATURE:
<221> NAME/KEY: VARIANT
<222> LOCATION: (2)..(2)
<223> OTHER INFORMATION: not C or absent
<220> FEATURE:
<221> NAME/KEY: VARIANT
<222> LOCATION: (3)..(3)
<223> OTHER INFORMATION: not C
<220> FEATURE:
<221> NAME/KEY: VARIANT
<222> LOCATION: (5)..(5)
<223> OTHER INFORMATION: not C
<220> FEATURE:
<221> NAME/KEY: VARIANT
<222> LOCATION: (6)..(6)
<223> OTHER INFORMATION: not C
<220> FEATURE:
<221> NAME/KEY: MOD_RES
<222> LOCATION: (8)..(8)
<223> OTHER INFORMATION: alanine variant comprising
      D3-X3-C(=O)-D2-X1-(C=O)-D1-R1' linked to the methyl side chain,
      wherein D3 is bond or C1-3 alkylene, X3 is -NH-, -O-, or -S-, D2
      is alkylene, alkenylene, or alkynylene,
<220> FEATURE:
<221> NAME/KEY: MOD_RES
<222> LOCATION: (8)..(8)
<223> OTHER INFORMATION: alanine variant (contd), wherein X1 is an
      element more electronegative than carbon, D1 is bond or alkylene,
      alkenylene, or alkynylene, and R1' is a first chemical functional
      group
<220> FEATURE:
<221> NAME/KEY: VARIANT
<222> LOCATION: (10)..(10)
<223> OTHER INFORMATION: E or N
<220> FEATURE:
<221> NAME/KEY: VARIANT
<222> LOCATION: (13)..(13)
<223> OTHER INFORMATION: W, F or naphthylalanine
<220> FEATURE:
<221> NAME/KEY: VARIANT
<222> LOCATION: (15)..(15)
<223> OTHER INFORMATION: not C
<220> FEATURE:
<221> NAME/KEY: VARIANT
<222> LOCATION: (16)..(16)
<223> OTHER INFORMATION: not C or absent
<220> FEATURE:
<221> NAME/KEY: VARIANT
<222> LOCATION: (17)..(17)
<223> OTHER INFORMATION: not C or absent

<400> SEQUENCE: 12

Xaa Xaa Xaa Cys Xaa Xaa His Xaa Gly Xaa Leu Val Xaa Cys Xaa Xaa
1               5                   10                  15

Xaa


<210> SEQ ID NO 13
<211> LENGTH: 13
```

<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: alanine variant

<400> SEQUENCE: 13

Asp Cys Ala Trp His Xaa Gly Glu Leu Val Trp Cys Thr
1 5 10

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: not C
<220> FEATURE:
<221> NAME/KEY: VARIANT
<222> LOCATION: (2)..(2)
<223> OTHER INFORMATION: not C
<220> FEATURE:
<221> NAME/KEY: MOD_RES
<222> LOCATION: (4)..(4)
<223> OTHER INFORMATION: alanine variant comprising
D3-X3-C(=O)-D2-X1-(C=O)-D1-H1 linked to the methyl side chain,
wherein D3 is bond or C1-3 alkylene, X3 is -NH-, -O-, or -S-, D2
is alkylene, alkenylene, or alkynylene,
<220> FEATURE:
<221> NAME/KEY: MOD_RES
<222> LOCATION: (4)..(4)
<223> OTHER INFORMATION: alanine variant (contd), wherein X1 is an
element more electronegative than carbon, D1 is bond or alkylene,
alkenylene, or alkynylene, and H1 is a first click-chemistry
functional group
<220> FEATURE:
<221> NAME/KEY: VARIANT
<222> LOCATION: (6)..(6)
<223> OTHER INFORMATION: E or N
<220> FEATURE:
<221> NAME/KEY: VARIANT
<222> LOCATION: (9)..(9)
<223> OTHER INFORMATION: W, F or naphthylalanine

<400> SEQUENCE: 14

Xaa Xaa His Xaa Gly Xaa Leu Val Xaa
1 5

<210> SEQ ID NO 15
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: not C or absent
<220> FEATURE:
<221> NAME/KEY: VARIANT
<222> LOCATION: (2)..(2)
<223> OTHER INFORMATION: not C or absent
<220> FEATURE:
<221> NAME/KEY: VARIANT
<222> LOCATION: (3)..(3)
<223> OTHER INFORMATION: not C
<220> FEATURE:
<221> NAME/KEY: VARIANT
<222> LOCATION: (5)..(5)

```
<223> OTHER INFORMATION: not C
<220> FEATURE:
<221> NAME/KEY: VARIANT
<222> LOCATION: (6)..(6)
<223> OTHER INFORMATION: not C
<220> FEATURE:
<221> NAME/KEY: MOD_RES
<222> LOCATION: (8)..(8)
<223> OTHER INFORMATION: alanine variant comprising
      D3-X3-C(=O)-D2-X1-(C=O)-D1-H1 linked to the methyl side chain,
      wherein D3 is bond or C1-3 alkylene, X3 is -NH-, -O-, or -S-, D2
      is alkylene, alkenylene, or alkynylene,
<220> FEATURE:
<221> NAME/KEY: MOD_RES
<222> LOCATION: (8)..(8)
<223> OTHER INFORMATION: alanine variant (contd), wherein X1 is an
      element more electronegative than carbon, D1 is bond or alkylene,
      alkenylene, or alkynylene, and H1 is a first click-chemistry
      functional group
<220> FEATURE:
<221> NAME/KEY: VARIANT
<222> LOCATION: (10)..(10)
<223> OTHER INFORMATION: E or N
<220> FEATURE:
<221> NAME/KEY: VARIANT
<222> LOCATION: (13)..(13)
<223> OTHER INFORMATION: W, F or naphthylalanine
<220> FEATURE:
<221> NAME/KEY: VARIANT
<222> LOCATION: (15)..(15)
<223> OTHER INFORMATION: not C
<220> FEATURE:
<221> NAME/KEY: VARIANT
<222> LOCATION: (16)..(16)
<223> OTHER INFORMATION: not C or absent
<220> FEATURE:
<221> NAME/KEY: VARIANT
<222> LOCATION: (17)..(17)
<223> OTHER INFORMATION: not C or absent

<400> SEQUENCE: 15

Xaa Xaa Xaa Cys Xaa Xaa His Xaa Gly Xaa Leu Val Xaa Cys Xaa Xaa
1               5                   10                  15

Xaa


<210> SEQ ID NO 16
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: alanine variant comprising
      D3-X3-C(=O)-D2-X1-(C=O)-D1-H1 linked to the methyl side chain,
      wherein D3 is bond or C1-3 alkylene, X3 is -NH-, -O-, or -S-, D2
      is alkylene, alkenylene, or alkynylene,
<220> FEATURE:
<221> NAME/KEY: MOD_RES
<222> LOCATION: (6)..(6)
<223> OTHER INFORMATION: alanine variant (contd), wherein X1 is an
      element more electronegative than carbon, D1 is bond or alkylene,
      alkenylene, or alkynylene, and H1 is a fifirst click-chemistry
      functional group

<400> SEQUENCE: 16

Asp Cys Ala Trp His Xaa Gly Glu Leu Val Trp Cys Thr
1               5                   10


<210> SEQ ID NO 17
<211> LENGTH: 17
<212> TYPE: PRT
<213> ORGANISM: Artificial Sequence
```

-continued

```
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: lysine variant comprising -C(=O)-D1-R1', linked
      to the lysine side chain, wherein D1 is alkylene, alkenylene, or
      alkynylene, and R1' is a first chemical functional group

<400> SEQUENCE: 17

Gly Pro Ser Val Phe Leu Phe Pro Pro Xaa Pro Lys Asp Thr Leu Met
1               5                   10                  15

Ile


<210> SEQ ID NO 18
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: lysine variant comprising -C(=O)-D1-R1', linked
      to the lysine side chain, wherein D1 is alkylene, alkenylene, or
      alkynylene, and R1' is a first chemical functional group

<400> SEQUENCE: 18

Gly Pro Ser Val Phe Leu Phe Pro Pro Lys Pro Xaa Asp Thr Leu Met
1               5                   10                  15

Ile


<210> SEQ ID NO 19
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: lysine variant comprising -C(=O)-D1-R1', linked
      to the lysine side chain, wherein D1 is alkylene, alkenylene, or
      alkynylene, and R1' is a first chemical functional group
<220> FEATURE:
<221> NAME/KEY: MOD_RES
<222> LOCATION: (12)..(12)
<223> OTHER INFORMATION: lysine variant comprising -C(=O)-D1-R1', linked
      to the lysine side chain, wherein D1 is alkylene, alkenylene, or
      alkynylene, and R1' is a first chemical functional group

<400> SEQUENCE: 19

Gly Pro Ser Val Phe Leu Phe Pro Pro Xaa Pro Xaa Asp Thr Leu Met
1               5                   10                  15

Ile


<210> SEQ ID NO 20
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: lysine variant comprising -C(=O)-D1-H1, linked
      to the lysine side chain, wherein D1 is alkylene, alkenylene, or
      alkynylene, and H1 is a first click-chemistry functional group

<400> SEQUENCE: 20
```

Gly Pro Ser Val Phe Leu Phe Pro Pro Xaa Pro Lys Asp Thr Leu Met
1 5 10 15

Ile

<210> SEQ ID NO 21
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: lysine variant comprising -C(=O)-D1-H1, linked to the lysine side chain, wherein D1 is alkylene, alkenylene, or alkynylene, and H1 is a first click-chemistry functional group

<400> SEQUENCE: 21

Gly Pro Ser Val Phe Leu Phe Pro Pro Lys Pro Xaa Asp Thr Leu Met
1 5 10 15

Ile

<210> SEQ ID NO 22
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: lysine variant comprising -C(=O)-D1-H1, linked to the lysine side chain, wherein D1 is alkylene, alkenylene, or alkynylene, and H1 is a first click-chemistry functional group
<220> FEATURE:
<221> NAME/KEY: MOD_RES
<222> LOCATION: (12)..(12)
<223> OTHER INFORMATION: lysine variant comprising -C(=O)-D1-H1, linked to the lysine side chain, wherein D1 is alkylene, alkenylene, or alkynylene, and H1 is a first click-chemistry functional group

<400> SEQUENCE: 22

Gly Pro Ser Val Phe Leu Phe Pro Pro Xaa Pro Xaa Asp Thr Leu Met
1 5 10 15

Ile

<210> SEQ ID NO 23
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: lysine variant comprising -C(=O)-D1-B-Cm, linked to the lysine side chain, wherein D1 is alkylene, alkenylene, or alkynylene
<220> FEATURE:
<221> NAME/KEY: MOD_RES
<222> LOCATION: (10)..(10)
<223> OTHER INFORMATION: lysine variant (cont), wherein B is formed by a click chemistry reaction between a first click-chemistry functional group and a second click-chemistry functional group, and Cm is a cargo

<400> SEQUENCE: 23

Gly Pro Ser Val Phe Leu Phe Pro Pro Xaa Pro Lys Asp Thr Leu Met
1 5 10 15

-continued

Ile

<210> SEQ ID NO 24
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: lysine variant comprising -C(=O)-D1-B-Cm, linked to the lysine side chain, wherein D1 is alkylene, alkenylene, or alkynylene
<220> FEATURE:
<221> NAME/KEY: MOD_RES
<222> LOCATION: (12)..(12)
<223> OTHER INFORMATION: lysine variant (cont), wherein B is formed by a click chemistry reaction between a first click-chemistry functional group and a second click-chemistry functional group, and Cm is a cargo

<400> SEQUENCE: 24

Gly Pro Ser Val Phe Leu Phe Pro Pro Lys Pro Xaa Asp Thr Leu Met
1 5 10 15

Ile

<210> SEQ ID NO 25
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: lysine variant comprising -C(=O)-D1-B-Cm, linked to the lysine side chain, wherein D1 is alkylene, alkenylene, or alkynylene
<220> FEATURE:
<221> NAME/KEY: MOD_RES
<222> LOCATION: (10)..(10)
<223> OTHER INFORMATION: lysine variant (cont), wherein B is formed by a click chemistry reaction between a first click-chemistry functional group and a second click-chemistry functional group, and Cm is a cargo
<220> FEATURE:
<221> NAME/KEY: MOD_RES
<222> LOCATION: (12)..(12)
<223> OTHER INFORMATION: lysine variant comprising -C(=O)-D1-B-Cm, linked to the lysine side chain, wherein D1 is alkylene, alkenylene, or alkynylene
<220> FEATURE:
<221> NAME/KEY: MOD_RES
<222> LOCATION: (12)..(12)
<223> OTHER INFORMATION: lysine variant (cont), wherein B is formed by a click chemistry reaction between a first click-chemistry functional group and a second click-chemistry functional group, and Cm is a cargo

<400> SEQUENCE: 25

Gly Pro Ser Val Phe Leu Phe Pro Pro Xaa Pro Xaa Asp Thr Leu Met
1 5 10 15

Ile

SITE-SPECIFIC ANTIBODY CONJUGATION AND ANTIBODY-DRUG CONJUGATE AS SPECIFIC EMBODIMENT THEREOF

CROSS-REFERENCE TO RELATED APPLICATIONS

This application is a national phase application of PCT Application No. PCT/KR2020/003282, filed on Mar. 9, 2020, which claims priority to U.S. Provisional Patent Application No. 62/815,557, filed on Mar. 8, 2019. The entire disclosure of the applications identified in this paragraph is incorporated herein by reference.

This application contains references to amino acid sequences and/or nucleic acid sequences which have been submitted concurrently herewith as the sequence listing text file entitled "000072usnp_SequenceListing.TXT", file size 17,718 bytes, created on 21 Dec. 2023. The aforementioned sequence listing is hereby incorporated by reference in its entirety pursuant to 37 C.F.R. § 1.52(e)(5).

FIELD

The present invention relates to technology for selectively labeling a certain amino acid residue of an antibody with substances (low-molecular-weight compounds, synthetic polymers, biopolymers (i.e., peptides, carbohydrates, proteins, and the like)) or linking a molecule (hereinafter referred to as a "cargo") to be delivered to a certain target cell or tissue to the antibody. Also, the present invention relates to technology for labeling a certain site of an antibody with a desired number of substances or linking a desired number of cargos to certain amino acid residues of the antibody. In addition, the present invention encompasses an antibody complex prepared by the method or a method using a fragment complex of the antibody.

BACKGROUND

Antibodies are biomolecules that have a function of recognizing certain molecules, and have been used for various industrial applications. For example, an antibody may be used to detect or screen for a certain substance and check a route through which the certain substance moves in the body or cells. Also, the antibody may be used for therapeutic purposes by inducing an immune response against the certain substance.

To expand the functions of such an antibody, there has been attempts to improve the antibody's ability. Typically, there has been an attempt to label an antibody with foreign substances in order to supplement or expand the antibody's functions. Typically, when an antibody is labeled with a fluorescent substance, the antibody may be used for a fluorescence assay, or when an antibody is labeled with an agent for treating a certain disease, the antibody may be used to maximize a therapeutic effect of the antibody. These attempts and technology are generally referred to as "antibody labeling." The present invention relates to a novel method of labeling an antibody.

In the beginning, the antibody labeling was achieved by randomly attaching a foreign substance to an antibody. However, this method has a lot of problems. The antibodies thus prepared have a problem in that they have poor homogeneity. These antibodies have a problem in that their effects remain uneven because there are a difference in the number of substances attached to each of the antibodies and a difference in binding sites for the antibodies. This problem is a great barrier to the development of antibody-drug conjugate (ADC) technology that requires high safety and reproducibility.

Also, the method has a problem in that an antibody's ability to recognize may be significantly degraded. An antibody consists of an Fab domain including an antigen-binding domain that recognizes an antigen, and an Fc domain involved in the crystallization of the antibody. Random labeling resulted in a highly degraded antibody's ability to recognize by allowing a foreign substance to bind to an antigen-binding domain of an antibody or a site adjacent to the antigen-binding domain.

Therefore, there has been a demand for technology for uniformly labeling an antibody in a site-specific manner in the related art. Although some techniques were developed, e.g., genetically modulating or modifying an antibody and the like, most of them are ineffective in technical and economic aspects. Accordingly, the present invention is designed to solve the problems, and thus is directed to technology capable of specifically linking a certain substance (or a "moiety") to a certain site of an antibody without any additional modulation of the antibody and delivering a certain substance (a drug or a labeled substance) into cells or tissues using the antibody as well.

SUMMARY

Technical Problem

The present invention provides technology for specifically transferring a chemical functional group to a certain site of an antibody. In one specific embodiment, the present invention provides technology for specifically transferring a chemical functional group to lysine 246 in the antibody. In another specific embodiment, the present invention provides technology for specifically transferring a chemical functional group to lysine 248 in the antibody. In still another specific embodiment, the present invention provides technology for specifically transferring a chemical functional group to lysine 246 and 248 in the antibody.

The present invention provides technology capable of linking a desired number of chemical functional groups to an antibody. In one specific embodiment, the present invention provides an antibody or a fragment thereof, which has two certain moieties bound thereto. In another specific embodiment, the present invention provides an antibody or a fragment thereof, which has four certain moieties bound thereto.

The present invention provides technology for specifically linking a cargo moiety to a certain site of an antibody. In one specific embodiment, the present invention provides technology for specifically linking a cargo moiety to lysine 246 in the antibody. In another specific embodiment, the present invention provides technology for specifically linking a cargo moiety to lysine 248 in the antibody. In still another specific embodiment, the present invention provides technology for specifically linking a cargo moiety to lysine 246 and 248 in the antibody.

The present invention provides technology for linking a desired number of cargo moieties to an antibody. In one specific embodiment, the present invention provides an antibody or a fragment thereof, which has two cargo moieties bound thereto. In another specific embodiment, the present invention provides an antibody or a fragment thereof, which has four cargo moieties bound thereto.

The present invention provides a method of using the aforementioned antibody or antibody fragment. In one specific embodiment, the present invention provides a method of treating a certain disease using an antibody-drug complex.

Technical Solution

The present application provides A compound of Formula 2:

[formula 2]

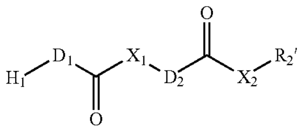

wherein, $H_1$ is a first click chemistry functional group, $D_1$ is selected from a covalent bond, $C_{1-4}$alkylene, $C_{2-4}$alkenylene, $C_{2-4}$alkynlene, and $C_{3-8}$cycloalkylene, $X_1$ is S, $D_2$ is selected from $C_{1-7}$alkylene, $C_{2-7}$alkenylene, $C_{2-7}$alkynylene, and $C_{3-8}$cycloalkynlene, $X_2$ is O, $R_2'$ is N-succinimide, p-nitrophenyl, or pentafluorophenyl.

Also, the present application provides the compound wherein $H_1$ is selected from terminal alkyne, azide, strained alkyne, diene, dienophile, alkene, thiol, and tetrazine. Furthermore, the present application provides the compound wherein $H_1$ is selected from norbornene, tetrazine, azide and dibenzocyclooctyne-amine.

Additionally, the present application provides the compound wherein $R_2'$ is N-succinimide.

Additionally, the present application provides the compound wherein the formula 2 is formula 2-1, 2-2, or 2-3:

[formula 2-1]

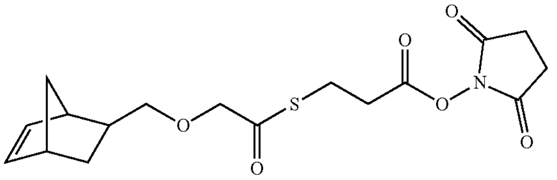

[formula 2-2]

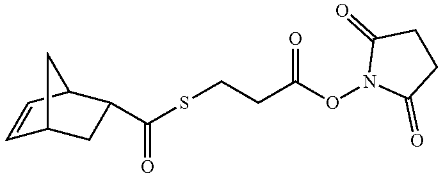

[formula 2-3]

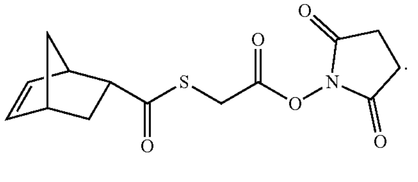

the present application provides a peptide of formula 4-2:

$(Xaa)_{1-3}$-C-$(Xaa)_2$-H-$Xa_1$-G-$Xa_2$-L-V-$Xa_3$-C-$(Xaa)_{1-3}$ [formula 4-2]

wherein, each Xaa is independently any amino acid residue that is not a cysteine residue, C is a cysteine residue, H is a histidine residue, G is a glycine residue, $Xa_2$ is a glutamic acid residue or an asparagine residue, L is a leucine residue, V is a valine residue, $Xa_3$ is selected from a tryptophan residue, a naphthylalanine residue, and a phenylalanine residue, and $Xa_1$ is

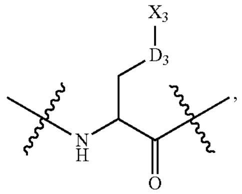

wherein $D_3$ is a covalent bond or $C_{1-3}$alkylene and $X_3$ is $NH_2$, wherein the peptide consists of 13 to 17 amino acid residues, wherein the peptide exhibits the activity of binding to human immunoglobulin G (IgG), and wherein the cysteine residue that is between two to four amino acids from the N-terminus of formula 4-2 and the cysteine residue that is between two to four amino acids from the C-terminus of formula 4-2 are optionally linked.

Also, the present application provides the peptide wherein $D_3$ is a covalent bond, methylene, or ethylene Additionally, the present application provides the peptide wherein the formula 4-2 is formula 4-6:

D-C-A-W-H-$Xa_1$-G-E-L-V-W-C-T [formula 4-6]

wherein, D is an aspartic acid residue, A is an alanine residue, E is a glutamic acid residue, W is a tryptophan residue, and T is a threonine residue.

The present application provides a peptide-compound conjugate of formula 6-2:

$(Xaa)_{1-3}$-C-$(Xaa)_2$-H-$(Xa_1)'$-G-$Xa_2$-L-V-$Xa_3$-C-$(Xaa)_{1-3}$ [formula 6-2]

wherein, each Xaa is independently any amino acid residue that is not a cysteine residue, C is a cysteine residue, H is a histidine residue, G is a glycine residue, $Xa_2$ is a glutamic acid residue or an asparagine residue, L is a leucine residue, V is a valine residue, $Xa_3$ is selected from a tryptophan residue, a naphthylalanine residue, and a phenylalanine residue, and $(Xa_1)'$ is

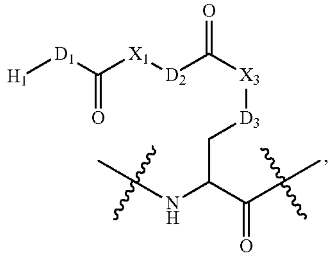

wherein $H_1$ is a first click chemistry functional group, $D_1$ is selected from a covalent bond, $C_{1-4}$alkylene, $C_{2-4}$alkenylene, $C_{2-4}$alkynylene, and $C_{3-8}$cycloalkynlene, $X_1$ is S, $D_2$ is selected from $C_{1-7}$alkylene, $C_{2-7}$alkenylene, $C_{2-7}$alkynylene, and $C_{3-8}$cycloalkynlene, $D_3$ is a covalent bond, or $C_{1-3}$alkylene, and $X_3$ is NH, wherein the peptide consists of 13 to 17 amino acid residues, wherein the peptide exhibits the activity of binding to human immunoglobulin G (IgG), and wherein the cysteine residue that is between two to four amino acids from the N-terminus of formula 6-2 and the cysteine residue that is between two to four amino acids from the C-terminus of formula 6-2 are optionally linked.

Also, the present application provides the peptide-compound conjugate wherein a distance from a beta carbon of the $(Xa_1)'$ to a first carbonyl carbon of the $(Xa_1)'$ is less than approx. 11.668 Å.

Additionally, the present application provides the peptide-compound conjugate wherein $D_2$ is $C_y$alkylene, $C_y$alkenylene, or $C_y$alkynylene, $D_3$ is $C_x$alkylene, wherein y is an integer greater than or equal to 1, and $1 \leq x+y \leq 5$.

Additionally, the present application provides the peptide-compound conjugate wherein a distance from a beta carbon of the $(Xa_1)'$ to a first carbonyl carbon of the $(Xa_1)'$ is greater than approx. 16.208 Å.

Additionally, the present application provides the peptide-compound conjugate wherein $D_2$ is $C_y$alkylene, $C_y$alkenylene, or $C_y$alkynylene, and $D_3$ is $C_x$alkylene, wherein y is an integer greater than or equal to 1, and $9 \leq x+y \leq 12$. Furthermore, the present application provides the peptide-compound conjugate wherein $D_2$ is $C_y$alkenylene, or $C_y$alkynylene.

Additionally, the present application provides the peptide-compound conjugate wherein a distance from a beta carbon of the $(Xa_1)'$ to a first carbonyl carbon of the $(Xa_1)'$ is approx. 11.668 Å to approx. 16.208 Å.

Additionally, the present application provides the peptide-compound conjugate wherein $D_2$ is $C_y$alkylene, $C_y$alkenylene, or $C_y$alkynylene, and $D_3$ is $C_x$alkylene, wherein y is an integer greater than or equal to 1, and $6 \leq x+y \leq 8$.

Additionally, the present application provides the peptide-compound conjugate wherein the formula 6-2 is formula 6-3:

D-C-A-W-H-$(Xa_1)'$-G-E-L-V-W-C-T [formula 6-3]

wherein, D is an aspartic acid residue, A is an alanine residue, E is a glutamic acid residue, W is a tryptophan residue, T is a threonine residue.

Additionally, the present application provides the peptide-compound conjugate wherein $D_1$ is a covalent bond and $D_2$ is methylene.

The present application provides a method for preparing an agent for transferring a first click chemical functional group to an antibody comprising reacting a compound of formula 2:

[formula 2]

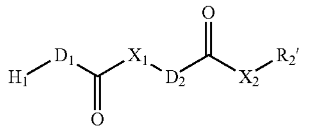

wherein, $H_1$ is a first click chemistry functional group, $D_1$ is selected from a covalent bond, $C_{1-4}$alkylene, $C_{2-4}$alkenylene, $C_{2-4}$alkynylene, and $C_{3-8}$cycloalkynlene, $X_1$ is S, $D_2$ is selected from $C_{1-7}$alkylene, $C_{2-7}$alkenylene, $C_{2-7}$alkynylene, and $C_{3-8}$cycloalkynlene, $X_2$ is O, $R_2'$ is N-succinimide, p-nitrophenyl, or pentafluorophenyl, with a peptide of formula 4-2:

$(Xaa)_{1-3}$-C-$(Xaa)_2$-H-$Xa_1$-G-$Xa_2$-L-V-$Xa_3$-C-$(Xaa)_{1-3}$ [formula 4-2]

wherein, each Xaa is independently any amino acid residue that is not a cysteine residue, C is a cysteine residue, H is a histidine residue, G is a glycine residue, $Xa_2$ is a glutamic acid residue or an asparagine residue, L is a leucine residue, V is a valine residue, $Xa_3$ is selected from a tryptophan residue, a naphthylalanine residue, and a phenylalanine residue, and $Xa_1$ is

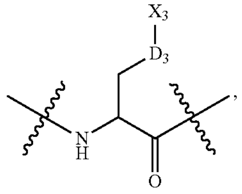

wherein $D_3$ is a covalent bond or $C_{1-3}$alkylene and $X_3$ is $NH_2$, wherein the peptide consists of 13 to 17 amino acid residues, wherein the peptide exhibits the activity of binding to human immunoglobulin G (IgG), and wherein the cysteine residue that is between two to four amino acids from the N-terminus of formula 4-2 and the cysteine residue that is between two to four amino acids from the C-terminus of formula 4-2 are optionally linked.

Also, the present application provides the method for preparing an agent for transferring a first click chemical functional group to an antibody wherein $D_2$ is $C_y$alkylene, $C_y$alkenylene, or $C_y$alkynylene, and $D_3$ is $C_x$alkylene, wherein y is an integer greater than or equal to 1, and $1 \leq x+y \leq 5$, characterized in that the agent for transferring a first click chemical functional group to an antibody prepared by the method can react with an antibody to deliver the first click chemistry functional group specifically to a 248 a lysine residue of an Fc domain of the antibody.

Additionally, the present application provides the method for preparing an agent for transferring a first click chemical functional group to an antibody wherein $D_2$ is $C_y$alkylene, $C_y$alkenylene, or $C_y$alkynylene, and $D_3$ is $C_x$alkylene, wherein y is an integer greater than or equal to 1, and $1 \leq x+y \leq 5$, characterized in that the agent for transferring a first click chemical functional group to an antibody prepared by the method can react with an antibody to deliver the first click chemistry functional group specifically to a 248 a lysine residue of an Fc domain of the antibody.

Additionally, the present application provides the method for preparing an agent for transferring a first click chemical functional group to an antibody wherein $D_2$ is $C_y$alkylene, $C_y$alkenylene, or $C_y$alkynylene, and $D_3$ is $C_x$alkylene, wherein y is an integer greater than or equal to 1, and $9 \leq x+y \leq 12$, characterized in that the agent for transferring a first click chemical functional group to an antibody prepared by the method can react with an antibody to deliver the first click chemistry functional group specifically to a 246 a lysine residue of an Fc domain of the antibody.

Additionally, the present application provides the method for preparing an agent for transferring a first click chemical functional group to an antibody wherein $D_2$ is Cyalkylene, $C_y$alkenylene, or $C_y$alkynylene, and $D_3$ is $C_x$alkylene, wherein y is an integer greater than or equal to 1, and $6 \leq x+y \leq 8$, characterized in that the agent for transferring a first click chemical functional group to an antibody prepared by the method can react with an antibody to deliver the first click chemistry functional group selectively to a 246 a lysine residue or a 248 a lysine residue of an Fc domain of the antibody The present application provides a kit for preparing a first click chemistry functional group transferring to an antibody comprising a compound of formula 2:

[formula 2]

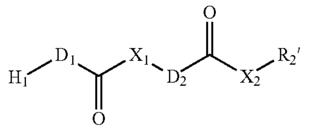

wherein, $H_1$ is a first click chemistry functional group, $D_1$ is selected from a covalent bond, $C_{1-4}$alkylene, $C_{2-4}$alkenylene, $C_{2-4}$alkynylene, and $C_{3-8}$cycloalkynlene, $X_1$ is S, $D_2$ is selected from $C_{1-7}$alkylene, $C_{2-7}$alkenylene, $C_{2-7}$alkynylene, and $C_{3-8}$cycloalkynlene, $X_2$ is O, $R_2'$ is N-succinimide, p-nitrophenyl, or pentafluorophenyl; and a peptide of formula 4-2:

$(Xaa)_{1-3}$-C-$(Xaa)_2$-H-$Xa_1$-G-$Xa_2$-L-V-$Xa_3$-C-$(Xaa)_{1-3}$ [formula 4-2]

wherein, each Xaa is independently any amino acid residue that is not a cysteine residue, C is a cysteine residue, H is a histidine residue, G is a glycine residue, $Xa_2$ is a glutamic acid residue or an asparagine residue, L is a leucine residue, V is a valine residue, $Xa_3$ is selected from a tryptophan residue, a naphthylalanine residue, and a phenylalanine residue, and $Xa_1$ is

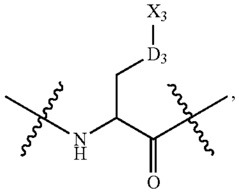

wherein $D_3$ is a covalent bond or $C_{1-3}$alkylene and $X_3$ is $NH_2$, wherein the peptide consists of 13 to 17 amino acid residues, wherein the peptide exhibits the activity of binding to human immunoglobulin G (IgG), and wherein the cysteine residue that is between two to four amino acids from the N-terminus of formula 4-2 and the cysteine residue that is between two to four amino acids from the C-terminus of formula 4-2 are optionally linked.

The present application provides an antibody or a fragment thereof comprising one or more amino acid sequence selected from formula 8-1, formula 8-2, and formula 8-3:

G-P-S-V-F-L-F-P-P-(K)'-P-K-D-T-L-M-I [formula 8-1]

G-P-S-V-F-L-F-P-P-K-P-(K)-D-T-L-M-I [formula 8-2]

G-P-S-V-F-L-F-P-P-(K)'-P-(K)'-D-T-L-M-I [formula 8-3]

wherein, G is a glycine residue, P is a proline residue, S is a serine residue, V is a valine residue, F is a phenylalanine residue, L is a leucine residue, K is a lysine residue, D is an aspartic acid residue, T is a threonine residue, M is a methionine residue, I is an isoleucine residue, and (K)' is

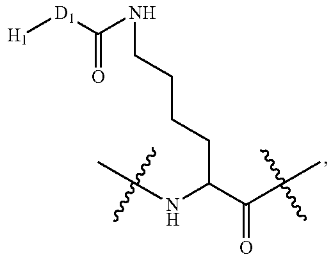

wherein $H_1$ is a first click chemistry functional group, $D_1$ is selected from a covalent bond, $C_{1-4}$alkylene, $C_{2-4}$alkenylene, $C_{2-4}$alkynylene, and $C_{3-8}$cycloalkynlene.

Also, the present application provides the antibody or a fragment thereof wherein $D_1$ is a covalent bond.

Additionally, the present application provides the antibody or a fragment thereof comprising the amino acid sequence of formula 8-1 and not comprising the amino acid sequence of formula 8-2 and 8-3. Furthermore, the present application provides the antibody or a fragment thereof comprising the amino acid sequence of formula 8-1 in both two Fc domains.

Additionally, the present application provides the antibody or a fragment thereof comprising the amino acid sequence of formula 8-2 and not comprising the amino acid sequence of formula 8-1 and 8-3. Furthermore, the present application provides the antibody or a fragment thereof comprising the amino acid sequence of formula 8-2 in both two Fc domains Additionally, the present application provides the antibody or a fragment thereof comprising the amino acid sequence of formula 8-3 and not comprising the amino acid sequence of formula 8-1 and 8-2. Furthermore, the present application provides the antibody or a fragment thereof comprising the amino acid sequence of formula 8-3 in both two Fc domains.

The present application provides a method for preparing an antibody or a fragment thereof comprising first click chemistry functional group comprising reacting a peptide-compound conjugate of formula 6-2:

$(Xaa)_{1-3}$-C-$(Xaa)_2$-H-$(Xa_1)'$-G-$Xa_2$-L-V-$Xa_3$-C-$(Xaa)_{1-3}$ [formula 6-2]

wherein, each Xaa is independently any amino acid residue that is not a cysteine residue, C is a cysteine residue, H is a histidine residue, G is a glycine residue, $Xa_2$ is a glutamic acid residue or an asparagine residue, L is a leucine residue, V is a valine residue, $Xa_3$ is selected from a tryptophan residue, a naphthylalanine residue, and a phenylalanine residue, and $(Xa_1)'$ is

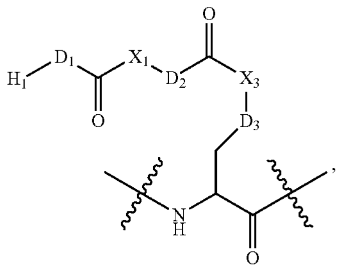

wherein $H_1$ is a first click chemistry functional group, $D_1$ is selected from a covalent bond, $C_{1-4}$alkylene, $C_{2-4}$alkenylene, $C_{2-4}$alkynylene, and $C_{3-8}$cycloalkynlene, $X_1$ is S, $D_2$ is selected from $C_{1-7}$alkylene, $C_{2-7}$alkenylene, $C_{2-7}$alkynylene, and $C_{3-8}$cycloalkynlene, $D_3$ is a covalent bond or $C_{1-3}$alkylene and $X_3$ is NH, wherein the peptide consists of 13 to 17 amino acid residues, wherein the peptide exhibits the activity of binding to human immunoglobulin G (IgG), and wherein the cysteine residue that is between two to four amino acids from the N-terminus of formula 6-2 and the cysteine residue that is between two to four amino acids from the C-terminus of formula 6-2 are optionally linked, with an antibody or a fragment thereof.

The present application provides a kit for preparing an antibody or a fragment thereof comprising first click chemistry functional group comprising a peptide-compound conjugate of formula 6-2:

$(Xaa)_{1-3}$-C-$(Xaa)_2$-H-$(Xa_1)'$-G-$Xa_2$-L-V-$Xa_3$-C-$(Xaa)_{1-3}$ [formula 6-2]

wherein, each Xaa is independently any amino acid residue that is not a cysteine residue, C is a cysteine residue, H is a histidine residue, G is a glycine residue, $Xa_2$ is a glutamic acid residue or an asparagine residue, L is a leucine residue, V is a valine residue, W is a tryptophan residue, and $(Xa_1)'$ is

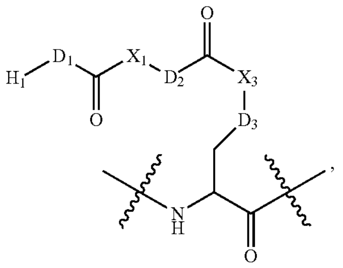

wherein $H_1$ is a first click chemistry functional group, $D_1$ is selected from a covalent bond, $C_{1-4}$alkylene, $C_{2-4}$alkenylene, $C_{2-4}$alkynylene, and $C_{3-8}$cycloalkynlene, $X_1$ is S, $D_2$ is selected from $C_{1-7}$alkylene, $C_{2-7}$alkenylene, $C_{2-7}$alkynylene, and $C_{3-8}$cycloalkynlene, $D_3$ is a covalent bond or $C_{1-3}$alkylene and $X_3$ is NH, wherein the peptide consists of 13 to 17 amino acid residues, wherein the peptide exhibits the activity of binding to human immunoglobulin G (IgG), and wherein the cysteine residue that is between two to four amino acids from the N-terminus of formula 6-2 and the cysteine residue that is between two to four amino acids from the C-terminus of formula 6-2 are optionally linked; and an antibody or a fragment thereof.

The present application provides a compound of formula 9:

$C_m$—$H_2$ [formula 9]

wherein, $C_m$ is a cargo moiety, $H_2$ is a second click chemistry functional group.

The present application provides a method for preparing an antibody-drug conjugate comprising reacting an antibody or a fragment thereof comprising one or more amino acid sequence selected from formula 8-1, formula 8-2, and formula 8-3:

G-P-S-V-F-L-F-P-P-(K)'-P-K-D-T-L-M-I [formula 8-1]

G-P-S-V-F-L-F-P-P-K-P-(K)'-D-T-L-M-I [formula 8-2]

G-P-S-V-F-L-F-P-P-(K)'-P-(K)'-D-T-L-M-I [formula 8-3]

wherein, G is a glycine residue, P is a proline residue, S is a serine residue, V is a valine residue, F is a phenylalanine residue, L is a leucine residue, K is a lysine residue, D is an aspartic acid residue, T is a threonine residue, M is a methionine residue, I is an isoleucine residue, and (K)' is

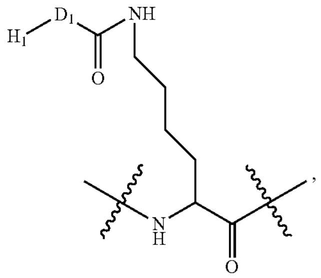

wherein $H_1$ is a first click chemistry functional group, $D_1$ is selected from a covalent bond, $C_{1-4}$alkylene, $C_{2-4}$alkenylene, $C_{2-4}$alkynylene, and $C_{3-8}$cycloalkynlene, with a compound of formula 9:

$C_m$—$H_2$ [formula 9]

wherein, $C_m$ is a cargo moiety, $H_2$ is a second click chemistry functional group which is complementary with the first click chemistry functional group.

The present application provides a kit for preparing an antibody-drug conjugate comprising an antibody or a fragment thereof comprising one or more amino acid sequence selected from formula 8-1, formula 8-2, and formula 8-3:

G-P-S-V-F-L-F-P-P-(K)'-P-K-D-T-L-M-I [formula 8-1]

G-P-S-V-F-L-F-P-P-K-P-(K)'-D-T-L-M-I [formula 8-2]

G-P-S-V-F-L-F-P-P-(K)'-P-(K)'-D-T-L-M-I [formula 8-3]

wherein, G is a glycine residue, P is a proline residue, S is a serine residue, V is a valine residue, F is a phenylalanine residue, L is a leucine residue, K is a lysine residue, D is an aspartic acid residue, T is a threonine residue, M is a methionine residue, I is an isoleucine residue, and (K)' is

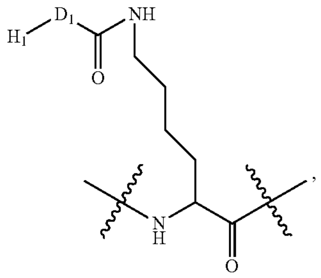

wherein $H_1$ is a first click chemistry functional group, $D_1$ is selected from a covalent bond, $C_{1-4}$alkylene, $C_{2-4}$alkenylene, $C_{2-4}$alkynylene, and $C_{3-8}$cycloalkynlene; and a compound of formula 9:

$C_m$—$H_2$ [formula 9]

wherein, $C_m$ is a cargo moiety, $H_2$ is a second click chemistry functional group which is complementary with the first click chemistry functional group.

The present application provides an antibody or a fragment thereof comprising one or more amino acid sequence selected from formula 10-1, formula 10-2, and formula 10-3:

G-P-S-V-F-L-F-P-P-(K)"-P-K-D-T-L-M-I [formula 10-1]

G-P-S-V-F-L-F-P-P-K-P-(K)"-D-T-L-M-I [formula 10-2]

G-P-S-V-F-L-F-P-P-(K)"-P-(K)"-D-T-L-M-I [formula 10-3]

wherein, G is a glycine residue, P is a proline residue, S is a serine residue, V is a valine residue, F is a phenylalanine residue, L is a leucine residue, K is a lysine residue, D is an aspartic acid residue, T is a threonine residue, M is a methionine residue, I is an isoleucine residue, and (K)" is

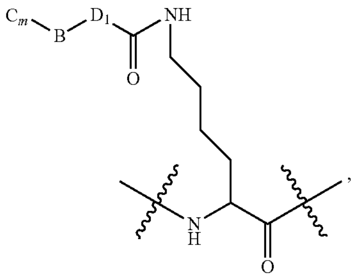

wherein $C_m$ is a cargo moiety, B is selected from

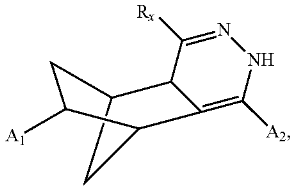

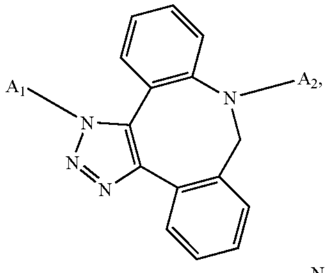

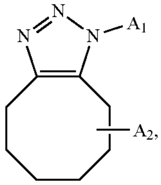

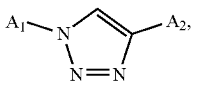

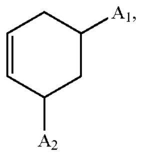

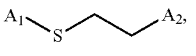

and

-continued

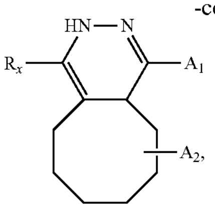

wherein $A_1$ and $A_2$ is connected to the cargo moiety or $D_1$ and they are not both connected to same, Rx is selected from H, halogen, and $C_{1-3}$alkyl, $D_1$ is selected from a covalent bond, $C_{1-4}$alkylene, $C_{2-4}$alkenylene, $C_{2-4}$alkynylene, and $C_{3-8}$cycloalkynlene.

Also, the present application provides the antibody or a fragment thereof comprising the amino acid sequence of formula 10-1 and not comprising the amino acid sequence of formula 10-2 and 10-3. Furthermore, the present application provides the antibody or a fragment thereof comprising the amino acid sequence of formula 10-1 in both two Fc domains.

Additionally, the present application provides the antibody or a fragment thereof comprising the amino acid sequence of formula 10-2 and not comprising the amino acid sequence of formula 10-1 and 10-3. Furthermore, the present application provides the antibody or a fragment thereof comprising the amino acid sequence of formula 10-2 in both two Fc domains.

Additionally, the present application provides the antibody or a fragment thereof comprising the amino acid sequence of formula 10-3 and not comprising the amino acid sequence of formula 10-1 and 10-2. Furthermore, the present application provides the antibody or a fragment thereof comprising the amino acid sequence of formula 10-3 in both two Fc domains.

Additionally, the present application provides the antibody or a fragment thereof wherein the cargo moiety comprises a drug moiety. Further, the present application provides the antibody or a fragment thereof wherein the cargo moiety comprises more than one drug moiety. Or further, the present application provides the antibody or a fragment thereof wherein the drug moiety is an anticancer agent. Furthermore, the present application provides the antibody or a fragment thereof wherein the anticancer agent is at least one selected from DM1, DM3, DM4, abrin, ricin A, pseudomonas exotoxin, cholera toxin, diphtheria toxin, tumor necrosis factor, α-interferon, β-interferon, nerve growth factor, platelet derived growth factor, tissue plasminogen activator, a cytokine, an apoptotic agen, an anti-angiogenic agent, a lymphokine, taxane, a DNA-alkylating agent, anthracycline, tubulysin analogs, duocarmycin analogs, auristatin E, auristatin F, maytansinoid, a cytotoxic agent comprising a reactive polyethylene glycol moiety, taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, methotrexate, 6-mercaptopurine, 6-thioguanine, cytarabine, 5-fluorouracil decarbazine, mechlorethamine, thiotepachlorambucil, meiphalan, carmustine, lomustine, cyclophosphamide, busulfan, dibromomannitol, streptozotocin, mitomycin C, cisplatin, dactinomycin, bleomycin, anthramycin, calicheamicin, Gemcitabine, bendamustine, bortezomib, carboplatin, cabazitaxel, dasatinib, docetaxel, epirubicin, erlotinib, everolimus, gemcitabine, gefitinib, idarubicin, imatinib, hydroxyurea, lapatinib, leuprorelin, melphalan, nedaplatin, nilotinib, oxaliplatin, pazopanib, pemetrexed, picoplatin, romidepsin, satraplatin, sorafenib, vemurafenib, sunitinib, teniposide, triplatin, and vinorelbine.

The present application provides a pharmaceutical composition for treating cancer comprising aforementioned antibody-drug conjugate Also, the present application provides the pharmaceutical composition for treating cancer wherein the cancer is selected from bladder cancer, bone cancer, brain tumor, breast cancer, heart cancer, cervical cancer, colorectal cancer, rectal cancer, esophageal cancer, fibrosarcoma, gastric cancer, gastrointestinal cancer, head and neck cancer, Kaposi sarcoma, renal cancer, leukemia, liver cancer, lung cancer, lymphoma, melanoma, myeloma, ovarian cancer, pancreatic cancer, penile cancer, prostate cancer, testicular germ cell cancer, thymoma and thymic carcinoma.

Additionally, the present application provides the pharmaceutical composition for treating cancer wherein the cancer is breast cancer.

The present application provides a method for treating cancer comprising administering a pharmaceutical composition comprising aforementioned antibody-drug conjugate to a subject.

Also, the present application provides the method for treating cancer wherein the cancer is selected from bladder cancer, bone cancer, brain tumor, breast cancer, heart cancer, cervical cancer, colorectal cancer, rectal cancer, esophageal cancer, fibrosarcoma, gastric cancer, gastrointestinal cancer, head and neck cancer, Kaposi sarcoma, renal cancer, leukemia, liver cancer, lung cancer, lymphoma, melanoma, myeloma, ovarian cancer, pancreatic cancer, penile cancer, prostate cancer, testicular germ cell cancer, thymoma and thymic carcinoma.

Furthermore, the present application provides the method for treating cancer wherein the cancer is breast cancer.

Advantageous Effects

An antibody product according to the present invention can have a certain number of chemical functional groups or cargo moieties labeled at a certain site thereof. Therefore, the present invention can provide an antibody product having high uniformity. Also, the present invention can provide an antibody product whose antibody functions are not degraded. That is, the present invention can provide an antibody product whose antibody binding affinity and half-life are not degraded. The present invention is of great significance as being the first technology allowing site-specific labeling of an antibody without any complicated processes.

BRIEF DESCRIPTION OF THE DRAWINGS

FIG. 1 shows a partial sequence of an Fc domain and numbers in the sequence numbered according to the EU numbering system.

DETAILED DESCRIPTION

Definitions

Figure 2:
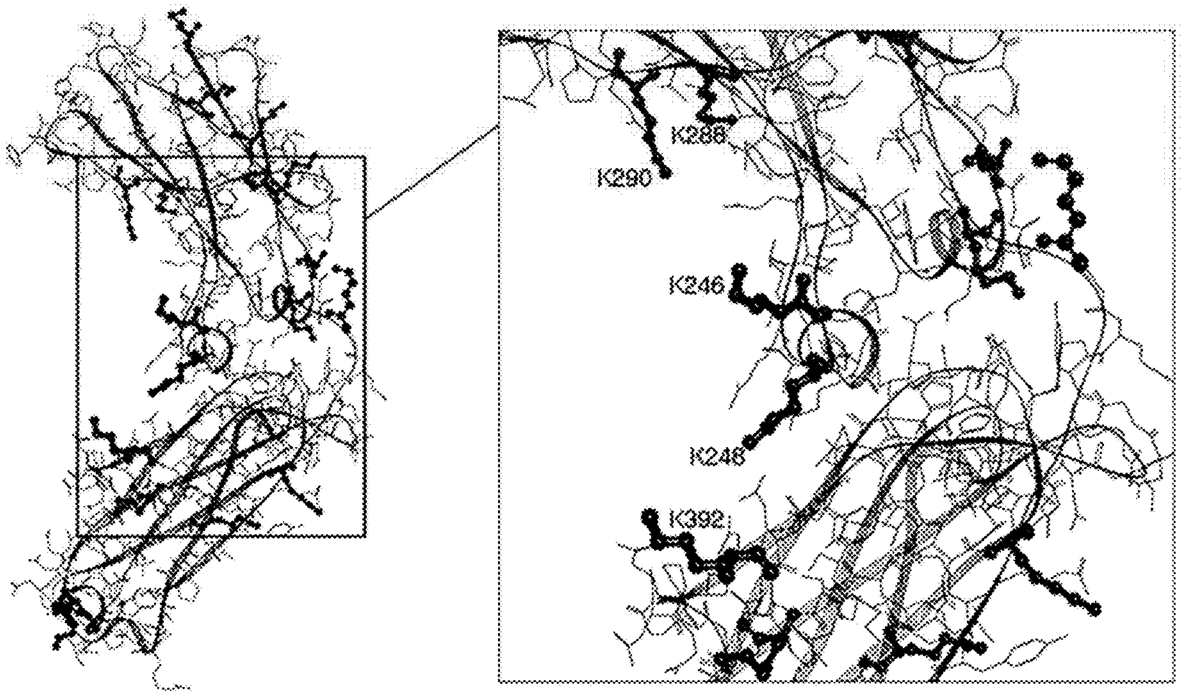
FIG. 2 shows positions of lysine residues in an Fc domain including lysine 246 and 248.

Unless otherwise defined, all technical and scientific terms used in the present invention have the same meaning as commonly understood by one of ordinary skill in the art to which this invention belongs. The following references are provided to give a number of common definitions of the terms used in the present invention to those skilled in the related art: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Unless otherwise clearly specified, the following terms used in the present invention shall have the meanings ascribed to them as follows.

In some embodiments, a chemical structure is disclosed together with the corresponding chemical name. When the terms contradict or conflict with each other, the chemical structure takes precedence over the chemical name to understand the meaning of a compound through the chemical structure.

The term "hetero" used in the present invention refers to a compound or a group of compounds including at least one heteroatom. The term "heteroatom" refers to an atom other than a carbon or hydrogen atom, and, for example, includes B, Si, N, P, O, S, and Se. Preferably, the heteroatom includes, among others, polyvalent elements such as N, O, and S, or monovalent elements such as F, Cl, Br, and I, but the present invention is not limited thereto.

The term "lower" used in the present invention is used to modify hydrocarbons, for example, alkylenes, and the like, and thus means that the corresponding hydrocarbon has 6 or less carbon atoms. For example, a $C_{1-6}$ linear or branched alkyl group are referred to by another name such as a "lower alkyl" group.

The term "oxy" used in the present invention refers to a secondary radical (—O—) of an oxygen atom.

The term "alkyl" or "alkane" refers to a linear or branched non-aromatic hydrocarbon that is completely saturated. Unless otherwise defined, a linear or branched alkyl group typically has a 1 to approximately 20 carbon atoms, preferably 1 to approximately 10 carbon atoms. The linear and branched alkyl group includes methyl, ethyl, n-propyl, isopropyl, n-butyl, sec-butyl, tert-butyl, pentyl, hexyl, pentyl, and octyl.

The term "alkenyl" or "alkene" refers to a linear or branched non-aromatic hydrocarbon that contains at least one double bond. Unless otherwise defined, a linear or branched alkenyl group typically has 1 to approximately 20 carbon atoms, preferably 1 to approximately 10 carbon atoms.

The term "alkynyl" or "alkyne" refers to a linear or branched non-aromatic hydrocarbon that contains at least one triple bond. Unless otherwise defined, a linear or branched alkynyl group typically has 1 to approximately 20 carbon atoms, preferably 1 to approximately 10 carbon atoms.

The term "cycloalkane" or "cycloalkyl" group refers to a completed saturated cyclic hydrocarbon. The "cycloalkyl" includes monocyclic and polycyclic rings. Unless otherwise defined, a monocyclic cycloalkyl group generally has 3 to approximately 10 carbon atoms, more generally 3 to 8 carbon atoms. Rings other than the first ring of the polycyclic cycloalkyl may be selected from saturated, unsaturated, and aromatic rings. The cycloalkyl includes a bicyclic molecule that contains 1, 2, or 3 or more atoms shared between two rings. The term "fused cycloalkyl" refers to a polycyclic cycloalkyl in which one ring shares two adjacent atoms with another ring. Rings other than the first ring of the fused polycyclic cycloalkyl may be selected from saturated, unsaturated, and aromatic rings.

The term "cycloalkyne" or "cycloalkynyl" refers to a cyclic hydrocarbon that contains at least one triple bond, which is also referred to as a "strained alkyne." The "cycloalkynyl" includes monocyclic and polycyclic rings. Unless otherwise defined, a monocyclic cycloalkynyl generally has 3 to approximately 10 carbon atoms, more generally 3 to 8 carbon atoms. Rings other than the first ring of the polycyclic cycloalkynyl may be selected from saturated, unsaturated and aromatic rings. The cycloalkynyl is a bicyclic molecule that contains 1, 2, or 3 or more atoms shared between two rings. The term "fused cycloalkynyl" refers to a polycyclic cycloalkynyl in which one ring shares two adjacent atoms with another ring. Rings other than the first ring of the fused polycyclic cycloalkynyl may be selected from saturated, unsaturated, and aromatic rings.

The term "alkylene" used as a molecule itself or used as part of another molecule refers to a divalent radical derived from an alkane. For example, the group includes $—CH_2CH_2—$, and $—CH_2CH_2CH_2CH_2—$, all of which contain 10 or less carbon atoms, but the present invention is not limited thereto. The term "lower alkylene" refers to a short alkylene group that generally has 6 or less carbon atoms. Unless stated otherwise, the term "alkylene" is intended to encompass groups represented by the "heteroalkylene" in the present invention.

The term "heteroalkylene" refers to a divalent radical derived from a heteroalkyl, and, for example, includes $—CH_2—CH_2—S—CH_2—CH_2—$, and $—CH_2—S—CH_2—CH_2—NH—CH_2—$, but the present invention is not limited thereto. A heteroalkylene group may contain the same or different heteroatoms at each end or all ends of a chain thereof (including an alkyleneoxy, an alkylenedioxy, an alkyleneamino, an alkylenediamino, an aminooxyalkylene, and the like, but the present invention is not limited thereto). Further, an indication of connection of both ends of the chain is independent of the arrangement of groups of a formula. For example, the formula $—C(O)_2R'—$ refers to both $—C(O)_2R'—$ and $—R'(O)_2C—$.

The term "alkenylene" used as a molecule itself or used as part of another molecule refers to a divalent radical derived from an alkene. For example, the group includes $—CH{=}CH—$, $—CH_2CH{\equiv}CHCH_2—$, and $—CH{=}CH—CH{=}CH—$, all of which have 10 or less carbon atoms, but the present invention is not limited thereto. Unless stated otherwise, the term "alkenylene" is intended to encompass heteroalkenylenes in the present invention.

The term "alkynylene" used as a molecule itself or used as part of another molecule refers to a divalent radical derived from an alkyne. For example, the group includes $—C{\equiv}C—$, $—CH_2C{\equiv}CCH_2—$, and $—C{\equiv}C—C{\equiv}C—$, all of which have 10 or less carbon atoms, but the present invention is not limited thereto. Unless stated otherwise, the term "alkynylene" is intended to encompass heteroalkynylenes in the present invention.

The term "cycloalkylene" used as a molecule itself or used as part of another molecule refers to a divalent radical derived from a cycloalkene. Unless stated otherwise, the "cycloalkylene" is intended to encompass heterocycloalkylenes in the present invention.

The term "alkylene" used in this specification, examples, and the claims is intended to encompass both "unsubstituted alkylene" and "substituted alkylene." Among these, the latter refers to an alkylene group that has a substituent replacing a hydrogen atom on one or more carbon atoms of the hydrocarbon. Unless otherwise clearly specified, the substituent may, for example, include a halogen, a hydroxyl group, a carbonyl group (for example, carboxyl, alkoxycarbonyl, formyl, or acyl), a thiocarbonyl group (for example, thioester, thioacetate, or thioformate), an alkoxy group, a phosphoryl group, a phosphate group, a phosphonate group, a phosphinate group, an amino group, an amido group, an amidine group, an imine group, a cyano group, a nitro group, an azido group, a sulfhydryl group, an alkylthio group, a sulfate group, a sulfonate group, a sulfamoyl group, a sulfonamido group, a sulfonyl group, a heterocyclyl group, an aralkyl group, or an aromatic or heteroaromatic group. When properly substituted, it may be understood by those skilled in the related art that a substituted residue on a hydrocarbon chain may itself be substituted. For example, the substituent of the substituted alkylene may include substituted and unsubstituted amino, azido, imino, amido, phosphoryl (including phosphonates and phosphinates), sulfonyl (including sulfates, sulfonamidos, sulfamoyls, and sulfonates), and silyl groups, and may also include ethers, alkylthios, carbonyls (including ketones, aldehydes, carboxylates, and esters), —CF3, —CN, and equivalents thereof. Exemplary substituted alkyls are as described below. The cycloalkylene may be further substituted with an alkyl, an alkenyl, an alkoxy, an alkylthio, an aminoalkyl, a carbonyl-substituted alkyl, —CF3, —CN, and equivalents thereof. This content is also equally applicable to the alkenylene and the alkynylene.

When used together with a residue such as an alkylene, an alkenylene, or an alkynylene, the term "$C_{x-y}$" is, for example, intended to encompass residues containing x to y carbon atoms in the chain thereof. For example, the term "$C_{x-y}$ alkylene" refers to a substituted or unsubstituted, linear or branched alkylene group that contains x to y carbon atoms in the chain thereof. For example, it is meant to exemplarily include a haloalkylene group such as difluoromethylene, 2,2,2-trifluoroethylene, and the like. The $C_0$ alkylene refers to a covalent bond. The terms "$C_{2-y}$ alkenylene" and "$C_{2-y}$ alkynylene" refers to a substituted or unsubstituted unsaturated aliphatic residue to which a definition of length and possible substitution is applied as described in the definition of the alkylene. However, this means that each contains at least one double or triple bond.

The term "click-chemistry reaction" is used as a chemical concept introduced by K. Barry Sharpless of the Scripps Research Institute to explain complementary chemical functional groups and a chemical reaction designed so that two molecules can rapidly and stably form a covalent bond. The click-chemistry reaction does not refer to a certain reaction, but refers to a concept of such a rapid and stable reaction. In any embodiment, the click-chemistry reaction must be modular, wide in scope, give high yields, generate only insignificant by-products, be stereospecific, physiologically stable, driven by a thermodynamic driving force (for example, greater than 84 KJ/mol), and/or have high atom economy. Some reactions are known to satisfy the requirements:

(1) Huisgen 1,3-dipolar cycloaddition (for example, including a Cu(I)-catalyzed cycloaddition reaction, which is often commonly referred to as a "click reaction"; see Tornoe et al., Journal of Organic Chemistry (2002) 67: 3057-3064): Copper or ruthenium is generally used as a catalyst;

[Schematic Diagram of Huisgen 1,3-Dipolar Cycloaddition]

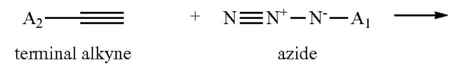

1,3-dipolar cycloaddition

-continued

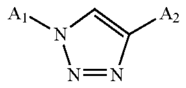

(2) Diels-Alder reaction, for example cycloaddition (for example, strain-promoted cycloaddition (SPAAC)) including a normal electron-demand Diels-Alder reaction and an inverse electron-demand Diels-Alder reaction, but the present invention is not limited thereto);

[Schematic Diagram of Diels-Alder Reaction]

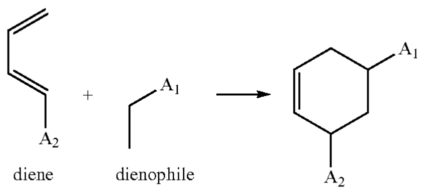

Diels-Alder reaction

[Example of Diels-Alder Reaction; TCO and Tetrazine]

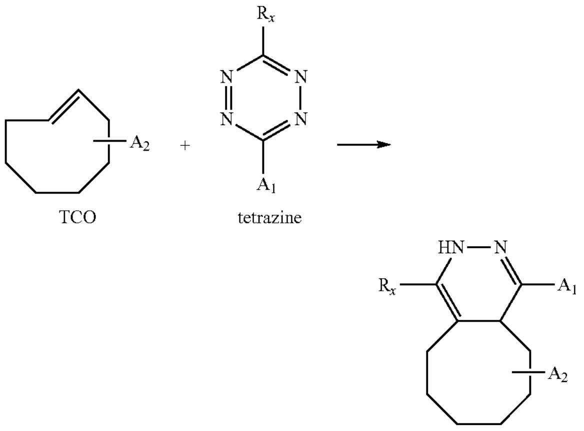

[Schematic Diagram of Strain-Promoted Cycloaddition]

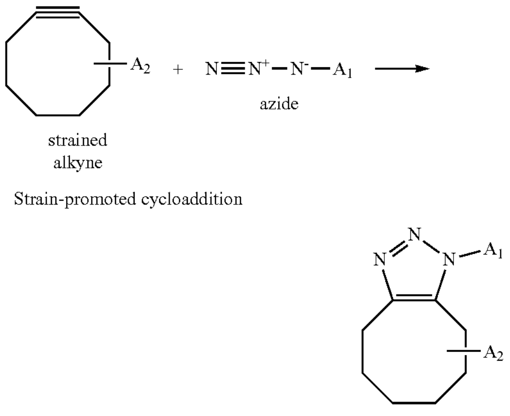

Strain-promoted cycloaddition

[Example of Strain-Promoted Cycloaddition; Azide and DBCO]

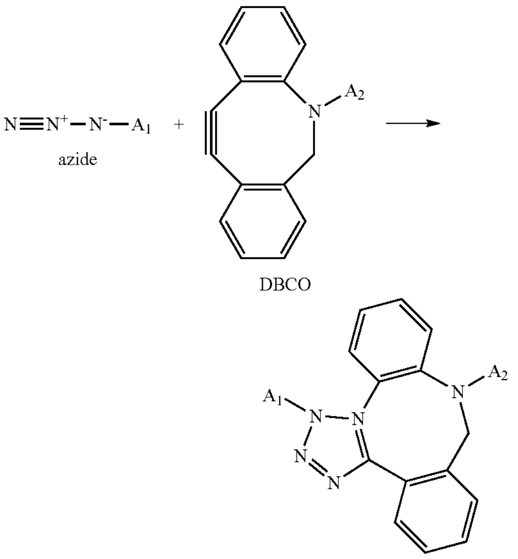

(3) Nucleophilic addition to small strained rings such as epoxides and aziridines;

(4) Nucleophilic addition to activated carbonyl groups;

(5) Addition to carbon-carbon double bonds or triple bonds.

[Addition of Thiol and Alkene]

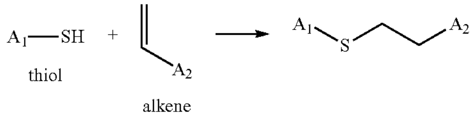

The term "click-chemistry functional group" used in the present invention refers to a functional group that participates in a click-chemistry reaction. For example, a strained alkyne (for example, a cyclooctyne) corresponds to a click-chemistry functional group. In general, the click-chemistry reaction requires at least two molecules, each of which contains click-chemistry functional groups complementary to each other. In this way, a pair of click-chemistry functional groups having reactivity with each other is often referred to as "partner click-chemistry functional groups" in the present invention. In strain-promoted cycloaddition of a cyclooctyne with an azide, for example, the azide is a partner click-chemistry functional group for the cyclooctyne and other alkynes. Exemplary click-chemistry functional groups used in the present invention include a terminal alkyne, an azide, a strained alkyne, a diene, a dienophile, a trans-cyclooctene, an alkene, a thiol, and a tetrazine, but the present invention is not limited thereto. Other click-chemistry functional groups are known to those skilled in the related art.

The term "leaving group" used in the present invention has the same concept as well known to those skilled in the related art (Advanced Organic Chemistry: reactions, mechanisms and structure-Fourth Edition of Jerry March, John Wiley and Sons Ed.; 1992, pages 351-357), and refers to a chemical functional group linked to any reactant, which moves when the reactant is subjected to a substitution reaction (displacement reaction), for example, a nucleophilic substitution reaction. A good leaving group refers to a leaving group that easily moves during the nucleophilic substitution reaction. Exemplary good leaving groups include a halogen (F, Cl, Br, and I), a tosylate, a mesylate, a triflate, an acetate, a trifluoromethylacetate, a camphorsulfonate, 2-thioxobenzo[d]thiazol-3 (2H)-yl, N-hydrosuccinimide, N-aryloxide, and an aryloxide substituted with one or more electron-withdrawing groups (EWGs), but the present invention is not limited thereto. For example, the aryloxide substituted with one or more electron-withdrawing groups include 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-chlorophenoxide, and the electron-withdrawing group, for example, includes a halogen (F, Cl, Br, or I), —$NO_2$, —CN, —C(O)($C_{1-6}$ alkyl), —C(O)(aryl), —C(O)O($C_{1-6}$ alkyl), —C(O)O(aryl), and the like.

The term "interactome" used in the present invention refers to a protein or a peptide that participates in a protein-protein interaction when there is a protein-protein interaction (PPI) between proteins or between peptides. For example, a chaperone protein and its passenger protein are mutual interactomes. The "protein-protein interaction" means that two or more proteins or peptide molecules interact to come into physical contact with each other with high specificity. In this case, the causative interaction includes an electromagnetic force, a hydrogen bond, and a hydrophobic interaction, but the present invention is not limited thereto.

The term "antibody interactome" used in the present invention refers to an interactome for an antibody including immunoglobulins. Exemplary antibody interactomes are listed in Table 1. Among these, peptides such as Fc-III, and the like are known to have binding activity for an Fc domain of an immunoglobulin. In this case, the peptides are also referred to as "Fc interactomes."

TABLE 1

List of SSAIs

| Peptide | Binding Constant | Binding Capacity | Elution pH | Remarks |
|---|---|---|---|---|
| PAM | $K_d$ = 0.3 μM | n.a. | 3 or 9 | Dendrimer comb. library |
| D-PAM | n.a. | 50 | 3.5 | SpA mimic |
| D-PAM-Φ | n.a. | 10 | 4 | |
| TWKTSRISIF | n.a. | n.a. | n.a. | Phage display library |
| FGRLVSSAIRY | n.a. | n.a. | n.a. | SpA mimic |
| Fc-III (DeLano et al.) Fc-III-Sepharose) | $K_d$ = 16 nM | 26.6 mg/μmol | 3.5 | Phage display cyclic peptide library SpA mimic |
| FcBP-2 | $K_d$ = 1.8 nM | n.a. | n.a. | Bicyclic peptide |
| Fc-III-4C | $K_d$ = 2.5 nM | n.a. | 3.5 | Bicyclic peptide |
| EFIHRSTLTALL | n.a. | 320 μg/g | n.a. | Phage display library SpA mimic |
| APAR | $K_d$ = 94 nM | 9.1 | n.a. | Comb. tetrapeptide library |
| FoRM | $K_d$ = 20 μM | n.a. | 2.7 | Synthetic cyclic peptide library, Fcv-receptor mimic |
| HWRGWV | $K_d$ = 10 μM | 28.4 | 4 | Comb. library |
| HYFKFD | $K_d$ = 11 μM | 27.0 | n.a. | (one-bead-one-peptide) |
| HFRRHL | $K_d$ = 26 μM | 33.6 | n.a. | SpA mimic |
| HWCitGWV | $K_d$ = 108 μM | 72 | n.a. | |
| $D_2$AAG | $K_a$ = 7.9 × $10^5 M^{-1}$ | 36.2 | 3.6 | Comb. library |
| DAAG | Ka = 2.6 × $10^5 M^{-1}$ | 49.6 | 3.6 | SpA mimic |
| cyclo [(Nα-Ac)S(A)-RWHYFK-Lact-E] | n.a. | n.a. | 3.5 | Cyclic peptide |
| cyclo [(Nα-Ac)Dap(A)-RWHYFK-Lact-E] | n.a. | n.a. | 3.5 | |
| cyclo[Link-M-WFRHYK] | $K_d$ = 7.6 μM | 19.7 | 4.0 | mRNA display library SpA mimic |
| NKFRGKYK | $K_a$ = 6.6 × $10^6 M^{-1}$ | DBBC-4.9 | 4.0 | Spot peptide array |
| NARKFYKG | $K_a$ = 6.5 × $10^6 M^{-1}$ | DBBC-5.0 | 4.0 | Fcv mimic |
| FYWHCLDE(1) | $K_d$ = 1.5 μM | 104.2 | 6.0 | Biometric design strategy |
| FYCHWALE(2) | $K_d$ = 6.1 μM | 87.6 | 6.0 | Fc-binder (SpA mimic) |
| FYCHTIDE(3) | $K_d$ = 5.7 μM | 63.7 | 6.0 | Dual affinity ligand |
| Dual 1/3 (2:1) | $K_d$ = 0.69 μM | 137.9 | 6.0 | |
| RRGW | $K_d$ = 0.5 μM | n.a. | n.a. | Computer design strategy Fc-binder |
| KHRFNKD | $K_d$ = 20 μM | n.a. | n.a. | Phage-display library SpA mimic |

* Maximal binding capacity ($q_m$) in mg/mL,
DBC: Dynamic binding capacity.
The depicted values are towards IgG and may not be directly compared to each other because they were obtained at different conditions or by different methods.
n.a.: Not available.

According to the present invention, the term "antibody" refers to an immunoglobulin molecule or a fragment thereof. Immunoglobulins are generally well known, and have an ability to specifically bind to a certain antigen. However, because the antibody according to the present invention is a concept that also encompasses a fragment thereof, the antibody does not have to show binding ability to a certain antigen as in case of the Fc fragment. In addition to the naturally occurring immunoglobulins, the antibody is also intended to encompass all recombinant proteins, fusion proteins, chimeric proteins, human immunoglobulins, non-human animal immunoglobulins, and the like, which have the same or similar structures.

According to the present invention, the term "conjugate" refers to a heterogeneous molecule made when conjugate partners are taken together to form a covalent bond. The covalent bond may be preferably formed by means of a click-chemistry reaction. The term “conjugate partner” refers to each of molecules intended to form a conjugate. In this case, when one wishing to perform conjugation intends to link a certain molecule to any other molecule, the certain molecule may be generally referred to as a “target molecule” or “target protein,” and the any other molecule may be generally referred to as a “cargo molecule” or “cargo moiety” for the sake of convenience.

According to the present invention, the term “carrier moiety” refers to a portion of molecule that constitutes a conjugate, that is, a molecule that functions to enhance serum stability of a molecule linked thereto or extend the half-life of the molecule. Molecules that may be used as the carrier moiety are well known in the related art. Representative examples of the carrier moiety include albumin, gelatin, elastin (including tropoelastin), an elastin-derived polypeptide (α-elastin and elastin-like polypeptides (ELPs)), gliadin, legumin, zein, a soy protein (for example, a soy protein isolate (SPI)), a milk protein, a whey protein, bilirubin, and the like, but the present invention is not limited thereto.

According to the present invention, the term “fluorescent moiety” is intended to encompass dyes or dye reagents used for fluorescence. Molecules that may be used as the dyes and dye reagents are well known in the related art. Representative examples of the fluorescent moiety are as listed in Table 2, but the present invention is not limited thereto (Immunotech-Coulter Corp. catalog, “Cytometry Monoclonal Reagent Guide,” 8/95, p. 3).

TABLE 2

List of fluorescent moieties

| Fluorochrome | Maximum Absorbance | Excitation at 488 nm | Maximum Emission | Fluorescence |
|---|---|---|---|---|
| Fluorescein isothiocyanate (FITC) | 495 nm | Yes | 525 nm | Green |
| Phycoerythrin (PE) | 488; 565 nm | Yes | 575 nm | Orange-red |
| Energy Coupled Dye [ECD] (PE-Texas-Red) | 488; 565 nm | Yes | 610-635 nm | Red Deep-red |
| Phycoerythrin-Cyanin 5 (PE-Cys) | 488; 565; 652 nm | Yes | 670 nm | |

According to the present invention, the term “drug moiety” refers to a molecule that has a therapeutic effect on any disease. The drug moiety according to the present invention includes those known to a person having ordinary skill in the art as being effective against any disease. Typically, the drug moiety having an anti-cancer effect includes DM1, DM3, DM4, Abrin, Ricin A, a Pseudomonas exotoxin, a Cholera toxin, a Diphtheria toxin, a tumor necrosis factor, a interferon, β interferon, a nerve growth factor, a platelet-derived growth factor, a tissue plasminogen activator, a cytokine, an apoptosis-inducing agent, an anti-angiogenic agent, a lymphokine, taxane, a DNA-alkylating agent, anthracyclin, a Tubulysin analogue, a duocarmycin analogue, auristatin E, auristatin F, a maytansinoid, a cytotoxic agent including a reactive polyethylene glycol residue, taxon, cytochalasin B, gramicidin D, ethidium bromide, emetine, mitomycin, etoposide, tenoposide, vincristine, vinblastine, T. Colchicine, doxorubicin, daunorubicin, dihydroxy anthracin dione, mitoxantrone, mithramycin, actinomycin D, 1-dihydrotestosterone, a glucocorticoid, procaine, tetracaine, lidocaine, propranolol, puromycin, methotrexate, 6-mercaptopurine, 6-thioguanine, cytarabine, 5-fluorouracil decarbazine, mechlorethamine, thiotepa, chlorambucil, Meiphalan, carmustine, lomustine, cyclophosphamide, busulfan, dibromomannitol, streptozotocin, mitomycin C, cisplatin, dactinomycin, bleomycin, anthramycin, calicheamicin, abiraterone, bendamustine, bortezomib, carboplatin, cabazitaxel, dasatinib, doxetaxel, epirubicin, erlotinib, everolimus, gemcitabine, gefitinib, idarubicin, imatinib, hydroxyurea, lapatinib, leuprorelin, melphalan, nedaplatin, nilotinib, oxaliplatin, pazopanib, pemetrexed, picoplatin, romidepsin, satraplatin, sorafenib, vemurafenib, sunitinib, teniposide, triplatin, and vinorelbine, but the present invention is not limited thereto.

According to the present invention, the term “radioactive moiety” refers to a moiety including a radioisotope. Radioisotopic labeling is useful for diagnostic imaging and radiotherapy. Representative radioactive moieties include $^{18}F$, $^{11}C$, $^{125}I$, $^{123}I$, $^{124}I$, $^{131}I$, and $^{99m}Tc$, but the present invention is not limited thereto.

The term “pharmaceutically acceptable carrier” may be used in the sense of including an excipient, a diluent, or an adjuvant. The carrier may be, for example, selected from the group consisting of lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinyl pyrrolidone, water, physiological saline, a buffer such as PBS, methylhydroxy benzoate, propylhydroxy benzoate, talc, magnesium stearate, and mineral oil. The carrier may include a filler, an anti-agglomerating agent, a lubricant, a wetting agent, a flavoring agent, an emulsifying agent, a preservative, or a combination thereof.

The term “pharmaceutically acceptable salt” refers to a salt in which biological effectiveness and properties of a proteome and a compound according to the present invention are preserved and that is not undesirable in biological or other aspects. In many cases, the proteome and compound of the present invention may form an acidic and/or basic salt in the presence of a charged group, for example, a charged amino and/or carboxyl group or the likes. A pharmaceutically acceptable acid addition salt may be prepared from an inorganic and organic acid, and a pharmaceutically acceptable base addition salt may be prepared from an inorganic and organic base.

The term “treatment” refers to an approach to obtain beneficial or desirable clinical outcomes. For the object of the present invention, non-limiting examples of the beneficial or desirable clinical outcomes include palliation of symptoms, reduction of a disease range, stabilization (i.e., not worsening) of a disease state, delay of progression or reduction of a progression rate of a disease, (partially or totally) improvement or temporal palliation and mitigation of a disease condition, and whether detectable or not. The treatment denotes all therapeutic treatments, and prophylactic or preventative methods. The treatments include treatments required for disorders to be prevented and already-occurring disorders. "Palliating" a disease means that a range of disease conditions and/or undesirable clinical signs are lowered and/or a time course of progression of the disease is delayed or extended, compared to when the disease is not treated.

The "therapeutically effective amount" (or "effective amount") refers to a sufficient amount of an active ingredient, for example, an agent according to the present invention, to achieve the treatment when administered to a subject or a patient. Therefore, what constitutes a therapeutically effective amount of a composition according to the present invention may be easily determined by those skilled in the related art. In the context of vision therapy, the "therapeutically effective amount" is an amount that causes an objectively measured change in one or more parameters associated with the treatment of eye diseases or conditions, which include an increase or decrease in expression of one or more genes associated with the eye diseases or conditions, an induction of apoptosis or other cell death pathways, a clinical improvement in symptoms, a decrease in abnormal neovascularization or inflammation, and the like. Of course, the therapeutically effective amount may vary depending on a certain subject and condition to be treated, the weight and age of a subject, the severity of a disease condition, a certain compound to be selected, a subsequent dosing schedule, the administration time adjustment, a mode of administration, and the like, all of which may be easily determined by those skilled in the related art. In the context of combination therapy, it should be understood that what constitutes a therapeutically effective amount of a certain active ingredient may be different from what constitutes a therapeutically effective amount of an active ingredient that is administered for monotherapy (that is, a treatment regimen using one chemical entity as the active ingredient).

The "subject" or "patient" refers to an animal in need of treatment which may be achieved by the molecule of the present invention. The animal to be treated according to the present invention includes a vertebrate. Particularly preferred examples of the animal include mammals, for example, bovine, canine, equine, feline, ovine, porcine, and primate animals (including human and non-human primates).

The term "about" or "approximately" refers to an amount, level, value, number, frequency, percentage, dimension, size, quantity, weight, or length that varies by 30, 25, 20, 25, 10, 9, 8, 7, 6, 5, 4, 3, 2, or 1% with respect to the reference amount, level, value, number, frequency, percentage, dimension, size, quantity, weight, or length.

1. Antibody

It should be understood that the description of the present invention is intended to provide a description of the structure, academic system, and physiological action of an antibody provided to aid in understanding the present invention, and the antibody falling within the scope of rights of the present invention is not intended to limit the description of the present invention.

An antibody consists of two heavy chains and two light chains as known in the art. When an antibody is simply divided in a functional aspect, the antibody is divided into a fragment antigen-binding variable region (Fab) including a light chain and a fragment crystallizable region composed as a portion of a heavy chain. The Fab includes a paratope that binds to an antigen, and refers to a region that allows an antibody to have specific binding activity for an antigen as known in the art. As the Fc domain is a ligand for an Fc receptor (FcR) in cells, it plays an important role in inducing an immune response. Also, the Fc domain plays an important role in extending the half-life of an antibody by binding to a neonatal Fc receptor so that the antibody can be repeatedly internalized into the cells.

From these facts, it is possible to deduce some desirable directivity of labeling an antibody: (1), First, it is desirable to label an antibody at a position spaced apart from a paratope of the antibody. When the labeling is performed on the paratope or at a position adjacent to the paratope, a binding affinity of the antibody for an antigen may be significantly lowered. (2) Second, it is desirable to label an antibody at a position spaced apart from a recognition site of FcR including FcRn. When the labeling is performed on the recognition site of the receptor or at a position adjacent to the recognition site, an immune response-inducing function of the antibody may be reduced, or the half-life of the antibody may be shortened. Information on the binding activity motif of the Fc domain may be found in DeLano, W. L. (2000): Convergent Solutions to Binding at a Protein-Protein Interface; Science, 287(5456), 1279-1283, and W. Lance Martin et al. (2001), Molecular Cell, Vol. 7, 867-877, April 2001.

In the present invention, when reference to an amino acid sequence of the Fc domain of the antibody is made, numbers in the sequence are numbered according to the EU numbering system unless stated otherwise. The EU numbering system has been widely used as a sequencing system for the Fc domain after research on the sequence of IgG, as described in Edelman G M, et al., The covalent structure of an entire gamma-G immunoglobulin molecule; Proc. Natl. Acad. Sci. USA, 1969 May; 63(1): 78-85.

1.1. Search for Desirable Labeling Site

A labeling site of an antibody may be designed in consideration of the criteria for the labeling site, that is, (1) a site spaced apart from a paratope; and (2) a site spaced apart from a recognition site of FcR including FcRn. Examples of the amino acids used in a bioconjugation reaction typically include lysine, cysteine, and tyrosine. Lysine 246 (Lys246) and lysine 248 (Lys248) present in an Fc domain of the antibody are residues that satisfy all the requirements, and thus are both desirable labeling sites. A sequence of the Fc domain including the Lys246 and Lys248 residues is GPSVFLFPPKPKDTLMI, and the sequence and numbers in the sequence numbered according to the EU numbering system are shown in FIG. 1 (FIG. 1, SEQ ID NO: 1).

In specific embodiments, the antibody according to the present invention may include a sequence of SEQ ID NO: 1 or derivatives thereof. Also, the antibody according to the present invention may include a derivative of SEQ ID NO: 1 in which lysine 246 is substituted. In addition, the antibody according to the present invention may include a derivative of SEQ ID NO: 1 in which lysine 248 is substituted. Furthermore, the antibody according to the present invention may include a derivative of SEQ ID NO: 1 in which lysine 246 and 248 are substituted.

The sequence of SEQ ID NO: 1 or derivatives thereof include sequences mutated in an acceptable range. In specific embodiments, the mutated sequences may have a homology that is greater than or equal to approximately 90%, approximately 85%, approximately 80%, approximately 75%, or approximately 70% with respect to the sequence of SEQ ID NO: 1 or derivatives thereof. In specific embodiment specified below, it should be understood that the derivatives of SEQ ID NO: 1 represented by Formulas 7-1 to 7-3, 8-1 to 8-3, and 10-1 to 10-3 also include sequences mutated in an acceptable range.

FIG. 2 shows positions of lysine residues in an Fc domain including lysine 246 and 248.

2. Linker ($R_1$'-$L_1$)

The present invention discloses a novel compound capable of being used to label an antibody. For the sake of convenience, such a compound is herein referred to as a linker, which is indicated by the symbol "$R_1$'-$L_1$."

The present invention provides a compound having a structure of the following Formula 1:

[Formula 1]

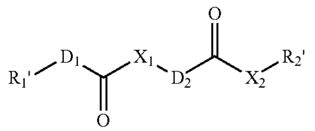

wherein $R_1$' is a first chemical functional group, $D_1$ is any alkylene, alkenylene, or alkynylene, $X_1$ is an element that is more electronegative than carbon, $D_2$ is any alkylene, alkenylene, or alkynylene, $X_2$ is an element that is more electronegative than carbon, and $R_2$' is a second chemical functional group.

In Formula 1, a carbonyl group connected to $D_1$ is referred to as a first carbonyl group. Also, a carbonyl group connected to $D_2$ is referred to as a second carbonyl group.

In specific embodiments, $R_1$' may include a click-chemistry functional group. Also, the click-chemistry functional group may include one or more selected from an alkyne, an azide, a strained alkyne, a diene, a dienophile, an alkene, a thiol, and a tetrazine. Furthermore, the click-chemistry functional group may be selected from an azide, or a strained alkyne. Further, the click-chemistry functional group may be selected from an azide, or dibenzocyclooctyne-amine. Additionally, the click-chemistry functional group may be selected from a diene, or a dienophile. Further, the click-chemistry functional group may be selected from a tetrazine, or a norbornene. Alternatively, the click-chemistry functional group may be selected from a tetrazine, or a trans-cyclooctene. In addition, $R_1$' may include two or more click-chemistry functional groups.

In other specific embodiments, $R_1$' may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond. When $D_1$ is a covalent bond, $R_1$' and the carbon of the first carbonyl group are directly connected to each other. Hereinafter, when describing a structure of a compound, all the alkylene, the alkenylene, the alkynylene, and the cycloalkylene are intended to include a heteroalkylene, a heteroalkenylene, a heteroalkynylene, and heterocycloalkylene, respectively, the contents of which are also specified in the section "Definitions."

In specific embodiments, $X_1$ may be $NR_1$, S, or O, wherein $R_1$ may be H, a halogen, or a substituted or unsubstituted $C_{1-3}$ alkylene. Also, $X_1$ may be S. $X_1$ may attract electrons from the carbon of the first carbonyl group to activate the first carbonyl group.

In specific embodiments, $D_2$ may include any one selected from a $C_{1-7}$ alkylene, a $C_{2-7}$ alkenylene, a $C_{2-7}$ alkynylene, and a $C_{3-8}$ cycloalkylene. Also, $D_2$ may be a $C_{1-2}$ alkylene. Furthermore, $D_2$ may be methylene.

In specific embodiments, $X_2$ may be $NR_1$, S, or O, wherein $R_1$ may be H, a halogen, or a substituted or unsubstituted $C_{1-3}$ alkylene. Also, $X_2$ may be O. $X_2$ may attract electrons from the carbon of the second carbonyl group to activate the second carbonyl group.

In specific embodiments, $R_2$' may be a halogen, N-succinimide, p-nitrophenyl, or pentafluorophenyl.

In specific embodiments, $R_2$' and $X_2$ taken together may form a leaving group. For example, $X_2$ may be O, and $R_2$' may be N-succinimide, p-nitrophenyl, or pentafluorophenyl. Also, $R_2$' may be N-succinimide. When a good leaving group is connected to the second carbonyl group, reactivity of the second carbonyl group may be enhanced. For example, an N-hydroxysuccinimide ester (an NHS ester) is known to show very high reactivity.

The present invention provides a compound having a structure of the following Formula 1-2:

[Formula 1-2]

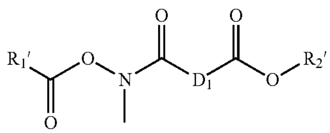

wherein $R_1$' is a first chemical functional group, $D_1$ is any alkylene, alkenylene, or alkynylene, and $R_2$' is a second chemical functional group.

In specific embodiments, $R_1$' may include a click-chemistry functional group. Also, the click-chemistry functional group may include one or more selected from an alkyne, an azide, a strained alkyne, a diene, a dienophile, an alkene, a thiol, and a tetrazine. Furthermore, the click-chemistry functional group may be selected from an azide, or a strained alkyne. Further, the click-chemistry functional group may be selected from an azide, or dibenzocyclooctyne-amine. Additionally, the click-chemistry functional group may be selected from a diene, or a dienophile. Further, the click-chemistry functional group may be selected from a tetrazine, or a norbornene. Alternatively, the click-chemistry functional group may be selected from a tetrazine, or a trans-cyclooctene. In addition, $R_1$' may include two or more click-chemistry functional groups.

In other specific embodiments, $R_1$' may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, $D_1$ may include any one selected from a $C_{1-7}$ alkylene, a $C_{2-7}$ alkenylene, a $C_{2-7}$ alkynylene, and a $C_{3-8}$ cycloalkylene. Also, $D_1$ may be a $C_{1-2}$ alkylene. Furthermore, $D_1$ may be methylene.

In specific embodiments, $R_2$' and O taken together may form a leaving group. In this case, $R_2$' may be N-succinimide, p-nitrophenyl, or pentafluorophenyl. Also, $R_2$' may be N-succinimide.

In specific embodiments, the compound represented by Formula 1-2 may have a structure of the following Formula 1-3:

[Formula 1-3]

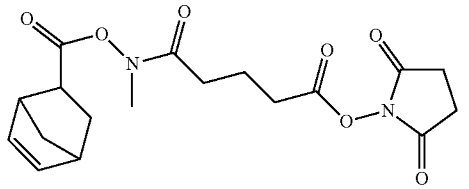

2.1. Linker Including First Click-Chemistry Functional Group ($H_1$-$L_1$)

The present invention provides a compound having a structure of the following Formula 2:

[Formula 2]

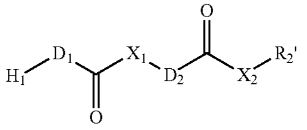

wherein $H_1$ is a first click-chemistry functional group, $D_1$ is any alkylene, alkenylene, or alkynylene, $X_1$ is an element that is more electronegative than carbon, $D_2$ is any alkylene, alkenylene, or alkynylene, $X_2$ is an element that is more electronegative than carbon, and $R_2$' is a second chemical functional group. The linker having the structure of Formula 2 is herein referred to as a "linker including a first click-chemistry functional group," which is indicated by the symbol "$H_1$-$L_1$."

In Formula 2, a carbonyl group connected to $D_1$ is referred to as a first carbonyl group. Also, a carbonyl group connected to $D_2$ is referred to as a second carbonyl group.

In specific embodiments, $H_1$ may include any one selected from an alkyne, an azide, a strained alkyne, a diene, a dienophile, an alkene, a thiol, and a tetrazine. Furthermore, $H_1$ may be an azide, or a strained alkyne. Further, $H_1$ may be an azide, or dibenzocyclooctyne-amine. Additionally, $H_1$ may be a diene, or a dienophile. Further, $H_1$ may be a tetrazine, or a norbornene. Alternatively, $H_1$ may be a tetrazine, or a trans-cyclooctene.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond.

In specific embodiments, $X_1$ may be $NR_1$, S, or O, wherein $R_1$ may be H, a halogen, or a substituted or unsubstituted $C_{1-3}$ alkylene. Also, $X_1$ may be S.

In specific embodiments, $D_2$ may include any one selected from a $C_{1-7}$ alkylene, a $C_{2-7}$ alkenylene, a $C_{2-7}$ alkynylene, and a $C_{3-8}$ cycloalkylene. Also, $D_2$ may be a $C_{1-2}$ alkylene. Furthermore, $D_2$ may be methylene.

In specific embodiments, $X_2$ may be $NR_1$, S, or O, wherein $R_1$ may be H, a halogen, or a substituted or unsubstituted $C_{1-3}$ alkylene. Also, $X_2$ may be O.

In specific embodiments, $R_2$' may be a halogen, N-succinimide, p-nitrophenyl, or pentafluorophenyl.

In specific embodiments, $R_2$' and $X_2$ taken together may form a leaving group. For example, $X_2$ may be O, and $R_2$' may be N-succinimide, p-nitrophenyl, or pentafluorophenyl. Also, $R_2$' may be N-succinimide.

In specific embodiments, the compound represented by Formula 2 may have any one structure selected from the following Formulas 2-1 to 2-3:

[Formula 2-1]

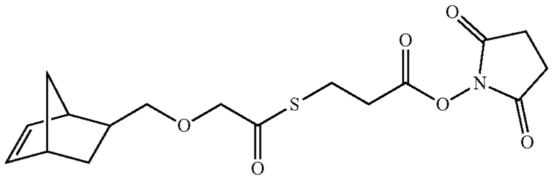

[Formula 2-2]

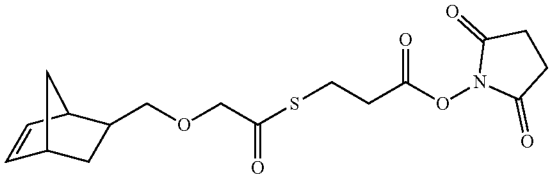

[Formula 2-3]

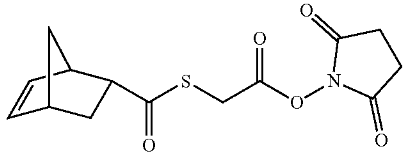

2.2. The position at which a substitution reaction occurs may be specifically determined due to the difference in reactivity between the first carbonyl group and the second carbonyl group When the linkers of Formulas 1 and 2, and sub-examples thereof are designed, sites for substitution reaction may be specified based on the design of $X_1$, $X_2$, and $R_2$'.

The linker disclosed in the present invention functions to transfer $R_1$' to a target molecule by means of a substitution reaction occurring between the activated first and/or second carbonyl groups. Such a substitution reaction is schematically shown as in the following Scheme 1.

[Scheme 1]

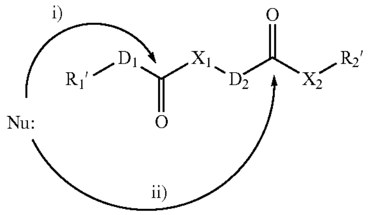

In Scheme 1, the target molecule is designated "Nu:" for the sake of convenience. The Nu: that serves as a nucleophile because it has an unshared electron pair causes a nucleophilic acyl substitution reaction with the first carbonyl group and/or second carbonyl group to form a bond with a linker. In the nucleophilic acyl substitution reaction, the reactivity of the carbonyl group may be determined by the basicity of the leaving group. Therefore, the reactivity of the carbonyl group is known to increase in the order of the carboxylate, the amide, the carboxylic acid, the ester, the thioester, and the acyl phosphate. Also, the carbonyl group such as an NHS ester, or the like is known to have high reactivity because the carbonyl group forms a very stable leaving group.

In specific embodiments, $X_1$ and $X_2$ may be elements that are more electronegative than carbon. Also, $X_1$ and $X_2$ may be $NR_1$, S, or O, wherein $R_1$ may be H, a halogen, or a substituted or unsubstituted $C_{1-3}$ alkylene. Because $X_1$ and $X_2$ taken together with the residue(s) to which they are attached may form a leaving group, the carbonyl group may be activated.

In this case, the activation of the carbonyl group may optionally allow Nu: to i) preferentially react with the first carbonyl group or ii) preferentially react with the second carbonyl group. This tendency of reaction may be determined depending on a difference in reactivity between the first carbonyl group and the second carbonyl group. For example, when the basicity of a leaving group including $X_1$ is lower than that of a leaving group including $X_2$, the first carbonyl group may react first. In another embodiment, when the basicity of the leaving group including $X_2$ is lower than that of the leaving group including $X_1$, the second carbonyl group may react first.

In preferred embodiments, the reactivity of the second carbonyl group is preferably higher than that of the first carbonyl group in the linker according to the present invention. According to the present invention, a selective reaction was achieved by allowing $X_2$-$R_2'$ connected to the second carbonyl group to form a good leaving group, and designing the first carbonyl group to be an amide, a thioester, an ester, and the like, which show mild reactivity. For example, in the case of the linker of Formula 1-3, the second carbonyl group may be an NHS ester, thereby allowing it to react faster than the first carbonyl group (a thioester).

The prior art disclosed in Publication Nos. US 2018/0141976 A1 and WO 2018/199337 A1 is similar to the present invention in terms of the form of an agent for transferring a first chemical functional group to an antibody (see section 4 below), but is different from the present invention in that the cross-linker includes two NHS esters. The two carbonyl groups of the cross-linker have the same reactivity, and it is difficult to prepare a desired agent for transferring a chemical functional group with high yield. Also, the cross-linker has a high probability of reacting with two SSFIs due to high reactivity of the NHS esters. According to the present invention, such problems have been solved by designing the first carbonyl group to be a thioester, and the like, which have mild reactivity.

3. Site-Specific Antibody Interactome (SSAI)

According to the present invention, there is disclosed a novel peptide for bringing a molecule to be labeled into close contact with a certain site of an antibody. For the sake of convenience, such a peptide is herein referred to as a site-specific antibody interactome, which is indicated by the symbol "SSAI."

The SSAI provided according to the present invention may have binding activity for a certain site of an antibody.

In specific embodiments, the SSAI may have binding activity for an Fab domain of the antibody. In this case, the SSAI may preferably have binding activity for a site spaced apart from a paratope of the antibody.

In specific embodiments, the SSAI may have binding activity for the Fc domain of the antibody. In this case, the SSAI may preferably have binding activity for an FcRn binding site of the antibody or a site spaced apart from residues of the antibody which affects the FcRn binding site of the antibody.

3.1: Site-Specific Fc Interactome (SSFI)

In the SSAI, a peptide having specific binding activity for the Fc domain is herein referred to as a "site-specific Fc interactome", which is indicated by the symbol "SSFI."

In specific embodiments, the SSFI may include an amino acid sequence represented by the following Formula 3:

[Formula 3]

(SEQ ID NO. 3)

$(Xaa)_2$-H-$Xa_1$-G-$Xa_2$-L-V-$Xa_3$ wherein each Xaa is independently any amino acid except cysteine, H is histidine, G is glycine, $Xa_2$ is glutamic acid or asparagine, L is leucine, V is valine, $Xa_3$ is selected from tryptophan, naphthylalanine, and phenylalanine, and $Xa_1$ is

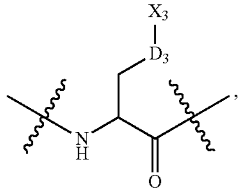
, wherein $D_3$ is a covalent bond or a $C_{1-3}$ alkylene, and $X_3$ is $NH_2$, OH, or SH. As an analogue of the sequence AWHLGELVW (SEQ ID NO: 2), which is a sequence found to have binding activity for the Fc domain in the articles "Dias, R. L. A., et al (2006), Protein Ligand Design: From Phage Display to Synthetic Protein Epitope Mimetics in Human Antibody Fc-Binding Peptidomimetics; Journal of the American Chemical Society, 128(8), 2726-2732; and DeLano, W. L., et al., Convergent solutions to binding at a protein-protein interface; Science 2000, 287, 1279-1283," it has binding activity for the Fc domain. The Fc binding activity motif according to the present invention has characteristics as follows: 1) First, key residues having Fc binding activity are specified. 2) The motif is also designed to allow a nucleophilic substitution reaction with a linker by changing the 4th leucine of SEQ ID NO: 2 into $Xa_1$ having a free electron pair. $(X)_n$ means that it consists of n Xs, and $(X)_{n-m}$ means that it consist of n or more and m or less Xs. Hereinafter, the carbon connected to $D_3$ is referred to as "beta carbon (β-carbon)."

Also, the amino acid sequence of Formula 3 may have a structure represented by the following Formula 3-1:

[Formula 3-1]

(SEQ ID NO. 4)

A-W-H-$Xa_1$-G-$Xa_2$-L-V-$Xa_3$ wherein A is alanine, H is histidine, G is glycine, $Xa_2$ is glutamic acid or asparagine, Lis leucine, V is valine, $Xa_3$ is selected from tryptophan, naphthylalanine, and phenylalanine, and $Xa_1$ is

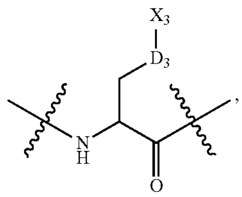

wherein $D_3$ is a covalent bond or a $C_{1-3}$ alkylene, and $X_3$ is $NH_2$, OH, or SH. In Formulas 3 and 3-1, $X_3$ may be $NH_2$. Alternatively, $Xa_2$ may be glutamic acid. Alternatively, $Xa_3$ may be tryptophan.

When the peptide including each of amino acid sequences of Formula 3 and sub-examples thereof is in a cyclic peptide form in which internal residues are connected to each other, the peptide is known to have better binding activity. The present invention provides a cyclic peptide including the amino acid sequence of Formula 3.

The present invention provides a cyclic peptide having a structure of the following Formula 4-1:

[Formula 4-1]

(SEQ ID NO: 5)

$^L$P-(Xaa)$_2$-H-$Xa_1$-G-$Xa_2$-L-V-$Xa_3$-$^D$P wherein N-terminal $^L$P and $^D$P form a D-proline-L-proline template, each Xaa is independently any amino acid except cysteine, H is histidine, G is glycine, $Xa_2$ is glutamic acid or asparagine, L is leucine, V is valine, $Xa_3$ is selected from tryptophan, naphthylalanine, and phenylalanine, and $Xa_1$ is

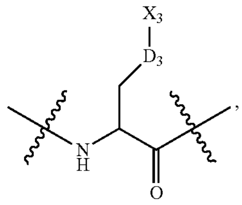

wherein $D_3$ is a covalent bond or a $C_{1-3}$ alkylene, and $X_3$ is $NH_2$, OH, or SH.

In specific embodiments, $X_3$ may be $NH_2$. In specific embodiments, $(X)_2$ may be AW. In specific embodiments, $Xa_2$ may be glutamic acid. In specific embodiments, $Xa_3$ may be tryptophan.

The present invention provides a cyclic peptide having a structure of the following Formula 4-2:

[Formula 4-2]

(SEQ ID NO: 6)

(Xaa)$_{1-3}$-C-(Xaa)$_2$-H-$Xa_1$-G-$Xa_2$-L-V-$Xa_3$-C-(Xaa)$_{1-3}$ wherein each Xaa is independently any amino acid except cysteine, C is cysteine, H is histidine, G is glycine, $Xa_2$ is glutamic acid or asparagine, L is leucine, V is valine, $Xa_3$ is selected from tryptophan, naphthylalanine, and phenylalanine, and $Xa_1$ is

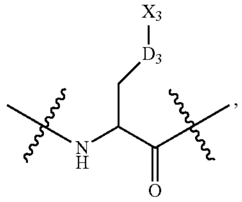

wherein $D_3$ is a covalent bond or a $C_{1-3}$ alkylene, and $X_3$ is $NH_2$, OH, or SH.

In specific embodiments, the peptide may consist of 13 or more and 17 or less amino acid residues.

In specific embodiments, cysteine located 2 to 4 amino acids from the N-terminus and cysteine located 2 to 4 amino acids from the C-terminus may be optionally connected to each other.

In specific embodiments, $X_3$ may be $NH_2$. In specific embodiments, $(X)_2$ may be AW. In specific embodiments, $Xa_2$ may be glutamic acid. In specific embodiments, $Xa_3$ may be tryptophan.

In specific embodiments, one of the residues constituting the N-terminal $(X)_{1-3}$ and one of the residues constituting the C-terminal $(X)_{1-3}$ may be bound to each other. In one exemplary embodiment, the peptide of Formula 4-2 may have a structure of the following Formula 4-3:

[Formula 4-3]

(SEQ ID NO: 7)

$^L$P-D-C-(Xaa)$_2$-H-$Xa_1$-G-$Xa_2$-L-V-$Xa_3$-C-T-$^D$P wherein N-terminal $^L$P와$^D$P may form a D-proline-L-proline template.

In another exemplary embodiment, the peptide of Formula 4-2 may have a structure of the following Formula 4-4:

[Formula 4-4]

(SEQ ID NO: 5)

C-D-C-(Xaa)$_2$-H-$Xa_1$-G-$Xa_2$-L-V-$Xaa_3$-C-T-C wherein the N-terminal cysteine and the C-terminal cysteine may be connected to each other.

The present invention provides a cyclic peptide having a structure of the following Formula 4-5:

[Formula 4-5]

(SEQ ID NO: 9)

D-C-(Xaa)$_2$-H-$Xa_1$-G-$Xa_2$-L-V-$Xa_3$-C-T wherein D is aspartic acid, T is threonine, each Xaa is independently any amino acid except cysteine, C is cysteine, H is histidine, G is glycine, $Xa_2$ is glutamic acid or asparagine, L is leucine, V is valine, $Xa_3$ is selected from tryptophan, naphthylalanine, and phenylalanine, and $Xa_1$ is

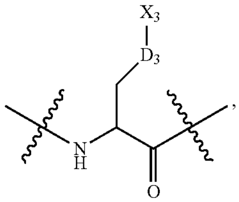

wherein $D_3$ is a covalent bond or a $C_{1-3}$ alkylene, and $X_3$ is $NH_2$, OH, or SH.

In specific embodiments, the peptide may consist of 13 or more and 17 or less amino acid residues.

In specific embodiments, cysteine located 2 amino acids from the N-terminus and cysteine located 2 amino acids from the C-terminus may be optionally connected to each other. In specific embodiments, $X_3$ may be $NH_2$. In specific embodiments, $(X)_2$ may be AW. In specific embodiments, $Xa_2$ may be glutamic acid. In specific embodiments, $Xa_3$ may be tryptophan.

In specific embodiments, the Formula 4-5 may be identical to the following Formula 4-6:

[Formula 4-6]

(SEQ ID NO: 10)

D-C-A-W-H-$Xa_1$-G-E-L-V-W-C-T wherein A is alanine, and E is glutamic acid.

The peptides having the structures of Formulas 4-1 to 4-6 may have binding activity for an antibody. Also, the peptides may have binding activity for immunoglobulin G (IgG). In addition, the peptides may have binding activity for an Fc domain of the antibody.

In specific embodiments, the N-terminus of the SSFI according to the present invention may be succinylated. In specific embodiments, the SSFI according to the present invention may include a polar amino acid residue at the N-terminal $(X)_{1-3}$ thereof. In other specific embodiments, the SSFI according to the present invention may include a polar amino acid residue at the C-terminal $(X)_{1-3}$ thereof. In this case, the polar amino acid residue includes an acidic amino acid and a basic amino acid. Also, the polar amino acid residue may include glutamic acid or aspartic acid.

3.2. Site-specific Fc interactome according to the present invention may be arranged with an Fc domain of an antibody with a specific topology.

In the present content, the compound of Formula 4-6 is provided as one example to aid in understanding the present invention, but the scope of the present invention is not limited thereto. It will be noted that the following description also applies to the compounds of Formulas 3, 3-1, and 4-1 to 4-6, and the compound of Formula 4-6 is merely provided as one example for the sake of convenience.

As previously described above, the SSFI according to the present invention has binding activity for the Fc domain of the antibody. In this case, the SSFI may be arranged with the Fc domain with a specific topology due to the interaction between amino acid residues. The representative interaction between the SSFI sequence according to the present invention and the Fc domain includes (1) a salt linkage of the SSFI with histidine 433 in the Fc domain, (2) a hydrogen bond of the SSFI with asparagine 434, (3) a salt linkage of the SSFI with glutamic acid 380, (4) a salt linkage of the SSFI with arginine 255, and the like. These interactions and specific topologies thus formed may be determined from the research results already known in the art (see DeLano, W. L., et al., Convergent solutions to binding at a protein-protein interface; Science 2000, 287, 1279-1283).

When the SSFI according to the present invention is designed, it is important for the SSFI to form a stable topology with the Fc domain. This is because an agent for transferring a first chemical functional group to the antibody according to the present invention, and a labeling process using the same are designed based on the topology between the SSFI and the Fc domain found in research (see the following sections 5.2, 5.3, and 5.4). When the interaction between the SSFI and the Fc domain becomes unstable during the design of SSFI to disturb a topology between their molecules, it is unfavorable as the interaction may give a negative effect on the labeling process.

One embodiment of the design principle will be described with reference to an exemplary compound. The SSFI represented by Formula 4-6 has a structure as follows:

[Formula 4-6]

(SEQ ID NO: 10)

D-C-A-W-H-$Xa_1$-G-E-L-V-W-C-I

Figure 3:
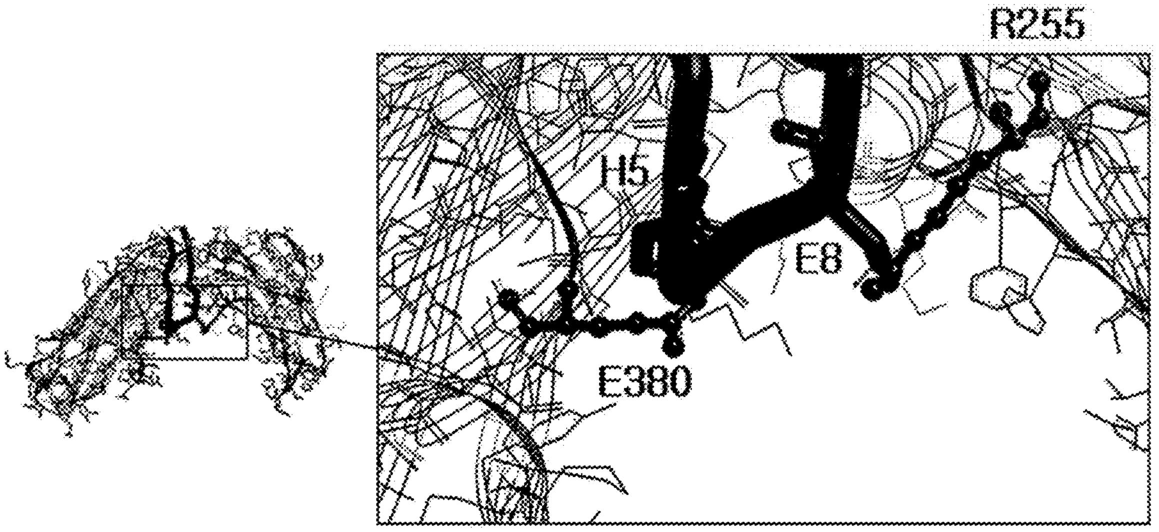
FIG. 3 and FIG. 4 show the topology between SSFI and the Fc domain.
Figure 4:
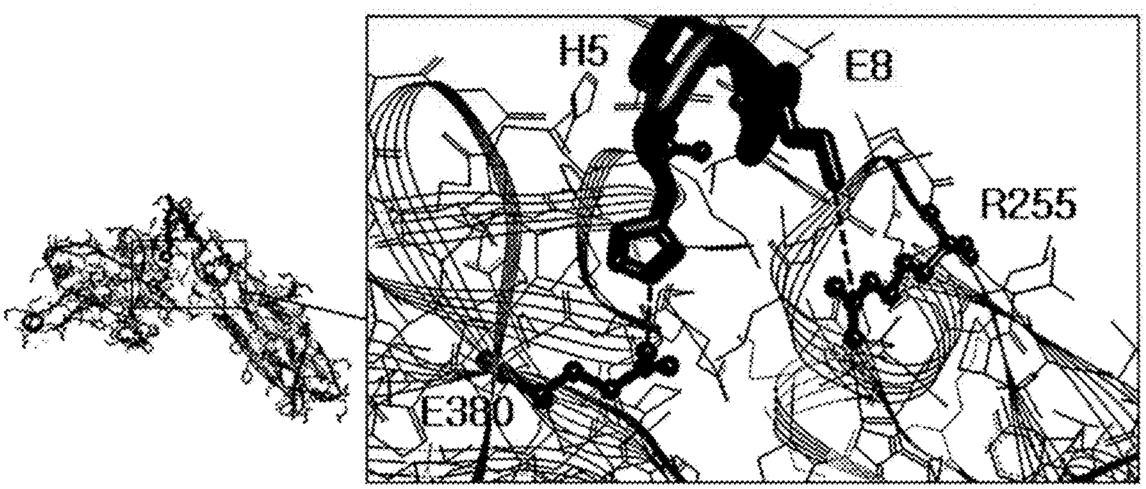

The results of simulating the topology between SSFI set forth in SEQ ID NO: 10 and the Fc domain based on the data in the articles, and the like are shown in FIGS. 3 and 4 (see DeLano, W. L., et al., Convergent solutions to binding at a protein-protein interface; Science 2000, 287, 1279-1283). In this case, a histidine residue at position 5 in the SSFI forms a salt linkage with glutamic acid 380 in the Fc domain, indicating that this salt linkage has a significant effect on the topology between the SSFI and the Fc domain (see a dotted line in FIG. 4). Therefore, it is desirable that the histidine residue and its position are not changed during the design of the SSFI (see 'H' next to the residue $Xa_1$ in Formulas 3, 3-1, and 4-1 to 4-6). In addition, it was confirmed that glutamic acid 8 is a residue that shows electronegativity, and thus forms a salt linkage with arginine 255 in the Fc domain, which shows electropositivity, thereby exerting a significant effect on the topology between the SSFI and the Fc domain (see a dotted line in FIG. 4). Therefore, the corresponding residue is preferably an acidic amino acid that may correspond to glutamic acid, and may be replaced with asparagine (see the residue $Xa_2$ in Formulas 3, 3-1, and 4-1 to 4-6). When the amino acid residues are replaced with other amino acid residues or are substituted with any functional groups, this may have an effect on the intermolecular interaction, thereby exerting an effect on the topology between the SSFI and the Fc domain.

In addition, glycine at position 7 in the sequence of SEQ ID NO: 10 is a small amino acid that is required to form a bent structure of the SSFI. Therefore, it is desirable that the glycine residue and its position are not changed during the design of the SSFI (see 'G' between the residues $Xa_1$ and $Xa_2$ in Formulas 3, 3-1, and 4-1 to 4-6).

Figure 5:
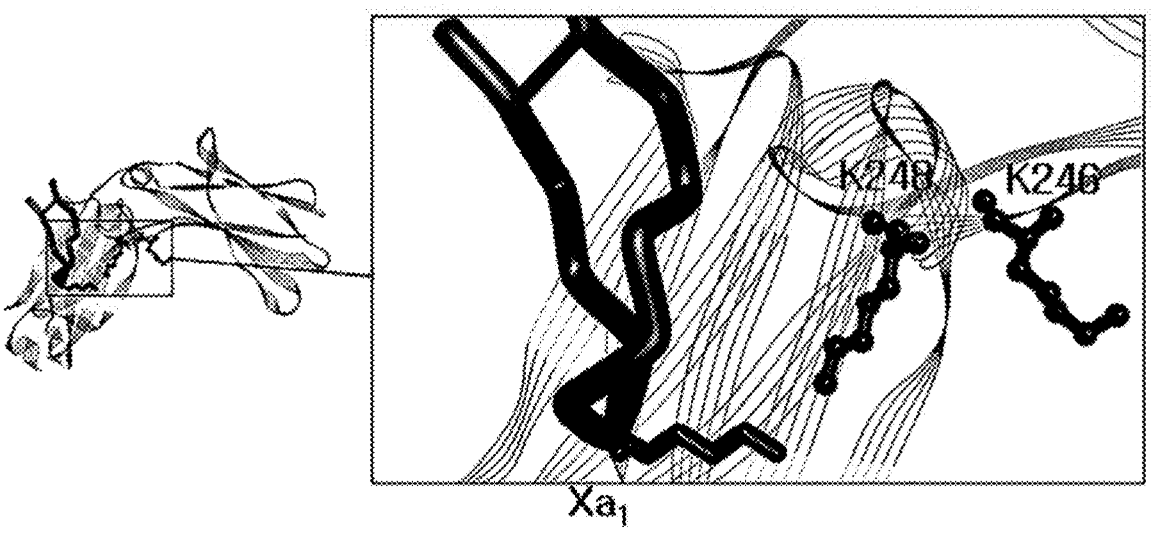
FIG. 5 shows $Xa_1$ of the SSFI and lysine 246 and 248 in the Fc domain.

FIG. 5 shows a topology between lysine residues of the Fc domain and the SSFI. Based on the topology, it can be seen that the lysine residues of the Fc domain located closest to the residue $Xa_1$ are lysine 246 and 248 (FIG. 5).

Figure 6:
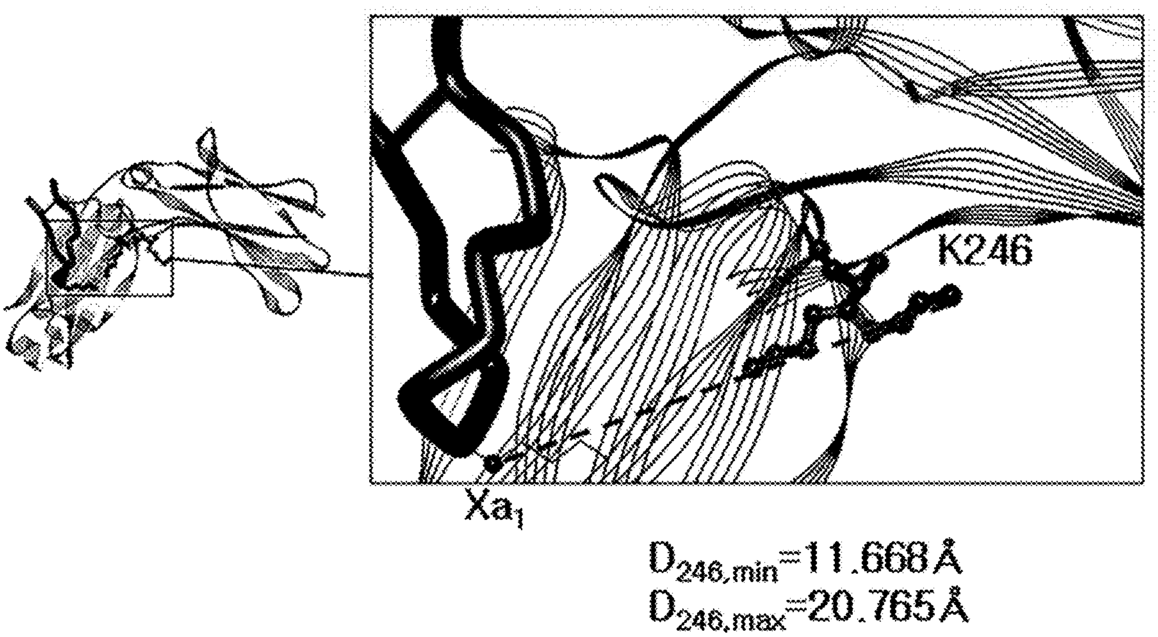
FIG. 6 shows a distance between an amine group of the lysine 246 and a beta carbon of the $Xa_1$ of the SSFI.

A distance between an amine group of lysine 246 and the beta carbon of $Xa_1$ was measured. As a result, it was confirmed that the minimum distance is measured to be approximately 11.668 Å (hereinafter referred to as "$D_{246,min}$"), and the maximum distance is measured to be approximately 20.765 Å (hereinafter referred to as "$D_{246,max}$") as the bonds constituting a lysine branch rotate (FIG. 6).

Figure 7:
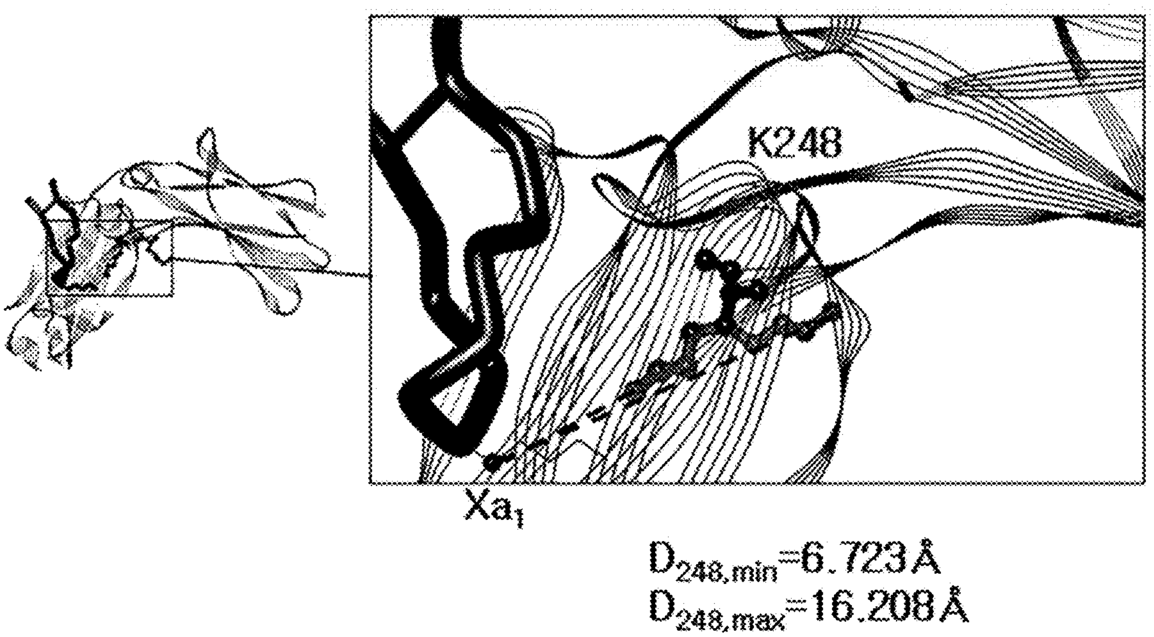
FIG. 7 shows a distance between an amine group of the lysine 248 and a beta carbon of the $Xa_1$ of the SSFI.

A distance between an amine group of lysine 248 and the beta carbon of $Xa_1$ was measured. As a result, it was confirmed that the minimum distance is measured to be approximately 6.723 Å (hereinafter referred to as "$D_{248,min}$"), and the maximum distance is measured to be approximately 16.208 Å (hereinafter referred to as "$D_{248,max}$") as the bonds constituting a lysine branch rotate (FIG. 7).

As will be described in the following section 5.3, the distance relationship may be an important consideration in the design of the linker and the SSFI, as well as the agent for transferring a first chemical functional group to an antibody.

4. Agent for Transferring First Chemical Functional Group to Antibody; Conjugate of $R_1$'-$L_1$ and SSAI ($R_1$'-$L_2$-SSAI)

According to the present invention, there is disclosed an agent for transferring a first chemical functional group to an antibody. Such a compound is herein indicated by the symbol "$R_1$'-$L_2$-SSAI." The compound is also referred to as a conjugate of $R_1$'-$L_1$ and SSAI (an $R_1$'-$L_2$-SSAI conjugate) depending on the structure thereof.

The present invention provides $R_1$'-$L_2$-SSAI having a structure of the following Formula 5:

[Formula 5]

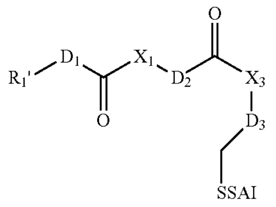

wherein $R_1$' is a first chemical functional group, $D_1$ is any alkylene, alkenylene, or alkynylene, $X_1$ is an element that is more electronegative than carbon, $D_2$ is any alkylene, alkenylene, or alkynylene, $D_3$ is a covalent bond or a $C_{1-3}$ alkylene, $X_3$ is NH, O, or S, and SSAI is a site-specific antibody interactome.

In specific embodiments, $R_1$' may include a click-chemistry functional group. Also, the click-chemistry functional group may include one or more selected from an alkyne, an azide, a strained alkyne, a diene, a dienophile, an alkene, a thiol, and a tetrazine. Furthermore, the click-chemistry functional group may be selected from an azide, or a strained alkyne. Further, the click-chemistry functional group may be selected from an azide, or dibenzocyclooctyne-amine. Additionally, the click-chemistry functional group may be selected from a diene, or a dienophile. Further, the click-chemistry functional group may be selected from a tetrazine, or a norbornene. Alternatively, the click-chemistry functional group may be selected from a tetrazine, or a trans-cyclooctene. In addition, $R_1$' may include two or more click-chemistry functional groups.

In other specific embodiments, $R_1$' may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond.

In specific embodiments, $X_1$ may be $NR_1$, S, or O, wherein $R_1$ may be H, a halogen, or a substituted or unsubstituted $C_{1-3}$ alkylene. Also, $X_1$ may be S.

In specific embodiments, $D_2$ may include any one selected from a $C_{1-7}$ alkylene, a $C_{2-7}$ alkenylene, a $C_{2-7}$ alkynylene, and a $C_{3-8}$ cycloalkylene. Also, $D_2$ may be a $C_{1-2}$ alkylene. Furthermore, $D_2$ may be methylene.

In specific embodiments, $X_3$ may be NH.

In specific embodiments, the SSAI may be a peptide sequence having binding activity for Fab. In other specific embodiments, the SSAI may be a peptide sequence having binding activity for the Fc domain.

When the SSAI in Formula 5 is SSFI, this is indicated by the symbol "$R_1$'-$L_2$-SSFI." The $R_1$'-$L_2$-SSFI according to the present invention is produced by means of a nucleophilic substitution reaction of $Xa_1$ of the SSFI according to the present invention with a second carbonyl group of $R_1$'-$L_1$ (see the following section 4-2 and Scheme 2). Therefore, the $R_1$'-$L_2$-SSFI according to the present invention includes those in which $Xa_1$ of the SSFI in Formulas 3, 3-1, and 4-1 to 4-6 is substituted with $(Xa_1)$', but the present invention is not limited to the following exemplary embodiments thereof.

The present invention provides an $R_1$'-$L_2$-SSFI including an amino acid sequence of the following Formula 5-1:

[Formula 5-1]

(SEQ ID NO: 11)

$(Xaa)_2$-H-$(Xa_1)$'-G-$Xa_2$-L-V-$Xa_3$ wherein each Xaa is independently any amino acid except cysteine, H is histidine, G is glycine, $Xa_2$ is glutamic acid or asparagine, L is leucine, V is valine, $Xa_3$ is selected from tryptophan, naphthylalanine, and phenylalanine, and $(Xa_1)$' is

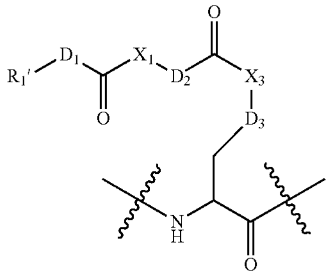

wherein $R_1$' is a first chemical functional group, $D_1$ is any alkylene, alkenylene, or alkynylene, $X_1$ is an element that is more electronegative than carbon, $D_2$ is any alkylene, alkenylene, or alkynylene, $D_3$ is a covalent bond or a $C_{1-3}$ alkylene, and $X_3$ is NH, O, or S.

In specific embodiments, $R_1$' may include a click-chemistry functional group. Also, the click-chemistry functional group may include one or more selected from an alkyne, an azide, a strained alkyne, a diene, a dienophile, an alkene, a thiol, and a tetrazine. Furthermore, the click-chemistry functional group may be selected from an azide, or a strained alkyne. Further, the click-chemistry functional group may be selected from an azide, or dibenzocyclooctyne-amine. Additionally, the click-chemistry functional group may be selected from a diene, or a dienophile. Further, the click-chemistry functional group may be selected from a tetrazine, or a norbornene. Alternatively, the click-chemistry functional group may be selected from a tetrazine, or a trans-cyclooctene. In addition, $R_1$' may include two or more click-chemistry functional groups.

In other specific embodiments, $R_1$' may include a carrier moiety, a fluorescent moiety, or a drug moiety. Also, $R_1$' may include a VC linker. In addition, $R_1$' may include a radioactive moiety. Also, $R_1$' may include a drug moiety. In other specific embodiments, $R_1$' may include an antibody or an analogue thereof, which includes a paratope.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond.

In specific embodiments, $X_1$ may be $NR_1$, S, or O, wherein $R_1$ may be H, a halogen, or a substituted or unsubstituted $C_{1-3}$ alkylene.

In specific embodiments, $D_2$ may include any one selected from a $C_{1-7}$ alkylene, a $C_{2-7}$ alkenylene, a $C_{2-7}$ alkynylene, and a $C_{3-8}$ cycloalkylene. Also, $D_2$ may be a $C_{1-2}$ alkylene. Furthermore, $D_2$ may be methylene.

In specific embodiments, $X_3$ may be NH.

In specific embodiments, $(X)_2$ may be AW. In specific embodiments, $Xa_2$ may be glutamic acid. In specific embodiments, $Xa_3$ may be tryptophan.

The present invention provides an $R_1$'-$L_2$-SSFI having a structure of the following Formula 5-2:

[Formula 5-2]

(SEQ ID NO: 12)

$(Xaa)_{1-3}$-C-$(Xaa)_2$-H-$(Xa_1)$'-G-$Xa_2$-L-V-$Xa_3$-C-$(Xaa)_{1-3}$ wherein each Xaa is independently any amino acid except cysteine, C is cysteine, H is histidine, G is glycine, $Xa_2$ is glutamic acid or asparagine, L is leucine, V is valine, $Xa_3$ is selected from tryptophan, naphthylalanine, and phenylalanine, and $(Xa_1)$' is

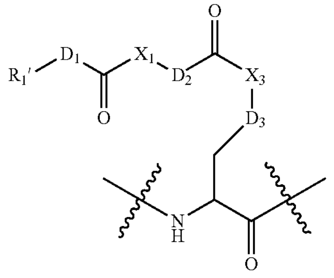

, wherein $R_1$' is a first chemical functional group, $D_1$ is any alkylene, alkenylene, or alkynylene, $X_1$ is an element that is more electronegative than carbon, $D_2$ is any alkylene, alkenylene, or alkynylene, $D_3$ is a covalent bond or a $C_{1-3}$ alkylene, and $X_3$ is NH, O, or S.

In specific embodiments, $R_1$' may include a click-chemistry functional group. Also, the click-chemistry functional group may include one or more selected from an alkyne, an azide, a strained alkyne, a diene, a dienophile, an alkene, a thiol, and a tetrazine. Furthermore, the click-chemistry functional group may be selected from an azide, or a strained alkyne. Further, the click-chemistry functional group may be selected from an azide, or dibenzocyclooctyne-amine. Additionally, the click-chemistry functional group may be selected from a diene, or a dienophile. Further, the click-chemistry functional group may be selected from a tetrazine, or a norbornene. Alternatively, the click-chemistry functional group may be selected from a tetrazine, or a trans-cyclooctene. In addition, $R_1$' may include two or more click-chemistry functional groups.

In other specific embodiments, $R_1$' may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond.

In specific embodiments, $X_1$ may be $NR_1$, S, or O, wherein $R_1$ may be H, a halogen, or a substituted or unsubstituted $C_{1-3}$ alkylene.

In specific embodiments, $D_2$ may include any one selected from a $C_{1-7}$ alkylene, a $C_{2-7}$ alkenylene, a $C_{2-7}$ alkynylene, and a $C_{3-8}$ cycloalkylene. Also, $D_2$ may be a $C_{1-2}$ alkylene. Furthermore, $D_2$ may be methylene.

In specific embodiments, Formula 5-2 may consist of 13 or more and 17 or less amino acid residues (including $(Xa_1)$').

In specific embodiments, cysteine located 2 to 4 amino acids from the N-terminus and cysteine located 2 to 4 amino acids from the C-terminus may be optionally connected to each other.

In specific embodiments, $X_3$ may be NH. In specific embodiments, $(X)_2$ may be AW. In specific embodiments, $Xa_2$ may be glutamic acid. In specific embodiments, $Xa_3$ may be tryptophan.

In specific embodiments, one of the residues constituting the N-terminal $(X)_{1-3}$ and one of the residues constituting the C-terminal $(X)_{1-3}$ may be bound to each other.

In specific embodiments, Formula 5-2 may be identical to Formula 5-3:

[Formula 5-3]

(SEQ ID NO: 13)

D-C-A-W-H-$(Xa_1)$'-G-E-L-V-W-C-T wherein A is alanine, and E is glutamic acid.

The $R_1$'-$L_2$-SSAI or $R_1$'-$L_2$-SSFI having the structures of Formulas 5 and 5-1 to 5-3 may have binding activity for an antibody. Also, the $R_1$'-$L_2$-SSAI or $R_1$'-$L_2$-SSFI may have binding activity for immunoglobulin G (IgG). In addition, the $R_1$'-$L_2$-SSAI or $R_1$'-$L_2$-SSFI may have binding activity for an Fc domain of the antibody.

4.1. Agent for Transferring First Click-Chemistry Functional Group to Antibody; Conjugate of $H_1$-$L_1$ and SSAI ($H_1$-$L_2$-SSAI)

According to the present invention, there is disclosed an agent for transferring a first click-chemistry functional group to an antibody. Such a compound is herein indicated by the symbol "$H_1$-$L_2$-SSAI." The compound is also referred to as a conjugate of $H_1$-$L_1$ and SSAI (an $H_1$-$L_2$-SSAI conjugate) depending on the structure thereof. In this case, when the SSAI is SSFI, this is indicated by the symbol '$H_1$-$L_2$-SSFI.'

The $H_1$-$L_2$-SSAI or $H_1$-$L_2$-SSFI according to the present invention includes those in which $R_1$' contains a click-chemistry functional group in the section '4. Agent for transferring first chemical functional group to antibody,' but the present invention is not limited to the following exemplary embodiments thereof.

The present invention provides an $H_1$-$L_2$-SSFI including an amino acid sequence of the following Formula 6-1:

```
[Formula 6-1]
                                        (SEQ ID NO: 14)
(Xaa)2-H-(Xa1)'-G-Xa2-L-V-Xa3
```

wherein each Xaa is independently any amino acid except cysteine,

H is histidine, G is glycine, $Xa_2$ is glutamic acid or asparagine, L is leucine, V is valine, $Xa_3$ is selected from tryptophan, naphthylalanine, and phenylalanine, and $(Xa_1)'$ is

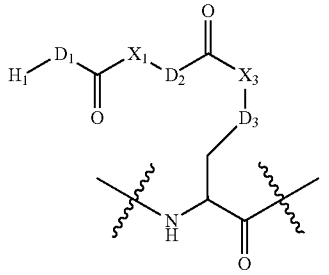

, wherein $H_1$ is a first click-chemistry functional group, $D_1$ is any alkylene, alkenylene, or alkynylene, $X_1$ is an element that is more electronegative than carbon, $D_2$ is any alkylene, alkenylene, or alkynylene, $D_3$ is a covalent bond or a $C_{1-3}$ alkylene, and $X_3$ is NH, O, or S.

In specific embodiments, $H_1$ may include any one selected from an alkyne, an azide, a strained alkyne, a diene, a dienophile, an alkene, a thiol, and a tetrazine. Furthermore, $H_1$ may be an azide, or a strained alkyne. Further, $H_1$ may be an azide, or dibenzocyclooctyne-amine. Additionally, $H_1$ may be a diene, or a dienophile. Further, $H_1$ may be a tetrazine, or a norbornene. Alternatively, $H_1$ may be a tetrazine, or a trans-cyclooctene.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $-CH_2OCH_2-$. In addition, $D_1$ may be a covalent bond.

In specific embodiments, $X_1$ may be $NR_1$, S, or O, wherein $R_1$ may be H, a halogen, or a substituted or unsubstituted $C_{1-3}$ alkylene.

In specific embodiments, $D_2$ may include any one selected from a $C_{1-7}$ alkylene, a $C_{2-7}$ alkenylene, a $C_{2-7}$ alkynylene, and a $C_{3-8}$ cycloalkylene. Also, $D_2$ may be a $C_{1-2}$ alkylene. Furthermore, $D_2$ may be methylene.

In specific embodiments, $X_3$ may be NH.

In specific embodiments, $(X)_2$ may be AW. In specific embodiments, $Xa_2$ may be glutamic acid. In specific embodiments, $Xa_3$ may be tryptophan.

The present invention provides an $H_1$-$L_2$-SSFI having a structure of the following Formula 6-2:

```
[Formula 6-2]
                                        (SEQ ID NO. 15)
(Xaa)1-3-C-(Xaa)2-H-(Xa1)'-G-Xa2-L-V-Xa3-C-
(Xaa)1-3
```

wherein each Xaa is independently any amino acid except cysteine,

C is cysteine, H is histidine, G is glycine, $Xa_2$ is glutamic acid or asparagine, L is leucine, V is valine, $Xa_3$ is selected from tryptophan, naphthylalanine, and phenylalanine, and $(Xa_1)'$ is

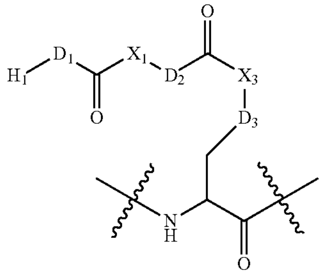

, wherein $H_1$ is a first click-chemistry functional group, $D_1$ is any alkylene, alkenylene, or alkynylene, $X_1$ is an element that is more electronegative than carbon, $D_2$ is any alkylene, alkenylene, or alkynylene, $D_3$ is a covalent bond or a $C_{1-3}$ alkylene, and $X_3$ is NH, O, or S.

In specific embodiments, $H_1$ may include any one selected from an alkyne, an azide, a strained alkyne, a diene, a dienophile, an alkene, a thiol, and a tetrazine. Furthermore, $H_1$ may be an azide, or a strained alkyne. Further, $H_1$ may be an azide, or dibenzocyclooctyne-amine. Additionally, $H_1$ may be a diene, or a dienophile. Further, $H_1$ may be a tetrazine, or a norbornene. Alternatively, $H_1$ may be a tetrazine, or a trans-cyclooctene.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $-CH_2OCH_2-$. In addition, $D_1$ may be a covalent bond.

In specific embodiments, $X_1$ may be $NR_1$, S, or O, wherein $R_1$ may be H, a halogen, or a substituted or unsubstituted $C_{1-3}$ alkylene.

In specific embodiments, $D_2$ may include any one selected from a $C_{1-7}$ alkylene, a $C_{2-7}$ alkenylene, a $C_{2-7}$ alkynylene, and a $C_{3-8}$ cycloalkylene. Also, $D_2$ may be a $C_{1-2}$ alkylene. Furthermore, $D_2$ may be methylene.

In specific embodiments, Formula 5-2 may consist of 13 or more and 17 or less amino acid residues (including $(Xa_1)'$).

In specific embodiments, cysteine located 2 to 4 amino acids from the N-terminus and cysteine located 2 to 4 amino acids from the C-terminus may be optionally connected to each other.

In specific embodiments, $X_3$ may be NH. In specific embodiments, $(X)_2$ may be AW. In specific embodiments, $Xa_2$ may be glutamic acid. In specific embodiments, $Xa_3$ may be tryptophan.

In specific embodiments, one of the residues constituting the N-terminal $(X)_{1-3}$ and one of the residues constituting the C-terminal $(X)_{1-3}$ may be bound to each other.

In specific embodiments, Formula 6-2 may be identical to Formula 6-3:

```
[Formula 6-3]
                                        (SEQ ID NO: 16)
D-C-A-W-H-(Xa1)'-G-E-L-V-W-C-T
```

wherein A is alanine, and E is glutamic acid.

The $H_1$-$L_2$-SSAI or $H_1$-$L_2$-SSFI having the structures of Formulas 6-1 to 6-3 may have binding activity for an antibody. Also, the $H_1$-$L_2$-SSAI or $H_1$-$L_2$-SSFI may have binding activity for immunoglobulin G (IgG). In addition, the $H_1$-$L_2$-SSAI or $H_1$-$L_2$-SSFI may have binding activity for an Fc domain of the antibody.

4.2. Method of Preparing Agent for Transferring First Chemical Functional Group to Antibody According to the present invention, there are disclosed methods of preparing the $R_1$'-$L_2$-SSAI, the $R_1$'-$L_2$-SSFI, the $H_1$-$L_2$-SSAI, and the $H_1$-$L_2$-SSFI (hereinafter generally referred to as "$R_1$'-$L_2$-SSAI"). It will be noted that a description of the following preparation methods is provided to aid in understanding the present invention.

For example, a method of preparing a compound of Formula 5 will be described. In specific embodiments, the compound of Formula 5 may be prepared through a reaction of the following Scheme 2.

[Scheme 2]

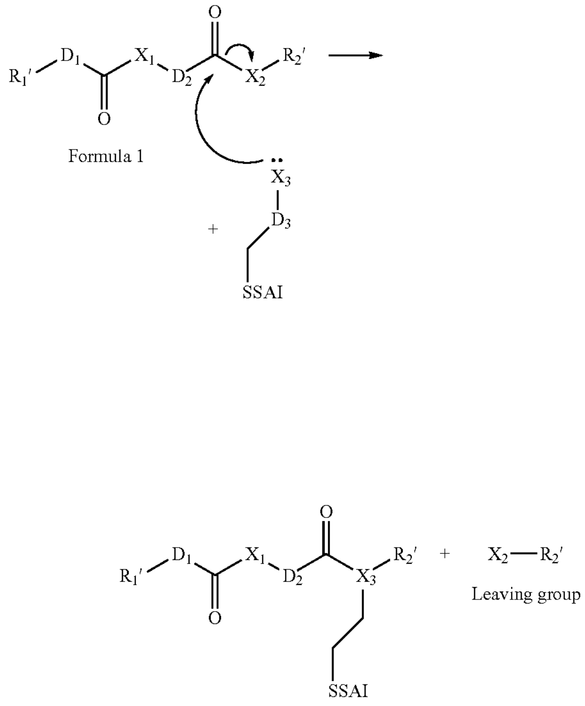

Formula 1

Formula 5

The $R_1$'-$L_2$-SSAI according to the present invention may be prepared by allowing a site-specific antibody interactome (SSAI) to react with the linker ($R_1$'-$L_1$) according to the present invention. The SSAI according to the present invention is designed to include a nucleophile $X_3$. The $X_3$ may attack an activated carbonyl group included in the linker to cause a nucleophilic substitution reaction. In this case, as the $X_3$ attacks the second carbonyl carbon, the $R_1$'-$L_2$-SSAI according to the present invention is prepared.

As a more specific example, a method of preparing a compound of Formula 6-3 will be described. In specific embodiments, the compound of Formula 6-3 may be prepared through a reaction of the following Scheme 3.

[Scheme 3]

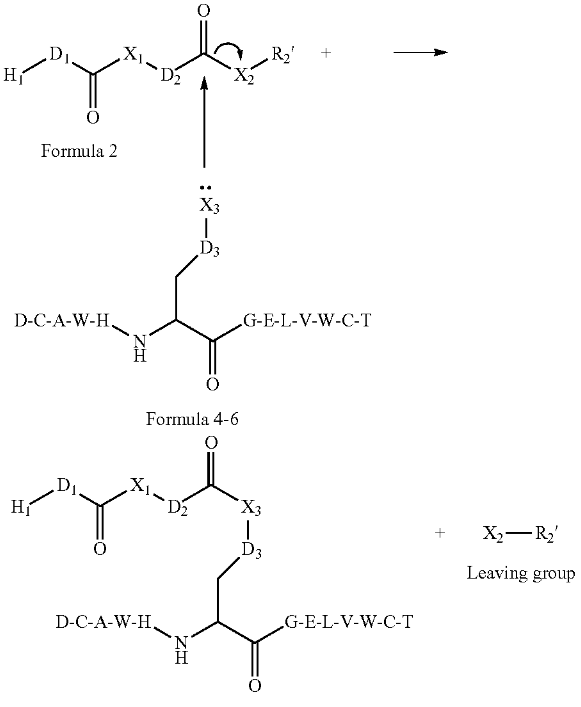

Formula 2

Formula 4-6

Formula 6-3

The SSAI including the amino acid sequence of Formula 3 or 3-1 according to the present invention and having each of the structures of Formulas 4-1 to 4-6 includes an $Xa_1$ residue including a nucleophile $X_3$. As the $X_3$ attacks the second carbonyl group included in the linker, the $R_1$'-$L_2$-SSAI according to the present invention is prepared.

In specific embodiments, the basicity of the leaving group including $X_2$ may be lower than that of the leaving group including $X_1$ in the linker according to the present invention. In specific embodiments, the linker according to the present invention may allow $X_2$-$R_2$' connected to the second carbonyl group to form a good leaving group. Also, $X_2$ may be O, and $R_2$' may be N-succinimide, p-nitrophenyl, or pentafluorophenyl. In this case, the reactivity of the second carbonyl group is higher than that of the first carbonyl group. Therefore, $X_3$ of the SSAI may specifically attack the second carbonyl group of the linker.

According to the present invention, there is disclosed a method of preparing an agent for transferring a first chemical functional group to an antibody.

The present invention provides a method of preparing an $R_1$'-$L_2$-SSAI, which comprises:

reacting a linker according to the present invention with a site-specific antibody interactome according to the present invention.

In specific embodiments, the linker may be any one selected from Formulas 1, 2, and 2-1 to 2-3.

In specific embodiments, the site-specific antibody interactome may include or have any one structure selected from Formulas 3, 3-1, and 4-1 to 4-6.

Also, the linker may have the structure of Formula 2, and the site-specific antibody interactome may have any one structure selected from Formulas 4-2 to 4-6. Furthermore, the site-specific antibody interactome may have the structure of Formula 4-6.

According to the present invention, there is disclosed a method of preparing an agent for transferring a first click-chemistry functional group to an antibody.

The present invention provides a method of preparing an $H_1$-$L_2$-SSAI, which comprises:

reacting a linker according to the present invention with a site-specific antibody interactome according to the present invention.

In specific embodiments, the linker may be any one selected from Formulas 2, and 2-1 to 2-3.

In specific embodiments, the site-specific antibody interactome may include or have any one structure selected from Formulas 3, 3-1, and 4-1 to 4-6.

Also, the linker may have the structure of Formula 2, and the site-specific antibody interactome may have any one structure selected from Formulas 4-2 to 4-6. Furthermore, the site-specific antibody interactome may have the structure of Formula 4-6.

According to the present invention, there is disclosed a kit for preparing an agent for transferring a first chemical functional group to an antibody.

The present invention provides a kit for preparing an agent for transferring a first chemical functional group to an antibody, which comprises the linker according to the present invention and the site-specific antibody interactome according to the present invention.

In specific embodiments, the linker may be any one selected from Formulas 1, 2, and 2-1 to 2-3.

In specific embodiments, the site-specific antibody interactome may include or have any one structure selected from Formulas 3, 3-1, and 4-1 to 4-6.

Also, the linker may have the structure of Formula 2, and the site-specific antibody interactome may have any one structure selected from Formulas 4-2 to 4-6. Furthermore, the site-specific antibody interactome may have the structure of Formula 4-6.

According to the present invention, there is disclosed a kit for preparing an agent for transferring a first click-chemistry functional group to an antibody.

The present invention provides a kit for preparing an agent for transferring a first click-chemistry functional group to an antibody, which comprises a linker containing the first click-chemistry functional group according to the present invention, and a site-specific antibody interactome.

In specific embodiments, the linker may be any one selected from Formulas 2, and 2-1 to 2-3.

In specific embodiments, the site-specific antibody interactome may include or have any one structure selected from Formulas 3, 3-1, and 4-1 to 4-6.

Also, the linker may have the structure of Formula 2, and the site-specific antibody interactome may have any one structure selected from Formulas 4-2 to 4-6. Furthermore, the site-specific antibody interactome may have the structure of Formula 4-6.

5. Antibody Containing First Chemical Functional Group ($R_1$'-Ab)

According to the present invention, there is disclosed an antibody containing a first chemical functional group. Such a compound is herein indicated by the symbol "$R_1$'-Ab."

The present invention provides an $R_1$'-Ab represented by Formula 7:

[Formula 7]

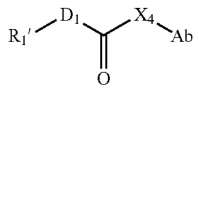

wherein $R_1$' is a first chemical functional group, $D_1$ is any alkylene, alkenylene, or alkynylene, $X_4$ is NH, O, or S, and Ab is an antibody.

In specific embodiments, $R_1$' may be a click-chemistry functional group. Also, $R_1$' may include any one selected from an alkyne, an azide, a strained alkyne, a diene, a dienophile, an alkene, a thiol, and a tetrazine. Furthermore, $R_1$' may be an azide, or a strained alkyne. Further, $R_1$' may be an azide, or dibenzocyclooctyne-amine. Additionally, $R_1$' may be a diene, or a dienophile. Further, $R_1$' may be a tetrazine, or a norbornene. Alternatively, $R_1$' may be a tetrazine, or a trans-cyclooctene.

In other specific embodiments, $R_1$' may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $-CH_2OCH_2-$. In addition, $D_1$ may be a covalent bond.

In one specific embodiment, $X_4$ may be NH.

In specific embodiments, Ab may be a human antibody. In other specific embodiments, Ab may be a non-human animal antibody. In specific embodiments, Ab may be immunoglobulin G (IgG). In specific embodiments, Ab may be a whole antibody. In other specific embodiments, Ab may be a fragment of the antibody.

In specific embodiments, $X_4$ and Ab may be connected via an Fab domain of Ab. In other specific embodiments, $X_4$ and Ab may be connected via an Fc domain of Ab. Also, $X_4$ and Ab may be connected via lysine 246 or 248 in the Fc domain of Ab. Furthermore, $X_4$ and Ab may be connected via lysine 246 in the Fc domain of Ab. Further, $X_4$ and Ab may be connected via lysine 248 in the Fc domain of Ab. Alternatively, $X_4$ and Ab may be connected via lysine 246 and 248 in the Fc domain of Ab. In specific embodiments, $X_4$ and Ab may be connected via only one of two Fc domains of Ab. In other specific embodiments, $X_4$ and Ab may be connected via both of the two Fc domains of Ab.

The present invention provides an antibody or a fragment thereof, which includes an amino acid sequence of the following Formula 7-1:

[Formula 7-1]

(SEQ ID NO: 17)

G-P-S-V-F-L-F-P-P-(K)'-P-K-D-T-L-M-I wherein G is glycine, P is proline, S is serine, V is valine, F is phenylalanine, L is leucine, K is lysine, D is aspartic acid, T is threonine, M is methionine, I is isoleucine, and (K)' is

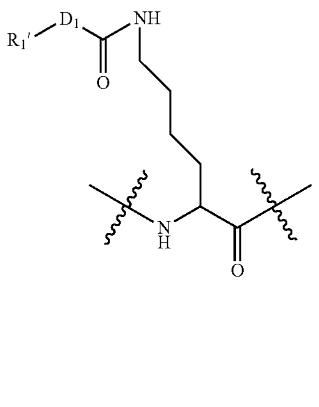
, wherein $R_1$' is a first chemical functional group, and $D_1$ is any alkylene, alkenylene, or alkynylene. The antibody or fragment thereof has $R_1$' connected via lysine 246 in an Fc domain thereof, or a site corresponding to the lysine 246.

In specific embodiments, $R_1$' may include a click-chemistry functional group. Also, the click-chemistry functional group may include one or more selected from an alkyne, an azide, a strained alkyne, a diene, a dienophile, an alkene, a thiol, and a tetrazine. Furthermore, the click-chemistry functional group may be selected from an azide, or a strained alkyne. Further, the click-chemistry functional group may be selected from an azide, or dibenzocyclooctyne-amine. Additionally, the click-chemistry functional group may be selected from a diene, or a dienophile. Further, the click-chemistry functional group may be selected from a tetrazine, or a norbornene. Alternatively, the click-chemistry functional group may be selected from a tetrazine, or a trans-cyclooctene. In addition, $R_1$' may include two or more click-chemistry functional groups.

In other specific embodiments, $R_1$' may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $—CH_2OCH_2—$. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody.

In specific embodiments, the antibody may include the amino acid sequence of Formula 7-1 in only one of the two Fc domains thereof. In other specific embodiments, the antibody may include the amino acid sequence of Formula 7-1 in both of the two Fc domains thereof.

The present invention provides an antibody or a fragment thereof, which includes an amino acid sequence of the following Formula 7-2:

```
[Formula 7-2]
                                        (SEQ ID NO: 18)
G-P-S-V-F-L-F-P-P-K-P-(K)'-D-T-L-M-I
```

wherein G is glycine, P is proline, S is serine, V is valine, F is phenylalanine, L is leucine, K is lysine, D is aspartic acid, T is threonine, M is methionine, I is isoleucine, and (K)' is

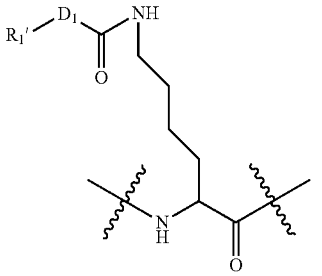

, wherein $R_1$' is a first chemical functional group, and $D_1$ is any alkylene, alkenylene, or alkynylene. The antibody or fragment thereof has $R_1$' connected via lysine 248 in an Fc domain thereof, or a site corresponding to the lysine 248.

In specific embodiments, $R_1$' may include a click-chemistry functional group. Also, the click-chemistry functional group may include one or more selected from an alkyne, an azide, a strained alkyne, a diene, a dienophile, an alkene, a thiol, and a tetrazine. Furthermore, the click-chemistry functional group may be selected from an azide, or a strained alkyne. Further, the click-chemistry functional group may be selected from an azide, or dibenzocyclooctyne-amine. Additionally, the click-chemistry functional group may be selected from a diene, or a dienophile. Further, the click-chemistry functional group may be selected from a tetrazine, or a norbornene. Alternatively, the click-chemistry functional group may be selected from a tetrazine, or a trans-cyclooctene. In addition, $R_1$' may include two or more click-chemistry functional groups.

In other specific embodiments, $R_1$' may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $—CH_2OCH_2—$. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody.

In specific embodiments, the antibody may include the amino acid sequence of Formula 7-2 in only one of the two Fc domains thereof. In other specific embodiments, the antibody may include the amino acid sequence of Formula 7-2 in both of the two Fc domains thereof.

The present invention provides an antibody or a fragment thereof, which includes an amino acid sequence of the following Formula 7-3:

```
[Formula 7-3]
                                        (SEQ ID NO: 19)
G-P-S-V-F-L-F-P-P-(K)'-P-(K)'-D-T-L-M-I
```

wherein G is glycine, P is proline, S is serine, V is valine, F is phenylalanine, Lis leucine, K is lysine, D is aspartic acid, T is threonine, M is methionine, I is isoleucine, and (K)' is

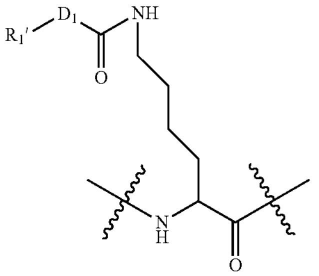

, wherein $R_1$' is a first chemical functional group, and $D_1$ is any alkylene, alkenylene, or alkynylene. The antibody or fragment thereof has $R_1$' connected via lysine 246 and 248 in an Fc domain thereof, or sites corresponding to the lysine 246 and 248.

In specific embodiments, $R_1$' may include a click-chemistry functional group. Also, the click-chemistry functional group may include one or more selected from an alkyne, an azide, a strained alkyne, a diene, a dienophile, an alkene, a thiol, and a tetrazine. Furthermore, the click-chemistry functional group may be selected from an azide, or a strained alkyne. Further, the click-chemistry functional group may be selected from an azide, or dibenzocyclooctyne-amine. Additionally, the click-chemistry functional group may be selected from a diene, or a dienophile. Further, the click-chemistry functional group may be selected from a tetrazine, or a norbornene. Alternatively, the click-chemistry functional group may be selected from a tetrazine, or a trans-cyclooctene. In addition, $R_1$' may include two or more click-chemistry functional groups.

In other specific embodiments, $R_1$' may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody.

In specific embodiments, the antibody may include the amino acid sequence of Formula 7-3 in only one of the two Fc domains thereof. In other specific embodiments, the antibody may include the amino acid sequence of Formula 7-3 in both of the two Fc domains thereof.

The present invention provides an antibody or a fragment thereof, which includes one or more amino acid sequences selected from Formulas 7-1, 7-2, and 7-3. In this case, the contents of the sequences of Formulas 7-1 to 7-3 are as described above.

In specific embodiments, $D_1$ may be a covalent bond.

In specific embodiments, the antibody or fragment thereof may include only the amino acid sequence of Formula 7-1 and may not include the amino acid sequences of Formulas 7-2 and 7-3. Also, the antibody or fragment thereof may include the amino acid sequence of Formula 7-1 in only one of the two Fc domains thereof. In addition, the antibody may include the amino acid sequence of Formula 7-1 in both of the two Fc domains thereof.

In other specific embodiments, the antibody or fragment thereof may include only the amino acid sequence of Formula 7-2 and may not include the amino acid sequences of Formulas 7-1 and 7-3. Also, the antibody or fragment thereof may include the amino acid sequence of Formula 7-2 in only one of the two Fc domains thereof. In addition, the antibody may include the amino acid sequence of Formula 7-2 in both of the two Fc domains thereof.

In specific embodiments, the antibody or fragment thereof may include only the amino acid sequence of Formula 7-3 and may not include the amino acid sequences of Formulas 7-1 and 7-2. Also, the antibody or fragment thereof may include the amino acid sequence of Formula 7-3 in only one of the two Fc domains thereof. In addition, the antibody may include the amino acid sequence of Formula 7-3 in both of the two Fc domains thereof.

5.1. Antibody Containing First Click-Chemistry Functional Group

According to the present invention, there is disclosed an antibody containing a first click-chemistry functional group. Such a compound is herein indicated by the symbol "$H_1$-Ab."

The present invention provides an $H_1$-Ab represented by Formula 8:

[Formula 8]

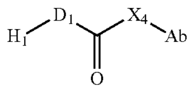

wherein $H_1$ is a first click-chemistry functional group, $D_1$ is any alkylene, alkenylene, or alkynylene, $X_4$ is NH, O, or S, and Ab is an antibody.

In specific embodiments, $H_1$ may include any one selected from an alkyne, an azide, a strained alkyne, a diene, a dienophile, an alkene, a thiol, and a tetrazine. Furthermore, $H_1$ may be an azide, or a strained alkyne. Further, $H_1$ may be an azide, or dibenzocyclooctyne-amine. Additionally, $H_1$ may be a diene, or a dienophile. Further, $H_1$ may be a tetrazine, or a norbornene. Alternatively, $H_1$ may be a tetrazine, or a trans-cyclooctene.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond.

In one specific embodiment, $X_4$ may be NH.

In specific embodiments, Ab may be a human antibody. In other specific embodiments, Ab may be a non-human animal antibody. In specific embodiments, Ab may be immunoglobulin G (IgG). In specific embodiments, Ab may be a whole antibody. In other specific embodiments, Ab may be a fragment of the antibody. In specific embodiments, Ab may be a wild-type antibody. In other specific embodiments, Ab may be a manipulated antibody.

In specific embodiments, $X_4$ and Ab may be connected via an Fab domain of Ab. In other specific embodiments, $X_4$ and Ab may be connected via an Fc domain of Ab. Also, $X_4$ and Ab may be connected via lysine 246 or 248 in the Fc domain of Ab. Furthermore, $X_4$ and Ab may be connected via lysine 246 in the Fc domain of Ab. Further, $X_4$ and Ab may be connected via lysine 248 in the Fc domain of Ab. Alternatively, $X_4$ and Ab may be connected via lysine 246 and 248 in the Fc domain of Ab. In specific embodiments, $X_4$ and Ab may be connected via only one of two Fc domains of Ab. In other specific embodiments, $X_4$ and Ab may be connected via both of the two Fc domains of Ab.

The present invention provides an antibody or a fragment thereof, which includes an amino acid sequence of the following Formula 8-1:

[Formula 8-1]

(SEQ ID NO. 20)

G-P-S-V-F-L-F-P-P-(K)'-P-K-D-T-L-M-I wherein G is glycine, P is proline, S is serine, V is valine, F is phenylalanine, L is leucine, K is lysine, D is aspartic acid, T is threonine, M is methionine, I is isoleucine, and (K)' is

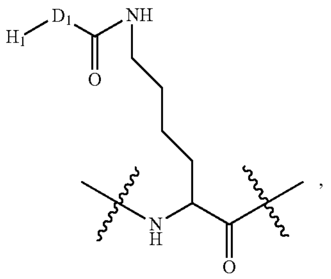

wherein $H_1$ is a first click-chemistry functional group, and $D_1$ is any alkylene, alkenylene, or alkynylene. The antibody or fragment thereof has $H_1$ connected via lysine 246 in an Fc domain thereof, or a site corresponding to the lysine 246.

In specific embodiments, $H_1$ may include any one selected from an alkyne, an azide, a strained alkyne, a diene, a dienophile, an alkene, a thiol, and a tetrazine. Furthermore, $H_1$ may be an azide, or a strained alkyne. Further, $H_1$ may be an azide, or dibenzocyclooctyne-amine. Additionally, $H_1$ may be a diene, or a dienophile. Further, $H_1$ may be a tetrazine, or a norbornene. Alternatively, $H_1$ may be a tetrazine, or a trans-cyclooctene.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $—CH_2OCH_2—$. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody. In specific embodiments, the antibody may be a wild-type antibody. In other specific embodiments, the antibody may be a manipulated antibody.

In specific embodiments, the antibody may include the amino acid sequence of Formula 8-1 in only one of the two Fc domains thereof. In other specific embodiments, the antibody may include the amino acid sequence of Formula 8-1 in both of the two Fc domains thereof.

The present invention provides an antibody or a fragment thereof, which includes an amino acid sequence of the following Formula 8-2:

```
[Formula 8-2]
                                  (SEQ ID NO: 21)
G-P-S-V-F-L-F-P-P-K-P-(K)'-D-T-L-M-I
```

wherein G is glycine, P is proline, S is serine, V is valine, F is phenylalanine, L is leucine, K is lysine, D is aspartic acid, T is threonine, M is methionine, I is isoleucine, and (K)' is

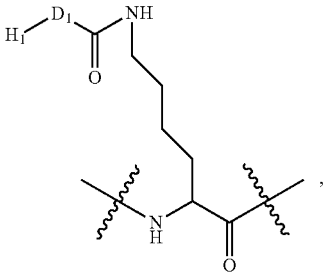

wherein $H_1$ is a first click-chemistry functional group, and $D_1$ is any alkylene, alkenylene, or alkynylene. The antibody or fragment thereof has $H_1$ connected via lysine 248 in an Fc domain thereof, or a site corresponding to the lysine 248.

In specific embodiments, $H_1$ may include any one selected from an alkyne, an azide, a strained alkyne, a diene, a dienophile, an alkene, a thiol, and a tetrazine. Furthermore, $H_1$ may be an azide, or a strained alkyne. Further, $H_1$ may be an azide, or dibenzocyclooctyne-amine. Additionally, $H_1$ may be a diene, or a dienophile. Further, $H_1$ may be a tetrazine, or a norbornene. Alternatively, $H_1$ may be a tetrazine, or a trans-cyclooctene.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $—CH_2OCH_2—$. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody. In specific embodiments, the antibody may be a wild-type antibody. In other specific embodiments, the antibody may be a manipulated antibody.

In specific embodiments, the antibody may include the amino acid sequence of Formula 8-2 in only one of the two Fc domains thereof. In other specific embodiments, the antibody may include the amino acid sequence of Formula 8-2 in both of the two Fc domains thereof.

The present invention provides an antibody or a fragment thereof, which includes an amino acid sequence of the following Formula 8-3:

```
[Formula 8-3]
                                  (SEQ ID NO: 22)
G-P-G-V-P-L-P-P-P-(K)'-P-(K)'-D-T-L-M-I
```

wherein G is glycine, P is proline, S is serine, V is valine, F is phenylalanine, L is leucine, K is lysine, D is aspartic acid, T is threonine, M is methionine, I is isoleucine, and (K)' is

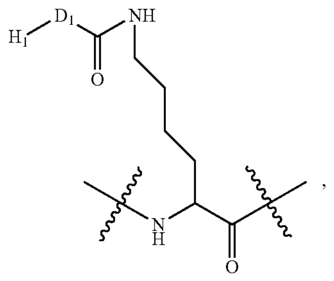

wherein $H_1$ is a first click-chemistry functional group, and $D_1$ is any alkylene, alkenylene, or alkynylene. The antibody or fragment thereof has $H_1$ connected via lysine 246 and 248 in an Fc domain thereof, or sites corresponding to the lysine 246 and 248.

In specific embodiments, $H_1$ may include any one selected from an alkyne, an azide, a strained alkyne, a diene, a dienophile, an alkene, a thiol, and a tetrazine. Furthermore, $H_1$ may be an azide, or a strained alkyne. Further, $H_1$ may be an azide, or dibenzocyclooctyne-amine. Additionally, $H_1$ may be a diene, or a dienophile. Further, $H_1$ may be a tetrazine, or a norbornene. Alternatively, $H_1$ may be a tetrazine, or a trans-cyclooctene.

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $-CH_2OCH_2-$. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody. In specific embodiments, the antibody may be a wild-type antibody. In other specific embodiments, the antibody may be a manipulated antibody.

In specific embodiments, the antibody may include the amino acid sequence of Formula 8-3 in only one of the two Fc domains thereof. In other specific embodiments, the antibody may include the amino acid sequence of Formula 8-3 in both of the two Fc domains thereof.

The present invention provides an antibody or a fragment thereof, which includes one or more amino acid sequences selected from Formulas 8-1, 8-2, and 8-3. In this case, the contents of the sequences of Formulas 8-1 to 8-3 are as described above.

In specific embodiments, $D_1$ may be a covalent bond.

In specific embodiments, the antibody or fragment thereof may include only the amino acid sequence of Formula 8-1 and may not include the amino acid sequences of Formulas 8-2 and 8-3. Also, the antibody or fragment thereof may include the amino acid sequence of Formula 8-1 in only one of the two Fc domains thereof. In addition, the antibody may include the amino acid sequence of Formula 8-1 in both of the two Fc domains thereof.

In other specific embodiments, the antibody or fragment thereof may include only the amino acid sequence of Formula 8-2 and may not include the amino acid sequences of Formulas 8-1 and 8-3. Also, the antibody or fragment thereof may include the amino acid sequence of Formula 8-2 in only one of the two Fc domains thereof. In addition, the antibody may include the amino acid sequence of Formula 8-2 in both of the two Fc domains thereof.

In specific embodiments, the antibody or fragment thereof may include only the amino acid sequence of Formula 8-3 and may not include the amino acid sequences of Formulas 8-1 and 8-2. Also, the antibody or fragment thereof may include the amino acid sequence of Formula 8-3 in only one of the two Fc domains thereof. In addition, the antibody may include the amino acid sequence of Formula 8-3 in both of the two Fc domains thereof.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody. In specific embodiments, the antibody may be a wild-type antibody. In other specific embodiments, the antibody may be a manipulated antibody.

5.2. Method of Preparing Antibody Containing First Chemical Functional Group

According to the present invention, there is disclosed a method of preparing the $R_1$'-Ab, and $H_1$-Ab (hereinafter generally referred to as "$R_1$'-Ab"). It will be noted that a description of the following preparation methods is provided to aid in understanding the present invention.

For example, a method of preparing a compound of Formula 7 will be described. In specific embodiments, the compound of Formula 7 may be prepared through a reaction of the following Scheme 4.

[Scheme 4]

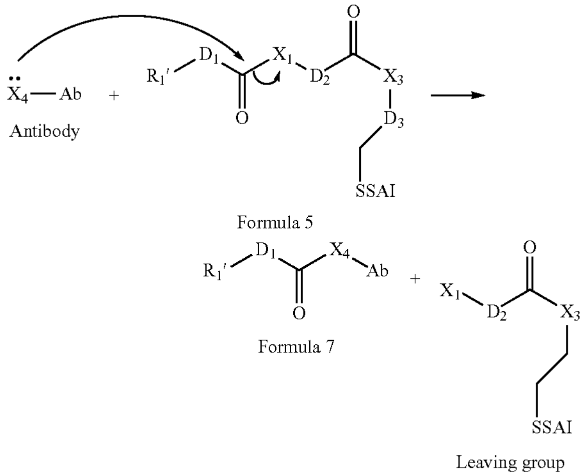

Because a first carbonyl group of the linker according to the present invention has mild reactivity, cross-linking may be realized when the first carbonyl group of the linker has a close positional relationship with an amine group of an antibody. First, the $R_1$'-$L_2$-SSAI represented by Formula 5 is brought into close contact with a certain site of the antibody to create an environment in which a reaction may occur. Because the $R_1$'-$L_2$-SSAI according to the present invention has an activated carbonyl group (i.e., a carbonyl group connected to $X_1$) corresponding to the first carbonyl group of the linker, the $R_1$'-$L_2$-SSAI of the present invention may trigger a nucleophilic substitution reaction. In this case, the compound of Formula 7 may be prepared since an atom ($X_4$) having a free electron pair present in the antibody serves as a nucleophile to attack the carbonyl group. In this case, by design of the linker, a site-specific antibody interactome (SSAI) leaves while being included in a leaving group and the SSAI is removed from the final product. These characteristics have a positive effect on physical properties of an antibody product, as shown in the section 5.8 below.

In specific embodiments, the $X_4$ may be $NH_2$. Also, the $X_4$ may be $NH_2$ of a lysine residue. In other specific embodiments, the $X_4$ may be SH. Also, the $X_4$ may be SH of a cysteine residue. In other specific embodiments, the $X_4$ may be OH.

As a more specific example, a method of preparing an antibody or a fragment thereof, which includes the amino acid sequence of Formula 8-3, will be described. In specific embodiments, the compound including the amino acid sequence of Formula 8-3 may be prepared through a reaction of the following Scheme 5.

According to the present invention, there is disclosed a method of preparing an antibody containing a first chemical functional group.

The present invention provides a method of preparing an $R_1$'-Ab, which includes:

reacting an agent for transferring a first chemical functional group to an antibody according to the present invention with an antibody or a fragment thereof.

In specific embodiments, the agent for transferring a first chemical functional group to an antibody may be any one selected from Formulas 5, 5-1 to 5-3, and 6-1 to 6-3.

In specific embodiments, the antibody or fragment thereof may be a human antibody. In other specific embodiments, the antibody or fragment thereof may be a non-human animal antibody. In specific embodiments, the antibody or

[Scheme 5]

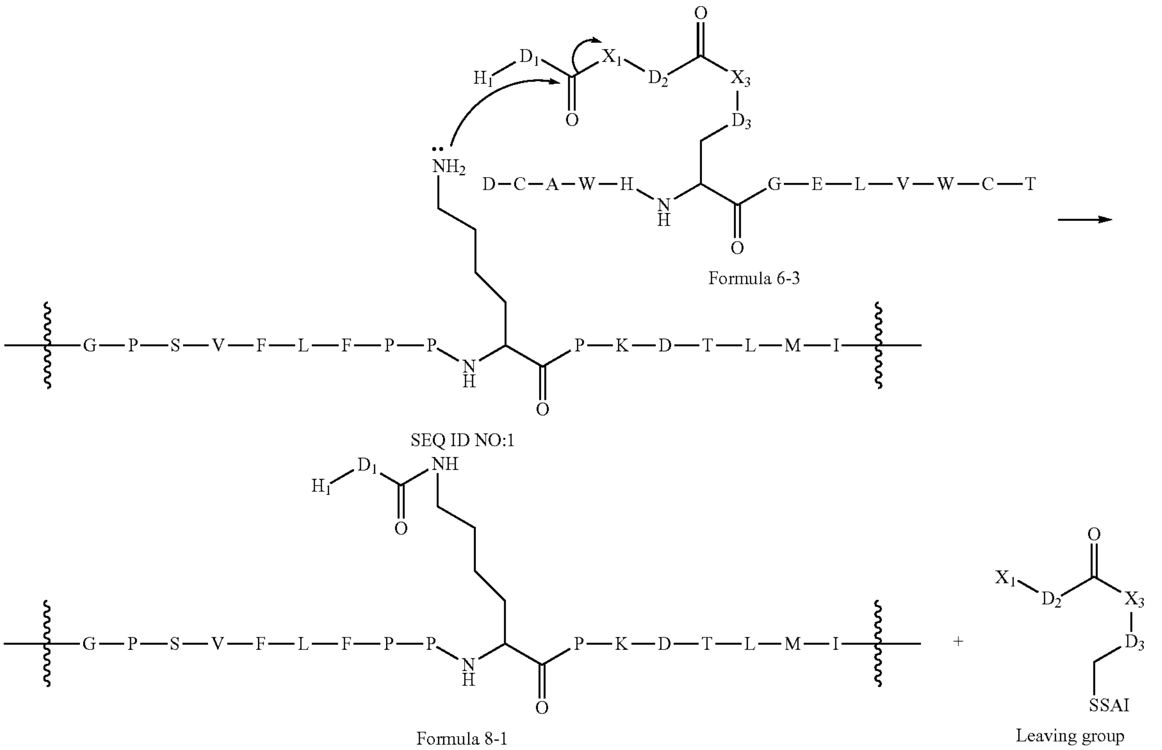

The compound having a structure of Formula 6-3 (a structure in which two cysteine residues are optionally connected) is directed towards the Fc domain of the antibody because the compound has an SSFI sequence (see section 3.2). In this case, the antibody including an amino acid sequence of SEQ ID NO: 1 includes lysine residues in an Fc domain thereof, and such a lysine residue may serve as a nucleophile. The exemplary embodiment shows a case where lysine 246 in the Fc domain or a residue corresponding to the lysine 246 (hereinafter referred to as "lysine 246") serves as a nucleophile. In this case, an amine group of the lysine 246 attacks a first carbonyl group of Formula 6-3 to produce a compound of Formula 8-1. In this way, $H_1$ or $R_1$ may be transferred to the lysine residue of the Fc domain of the antibody. In this case, to which certain lysine residue the chemical functional group is transferred may depend on the design of the linker, the SSAI, and the $R_1$'-$L_2$-SSAI, as described in the sections 5.3 and 5.4 below.

fragment thereof may be immunoglobulin G (IgG). In specific embodiments, the antibody or fragment thereof may be a whole antibody. In other specific embodiments, the antibody or fragment thereof may be a fragment of the antibody. In specific embodiments, the antibody or fragment thereof may be a wild-type antibody. In other specific embodiments, the antibody or fragment thereof may be a manipulated antibody.

In specific embodiments, the present invention provides a method of preparing an antibody having a first chemical functional group transferred to a specific lysine residue of an Fc domain thereof. In this case, those of aspects as described in the section 5.4 below may be used as the agent for transferring a first chemical functional group to an antibody.

According to the present invention, there is disclosed a method of preparing an antibody containing a first click-chemistry functional group.

The present invention provides a method of preparing an $H_1$-Ab, which includes:

reacting an agent for transferring a first click-chemistry functional group to an antibody according to the present invention with an antibody or a fragment thereof.

In specific embodiments, the agent for transferring a first click-chemistry functional group to an antibody may be any one selected from Formulas 6-1 to 6-3. Also, the agent for transferring a first click-chemistry functional group to an antibody may have the structure of Formula 6-3.

In specific embodiments, the antibody or fragment thereof may be a human antibody. In other specific embodiments, the antibody or fragment thereof may be a non-human animal antibody. In specific embodiments, the antibody or fragment thereof may be immunoglobulin G (IgG). In specific embodiments, the antibody or fragment thereof may be a whole antibody. In other specific embodiments, the antibody or fragment thereof may be a fragment of the antibody. In specific embodiments, the antibody or fragment thereof may be a wild-type antibody. In other specific embodiments, the antibody or fragment thereof may be a manipulated antibody.

In specific embodiments, the present invention provides a method of preparing an antibody having a first click-chemistry functional group transferred to a specific lysine residue of an Fc domain thereof. In this case, those of aspects as described in the section 5.4 below may be used as the agent for transferring a first click-chemistry functional group to an antibody.

According to the present invention, there is disclosed a kit for preparing an antibody or a fragment thereof containing a first chemical functional group.

The present invention provides a kit for preparing an antibody or a fragment thereof containing a first chemical functional group, which includes an agent for transferring a first chemical functional group to an antibody according to the present invention, and an antibody or a fragment thereof.

In specific embodiments, the agent for transferring a first chemical functional group to an antibody may be any one selected from Formulas 5, 5-1 to 5-3, and 6-1 to 6-3.

In specific embodiments, the antibody or fragment thereof may be a human antibody. In other specific embodiments, the antibody or fragment thereof may be a non-human animal antibody. In specific embodiments, the antibody or fragment thereof may be immunoglobulin G (IgG). In specific embodiments, the antibody or fragment thereof may be a whole antibody. In other specific embodiments, the antibody or fragment thereof may be a fragment of the antibody. In specific embodiments, the antibody or fragment thereof may be a wild-type antibody. In other specific embodiments, the antibody or fragment thereof may be a manipulated antibody.

Also, the present invention provides a kit for preparing an antibody or a fragment thereof containing a first chemical functional group, which includes:

a linker ($R_1$'-$L_1$) according to the present invention;

a site-specific antibody interactome according to the present invention; and an antibody or a fragment thereof.

In specific embodiments, the linker may be any one selected from Formulas 1, 2, and 2-1 to 2-3.

In specific embodiments, the site-specific antibody interactome may be any one selected from Formulas 3, 3-1, and 4-1 to 4-6.

In specific embodiments, the antibody or fragment thereof may be a human antibody. In other specific embodiments, the antibody or fragment thereof may be a non-human animal antibody. In specific embodiments, the antibody or fragment thereof may be immunoglobulin G (IgG). In specific embodiments, the antibody or fragment thereof may be a whole antibody. In other specific embodiments, the antibody or fragment thereof may be a fragment of the antibody. In specific embodiments, the antibody or fragment thereof may be a wild-type antibody. In other specific embodiments, the antibody or fragment thereof may be a manipulated antibody.

The present invention provides a kit for preparing an antibody having a first chemical functional group transferred to a specific lysine residue of an Fc domain thereof. In this case, those of aspects as described in the section 5.4 below may be used as the agent for transferring a first chemical functional group to an antibody, the linker, and the site-specific antibody interactome.

According to the present invention, there is disclosed a kit for preparing an antibody or a fragment thereof containing a first click-chemistry functional group.

The present invention provides a kit for preparing an antibody or a fragment thereof containing a first click-chemistry functional group, which includes an agent for transferring a first click-chemistry functional group to an antibody according to the present invention, and an antibody or a fragment thereof.

In specific embodiments, the agent for transferring a first click-chemistry functional group to an antibody may be any one selected from Formulas 6-1 to 6-3. Also, the agent for transferring a first click-chemistry functional group to an antibody may have the structure of Formula 6-3.

In specific embodiments, the antibody or fragment thereof may be a human antibody. In other specific embodiments, the antibody or fragment thereof may be a non-human animal antibody. In specific embodiments, the antibody or fragment thereof may be immunoglobulin G (IgG). In specific embodiments, the antibody or fragment thereof may be a whole antibody. In other specific embodiments, the antibody or fragment thereof may be a fragment of the antibody. In specific embodiments, the antibody or fragment thereof may be a wild-type antibody. In other specific embodiments, the antibody or fragment thereof may be a manipulated antibody.

Also, the present invention provides a kit for preparing an antibody or a fragment thereof containing a first click-chemistry functional group, which includes:

a linker ($H_1$-$L_1$) according to the present invention;

a site-specific antibody interactome according to the present invention; and an antibody or a fragment thereof.

In specific embodiments, the linker may be any one selected from Formulas 2, and 2-1 to 2-3.

In specific embodiments, the site-specific antibody interactome may be any one selected from Formulas 3, 3-1, and 4-1 to 4-6.

In specific embodiments, the antibody or fragment thereof may be a human antibody. In other specific embodiments, the antibody or fragment thereof may be a non-human animal antibody. In specific embodiments, the antibody or fragment thereof may be immunoglobulin G (IgG). In specific embodiments, the antibody or fragment thereof may be a whole antibody. In other specific embodiments, the antibody or fragment thereof may be a fragment of the antibody. In specific embodiments, the antibody or fragment thereof may be a wild-type antibody. In other specific embodiments, the antibody or fragment thereof may be a manipulated antibody.

The present invention provides a kit for preparing an antibody having a first click-chemistry functional group transferred to a specific lysine residue of an Fc domain thereof. In this case, those of aspects as described in the section 5.4 below may be used as the agent for transferring a first click-chemistry functional group to an antibody, the linker, and the site-specific antibody interactome.

5.3. Function of $(Xa_1)'$ and Design Principle of Location of $(Xa_1)'$ on $R_1'$-$L_2$-SSFI In the present content, the compound of Formula 6-3 is provided as one example to aid in understanding the present invention, but the scope of the present invention is not limited thereto. It will be noted that the following description also applies to the compounds of Formulas 5, 5-1 to 5-3, and 6-1 to 6-3, and the compound of Formula 6-3 is merely provided as one example for the sake of convenience.

As discussed in the section 5.2, $(Xa_1)'$ of the $R_1'$-$L_2$-SSFI functions to transfer $R_1'$ to an antibody by means of a nucleophilic substitution reaction. According to the present invention, it is assumed that the conditions for facilitating a nucleophilic substitution reaction satisfy the following requirements: (1) $(Xa_1)'$ is adjacent to a lysine residue of an Fc domain, and (2) a side chain to which $R_1'$ is bound is directed towards the lysine residue. It was expected that the yield and uniformity of a process would drop as the position of $(Xa_1)'$ and the direction of the side chain become farther from the lysine residue of the Fc domain. Also, (3) it will be preferred that a substitution position of $(Xa_1)'$ does not have a great influence on the interaction between the SSFI and the Fc domain (see section 3.2).

As indirectly seen in FIGS. 3 and 5, it was confirmed that the positions in the SSFI that satisfy the requirement of (1) in relation to lysine 246 and 248 in the Fc domain are positions 5, 6, 7, and 8 based on the following Formula 6-3.

D-C-A-W-H-$(Xa_1)'$-G-E-L-V-W-C-T [Formula 6-3]

In this case, as histidine corresponding to position 5 forms a salt linkage with glutamic acid 380 in the Fc domain, replacement of the histidine may affect the interaction between the SSFI and the Fc domain. Therefore, this does not satisfy the requirement of (3). Also, because the direction of this side chain is not close to the lysine 246 and 248, this does not satisfy the requirement of (2). Because glycine corresponding to position 7 helps to form a bent structure of the SSFI, it is not desirable to replace the glycine residue with a large $(Xa_1)'$ residue. As glutamic acid corresponding to position 8 forms a salt linkage with arginine 255 in the Fc domain, replacement of the glutamic acid may affect the interaction between the SSFI and the Fc domain. Therefore, this does not satisfy the requirement of (3) (see section 3.2). It was judged that position 6 is most suitable for the position of $(Xa_1)'$ because position 6 satisfies all the requirements of (1), (2), and (3). Therefore, the $R_1'$-$L_2$-SSFI according to the present invention has been completed based on these facts.

5.4. The position of $R_1'$ transferred to an antibody may vary depending on the length of $D_2$ in $R_1'$-$L_1$ and $D_3$ in SSFI.

The present content is intended to explain a preferred design principle of the $R_1'$-$L_2$-SSFI according to the present invention. According to the design of the $R_1'$-$L_2$-SSFI, it is possible to specifically transfer $R_1'$ to a specific lysine residue of the Fc domain. Also, the present content is intended to explain a design principle of the $R_1'$-$L_1$ and SSFI to prepare a preferred $R_1'$-$L_2$-SSFI.

A person of ordinary skill in the art who reads the section 5.2 as described above may recognize that a nucleophilic substitution reaction may occur when the first carbonyl carbon of $(Xa_1)'$ of the $R_1'$-$L_2$-SSFI is located adjacent to an amine group of lysine of the Fc domain. Based on the description of the section 3.2 as described above, a person of ordinary skill in the art may also recognize that the $R_1'$-$L_2$-SSFI is arranged with the Fc domain with a specific topology, wherein amine groups of lysine 246 and 248 in the Fc domain are spaced apart a certain distance from the beta carbon of $(Xa_1)'$ (FIG. 5). By using this combination to design the $R_1'$-$L_2$-SSFI, it was expected that it is possible to specifically label a desired lysine residue when (1) a distance (hereinafter generally referred to as "$L_c$") between the beta carbon of $(Xa_1)'$ and the first carbonyl carbon is the same as or similar to (2) a distance between the beta carbon of $(Xa_1)'$ and the amine groups of lysine 246 and 248 in the Fc domain in the specific topology.

Figure 8:
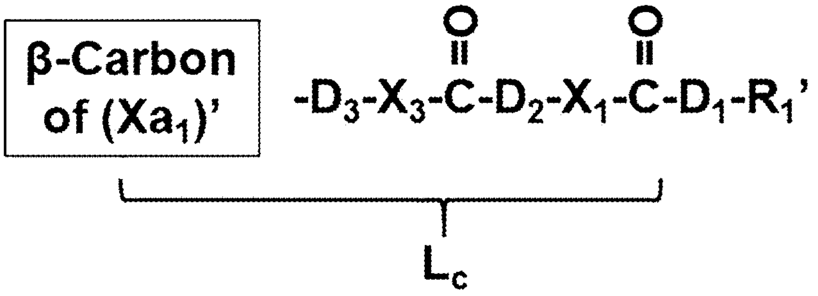
FIG. 8 shows a structure of $R_1$'-$L_2$-SSFI and a distance ($L_c$) between a beta carbon and a first carbonyl carbon of $(Xa_1)'$.

The structure of the $R_1'$-$L_2$-SSFI according to the present invention and the $L_c$ are shown in FIG. 8. As shown in FIG. 8, $D_3$, $X_3$, carbon atoms, $D_2$, and $X_1$ are located between the beta carbon of $(Xa_1)'$ and the first carbonyl carbon. Among these, $D_3$ and $X_3$ are associated with the design of SSFI, and $D_2$ and $X_1$ are associated with the design of $L_1$-$R_1$'.

For the sake of convenience, the invention was embodied on the assumption that $D_3$ is a $C_x$ alkylene, $X_3$ is N, $D_2$ is a $C_y$ alkylene, a $C_y$ alkenylene, or a $C_y$ alkynylene, and $X_1$ is S, wherein y is an integer greater than or equal to 1. In this case, it was assumed that the alkylene, the alkenylene, and the alkynylene have the same length. The structure of the linker shown in FIG. 8 was modeled using the software Discovery Studio to calculate $L_c$ values. As a result, the $L_c$ values determined with respect to the x+y value are listed in Table 3. In the calculation process, the chain was modeled when it had the longest length.

TABLE 3

Lc values with respect to x + y value

| x + y | Lc (Å) |
|---|---|
| 1 (x = 0, y = 1) | 6.616 |
| 2 | 7.784 |
| 3 | 9.102 |
| 4 | 10.299 |
| 5 | 11.599 |
| 6 | 12.816 |
| 7 | 14.100 |
| 8 | 15.334 |
| 9 | 16.601 |
| 10 | 17.848 |
| 11 | 19.099 |
| 12 | 20.357 |
| 13 | 21.592 |
| 14 | 22.357 |

Figure 9:
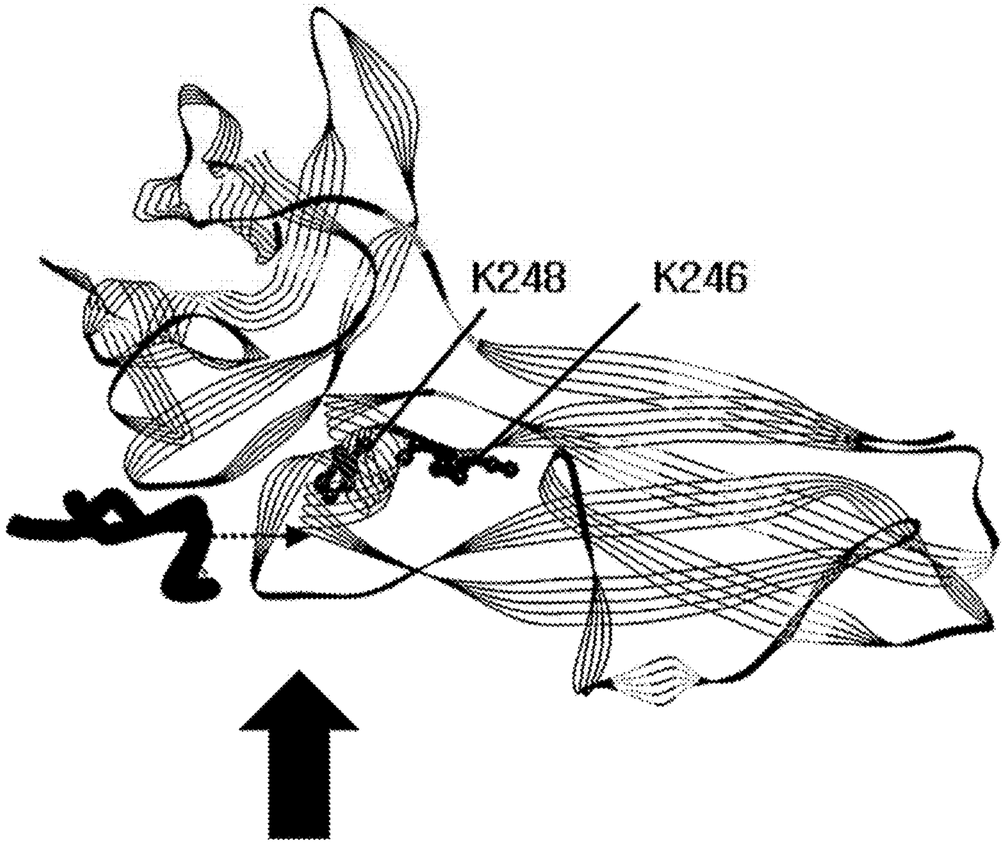
FIG. 9 shows the topology between the R1'-L2-SSFI and the Fc domain so that a side chain of $(Xa_1)'$ has a direction (a dotted arrow) parallel with the x axis on the drawing.
Figure 10:
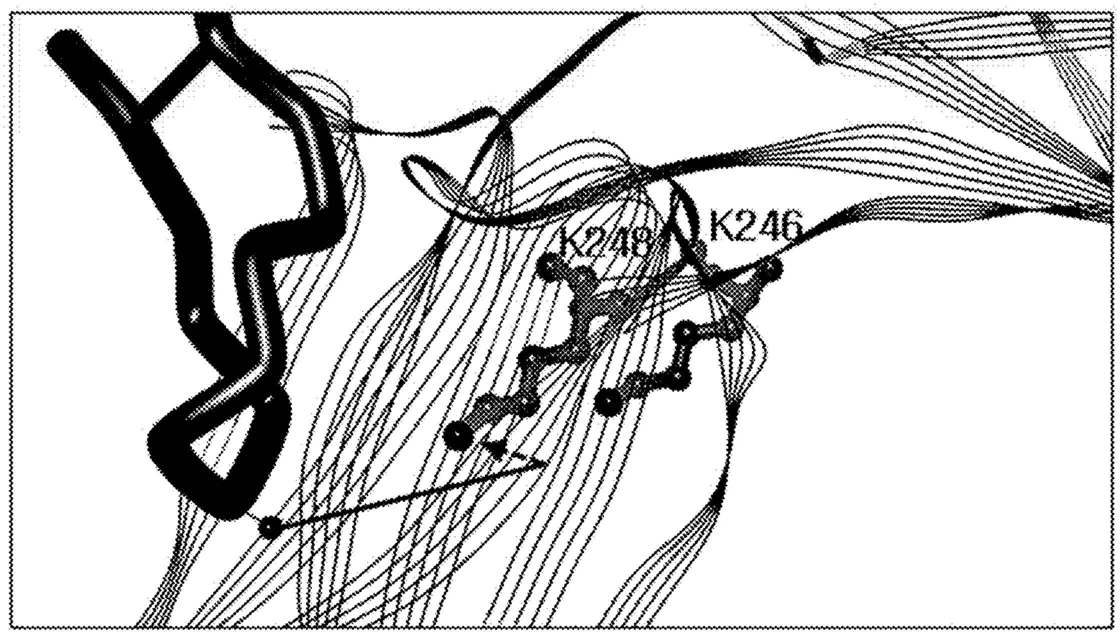
FIG. 10 shows the conditions used to allow the first carbonyl carbon to react well with lysine 248.
Figure 11:
FIG. 11 shows the conditions used to allow the first carbonyl carbon to react well with lysine 246.
Figure 12:
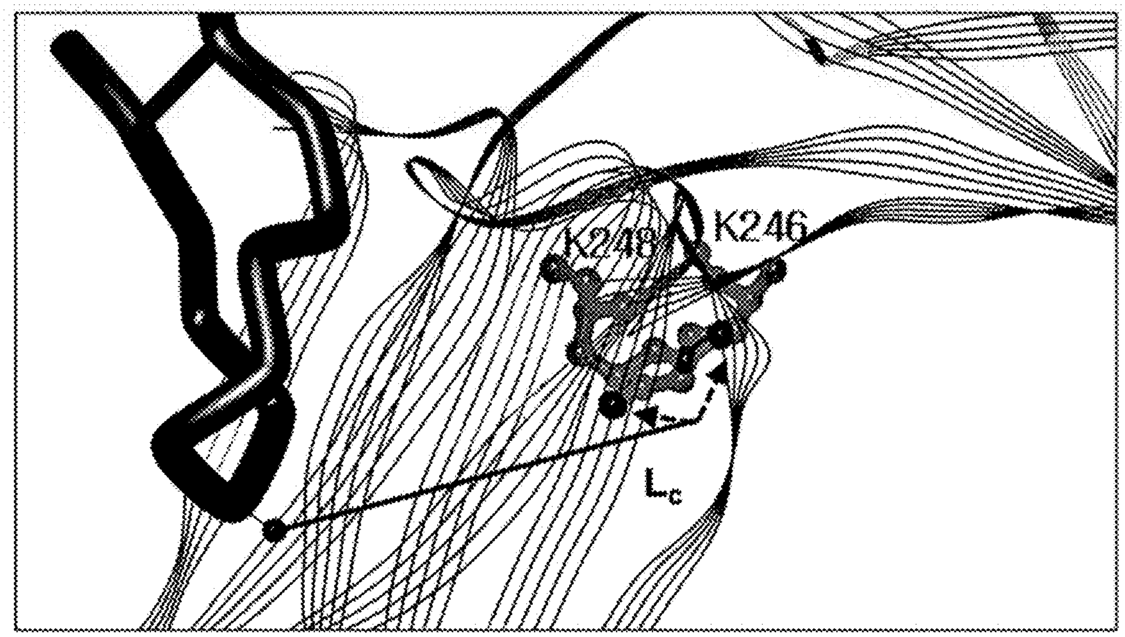
FIG. 12 shows the conditions used to allow the first carbonyl carbon to selectively react with lysine 246 or 248.

Hereinafter, the accompanying drawings provided to show a topology between the $R_1'$-$L_2$-SSFI and a lysine residue of the Fc domain are provided based on FIG. 9. FIG. 9 shows a topology between an $R_1'$-$L_2$-SSFI and an Fc domain so that a direction (a dotted arrow) of a side chain of $(Xa_1)'$ is parallel with the x axis in the drawing. As shown in FIG. 9, it can be seen that the side chain of $(Xa_1)'$ is directed towards the amine groups of the lysine 246 and 248 (see section 5.3). Also, it can be seen from the drawing that the side chain of $(Xa_1)'$ may specifically react with the lysine 246 or 248 depending on the length of $L_c$. FIGS. 10 to 12 are diagrams viewing a diagram of FIG. 9 in a direction (a thick solid line arrow) parallel with the y-axis in the drawing along the exemplary length of $L_c$.

The distances ($D_{246,min}$, $D_{246,max}$, $D_{248,min}$, and $D_{248,max}$) between the beta carbon of $(Xa_1)'$ and the amine groups of lysine 246 and 248 in the Fc domain are described in the section 3.2. The beta carbon of $(Xa_1)'$ is closer to the lysine 248 in the Fc domain than the lysine residue at position 246. Therefore, it was expected that the first carbonyl carbon would react well with the lysine 248 when the $L_c$ value is shorter than $D_{246,min}$ (FIG. 10), the first carbonyl carbon would react well with the lysine 246 when the $L_c$ value is longer than $D_{248,max}$ (FIG. 11), and the first carbonyl carbon would selectively react with the lysine 246 and 248 when the $L_c$ value is longer than or equal to $D_{246,min}$ and shorter than or equal to $D_{248,max}$ (FIG. 12).

According to the present invention, there is disclosed an $R_1$'-$L_2$-SSFI for specifically transferring a first chemical functional group to lysine 248 in an Fc domain of an antibody (see FIG. 11).

The present invention provides an agent for transferring a first chemical functional group to an antibody, characterized in that a distance ($L_c$) between the beta carbon of $(Xa_1)'$ and the first carbonyl carbon is shorter than $D_{246,min}$ (approximately 11.668 Å). In this case, $L_c$ may have a value of approximately 6.5 Å, approximately 7 Å, approximately 8 Å, approximately 9 Å, approximately 10 Å, approximately 11 Å, or approximately 11.5 Å.

In specific embodiments, when the $R_1$'-$L_2$-SSFI has any one structure selected from Formulas 5, 5-1 to 5-3, and 6-1 to 6-3, $D_3$ is a $C_x$ alkylene, $X_3$ is N, $D_2$ is a $C_y$ alkylene, a $C_y$ alkenylene, or a $C_y$ alkynylene, $X_1$ is S, wherein y may be an integer greater than or equal to 1, and the sum of x and y may be $1 \leq x+y \leq 5$. Also, the sum of x and y may be 1, 2, 3, 4, or 5. For example, x may be 0, and y may be $1 \leq y \leq 5$. In another exemplary embodiment, x may be 1, and y may be $1 \leq y \leq 4$. In still another exemplary embodiment, x may be 2, and y may be $1 \leq y \leq 3$. In yet another exemplary embodiment, x may be 3, and y may be $1 \leq y \leq 2$. The corresponding numerical range is determined based on the value listed in Table 3.

According to the present invention, there is disclosed an $R_1$'-$L_2$-SSFI for specifically transferring a first chemical functional group to lysine 246 in an Fc domain of an antibody.

According to one aspect of the present invention, the present invention provides an agent for transferring a first chemical functional group to an antibody, characterized in that a distance ($L_c$) between the beta carbon of $(Xa_1)'$ and the first carbonyl carbon is longer than $D_{248,max}$ (approximately 16.208 Å). For example, $L_c$ may have a value of approximately 16.5 Å, approximately 17 Å, approximately 18 Å, approximately 19 Å, approximately 20 Å, or approximately 20.5 Å.

In specific embodiments, when the $R_1$'-$L_2$-SSFI has any one structure selected from Formulas 5, 5-1 to 5-3, and 6-1 to 6-3, $D_3$ is a $C_x$ alkylene, $X_3$ is N, $D_2$ is a $C_y$ alkylene, a $C_y$ alkenylene, or a $C_y$ alkynylene, $X_1$ is S, wherein y may be an integer greater than or equal to 1, and the sum of x and y may be greater than or equal to 9. Also, the sum of x and y may be 9, 10, 11, or 12. For example, x may be 0, and y may be $9 \leq y \leq 12$. In another exemplary embodiment, x may be 1, and y may be $8 \leq y \leq 11$. In still another exemplary embodiment, x may be 2, and y may be $7 \leq y \leq 10$. In yet another exemplary embodiment, x may be 3, and y may be $6 \leq y \leq 9$. Optionally, $D_2$ may be an alkynylene. When $D_2$ is an alkynylene, the side chain of $(Xa_1)'$ may become stereoscopically rigid, thereby preventing bending of the side chain.

According to the present invention, there is disclosed an $R_1$'-$L_2$-SSFI for selectively transferring a first chemical functional group to lysine 246 or 248 in an Fc domain of an antibody.

According to one aspect of the present invention, the present invention provides an agent for transferring a first chemical functional group to an antibody, characterized in that a distance ($L_c$) between the beta carbon of $(Xa_1)'$ and the first carbonyl carbon has a value longer than or equal to $D_{246,min}$ (approximately 11.668 Å) and shorter than or equal to $D_{248,max}$ (approximately 16.208 Å). In this case, $L_c$ may have a value of approximately 11.668 Å, approximately 12 Å, approximately 13 Å, approximately 14 Å, approximately 15 Å, approximately 15.5 Å, approximately 16 Å, or approximately 16.208 Å.

In specific embodiments, when the $R_1$'-$L_2$-SSFI has any one structure selected from Formulas 5, 5-1 to 5-3, and 6-1 to 6-3, $D_3$ is a $C_x$ alkylene, $X_3$ is N, $D_2$ is a $C_y$ alkylene, a $C_y$ alkenylene, or a $C_y$ alkynylene, $X_1$ is S, wherein y may be an integer greater than or equal to 1, and the sum of x and y may be $6 \leq x+y \leq 8$. In this case, the sum of x and y may be 6, 7, or 8. For example, x may be 0, and y may be $6 \leq y \leq 8$. In another exemplary embodiment, x may be 1, and y may be $5 \leq y \leq 7$. In still another exemplary embodiment, x may be 2, and y may be $4 \leq y \leq 6$. In yet another exemplary embodiment, x may be 3, and y may be $3 \leq y \leq 5$.

According to the present invention, there is disclosed a method of preparing an $R_1$'-$L_2$-SSFI for specifically transferring a first chemical functional group to lysine 248 in an Fc domain of an antibody.

As one example of the method of preparing an agent for transferring first chemical functional group to an antibody as described in the section 4.2, the present invention provides a method of preparing an $R_1$'-$L_2$-SSAI, which is characterized by including:

reacting a linker according to the present invention with a site-specific antibody interactome according to the present invention, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $1 \leq x+y \leq 5$. Also, the $R_1$'-$L_2$-SSAI prepared by the method may react with an antibody to specifically transfer a first chemical functional group to lysine 248 in an Fc domain of the antibody.

According to the present invention, there is disclosed a kit for preparing an $R_1$'-$L_2$-SSFI for specifically transferring a first chemical functional group to lysine 248 in an Fc domain of an antibody.

As one example of the method of preparing an agent for transferring first chemical functional group to an antibody as described in the section 4.2, the present invention provides a kit for preparing an $R_1$'-$L_2$-SSAI, which is characterized by including:

a linker according to the present invention; and a site-specific antibody interactome according to the present invention, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $1 \leq x+y \leq 5$.

According to the present invention, there is disclosed a method of preparing an $R_1$'-$L_2$-SSFI for specifically transferring a first chemical functional group to lysine 246 in an Fc domain of an antibody.

As one example of the method of preparing an agent for transferring first chemical functional group to an antibody as described in the section 4.2, the present invention provides a method of preparing an $R_1$'-$L_2$-SSAI, which is characterized by including:

reacting a linker according to the present invention with a site-specific antibody interactome according to the present invention, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $9 \leq x+y \leq 12$. Also, the $R_1$'-$L_2$-SSAI prepared by the method may react with an antibody to specifically transfer a first chemical functional group to lysine 246 in an Fc domain of the antibody.

According to the present invention, there is disclosed a kit for preparing an $R_1$'-$L_2$-SSFI for specifically transferring a first chemical functional group to lysine 246 in an Fc domain of an antibody.

As one example of the method of preparing an agent for transferring first chemical functional group to an antibody as described in the section 4.2, the present invention provides a kit for preparing an $R_1$'-$L_2$-SSAI, which is characterized by including:

a linker according to the present invention; and a site-specific antibody interactome according to the present invention, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $9 \leq x+y \leq 12$.

According to the present invention, there is disclosed a method of preparing an $R_1$'-$L_2$-SSFI for selectively transferring a first chemical functional group to lysine 246 or 248 in an Fc domain of an antibody.

As one example of the method of preparing an agent for transferring first chemical functional group to an antibody as described in the section 4.2, the present invention provides a method of preparing an $R_1$'-$L_2$-SSAI, which is characterized by including:

reacting a linker according to the present invention with a site-specific antibody interactome according to the present invention, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $6 \leq x+y \leq 8$. Also, the $R_1$'-$L_2$-SSAI prepared by the method may react with an antibody to selectively transfer a first chemical functional group to lysine 246 or 248 in an Fc domain of the antibody.

According to the present invention, there is disclosed a kit for preparing an $R_1$'-$L_2$-SSFI for selectively transferring a first chemical functional group to lysine 246 or 248 in an Fc domain of an antibody.

As one example of the method of preparing an agent for transferring first chemical functional group to an antibody as described in the section 4.2, the present invention provides a kit for preparing an $R_1$'-$L_2$-SSAI, which is characterized by including:

a linker according to the present invention; and a site-specific antibody interactome according to the present invention, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $6 \leq x+y \leq 8$.

According to the present invention, there is disclosed a method of preparing an antibody having a first chemical functional group specifically transferred to lysine 248 in an Fc domain thereof.

As one example of the method of preparing an antibody containing a first chemical functional group as described in the section 5.2, the present invention provides a method of preparing an $R_1$'-Ab, which is characterized by including:

reacting an agent for transferring a first chemical functional group to an antibody according to the present invention with an antibody or a fragment thereof, wherein, in the agent for transferring a first chemical functional group to an antibody, a distance ($L_c$) between the beta carbon of $(Xa_1)$' and the first carbonyl carbon is shorter than approximately 11.668 Å.

In specific embodiments, in the agent for transferring a first chemical functional group to an antibody, $D_3$ is a $C_x$ alkylene, and $D_2$ is a $C_y$ alkylene, a $C_y$ alkenylene, or a $C_y$ alkynylene, wherein y may be an integer greater than or equal to 1, and the sum of x and y may be $1 \leq x+y \leq 5$.

According to the present invention, there is disclosed a kit for preparing an antibody having a first chemical functional group specifically transferred to lysine 248 in an Fc domain thereof.

As one example of the method of preparing an antibody containing a first chemical functional group as described in the section 5.2, the present invention provides a kit for preparing an $R_1$'-Ab, which is characterized by including:

an agent for transferring a first chemical functional group to an antibody according to the present invention; and an antibody or a fragment thereof, wherein, in the agent for transferring a first chemical functional group to an antibody, a distance ($L_c$) between the beta carbon of $(Xa_1)$' and the first carbonyl carbon is shorter than approximately 11.668 Å.

In specific embodiments, in the agent for transferring a first chemical functional group to an antibody, $D_3$ is a $C_x$ alkylene, and $D_2$ is a $C_y$ alkylene, a $C_y$ alkenylene, or a $C_y$ alkynylene, wherein y may be an integer greater than or equal to 1, and the sum of x and y may be $1 \leq x+y \leq 5$.

Optionally, as one example of the method of preparing an antibody containing a first chemical functional group as described in the section 5.2, the present invention provides a kit for preparing an $R_1$'-Ab, which is characterized by including:

a linker according to the present invention;

a site-specific antibody interactome according to the present invention; and an antibody or a fragment thereof, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $1 \leq x+y \leq 5$.

According to the present invention, there is disclosed a method of preparing an antibody having a first chemical functional group specifically transferred to lysine 246 in an Fc domain thereof.

As one example of the method of preparing an antibody containing a first chemical functional group as described in the section 5.2, the present invention provides a method of preparing an $R_1$'-Ab, which is characterized by including:

allowing an antibody or a fragment thereof to react with an agent for transferring a first chemical functional group to an antibody according to the present invention, wherein, in the agent for transferring a first chemical functional group to an antibody, a distance ($L_c$) between the beta carbon of $(Xa_1)'$ and the first carbonyl carbon is longer than approximately 16.208 Å.

In specific embodiments, in the agent for transferring a first chemical functional group to an antibody, $D_3$ is a $C_x$ alkylene, and $D_2$ is a $C_y$ alkylene, a $C_y$ alkenylene, or a $C_y$ alkynylene, wherein y may be an integer greater than or equal to 1, and the sum of x and y may be $9 \leq x+y \leq 12$.

According to the present invention, there is disclosed a kit for preparing an antibody having a first chemical functional group specifically transferred to lysine 246 in an Fc domain thereof.

As one example of the method of preparing an antibody containing a first chemical functional group as described in the section 5.2, the present invention provides a kit for preparing an $R_1$'-Ab, which is characterized by including:

an agent for transferring a first chemical functional group to an antibody according to the present invention; and an antibody or a fragment thereof, wherein, in the agent for transferring a first chemical functional group to an antibody, a distance ($L_c$) between the beta carbon of $(Xa_1)'$ and the first carbonyl carbon is longer than approximately 16.208 Å.

In specific embodiments, in the agent for transferring a first chemical functional group to an antibody, $D_3$ is a $C_x$ alkylene, and $D_2$ is a $C_y$ alkylene, a $C_y$ alkenylene, or a $C_y$ alkynylene, wherein y may be an integer greater than or equal to 1, and the sum of x and y may be $9 \leq x+y \leq 12$.

Optionally, as one example of the method of preparing an antibody containing a first chemical functional group as described in the section 5.2, the present invention provides a kit for preparing an $R_1$'-Ab, which is characterized by including:

a linker according to the present invention;

a site-specific antibody interactome according to the present invention; and an antibody or a fragment thereof, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $9 \leq x+y \leq 12$.

According to the present invention, there is disclosed a method of preparing an antibody having a first chemical functional group selectively transferred to lysine 246 or 248 in an Fc domain thereof.

As one example of the method of preparing an antibody containing a first chemical functional group as described in the section 5.2, the present invention provides a method of preparing an $R_1$'-Ab, which is characterized by including:

reacting an agent for transferring a first chemical functional group to an antibody according to the present invention with an antibody or a fragment thereof, wherein, in the agent for transferring a first chemical functional group to an antibody, a distance ($L_c$) between the beta carbon of $(Xa_1)'$ and the first carbonyl carbon is longer than or equal to approximately 11.668 Å and shorter than or equal to approximately 16.208 Å.

In specific embodiments, in the agent for transferring a first chemical functional group to an antibody, $D_3$ is a $C_x$ alkylene, and $D_2$ is a $C_y$ alkylene, a $C_y$ alkenylene, or a $C_y$ alkynylene, wherein y may be an integer greater than or equal to 1, and the sum of x and y may be $6 \leq x+y \leq 8$.

According to the present invention, there is disclosed a kit for preparing an antibody having a first chemical functional group selectively transferred to lysine 246 or 248 in an Fc domain thereof.

As one example of the method of preparing an antibody containing a first chemical functional group as described in the section 5.2, the present invention provides a kit for preparing an $R_1$'-Ab, which is characterized by including:

an agent for transferring a first chemical functional group to an antibody according to the present invention; and an antibody or a fragment thereof, wherein, in the agent for transferring a first chemical functional group to an antibody, a distance ($L_c$) between the beta carbon of $(Xa_1)'$ and the first carbonyl carbon is longer than or equal to approximately 11.668 Å and shorter than or equal to approximately 16.208 Å.

In specific embodiments, in the agent for transferring a first chemical functional group to an antibody, $D_3$ is a $C_x$ alkylene, and $D_2$ is a $C_y$ alkylene, a $C_y$ alkenylene, or a $C_y$ alkynylene, wherein y may be an integer greater than or equal to 1, and the sum of x and y may be $6 \leq x+y \leq 8$.

Optionally, as one example of the method of preparing an antibody containing a first chemical functional group as described in the section 5.2, the present invention provides a kit for preparing an $R_1$'-Ab, which is characterized by including:

a linker according to the present invention;

a site-specific antibody interactome according to the present invention; and an antibody or a fragment thereof, wherein $D_2$ in the linker is a $C_y$ alkylene, a $C_y$ alkenylene, or a $C_y$ alkynylene, and $D_3$ in the site-specific antibody interactome is a $C_x$ alkylene, wherein y is an integer greater than or equal to 1, and the sum of x and y is $6 \leq x+y \leq 8$.

According to the present invention, there is disclosed a method of preparing an antibody having a first chemical functional group transferred to both lysine 246 and 248 in an Fc domain thereof.

The present invention provides a method of preparing an $R_1$'-Ab, which includes:

reacting a first agent for transferring a first chemical functional group to an antibody with an antibody or a fragment thereof; and reacting a second agent for transferring a first chemical functional group to an antibody with the antibody or fragment thereof.

In specific embodiments, the first agent for transferring a first chemical functional group to an antibody may be an $R_1$'-$L_2$-SSFI for specifically transferring a first chemical functional group to lysine 248 in the Fc domain as described above, and the second agent for transferring a first chemical functional group to an antibody may be an $R_1$'-$L_2$-SSFI for specifically transferring a first chemical functional group to lysine 246 in the Fc domain as described above.

In specific embodiments, the first agent for transferring a first chemical functional group to an antibody may be an $R_1$'-$L_2$-SSFI for specifically transferring a first chemical functional group to lysine 246 in the Fc domain as described above, and the second agent for transferring a first chemical functional group to an antibody may be an $R_1$'-$L_2$-SSFI for specifically transferring a first chemical functional group to lysine 248 in the Fc domain as described above.

In specific embodiments, the reacting of the first agent for transferring a first chemical functional group to an antibody with the antibody or fragment thereof; and the reacting of the second agent for transferring a first chemical functional group to an antibody with the antibody or fragment thereof may be sequentially performed.

According to the present invention, there is disclosed a kit for preparing an antibody having a first chemical functional group transferred to both lysine 246 and 248 in an Fc domain thereof.

The present invention provides a kit for preparing an $R_1$'-Ab, which includes:

- a first agent for transferring a first chemical functional group to an antibody;
- a second agent for transferring a first chemical functional group to an antibody; and
- an antibody or a fragment thereof.

In specific embodiments, the first agent for transferring a first chemical functional group to an antibody may be an $R_1$'-$L_2$-SSFI for specifically transferring a first chemical functional group to lysine 248 in the Fc domain as described above, and the second agent for transferring a first chemical functional group to an antibody may be an $R_1$'-$L_2$-SSFI for specifically transferring a first chemical functional group to lysine 246 in the Fc domain as described above.

In specific embodiments, the first agent for transferring a first chemical functional group to an antibody may be an $R_1$'-$L_2$-SSFI for specifically transferring a first chemical functional group to lysine 246 in the Fc domain as described above, and the second agent for transferring a first chemical functional group to an antibody may be an $R_1$'-$L_2$-SSFI for specifically transferring a first chemical functional group to lysine 248 in the Fc domain as described above.

5.5. It is possible to transfer first chemical functional group more site-specifically by modulating the reactivity of the first carbonyl group.

As described above in the section 5.2, an antibody containing a first chemical functional group may be prepared by a nucleophile of the antibody attacking a first carbonyl group of the $R_1$'-$L_2$-SSFI. The first carbonyl group is characterized by having milder reactivity than the second carbonyl group of the linker (see section 2.2). The reactivity of the first carbonyl group may be modulated so that a certain amine group of the antibody can react with the first carbonyl group only when the certain amine group is in the vicinity of the first carbonyl group. In this way, the present invention allows the first carbonyl group not to react well with any amine group through the vicinity conditions for reaction, and enables high positional specificity of the reaction.

The prior art disclosed in Publication Nos. US 2018/0141976 A1 and WO 2018/199337 A1 aims to site-selectively modulate lysine 246 or 248 in an Fc domain using an analogue of Fc-III. Because the prior art uses a disuccinimidyl cross-linker, the first carbonyl group and the second carbonyl group are equally highly reactive (see section 2.2). Therefore, because the first carbonyl group has high reactivity and has no vicinity conditions for reaction, any lysine residue is highly likely to be labeled.

5.6. The antibody containing a first chemical functional group prepared according to the present invention has high uniformity and yield.

The technical problem and the technical solution to specifically transfer (1) "a desired number" of first chemical functional groups to (2) "certain sites of an antibody" have been described in detail with reference to the sections 5.3 and 5.4. As can be seen from Experimental Examples below, it can be seen that the chemical functional group of the antibody containing a first chemical functional group prepared by means of the technical solution is transferred to a certain lysine residue in the Fc domain thereof with high specificity and yield (see Experimental Example 3.3). Therefore, the present invention has been completed based on these facts.

As shown in the background art, the conjugate product having high uniformity due to antibody labeling has advantages in that (1) the functions of the antibody conjugate are uniformly guaranteed, (2) the antibody conjugate is safe due to its predictable effects, and (3) a drop in function of an antibody may be avoided because it is possible to label an antibody while avoiding a functional region of the antibody.

The prior art disclosed in Publication Nos. US 2018/0141976 A1 and WO 2018/199337 A1 aims to site-selectively modulate lysine 246 or 248 in an Fc domain using an analogue of Fc-III. However, according to the prior art, the uniformity and yield of the antibody may be inevitably low due to two reasons. According to the prior art, first, because a distance ($L_c$) between the beta carbon of $(Xa_1)'$ and the first carbonyl carbon is approximately 15 Å, it is possible to selectively label lysine at either position 246 or 248, but it is impossible to specifically select one of the lysine 246 and 248 to be labeled. Second, a first carbonyl group of a cross-linker according to the prior art has no vicinity conditions for reaction due to high reactivity (see section 5.5). As a result, the first carbonyl group is highly likely to react with any lysine residue. Therefore, the prior art has a drawback in that the uniformity and yield of an antibody-labeled product are inferior to those of the present invention.

5.7. No functions of the antibody are lowered because the antibody containing a first chemical functional group according to the present invention has no FcRn binding site blocked therein.

The design principle for the antibody labeling site being (1) spaced apart from the paratope; and (2) spaced apart from the recognition site of FcR including FcRn has been described above in the section 1.1. Because the lysine 246 and 248 are included in the Fc domain, the lysine 246 and 248 are spaced apart from the paratope, but the corresponding site may overlap the recognition site of FcRn, which may be problematic.

It is known that FcRn has various functions, and particularly plays an important role in extending the half-life of the antibody by participating in IgG recycling. When the antibody is used in vivo, that is, when the antibody is used as a therapeutic agent, a contrast medium, and the like, the interaction between FcRn and the antibody may not occur smoothly, thereby making it impossible for the antibody to function normally due to the short half-life of the antibody.

Figure 13:
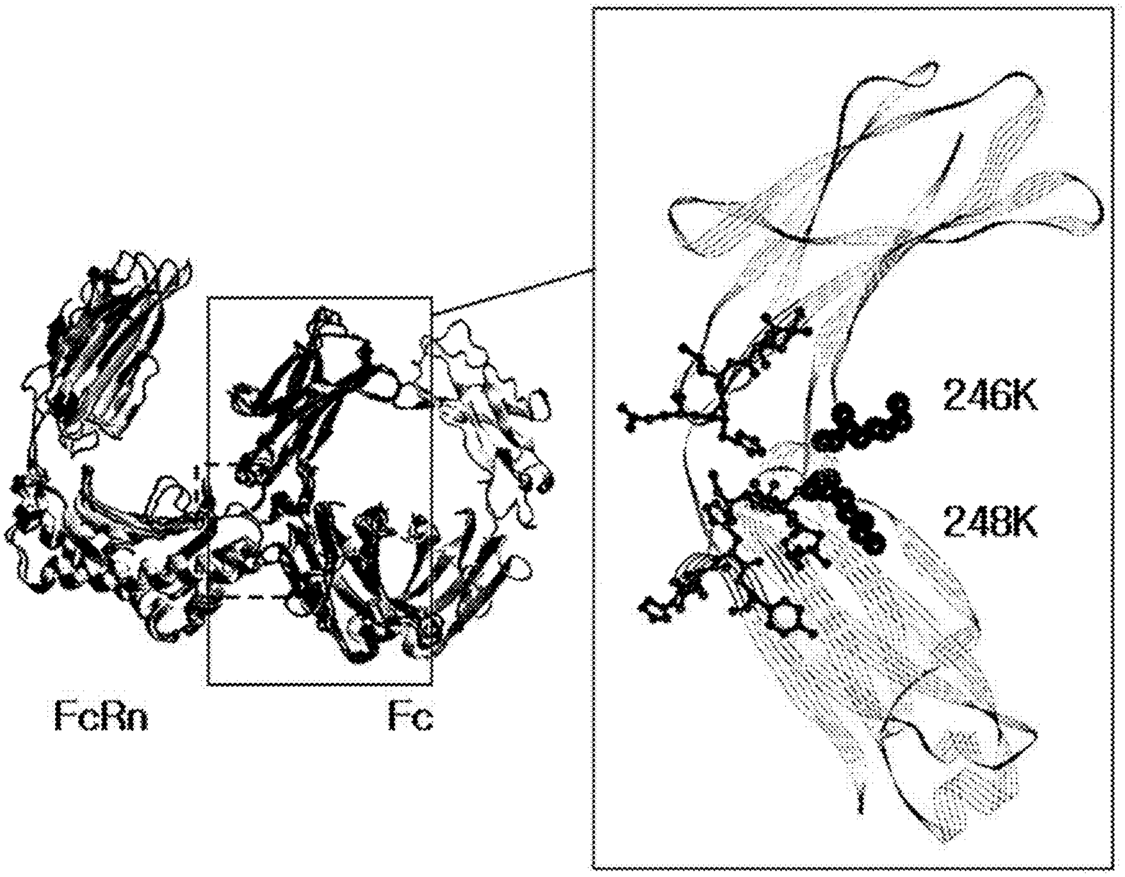
FIG. 13 shows an FcRn binding site and lysine 246 and 248 in the Fc domain.

5.7.1. Lysine 246 and lysine 248 are spaced apart from the FcRn binding site of the antibody The spacing between the lysine residues in the Fc domain and the FcRn binding site of Fc was an important consideration to choose the lysine residue in the Fc domain. FIG. 13 shows a binding structure between an Fc domain and FcRn and positions of the FcRn binding site and lysine 246 and 248 in the Fc domain. Papers and computer modeling were employed to show a binding structure between the Fc domain and FcRn (Ying T, Ju T W, Wang Y, Prabakaran P, Dimitrov D S., Interactions of IgG1 $CH_2$ and $CH_3$ Domains with FcRn; Front Immunol. 2014; 5:146, Monnet C, Jorieux S, Urbain R, et al., Selection of IgG Variants with Increased FcRn Binding Using Random and Directed Mutagenesis: Impact on Effector Functions. Front Immunol. 2015; 6:39.) (see the left image of FIG. 13). The FcRn binding site and the lysine 246 and 248 disclosed in the same article data are indicated in the Fc domain (see the right image of FIG. 13). Referring to the two images, it can be seen that side chains of the lysine 246 and 248 are directed in a direction opposite the FcRn binding site.

From these facts, it was contemplated that, when an antibody labeling site is chosen, the antibody labeling site does not affect the interaction between the FcRn and Fc domain. In effect, it was confirmed that the half-life of the prepared antibody is not reduced so that the antibody labeling site does not influence binding of FcRn as intended (see Experimental Example 5).

Figure 14:
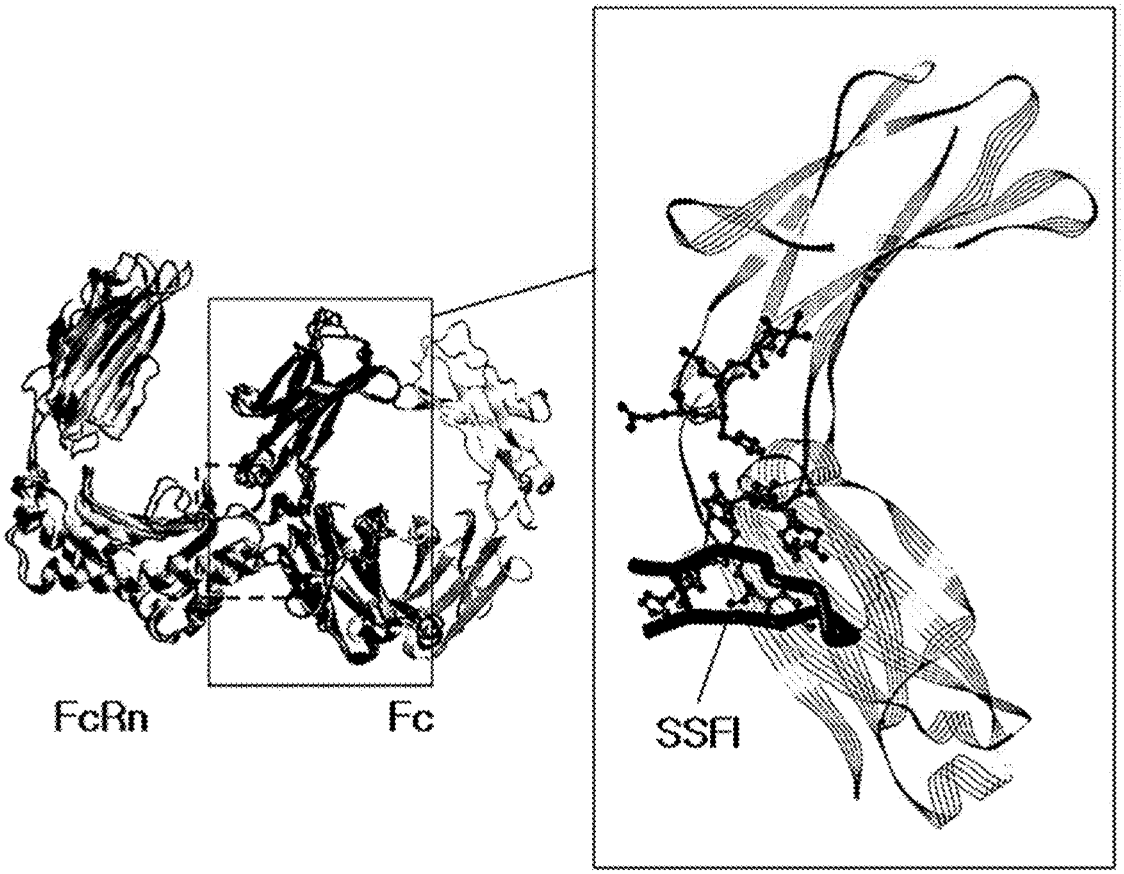
FIG. 14 shows the analysis of a binding structure between SSFI and the Fc domain in comparison with a binding site between Fc and of FcRn.

5.8. A process of preparing the antibody containing a first chemical functional group according to the present invention is characterized by SSAI leaving, As seen from Schemes 4 and 5 in the section 5.2, a process of preparing the $R_1$'-Ab according to the present invention is characterized in that SSAI leaves the final product $R_1$'-Ab because the SSAI is included in a leaving group of a nucleophilic substitution reaction. The binding structure between the Fc domain and the SSFI according to the present invention (see section 3.2) was analyzed in comparison with the binding site between Fc and FcRn. As a result, it was confirmed that a portion of the FcRn binding site is covered with the SSFI (FIG. 14). In this regard, it can be expected that, when the SSFI does not leave during the process of preparing the $R_1$'-Ab, the SSFI has a negative influence on the physical properties (e.g., half-life, and the like) of the antibody.

The prior art disclosed in Publication No. US 2018/0141976 A1 aims to site-selectively modulate lysine 246 or 248 in an Fc domain using an analogue of Fc-III. However, the corresponding prior art is different from the present invention in that SSFI is included in the final antibody-labeled product because the SSFI does not leave during the preparation process.

The prior art disclosed in Publication No. WO 2018/199337 A1 aims to site-selectively modulate lysine 246 or 248 in an Fc domain using an analogue of Fc-III, wherein SSFI is not included in the final antibody-labeled product. However, the corresponding prior art further includes cleaving a "cleavable linker that is a divalent group" in order to remove the SSFI during the preparation process, but the present invention has an advantage in that the SSFI leaves during a conjugation reaction without any additional processes. Also, the cleaving of the cleavable linker that is a divalent group according to the corresponding invention has a drawback in that a disulfide bond forming a structure of the antibody may be cleaved. Because the present invention uses a nucleophilic substitution reaction which occurs easily without any special conditions, this problem may be dramatically improved.

5.9. No side reactions other than a conjugate formation reaction occurs because the antibody containing a first click-chemistry functional group according to the present invention does not contain a highly bioreactive chemical functional group.

The antibody prepared by the method of preparing an $R_1$'-Ab according to the present invention has a structure represented by Formula 7:

[Formula 7]

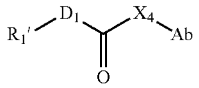

When $R_1$' is transferred to lysine 246 or 248, $X_4$ may be NH, and $D_1$ may be any alkylene, alkenylene, or alkynylene. In this case, —NH—(CO)— connected to the antibody is an amide bond that is generally stable in vivo. Also, $D_1$ generally has a structure which is not highly bioreactive. Therefore, it is expected that the $R_1$'-Ab prepared according to the present invention has high safety because a highly bioreactive structure is not added to molecules other than the labeled molecule ($R_1$').

In particular, when the $R_1$'-Ab is an $H_1$-Ab having a click-chemistry residue transferred thereto, a highly bioreactive structure is not added to the $R_1$'-Ab. Therefore, the yield of the click-chemistry reaction may be improved because no secondary reactions other than the click-chemistry reaction occur.

The prior art disclosed Publication No. WO 2018/199337 A1 aims to site-selectively modulate lysine 246 or 248 in an Fc domain using an analogue of Fc-III and use a biorthogonal functional group. However, the corresponding prior art is different from the present invention in that the antibody product according to the corresponding prior art is allowed to have an additional chemical functional group such as thiol, hydroxy, carboxylic acid, phosphoric acid, amine, and the like during the cleaving of the "cleavable linker that is a divalent group." Such an additional chemical functional group is a bioreactive functional group, and thus may affect the safety of the antibody product.

6. Payload ($C_m$—$H_2$)

According to the present invention, there is disclosed a payload. Such a compound is herein indicated by the symbol "$C_m$—$H_2$."

The present invention provides a $C_m$—$H_2$ represented by Formula 9:

$C_m$—$H_2$ [Formula 9]

wherein $C_m$ is a cargo moiety, $H_2$ is a second click-chemistry functional group.

In specific embodiments, $C_m$ may include a carrier moiety, a fluorescent moiety, a drug moiety, or a radioactive moiety. Also, $R_1$' may include a drug moiety. In addition, $R_1$' may include a VC linker. In other specific embodiments, $R_1$' may include an antibody or an analogue thereof, which includes a paratope.

In specific embodiments, when $C_m$ includes a drug moiety, the drug moiety may be an anti-cancer drug. Also, the anti-cancer drug may include one or more selected from DM1, DM3, DM4, Abrin, Ricin A, a Pseudomonas exotoxin, a Cholera toxin, a Diphtheria toxin, a tumor necrosis factor, a interferon, β interferon, a nerve growth factor, a platelet-derived growth factor, a tissue plasminogen activator, a cytokine, an apoptosis-inducing agent, an anti-angiogenic agent, a lymphokine, taxane, a DNA-alkylating agent, anthracyclin, a Tubulysin analogue, a duocarmycin analogue, auristatin E, auristatin F, a maytansinoid, a cytotoxic agent including a reactive polyethylene glycol residue, taxon, cytochalasin B, gramicidin D, ethidium bromide, emetine, mitomycin, etoposide, tenoposide, vincristine, vinblastine, T. Colchicin, doxorubicin, daunorubicin, dihydroxy anthracin dione, mitoxantrone, mithramycin, actinomycin D, 1-dihydrotestosterone, a glucocorticoid, procaine, tetracaine, lidocaine, propranolol, puromycin, methotrexate, 6-mercaptopurine, 6-thioguanine, cytarabine, 5-fluorouracil decarbazine, mechlorethamine, thiotepa, chlorambucil, Meiphalan, carmustine, lomustine, cyclophosphamide, busulfan, dibromomannitol, streptozotocin, mitomycin C, cisplatin, dactinomycin, bleomycin, anthramycin, calicheamicin, abiraterone, bendamustine, bortezomib, carboplatin, cabazitaxel, dasatinib, doxetaxel, epirubicin, erlotinib, everolimus, gemcitabine, gefitinib, idarubicin, imatinib, hydroxyurea, lapatinib, leuprorelin, melphalan, nedaplatin, nilotinib, oxaliplatin, pazopanib, pemetrexed, picoplatin, romidepsin, satraplatin, sorafenib, vemurafenib, sunitinib, teniposide, triplatin, and vinorelbine.

In specific embodiments, $C_m$ may include a plurality of carrier moieties, fluorescent moieties, drug moieties, or radioactive moieties. Also, $C_m$ may include two or more drug moieties. In addition, $C_m$ may include a VC linker.

In specific embodiments, $H_2$ may include any one selected from an alkyne, an azide, a strained alkyne, a diene, a dienophile, an alkene, a thiol, and a tetrazine. Furthermore, $H_2$ may be an azide, or a strained alkyne. Further, $H_2$ may be an azide, or dibenzocyclooctyne-amine. Additionally, $H_2$ may be a diene, or a dienophile. Further, $H_2$ may be a tetrazine, or a norbornene. Alternatively, $H_2$ may be a tetrazine, or a trans-cyclooctene.

In specific embodiments, when $H_2$ is to react with the $H_1$-Ab according to the present invention, $H_2$ may be complementary to the first click-chemistry functional group ($H_1$).

7. Antibody-Payload Conjugate ($C_m$-Ab)

According to the present invention, there is disclosed a conjugate of an antibody and a payload (i.e., an antibody-payload conjugate). Such a compound is herein indicated by the symbol "$C_m$-Ab."

The present invention provides a $C_m$-Ab represented by Formula 10:

[Formula 10]

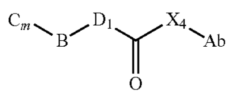

wherein $C_m$ is a cargo moiety,

B is a structure formed by a click-chemistry reaction between a first click-chemistry functional group and a second click-chemistry functional group, $D_1$ is any alkylene, alkenylene, or alkynylene, $X_4$ is NH, O, or S, and Ab is an antibody.

The contents of the cargo moiety apply to the contents disclosed in the section '6. Payload.'

In specific embodiments, B may be a structure formed by a click-chemistry reaction between any one selected from an alkyne, an azide, a strained alkyne, a diene, a dienophile, an alkene, a thiol, and a tetrazine and its partner "click-chemistry functional group." Also, B may be any one selected from

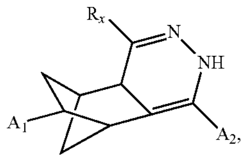

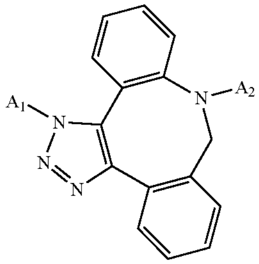

,

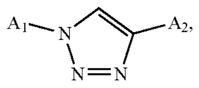

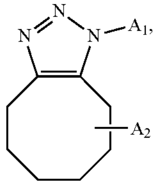

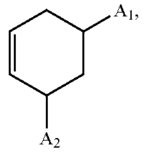

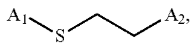

and

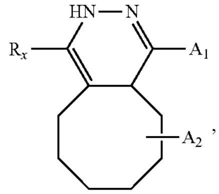

, wherein both $A_1$ and $A_2$ are connected to the cargo moiety or $D_1$ so that the $A_1$ and $A_2$ cannot be connected to the same moiety, and Rx may be selected from H, a halogen, and a $C_{1-3}$ alkyl. Furthermore, B may be

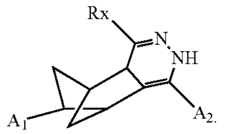

Additionally, B may be

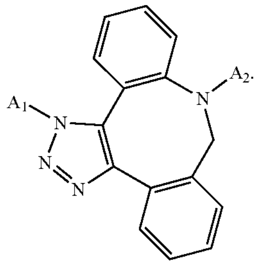

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond.

In one specific embodiment, $X_4$ may be NH.

In specific embodiments, Ab may be a human antibody. In other specific embodiments, Ab may be a non-human animal antibody. In specific embodiments, Ab may be immunoglobulin G (IgG). In specific embodiments, Ab may be a whole antibody. In other specific embodiments, Ab may be a fragment of the antibody.

In specific embodiments, $X_4$ and Ab may be connected via an Fab domain of Ab. In other specific embodiments, $X_4$ and Ab may be connected via an Fc domain of Ab. Also, $X_4$ and Ab may be connected via lysine 246 or 248 in the Fc domain of Ab. Furthermore, $X_4$ and Ab may be connected via lysine 246 in the Fc domain of Ab. Further, $X_4$ and Ab may be connected via lysine 248 in the Fc domain of Ab. Alternatively, $X_4$ and Ab may be connected via lysine 246 and 248 in the Fc domain of Ab. In specific embodiments, $X_4$ and Ab may be connected via only one of two Fc domains of Ab. In other specific embodiments, $X_4$ and Ab may be connected via both of the two Fc domains of Ab.

The present invention provides an antibody or a fragment thereof including an amino acid sequence of the following Formula 10-1:

```
[Formula 10-1]
                                    (SEQ ID NO: 23)
G-P-S-V-F-L-F-P-P-(K)"-P-K-D-T-L-M-I
```

wherein G is glycine, P is proline, S is serine, V is valine, F is phenylalanine, L is leucine, K is lysine, D is aspartic acid, T is threonine, M is methionine, I is isoleucine, and (K)" is

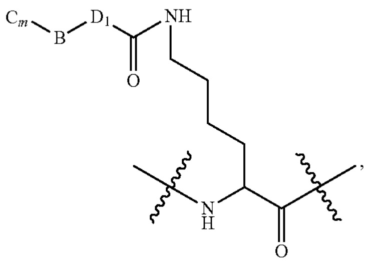

wherein $C_m$ is a cargo moiety,

B is a structure formed by a click-chemistry reaction between a first click-chemistry functional group and a second click-chemistry functional group, and $D_1$ is any alkylene, alkenylene, or alkynylene. The antibody or fragment thereof has a cargo moiety conjugated to lysine 246 in an Fc domain thereof, or a site corresponding to the lysine 246.

The contents of the cargo moiety apply to the contents disclosed in the section '6. Payload.'

In specific embodiments, B may be a structure formed by a click-chemistry reaction between any one selected from an alkyne, an azide, a strained alkyne, a diene, a dienophile, an alkene, a thiol, and a tetrazine and its partner "click-chemistry functional group." Also, B may be any one selected from

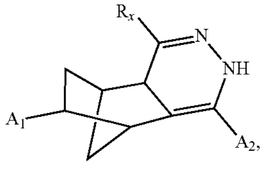

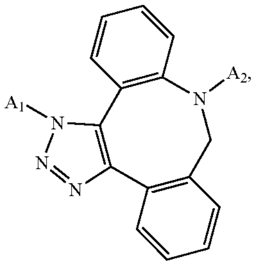

-continued

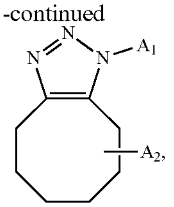

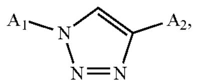

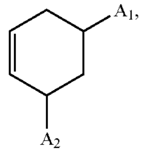

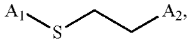

and

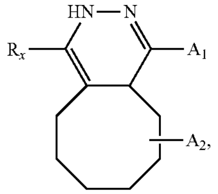

wherein both $A_1$ and $A_2$ are connected to the cargo moiety or $D_1$ so that the $A_1$ and $A_2$ cannot be connected to the same moiety, and Rx may be selected from H, a halogen, and a $C_{1-3}$ alkyl. Furthermore, B may be

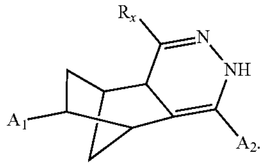

Additionally, B may be

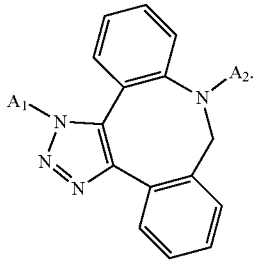

In specific embodiments, $D_1$ may include any one selected from a covalent bond, a $C_{1-4}$ alkylene, a $C_{2-4}$ alkenylene, a $C_{2-4}$ alkynylene, and a Cas cycloalkylene. Also, $D_1$ may be $—CH_2OCH_2—$. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody.

In specific embodiments, the antibody may include the amino acid sequence of Formula 10-1 in only one of the two Fc domains thereof. In other specific embodiments, the antibody may include the amino acid sequence of Formula 10-1 in both of the two Fc domains thereof.

The present invention provides an antibody or a fragment thereof including an amino acid sequence of the following Formula 10-2:

```
[Formula 10-2]
                                        (SEQ ID NO: 24)
G-P-S-V-F-L-F-P-P-K-P-(K)"-D-T-L-M-I
```

wherein G is glycine, P is proline, S is serine, V is valine, F is phenylalanine, L is leucine, K is lysine, D is aspartic acid, T is threonine, M is methionine, I is isoleucine, and (K)" is

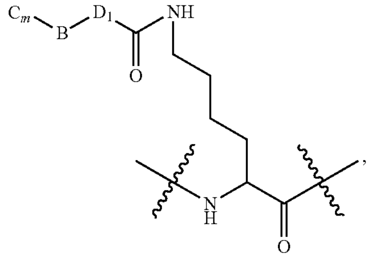

wherein $C_m$ is a cargo moiety,

B is a structure formed by a click-chemistry reaction between a first click-chemistry functional group and a second click-chemistry functional group, and $D_1$ is any alkylene, alkenylene, or alkynylene. The antibody or fragment thereof has a cargo moiety conjugated to lysine 246 in an Fc domain thereof, or a site corresponding to the lysine 246.

The contents of the cargo moiety apply to the contents disclosed in the section '6. Payload.'

In specific embodiments, B may be a structure formed by a click-chemistry reaction between any one selected from an alkyne, an azide, a strained alkyne, a diene, a dienophile, an alkene, a thiol, and a tetrazine and its partner "click-chemistry functional group." Also, B may be any one selected from

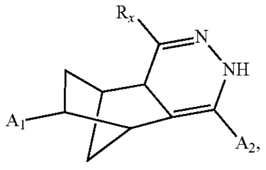

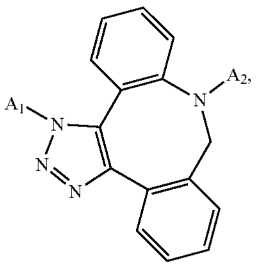

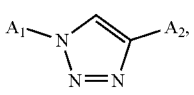

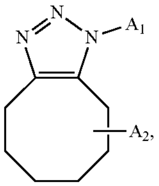

-continued

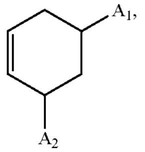

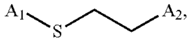 and

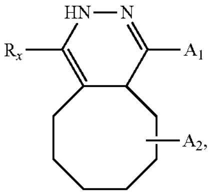

wherein both $A_1$ and $A_2$ are connected to the cargo moiety or $D_1$ so that the $A_1$ and $A_2$ cannot be connected to the same moiety, and Rx may be selected from H, a halogen, and a $C_{1-3}$ alkyl. Furthermore, B may be

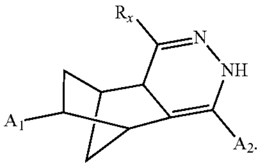

Additionally, B may be

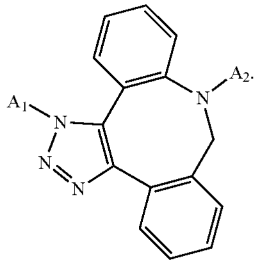

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be —$CH_2OCH_2$—. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody.

In specific embodiments, the antibody may include the amino acid sequence of Formula 10-2 in only one of the two Fc domains thereof. In other specific embodiments, the antibody may include the amino acid sequence of Formula 10-2 in both of the two Fc domains thereof.

The present invention provides an antibody or a fragment thereof including an amino acid sequence of the following Formula 10-3:

[Formula 10-3]

SEQ ID NO: 25

G-P-S-V-F-L-F-P-P-(K)"-P-(K)"-D-T-L-M-I wherein G is glycine, P is proline, S is serine, V is valine, F is phenylalanine, L is leucine, K is lysine, D is aspartic acid, T is threonine, M is methionine, I is isoleucine, and (K)" is each independently

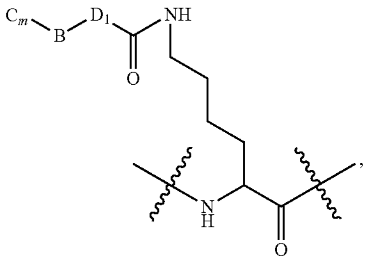

wherein $C_m$ is a cargo moiety,

B is a structure formed by a click-chemistry reaction between a first click-chemistry functional group and a second click-chemistry functional group, and $D_1$ is any alkylene, alkenylene, or alkynylene. The antibody or fragment thereof has a cargo moiety conjugated to lysine 246 in an Fc domain thereof, or a site corresponding to the lysine 246.

The contents of the cargo moiety apply to the contents disclosed in the section "6. Payload."

In specific embodiments, B may be a structure formed by a click-chemistry reaction between any one selected from an alkyne, an azide, a strained alkyne, a diene, a dienophile, an alkene, a thiol, and a tetrazine and its partner "click-chemistry functional group." Also, B may be any one selected from

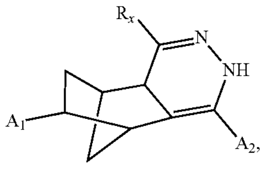

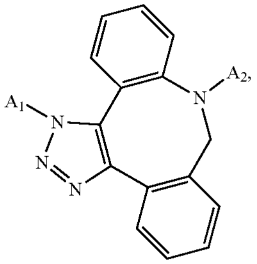

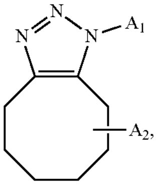

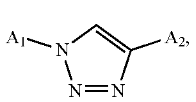

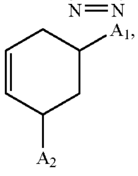

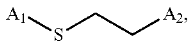

and

-continued

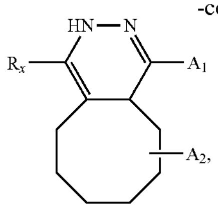

wherein both $A_1$ and $A_2$ are connected to the cargo moiety or $D_1$ so that the $A_1$ and $A_2$ cannot be connected to the same moiety, and Rx may be selected from H, a halogen, and a $C_{1-3}$ alkyl. Furthermore, B may be

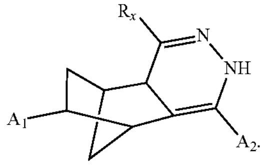

Additionally, B may be

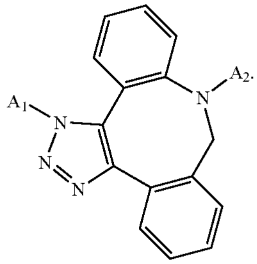

In specific embodiments, $D_1$ may include any one selected from a covalent bond, a $C_{1-4}$ alkylene, a $C_{2-4}$ alkenylene, a $C_{2-4}$ alkynylene, and a $C_{3-8}$ cycloalkylene. Also, $D_1$ may be $—CH_2OCH_2—$. In addition, $D_1$ may be a covalent bond.

In specific embodiments, the antibody may be a human antibody. In other specific embodiments, the antibody may be a non-human animal antibody. In specific embodiments, the antibody may be immunoglobulin G (IgG). In specific embodiments, the antibody may be a whole antibody. In other specific embodiments, the antibody may be a fragment of the antibody.

In specific embodiments, the antibody may include the amino acid sequence of Formula 10-3 in only one of the two Fc domains thereof. In other specific embodiments, the antibody may include the amino acid sequence of Formula 10-3 in both of the two Fc domains thereof.

The present invention provides an antibody or a fragment thereof including one or more amino acid sequences selected from Formulas 10-1, 10-2, and 10-3. In this case, the contents of Formulas 10-1 to 10-3 are as described above.

In specific embodiments, $D_1$ may be a covalent bond.

In specific embodiments, the antibody or fragment thereof may include only the amino acid sequence of Formula 10-1 and may not include the amino acid sequences of Formulas 10-2 and 10-3. Also, the antibody or fragment thereof may include the amino acid sequence of Formula 10-1 in only one of the two Fc domains thereof. In addition, the antibody may include the amino acid sequence of Formula 10-1 in both of the two Fc domains thereof.

In other specific embodiments, the antibody or fragment thereof may include only the amino acid sequence of Formula 10-2 and may not include the amino acid sequences of Formulas 10-1 and 10-3. Also, the antibody or fragment thereof may include the amino acid sequence of Formula 10-2 in only one of the two Fc domains thereof. In addition, the antibody may include the amino acid sequence of Formula 10-2 in both of the two Fc domains thereof.

In specific embodiments, the antibody or fragment thereof may include only the amino acid sequence of Formula 10-3 and may not include the amino acid sequences of Formulas 10-1 and 10-2. Also, the antibody or fragment thereof may include the amino acid sequence of Formula 10-3 in only one of the two Fc domains thereof. In addition, the antibody may include the amino acid sequence of Formula 10-3 in both of the two Fc domains thereof.

7.1. Antibody-Drug Conjugate (ADC)

According to the present invention, there is disclosed a novel antibody-drug conjugate (ADC). The ADC according to the present invention means that a payload in the antibody-payload conjugate includes a drug moiety.

The present invention provides a $C_m$-Ab according to the present invention in which a cargo moiety includes a drug moiety.

In specific embodiments, the cargo moiety may include two or more drug moieties.

In specific embodiments, the drug moiety may be an anti-cancer drug. Also, the anti-cancer drug may include one or more selected from DM1, DM3, DM4, Abrin, Ricin A, a Pseudomonas exotoxin, a Cholera toxin, a Diphtheria toxin, a tumor necrosis factor, a interferon, β interferon, a nerve growth factor, a platelet-derived growth factor, a tissue plasminogen activator, a cytokine, an apoptosis-inducing agent, an anti-angiogenic agent, a lymphokine, taxane, a DNA-alkylating agent, anthracyclin, a Tubulysin analogue, a duocarmycin analogue, auristatin E, auristatin F, a maytansinoid, a cytotoxic agent including a reactive polyethylene glycol residue, taxon, cytochalasin B, gramicidin D, ethidium bromide, emetine, mitomycin, etoposide, tenoposide, vincristine, vinblastine, T. Colchicin, doxorubicin, daunorubicin, dihydroxy anthracin dione, mitoxantrone, mithramycin, actinomycin D, 1-dihydrotestosterone, a glucocorticoid, procaine, tetracaine, lidocaine, propranolol, puromycin, methotrexate, 6-mercaptopurine, 6-thioguanine, cytarabine, 5-fluorouracil decarbazine, mechlorethamine, thiotepa, chlorambucil, Meiphalan, carmustine, lomustine, cyclophosphamide, busulfan, dibromomannitol, streptozotocin, mitomycin C, cisplatin, dactinomycin, bleomycin, anthramycin, calicheamicin, abiraterone, bendamustine, bortezomib, carboplatin, cabazitaxel, dasatinib, doxetaxel, epirubicin, erlotinib, everolimus, gemcitabine, gefitinib, idarubicin, imatinib, hydroxyurea, lapatinib, leuprorelin, melphalan, nedaplatin, nilotinib, oxaliplatin, pazopanib, pemetrexed, picoplatin, romidepsin, satraplatin, sorafenib, vemurafenib, sunitinib, teniposide, triplatin, and vinorelbine.

In specific embodiments, the cargo moiety may include a VC linker.

7.2. Method of Preparing Antibody-Payload Conjugate

According to the present invention, there is disclosed a method of preparing an antibody-payload conjugate.

The antibody-payload conjugate of the present invention may be prepared by allowing a $C_m$—$H_2$ to react with an $H_1$-Ab. In this case, the contents of the $H_1$-Ab apply to the contents disclosed in the section 5.1, and the contents disclosed in the section 6 apply for the $C_m$—$H_2$. When the first click-chemistry functional group of $H_1$-Ab and the second click-chemistry functional group of $C_m$—$H_2$ are complementary to each other, that is, when the first click-chemistry functional group of $H_1$-Ab and the second click-chemistry functional group of $C_m$—$H_2$ function as partner click-chemistry functional groups, a click-chemistry reaction may occur to prepare an antibody-payload conjugate according to the present invention. The contents of the click-chemistry reaction were sufficiently described above in the section "Definition." The click-chemistry reaction is a biorthogonal reaction, and has an advantage in that the reaction occurs at a very rapid reaction rate and is used to form a strong binding structure. Therefore, the click-chemistry reaction has the same advantages as in the following sections 7.3 and 7.4.

The present invention provides a method of preparing an antibody-payload conjugate, characterized in that the method includes reacting an antibody containing a first click-chemistry functional group according to the present invention with a payload according to the present invention, wherein $H_2$ of the payload is a second click-chemistry functional group complementary to the first click-chemistry functional group.

In this case, the antibody provided in the section 5.1 applies to the antibody containing the first click-chemistry functional group, and the payload provided in the section 6 applies to the payload. Because all the antibodies containing a first click-chemistry functional group in the lysine 246 and/or the lysine 248 are disclosed in the section 5.1, it is desirable that the antibody-payload conjugates in which a cargo moiety is conjugated to the lysine 246 and/or the lysine 248 are disclosed to a fully reproducible extent (see Formulas 10 and 10-1 to 10-3 in the section 7).

The present invention provides a kit for preparing an antibody-payload conjugate, characterized in that the kit includes an antibody containing a first click-chemistry functional group according to the present invention; and a payload according to the present invention, wherein $H_2$ of the payload is a second click-chemistry functional group complementary to the first click-chemistry functional group.

In this case, the antibody provided in the section 5.1 applies to the antibody containing the first click-chemistry functional group, and the payload provided in the section 6 applies to the payload.

Optionally, the present invention provides a kit for preparing an antibody-payload conjugate, which includes:

an antibody;

an agent for transferring a first click-chemistry functional group to an antibody according to the present invention;

a payload according to the present invention.

In specific embodiments, the agent for transferring a first click-chemistry functional group to an antibody may be an $H_1$-$L_2$-SSFI for specifically transferring a first click-chemistry functional group to lysine 246 or 248 in an Fc domain of an antibody according to the present invention. In other specific embodiments, the agent for transferring a first click-chemistry functional group to an antibody may be an $H_1$-$L_2$-SSFI for specifically transferring a first click-chemistry functional group to lysine 246 in an Fc domain of an antibody according to the present invention. In still another specific embodiment, the agent for transferring a first click-chemistry functional group to an antibody may be an $H_1$-$L_2$-SSFI for specifically transferring a first click-chemistry functional group to lysine 248 in an Fc domain of an antibody according to the present invention.

Optionally, the present invention provides a kit for preparing an antibody-payload conjugate, which includes:

an antibody;

a linker according to the present invention;

a site-specific antibody interactome according to the present invention; and a payload according to the present invention.

In specific embodiments, $D_2$ in the linker is a $C_y$ alkylene, a $C_y$ alkenylene, or a $C_y$ alkynylene, and $D_3$ in the site-specific antibody interactome is a $C_x$ alkylene, wherein y may be an integer greater than or equal to 1. Also, the sum of x and y may be $1 \le x+y \le 5$. In addition, the sum of x and y may be $6 \le x+y \le 8$. Further, the sum of x and y may be $9 \le x+y \le 12$.

7.3. The antibody-payload conjugate according to the present invention uses a biorthogonal reaction to form a stable bond.

The antibody-payload conjugate according to the present invention is formed through a click-chemistry reaction. The click-chemistry reaction is a biorthogonal reaction that does not influence biochemical phenomena naturally occurring in vivo. Also, a bond formed by the biorthogonal reaction is not recognized by in vivo lyases. Therefore, the antibody-payload conjugate according to the present invention has an advantage in that the antibody and the cargo moiety form a very stable bond in vivo.

7.4. The antibody-payload conjugate prepared according to the present invention has high uniformity and yield.

As described above in the section 5.6, the antibody containing a first click-chemistry functional group according to the present invention has high uniformity and yield. Therefore, the antibody-payload conjugate prepared from the antibody according to the present invention has an advantage in that it also has high uniformity and yield. The uniformity of $C_m$-Ab has to be high in order that the antibody conjugate has uniform performance.

In the case of the antibody conjugates prepared by the prior art disclosed in Publication Nos. US 2018/0141976 A1 and WO 2018/199337 A1, since the antibody conjugates have poor yield and uniformity, as described above in the section 5.6, there may be a negative effect on the uniformity of performance.

7.5. No functions of the antibody are lowered because the antibody-payload conjugate according to the present invention has no FcRn binding site blocked therein.

The $C_m$-Ab according to present invention has the same advantages as described in the sections 5.7 and 5.8. In particular, pharmacokinetic (PK) characteristics of the ADC used in vivo may be greatly improved because the ADC has an increased half-life.

An FcRn binding site of the ADC prepared by the prior art disclosed in Publication No. US 2018/0141976 A1 is blocked because SSFI is included in the final antibody-labeled product. Therefore, the ADC according to the present invention has superior PK characteristics, compared to the ADC according to the corresponding prior art.

7.6. The antibody-drug conjugate according to the present invention is stable because the antibody-drug conjugate does not contain a highly bioreactive chemical functional group.

The $C_m$-Ab according to the present invention has the same advantages as described in the section 5.9. In particular, pharmacodynamic (PD) characteristics of the ADC used in vivo may be greatly improved because the ADC enables a smooth antibody-drug action.

In the case of the ADC prepared by the prior art disclosed in Publication No. WO 2018/199337 A1, an additional chemical functional group such as thiol, hydroxy, a carboxylic acid, phosphoric acid, an amine, and the like are included in the final antibody-labeled product. Therefore, the ADC according to the present invention has superior PD characteristics, compared to the ADC according to the corresponding prior art.

8. Composition

According to the present invention, there is disclosed a composition including an antibody. In this case, the antibody may be an antibody containing a first chemical functional group according to the present invention. Alternatively, the antibody may be an antibody-payload conjugate according to the present invention. Also, the antibody may be an antibody-drug conjugate according to the present invention.

The composition according to the present invention may be used for various applications depending on the function of an antibody included in the composition. For example, when a first chemical functional group or a cargo moiety includes a radioactive moiety, the corresponding composition may be used as a radioactive contrast medium, and the like. Alternatively, when the first chemical functional group or the cargo moiety includes a fluorescent moiety, the corresponding composition may be used as a label used in an enzyme-linked immunosorbent assay (ELISA), and the like. Alternatively, when the first chemical functional group or the cargo moiety includes a drug moiety, the corresponding composition may be used as a pharmaceutical composition. In this case, components of the composition generally used in the related art fall within the scope of the present invention. Also, compositional ratios of the corresponding components generally used in the art also fall within the scope of the present invention.

The present invention provides a composition including an antibody containing a first chemical functional group according to the present invention. In specific embodiments, the antibody containing the first chemical functional group may be at least one selected from Formulas 7, 7-1 to 7-3, 8, and 8-1 to 8-3.

Also, the present invention provides a composition including an antibody containing a first click-chemistry functional group according to the present invention. In specific embodiments, the antibody containing the first click-chemistry functional group may be at least one selected from Formulas 8, and 8-1 to 8-3.

In addition, the present invention provides a composition including an antibody-payload conjugate according to the present invention. In this case, the contents described in the section 7 apply to the contents of the antibody-payload conjugate.

Optionally, the present invention provides a composition including an antibody-drug conjugate according to the present invention. In this case, the contents described in the section 7.1 apply to the contents of the antibody-drug conjugate.

Pharmaceutical Composition

The following content relates to the where the composition is a pharmaceutical composition used for diagnostic, prophylactic and/or therapeutic purposes. Only within the content "pharmaceutical composition" here, all the $R_1$'-Ab, $H_1$-Ab, $C_m$-Ab, and ADC according to the present invention are used interchangeably with the term "antibody or fragment thereof."

The present invention provides a pharmaceutical composition including an antibody or a fragment thereof according to the present invention. Also, the pharmaceutical composition may be a composition for treating cancer. Furthermore, the cancer may include any one selected from bladder cancer, bone cancer, brain cancer, breast cancer, heart cancer, cervical cancer, colon cancer, rectal cancer, esophageal cancer, fibrosarcoma, gastric cancer, stomach cancer, head and neck cancer, Kaposi's sarcoma, renal cancer, leukemia, liver cancer, lung cancer, lymphoma, melanoma, myeloma, ovarian cancer, pancreatic cancer, penile cancer, prostate cancer, testicular germ cell cancer, thymoma, and thymic carcinoma. Further, the cancer may be breast cancer.

The present invention provides a therapeutic method which includes administering a pharmaceutical composition including an antibody or a fragment thereof according to the present invention into a subject. Also, the therapeutic method may be a method of treating cancer. Furthermore, the cancer may include any one selected from bladder cancer, bone cancer, brain cancer, breast cancer, heart cancer, cervical cancer, colon cancer, rectal cancer, esophageal cancer, fibrosarcoma, gastric cancer, stomach cancer, head and neck cancer, Kaposi's sarcoma, renal cancer, leukemia, liver cancer, lung cancer, lymphoma, melanoma, myeloma, ovarian cancer, pancreatic cancer, penile cancer, prostate cancer, testicular germ cell cancer, thymoma, and thymic carcinoma. Further, the cancer may be breast cancer.

To prepare a pharmaceutical or sterilized composition including an antibody or a fragment thereof, the antibody or fragment thereof according to the present invention may be mixed with a pharmaceutically acceptable carrier or excipient. The composition may further include one or more other therapeutic agents which are suitable for treating or preventing cancer (e.g., breast cancer, colorectal cancer, lung cancer, multiple myeloma, ovarian cancer, liver cancer, gastric cancer, pancreatic cancer, acute myelogenous leukemia, chronic myelogenous leukemia, osteosarcoma, squamous cell carcinoma, peripheral nerve sheath tumors, schwannoma, head and neck cancer, bladder cancer, esophageal cancer, Barrett's esophageal cancer, glioblastoma, clear cell sarcoma of soft tissue, malignant mesothelioma, neurofibromatosis, kidney cancer, melanoma, prostate cancer, benign prostate hypertrophy (BPH), gynecomastia, rhabdomyosarcoma, and endometriosis).

A formulation of therapeutic and diagnostic agents may be prepared by mixing with a physiologically acceptable carrier, an excipient, or a stabilizing agent, for example, in the form of a freeze-dried powder, slurry, an aqueous solution, a lotion, or a suspension (see, for example, Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N. Y., 2000; Avis, et al. (eds.), Pharmaceutical Dosage Forms: Parenteral Medications, Marcel Dekker, NY, 1993; Lieberman, et al. (eds.), Pharmaceutical Dosage Forms: Tablets, Marcel Dekker, NY, 1990; Lieberman, et al. (eds.) Pharmaceutical Dosage Forms: Disperse Systems, Marcel Dekker, NY, 1990; Weiner and Kotkoskie, Excipient Toxicity and Safety, Marcel Dekker, Inc., New York, N.Y., 2000).

In specific embodiments, the clinical service form (CSF) of the antibody-drug conjugate according to the present invention is a lyophilisate present in a vial containing ADC, sodium succinate, and polysorbate 20. The lyophilisate may be reconstituted with water for injection, and the solution includes ADC, sodium succinate, sucrose and polysorbate 20 at approximately pH 5.0. For sequential intravenous administration, the resulting solution will be usually further diluted into a carrier solution.

The choice of a therapeutic dosing regimen depends on various factors including a rate of serum or tissue replacement of a substance, a level of symptoms, the immunogenicity of the substance, and the accessibility of target cells in a biological matrix. In specific embodiments, the dosing regimens maximize an amount of a therapeutic agent to be delivered to a patient so as to satisfy acceptable levels of side effects. Therefore, an amount of a biological agent to be administered depends in part on the certain substance and the severity of the condition being treated. Guidance is available for selection of the appropriate doses of antibodies, cytokines, and small molecules (see, for example, Wawrzynczak, Antibody Therapy, Bios Scientific Pub. Ltd, Oxfordshire, U K, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

The appropriate dose is, for example, determined by a clinical practitioner using parameters or factors known in the related art or suspected to affect treatment, or using parameters or factors expected to affect treatment. In general, the dose begins with an amount somewhat smaller than the optimal dose and then increases in small increments until the desirable or optimal effects are achieved relative to any negative side effects. Important diagnostic measures, for example, include symptoms of inflammation or levels of inflammatory cytokines produced.

An actual dose level of the active ingredient in the pharmaceutical composition according to the present invention may vary in order to achieve an effective amount of the active ingredient to realize desired therapeutic responses in a certain patient, a composition, and a mode of administration without causing any toxicity in patients. The chosen dose level may be determined depending on various pharmacokinetic factors including the activities of a certain composition of the present invention used, or esters, salts or amides thereof, a route of administration, an administration time, a secretion rate of a certain compound used, a duration of treatment, other drugs, compounds and/or substances used in combination with the certain compound used, the age, sex, weight, condition, overall health, and previous medical history of a patient to be treated, and other factors known in the medical field.

The composition including an antibody or a fragment thereof according to the present invention may be given by continuous infusion, or given in a single dose, for example, daily, weekly, 1 to 7 times per week, bi-weekly, once every three weeks, once every four weeks, once every five weeks, once every six weeks, once every seven weeks, or once every eight weeks. The dose may be given intravenously, subcutaneously, topically, orally, intranasally, intrarectally, intramuscularly, intracerebrally, or by inhalation. A certain dosing protocol involves the maximum dose or administration frequency that avoids significant unwanted side effects.

For the antibody or fragment thereof according to the present invention, the dose to be administered to a patient may be in a range of 0.0001 mg/kg to 100 mg/kg (patient weight). The dose may be in a range of 0.0001 mg/kg to 20 mg/kg, 0.0001 mg/kg to 10 mg/kg, 0.0001 mg/kg to 5 mg/kg, 0.0001 to 2 mg/kg, 0.0001 to 1 mg/kg, 0.0001 mg/kg to 0.75 mg/kg, 0.0001 mg/kg to 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg, or 0.01 to 0.10 mg/kg (patient weight). The dose of the antibody or fragment thereof according to the present invention may be calculated by multiplying the weight (kilogram (kg)) of a patient by the dose (mg/kg) to be administered.

The antibody or fragment thereof according to the present invention may be repeatedly administered, and the administration may be performed at intervals of at least a day, two days, three days, five days, 10 days, 15 days, 30 days, 45 days, 2 months, 75 days, 3 months, or at least 6 months. In specific embodiments, the antibody or fragment thereof according to the present invention may be repeatedly administered every three weeks.

An effective amount to be administered to a certain patient may vary depending on factors such as the condition to be treated, the overall health of a patient, the mode, route and dosage of administration, and the severity of side effects (see, for example, Maynard et al., A Handbook of SOPs for Good Clinical Practice, Interpharm Press, Boca Raton, Fla., 1996; Dent, Good Laboratory and Good Clinical Practice, Urch Publ., London, U K, 2001).

The route of administration may be, for example, by topical or skin application, by intravenous, intraperitoneal, intracerebral, intramuscular, intraocular, intra-arterial, intramedullary, intralesional injection or infusion, or by a sustained release system or an implant (see, for example, Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). When necessary, the composition may also include a solubilizing agent and a topical anesthetic (for example, lidocaine) for relieving pain at a site of injection. For example, the composition may also be formulated using an inhaler or a nebulizer, or may be used for pulmonary administration by formulation using an aerosolizing agent. See, for example, U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, the entire contents of which are hereby incorporated by reference.

Also, the composition of the present invention may be administered through one or more routes of administration using one or more various methods known in the related art. As recognized by a person of ordinary skill in the art, the route and/or mode of administration will depend on the desired results. The route of administration selected for the antibody or fragment thereof according to the present invention includes intravenous, intramuscular, intradermal, intraperitoneal, subcutaneous, intraspinal, or other parenteral routes of administration, for example, routes of administration by injection or infusion. Parenteral administration generally represents a mode of administration by injection other than the enteral and topical administration, and includes intravenous, intramuscular, intra-arterial, intrathecal, intracapsular, intraorbital, intracardial, intradermal, intraperitoneal, transtracheal, subcutaneous, subepidermal, intra-articular, subcapsular, subarachnoid, intraspinal, epidural, and intrasternal injections and infusions, but the present invention is not limited thereto. Alternatively, the composition of the present invention may be administered through a non-parenteral route of administration, for example, a topical, intraepidermal or intramucosal route of administration, and may be, for example, administered intranasally, orally, vaginally, intrarectally, sublingually, or topically. In one exemplary embodiment, the antibody or fragment thereof according to the present invention may be administered by infusion. In another exemplary embodiment, the antibody or fragment thereof according to the present invention may be subcutaneously administered.

When the antibody or fragment thereof according to the present invention is administered using a controlled or delayed release system, a pump may be used to achieve the controlled or delayed release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). A polymeric material may be used to achieve the controlled or delayed release in the therapy of the present invention (see, for example, Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; also see Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253). Examples of polymers used for a sustained release formulation include poly(2-hydroxyethyl methacrylate), poly(methyl methacrylate), poly(acrylic acid), poly(ethylene-co-vinyl acetate), poly(methacrylic acid), polyglycolide (PLG), a polyanhydride, poly(N-vinyl pyrrolidone), poly(vinyl alcohol), polyacrylamide, poly(ethylene glycol), polylactide (PLA), poly (lactide-co-glycolide) (PLGA), and a polyorthoester, but the present invention is not limited thereto. In one exemplary embodiment, the polymer used for a sustained release formulation is inert, has no filterable impurities, and is stable upon storage, sterilization, and biodegradability. The controlled or delayed release system may be located adjacent to a prophylactic or therapeutic target, and thus requires a portion of the systemic dose (see, for example, Goodson, in Medical Applications of Controlled Release, supra, vol. 2, pp. 115-138, 1984).

The controlled release system is discussed in the review of the article "Langer, Science 249:1527-1533, 1990." Any prior art known to a person of ordinary skill in the art may be used to produce a sustained release formulation including one or more antibodies or a fragments thereof according to the present invention. See, for example, U.S. Pat. No. 4,526,938, PCT Publication No. WO 91/05548, PCT Publication No. WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, the entire contents of which are hereby incorporated by reference.

When the antibody or fragment thereof according to the present invention is topically administered, the antibody or fragment thereof may be formulated into forms of an ointment, a cream, a transdermal patch, a lotion, a gel, a shampoo, a spray, an aerosol, a solution, or an emulsion, or other forms well known to a person of ordinary skill in the art. See, for example, Remington's Pharmaceutical Sciences and Introduction to Pharmaceutical Dosage Forms, 19th ed., Mack Pub. Co., Easton, Pa. (1995). A non-sprayable topical dosage form includes a carrier or one or more excipients suitable for topical application. In some cases, viscous, semisolid, or solid forms having a higher kinematic viscosity than water may be generally used as the topical dosage form. Suitable preparations include a solution, a suspension, an emulsion, a cream, an ointment, a powder, a liniment, a salve, and the like, all of which are sterilized, or mixed with an adjuvant (for example, a preservative, a stabilizing agent, a wetting agent, a buffer, or a salt) influencing various characteristics, for example, such as osmotic pressure, when necessary, but the present invention is not limited thereto. In some cases, other suitable topical dosage forms include a sprayable aerosol formulation filled in a mixture of compressed volatile substances (for example, a gaseous propellant such as freon) or a squeeze bottle after the active ingredient is combined with a solid or liquid inert carrier. When necessary, a moisturizing agent or a humectant may be also added to the pharmaceutical composition and the dosage form. Examples of such an additional component are known in the related art.

When the composition including an antibody or a fragment thereof is intranasally administered, the composition may be formulated into forms of an aerosol, a spray, mist, or drops. In particular, a prophylactic or therapeutic agent for use in the present invention may be conveniently delivered in an aerosol spray dosage form from a pressurized pack or an atomizer using a suitable propellant (for example, dichlorodifluoromethane, trichlorofluoromethane, dichlorotetrafluoroethane, carbon dioxide, or other suitable gases). In the case of the pressurized aerosol, the dosage unit may be determined by providing a valve to deliver a metered amount. A capsule and cartridge (for example, consisting of gelatin) for use in an inhaler or an insufflator may be formulated to include a powder mixture of compounds, and a suitable powder base, for example, lactose or starch.

Methods for co-administration or treatment with a second therapeutic agent, for example, a cytokine, a steroid, a chemotherapeutic agent, an antibiotic, or radiation are known in the related art (see, for example, Hardman et al., (eds.) (2001) Goodman and Gilman's The Pharmacological Basis of Therapeutics, $10^{th}$ ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of the therapeutic agent may reduce symptoms by at least 10%; at least 20%; at least approximately 30%; at least 40%, or at least 50%.

An additional therapy (for example, a prophylactic or therapeutic agent) that may be administered in combination with the antibody or fragment thereof according to the present invention may be administered together with the antibody or fragment thereof according to the present invention at intervals of less than 5 minutes, intervals of less than 30 minutes, intervals of an hour, intervals of approximately an hour, intervals of approximately 1 to approximately 2 hours, intervals of approximately 2 hours to approximately 3 hours, intervals of approximately 3 hours to approximately 4 hours, intervals of approximately 4 hours to approximately 5 hours, intervals of approximately 5 hours to approximately 6 hours, intervals of approximately 6 hours to approximately 7 hours, intervals of approximately 7 hours to approximately 8 hours, intervals of approximately 8 hours to approximately 9 hours, intervals of approximately 9 hours to approximately 10 hours, intervals of approximately 10 hours to approximately 11 hour, intervals of approximately 11 hour to approximately 12 hours, intervals of approximately 12 hours to 18 hours, intervals of 18 hours to 24 hours, intervals of 24 hours to 36 hours, intervals of 36 hours to 48 hours, intervals of 48 hours to 52 hours, intervals of 52 hours to 60 hours, intervals of 60 hours to 72 hours, intervals of 72 hours to 84 hours, intervals of 84 hours to 96 hours, or intervals of 96 hours to 120 hours. Two or more therapeutic agents may be administered during the same visit by a patient.

In specific embodiments, the antibody or fragment thereof according to the present invention may be formulated to insure a proper distribution in vivo. For example, the blood-brain barrier (BBB) excludes a number of highly hydrophilic compounds. To ensure therapeutic compounds of the invention cross the BBB (when necessary), they can be, for example, formulated in liposomes. For a method of preparing liposomes, for example, see U.S. Pat. Nos. 4,522,811; 5,374,548; and 5,399,331. The liposomes may include one or more moieties that are selectively transported into specific cells or organs, thereby enhancing targeted drug delivery (see, for example, Ranade, (1989) J. Clin. Pharmacol. 29:685). Exemplary targeting moieties include folate or biotin (see, for example, U.S. Pat. No. 5,416,016 (to Low et al.)); mannosides (see Umezawa et al., (1988) Biochem. Biophys. Res. Commun. 153:1038); antibodies (see Bloeman et al., (1995) FEBS Lett. 357:140; Owais et al., (1995) Antimicrob. Agents Chemother. 39:180); a surfactant protein A receptor (see Briscoe et al., (1995) Am. J. Physiol. 1233:134); p 120 (see Schreier et al., (1994) J. Biol. Chem. 269:9090), and the like. Also, see K. Keinanen; M. L. Laukkanen (1994) FEBS Lett. 346:123; J. J. Killion; I. J. Fidler (1994) Immunomethods 4:273.

The present invention provides a protocol for administering a pharmaceutical composition, which includes the antibody or fragment thereof according to the present invention, to a subject in need thereof alone or in combination with other therapies. The therapeutic agent (for example, a prophylactic or therapeutic agent) for combination therapy of the present invention may be simultaneously or sequentially administered to the subject. The therapeutic agent (for example, a prophylactic or therapeutic agent) for combination therapy of the present invention may also be administered periodically. A periodic therapy includes administering a first therapeutic agent (for example, a first prophylactic or therapeutic agent) for a predetermined period of time, administering a second therapeutic agent (for example, a second prophylactic or therapeutic agent) for a predetermined period of time, and then sequentially repeating the steps of administration, that is, a predetermined cycle for reducing the occurrence of resistance to one of the therapeutic agents (for example, agonists), and/or preventing or reducing side effects of one of the therapeutic agents (for example, agonists), and/or improving efficacy of the therapeutic agents.

The therapeutic agent (for example, a prophylactic or therapeutic agent) for combination therapy of the present invention may be simultaneously administered to a subject.

The term "simultaneously" means that therapies (for example, prophylactic or therapeutic agents) need not be administered at exactly the same time without limitation, but are rather administered to a subject sequentially with the pharmaceutical composition including an antibody or a fragment thereof according to the present invention, and are administered at time intervals that may serve to provide higher benefits compared to when the antibody of the present invention is administered at a different time from other therapy(ies). For example, the respective therapeutic agents may be sequentially administered to a subject at the same time or different points of time in any order; but should be administered at sufficiently short time intervals to provide a desire therapeutic or prophylactic effect when they are not administered at the same time. The respective therapeutic agents may be administered to a subject in any adequate form through any suitable route of administration. In various exemplary embodiments, the therapeutic agent (for example, a prophylactic or therapeutic agent) may be administered to a subject at intervals of less than 15 minutes, intervals of less than 30 minutes, intervals of less than an hour, intervals of approximately an hour, intervals of approximately 1 to approximately 2 hours, intervals of approximately 2 hours to approximately 3 hours, intervals of approximately 3 hours to approximately 4 hours, intervals of approximately 4 hours to approximately 5 hours, intervals of approximately 5 hours to approximately 6 hours, intervals of approximately 6 hours to approximately 7 hours, intervals of approximately 7 hours to approximately 8 hours, intervals of approximately 8 hours to approximately 9 hours, intervals of approximately 9 hours to approximately 10 hours, intervals of approximately 10 hours to approximately 11 hour, intervals of approximately 11 hour to approximately 12 hours, intervals of 24 hours, 48 hours, 72 hours, or intervals of a week. In other exemplary embodiments, two or more therapeutic agents (for example, prophylactic or therapeutic agents) may be administered during the same visit by a patient.

In the same pharmaceutical composition, the prophylactic or therapeutic agent for combination therapy may be administered to a subject. Alternatively, in the individual pharmaceutical compositions, the prophylactic or therapeutic agent for combination therapy may be simultaneously administered to a subject. The prophylactic or therapeutic agent may be administered to a subject through the same or different routes of administration.

Experimental Examples

1. Preparation Examples of Compounds for Preparing an Agent for Transferring a Site-Specific First Click-Chemistry Functional Group to an Antibody 1.1. Synthesis and Confirmation of Structure of Linker ($H_1$-$L_1$)

1.1.1.: Compound I (SO1 Linker: NHS & Norbornene)

[Scheme 6]

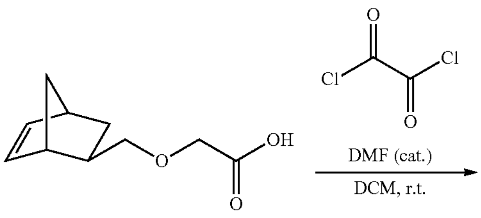

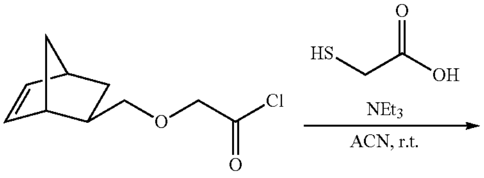

1

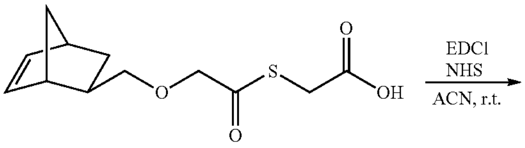

2

-continued

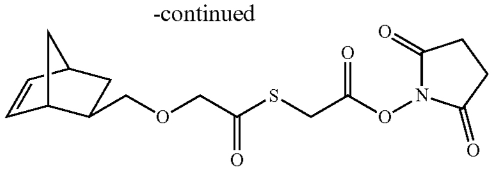

I

Figure 15:
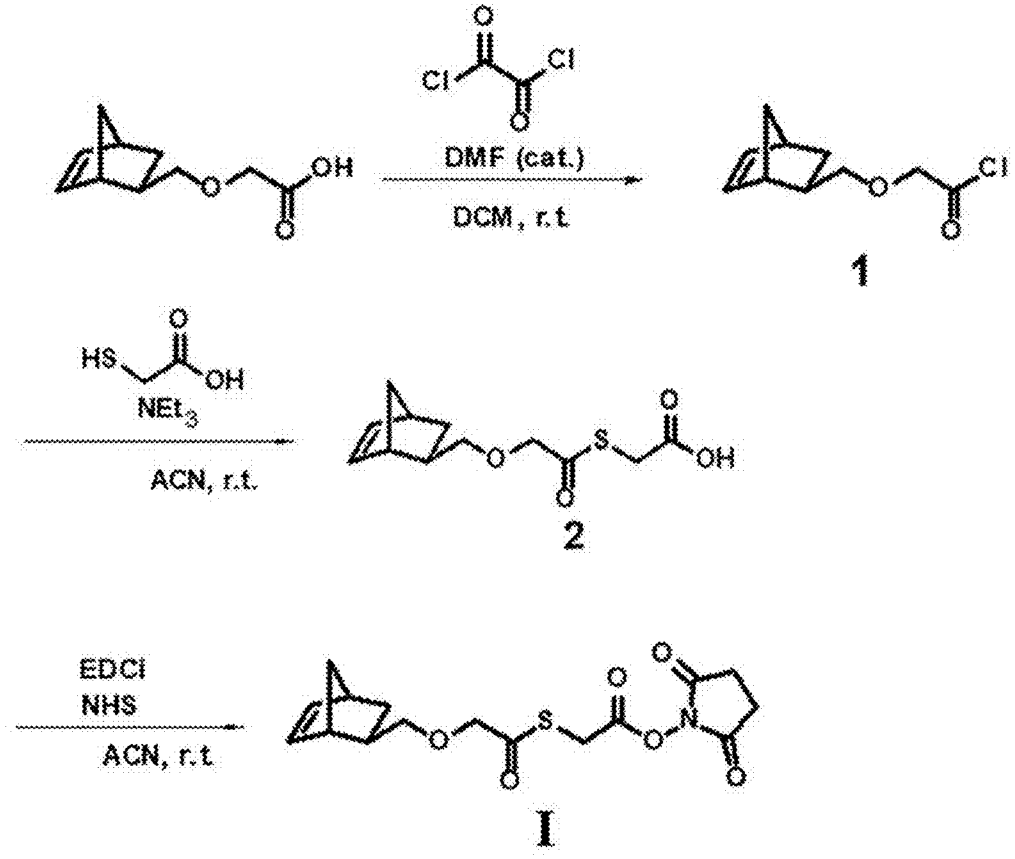
FIG. 15 shows a method of synthesizing Compound I.

Synthesis of Compound I (Scheme 6, FIG. 15)

Synthesis of Compound 1

2 g (10.98 mmol, 1.0 eq.) of 2-(bicyclo[2.2.1]hept-5-ene-2-ylmethoxy) acetic acid was dissolved in 50 mL of DCM, and 0.085 mL (1.098 mmol, 0.1 eq.) of DMF and 1.91 mL (21.96 mmol, 2.0 eq.) of oxalyl chloride were then added dropwise while stirring at room temperature. The reaction solution was stirred for 3 hours, and then concentrated under reduced pressure to obtain 1.97 g of a target compound (yield: 90%).

Synthesis of Compound 2

1.97 g (9.88 mmol, 1.0 eq.) of Compound 1 was dissolved in 20 mL of acetonitrile (ACN), and 0.68 mL (9.88 mmol, 1.0 eq.) of thioglycolic acid and 2.06 mL (14.82 mmol, 1.5 eq.) of triethylamine were then added dropwise while stirring at room temperature. The reaction solution was stirred for 18 hours, and then concentrated under reduced pressure. Subsequently, water was added to the reaction solution, and the reaction solution was extracted three times with ethyl acetate (EA). An organic layer was dried over magnesium sulfate, concentrated under reduced pressure, and then purified by column chromatography (DCM:MeOH=10:1) to obtain 2.05 g (yield: 79%) of a target compound.

$^1$H NMR (500 MHZ, $CDCl_3$) δ $^1$H NMR (500 MHZ, $CDCl_3$) δ 6.15-6.01 (m, 2H), 4.20 (t, J=5.0 Hz, 1H), 3.77-3.71 (m, 2H), 3.68-3.57 (m, 1H), 3.56-3.45 (m, 1H), 2.84 (s, 2H), 1.81-1.69 (m, 2H), 1.30 (ddd, J=19.8, 14.5, 8.6 Hz, 4H), 1.15 (ddd, J=16.0, 7.6, 3.3 Hz, 1H).

Synthesis of Compound I 2.05 g (7.81 mmol, 1.0 eq.) of Compound 2 was dissolved in 50 mL of ACN, and 2.76 g (14.44 mmol, 1.8 eq.) of 1-ethyl-3-(3-dimethylaminopropyl) carbodiimide (EDCi) and 2.21 g (19.25 mmol, 2.46 eq.) of N-hydroxysuccinimide (NHS) were then added while stirring at room temperature. The reaction solution was stirred for 18 hours, and then concentrated under reduced pressure. Subsequently, water was added to the reaction solution, and the reaction solution was extracted three times with EA. An organic layer was recovered, dried over magnesium sulfate, and then concentrated under reduced pressure. Then, the residue was purified on a silica gel column using chromatography (EA:Hex=2:1) to obtain 2.7 g (yield: 98%) of a target compound.

$^1$H NMR (500 MHZ, $CDCl_3$) δ 6.15-6.03 (m, 2H), 4.45 (s, 1H), 4.21 (d, J=5.0 Hz, 1H), 3.97 (s, 1H), 3.65 (dd, J=12.0, 7.3 Hz, 1H), 3.52 (t, J=8.9 Hz, 1H), 2.83 (dd, J=24.4, 11.8 Hz, 6H), 1.81-1.67 (m, 1H), 1.30 (dq, J=27.0, 9.5 Hz, 4H), 1.16 (ddd, J=15.3, 7.4, 3.8 Hz, 1H).

Confirmation of Structure of Compound I $^1$H NMR (500 MHZ, $CDCl_3$) δ 6.15-6.03 (m, 2H), 4.45 (s, 1H), 4.21 (d, J=5.0 Hz, 1H), 3.97 (s, 1H), 3.65 (dd, J=12.0, 7.3 Hz, 1H), 3.52 (t, J=8.9 Hz, 1H), 2.83 (dd, J=24.4, 11.8 Hz, 6H), 1.81-1.67 (m, 1H), 1.30 (dq, J=27.0, 9.5 Hz, 4H), 1.16 (ddd, J=15.3, 7.4, 3.8 Hz, 1H).

LRMS (ESI): m/z 371.2 [$M+NH_4^+$]

Figure 16:
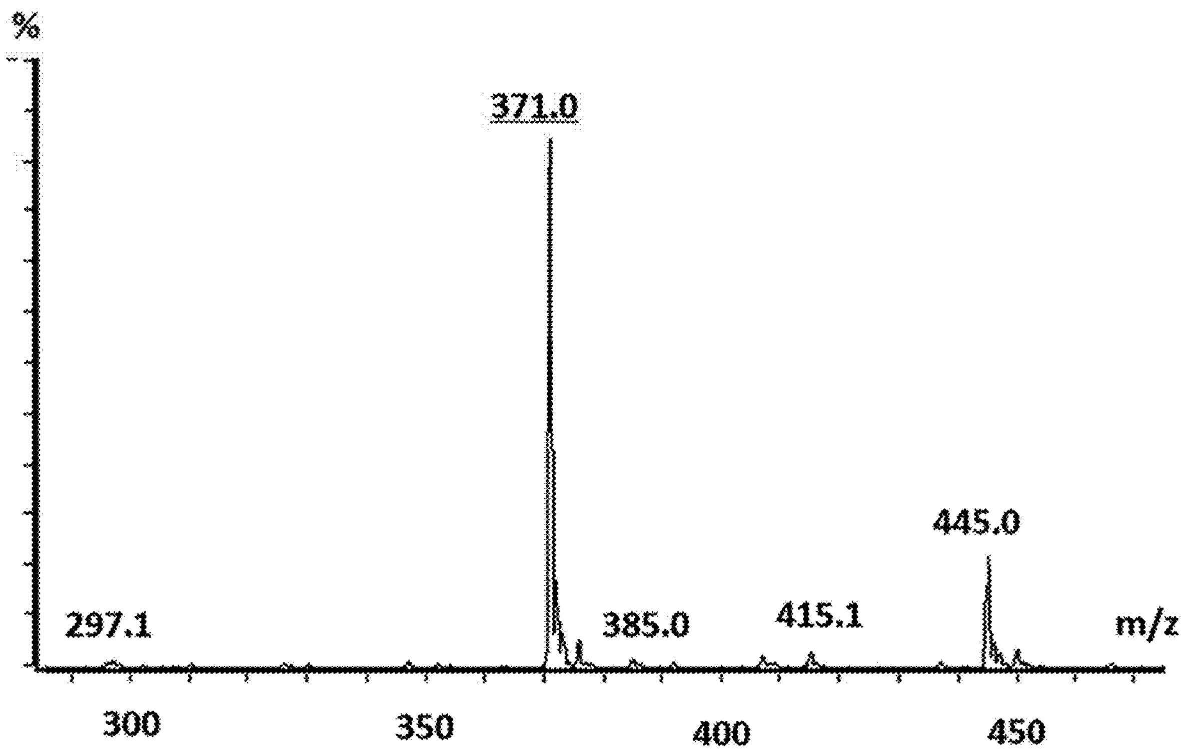
FIG. 16 shows the results of confirming a structure of Compound I by means of mass spectrometry.

The structure of Compound I was confirmed by mass spectrometry. The results are shown in FIG. 16.

1.1.2. Compound II (SO2 Linker: NHS & Norbornene)

[Scheme 7]

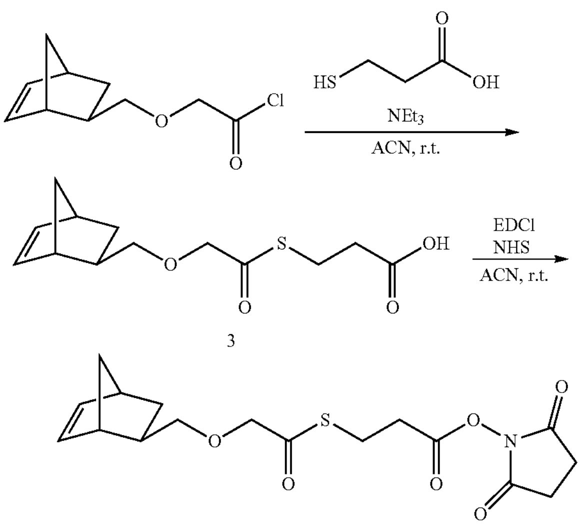

II

Figure 17:
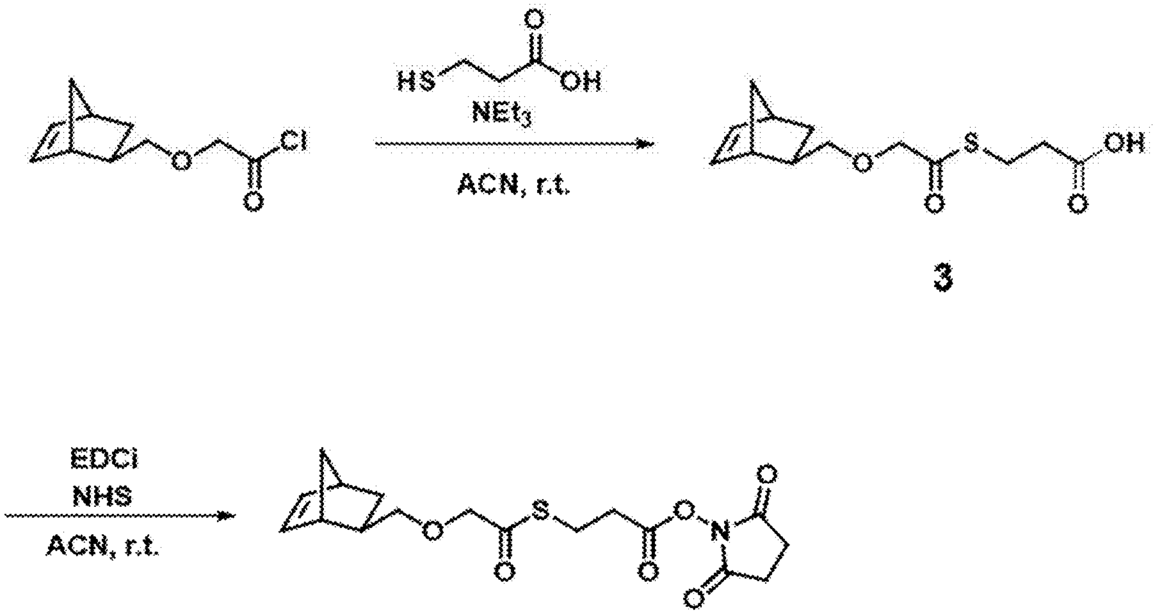
FIG. 17 shows a method of synthesizing Compound II.

Synthesis of Compound II (Scheme 7, FIG. 17)

Synthesis of Compound 3

0.55 g (2.33 mmol, 1.0 eq.) of Compound 1 was dissolved in 5 mL of acetonitrile (ACN), and 0.2 mL (2.33 mmol, 1.0 eq.) of 3-mercaptopropionic acid and 0.49 mL (3.49 mmol, 1.5 eq.) of triethylamine were then added dropwise while stirring at room temperature. The reaction solution was stirred for 11 hours, and then concentrated under reduced pressure. Subsequently, water was added to the reaction solution, and the reaction solution was extracted three times with ethyl acetate (EA). An organic layer was dried over magnesium sulfate, concentrated under reduced pressure, and then purified by silica gel column chromatography (DCM:MeOH=10:1) to obtain 0.56 g (yield: 89%) of a target compound.

Synthesis of Compound II 0.56 g (2.07 mmol, 1.0 eq.) of Compound 3 was dissolved in 10 mL of acetonitrile (ACN), and 0.81 g (4.21 mmol, 2.0 eq.) of 1-ethyl-3-(3-dimethylaminopropyl) carbodiimide (EDCi) and 0.65 g (5.61 mmol, 2.7 eq.) of N-hydroxysuccinimide (NHS) were added while stirring at room temperature. The reaction solution was stirred for 12 hours, and then concentrated under reduced pressure. Subsequently, water was added to the reaction solution, and the reaction solution was extracted three times with EA. An organic layer was dried over magnesium sulfate, and concentrated under reduced pressure. Then, the residue was purified by silica gel column chromatography (EA:Hex=2:1) to obtain 0.63 g (yield: 83%) of a target compound.

Confirmation of Structure of Compound II $^1$H NMR (500 MHZ, $CDCl_3$) δ 6.16-6.14 (m, 2H), 4.45 (s, 1H), 4.21-4.08 (m, 1H), 3.69-3.58 (m, 1H), 3.51 (dt, J=14.5, 8.9 Hz, 1H), 3.22 (t, J=7.1 Hz, 2H), 2.96 (t, J=7.1 Hz, 2H), 2.79-2.83 (m, 6H), 1.81-1.67 (m, 1H), 1.37-1.21 (m, 4H), 1.13-1.18 (m, 1H).

LRMS (ESI): m/z 385.1 [$M+NH_{4+}$]

Figure 18:
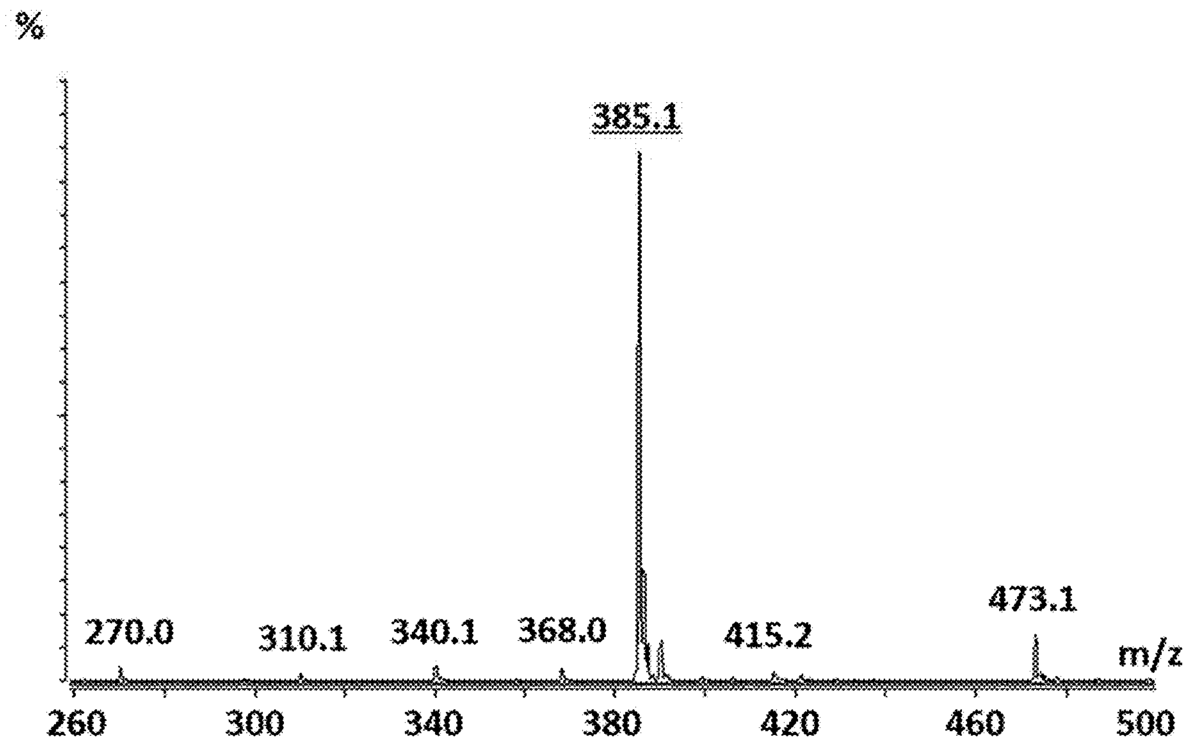
FIG. 18 shows the results of confirming a structure of Compound II by means of mass spectrometry.

The structure of Compound II was confirmed by mass spectrometry. The results are shown in FIG. 18.

1.1.3. Compound III (SO3 Linker: NHS & Norbornene)

[Scheme 8]

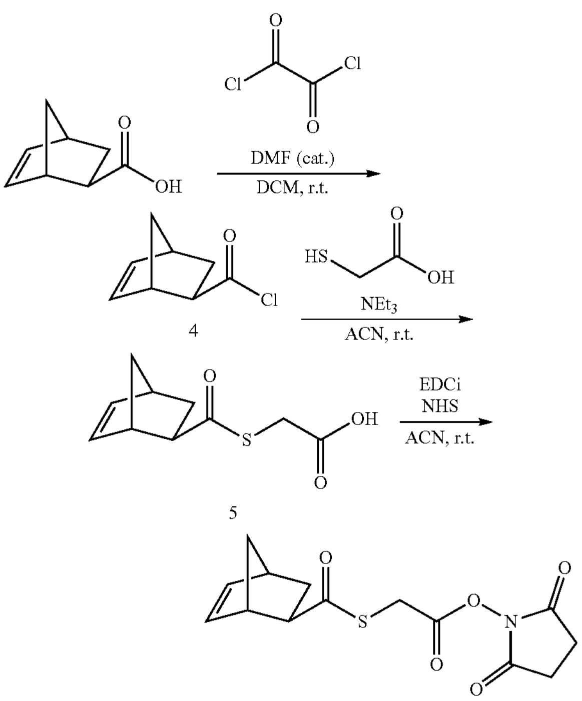

III

Figure 19:
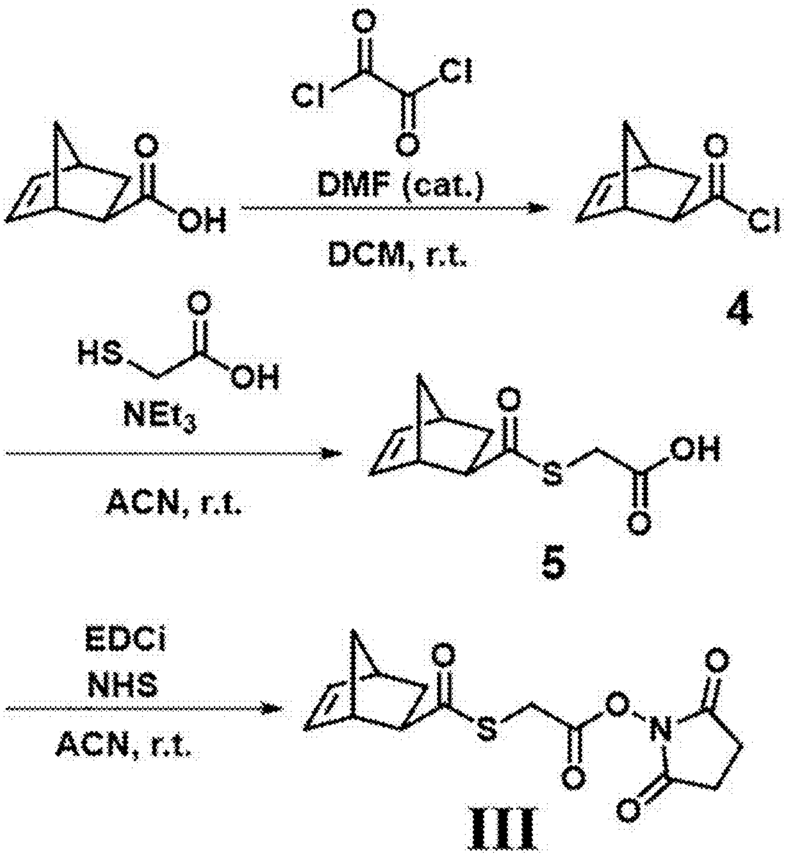
FIG. 19 shows a method of synthesizing Compound III.

Synthesis of Compound III (Scheme 8, FIG. 19)

Synthesis of Compound 4

0.5 g (3.62 mmol, 1.0 eq.) of exo-5-norbornenecarboxylic acid was dissolved in 20 mL of DCM, and 0.028 mL (0.37 mmol, 0.94 eq.) of DMF and 0.63 mL (7.24 mmol, 2.0 eq.) of oxalyl chloride were then added dropwise while stirring at room temperature. The reaction solution was stirred for 3 hours, and then concentrated under reduced pressure to obtain 0.47 g (yield: 83%) of a target compound.

Synthesis of Compound 5

0.47 g (3.0 mmol, 1.0 eq.) of Compound 4 was dissolved in 15 mL of acetonitrile (ACN), and 0.21 mL (3.0 mmol, 1.0 eq.) of thioglycolic acid and 0.63 mL (4.5 mmol, 1.5 eq.) of triethylamine were then added dropwise while stirring at room temperature. The reaction solution was stirred for 18 hours, and then concentrated under reduced pressure. Subsequently, water was added to the reaction solution, and the reaction solution was extracted three times with ethyl acetate (EA). An organic layer was dried over magnesium sulfate, concentrated under reduced pressure, and then purified by column chromatography (DCM:MeOH=10:1) to obtain 0.3 g (yield: 47%) of a target compound.

$^1$H NMR (500 MHZ, $CDCl_3$) δ 9.82 (brs, 1H), 6.24-6.07 (m, 2H), 3.76 (s, 2H), 3.12 (s, 1H), 2.97 (s, 1H), 2.54 (dd, J=9.0, 4.7 Hz, 1H), 2.04-1.87 (m, 1H), 1.57 (d, J=8.5 Hz, 1H), 1.48-1.35 (m, 2H).

Synthesis of Compound III 0.26 g (1.22 mmol, 1.0 eq.) of Compound 5 was dissolved in 15 mL of acetonitrile (ACN), and 0.35 g (1.83 mmol, 1.5 eq.) of 1-ethyl-3-(3-dimethylaminopropyl) carbodiimide (EDCi) and 0.28 g (2.44 mmol, 2.0 eq.) of N-hydroxysuccinimide (NHS) were added while stirring at room temperature. The reaction solution was stirred for 3 hours, and then concentrated under reduced pressure. Subsequently, water was added to the reaction solution, and the reaction solution was extracted three times with EA. An organic layer was recovered, dried over magnesium sulfate, and then concentrated under reduced pressure. Then, the residue was purified on a silica gel column using chromatography (EA:Hex=2:1) to obtain 0.32 g (yield: 85%) of a target compound.

Confirmation of Structure of Compound III $^1$H NMR (500 MHZ, $CDCl_3$) δ 6.21 (dd, J=5.5, 3.0 Hz, 1H), 6.15 (dd, J=5.5, 3.1 Hz, 1H), 4.01 (s, 2H), 3.15 (s, 1H), 2.98 (s, 1H), 2.86 (s, 4H), 2.54 (dd, J=9.2, 4.6 Hz, 1H), 2.02 (dt, J=11.9, 4.0 Hz, 1H), 1.59 (d, J=8.6 Hz, 1H), 1.46-1.36 (m, 2H).

LCMS (ESI): m/z 332.16 [$M+Na^+$]

Figure 20:
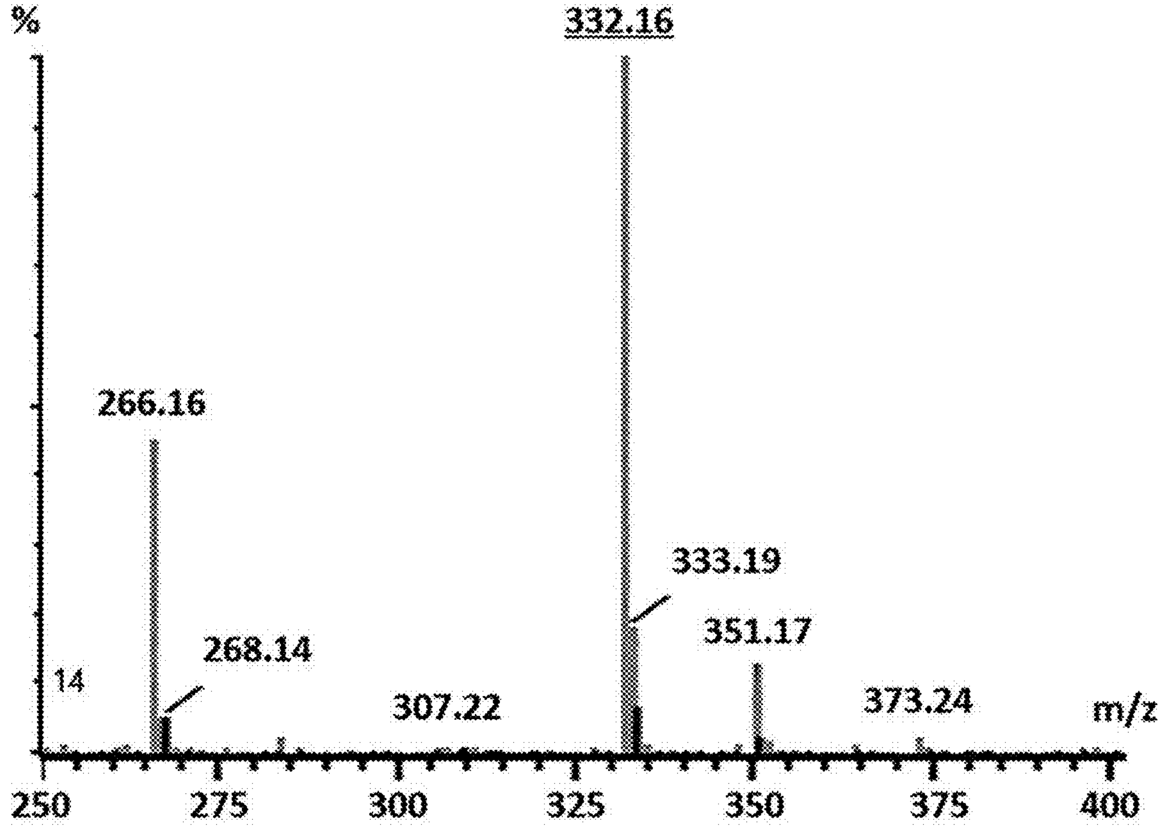
FIG. 20 shows the results of confirming a structure of Compound III by means of mass spectrometry.

The structure of Compound III was confirmed by mass spectrometry. The results are shown in FIG. 20.

1.1.4. Compound IV (SO4 Linker: NHS & Azide)

[Scheme 9]

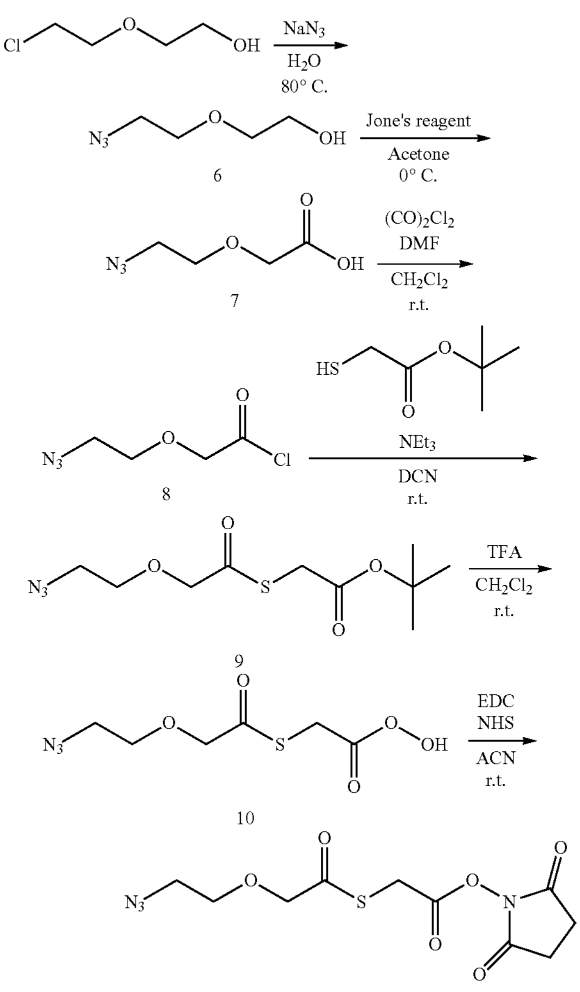

IV

Figure 21:
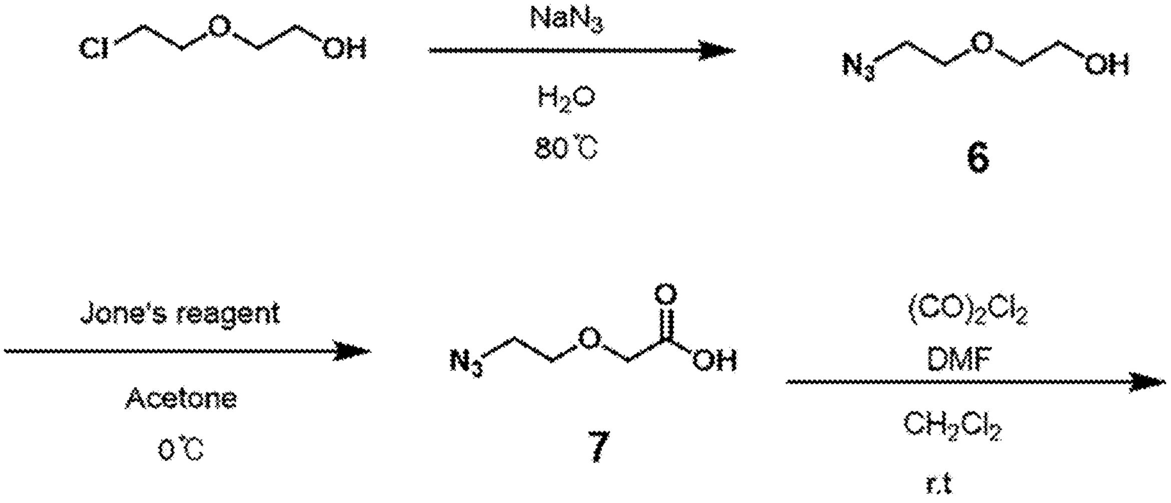
FIG. 21 and FIG. 22 show a method of synthesizing Compound IV.
Figure 22:
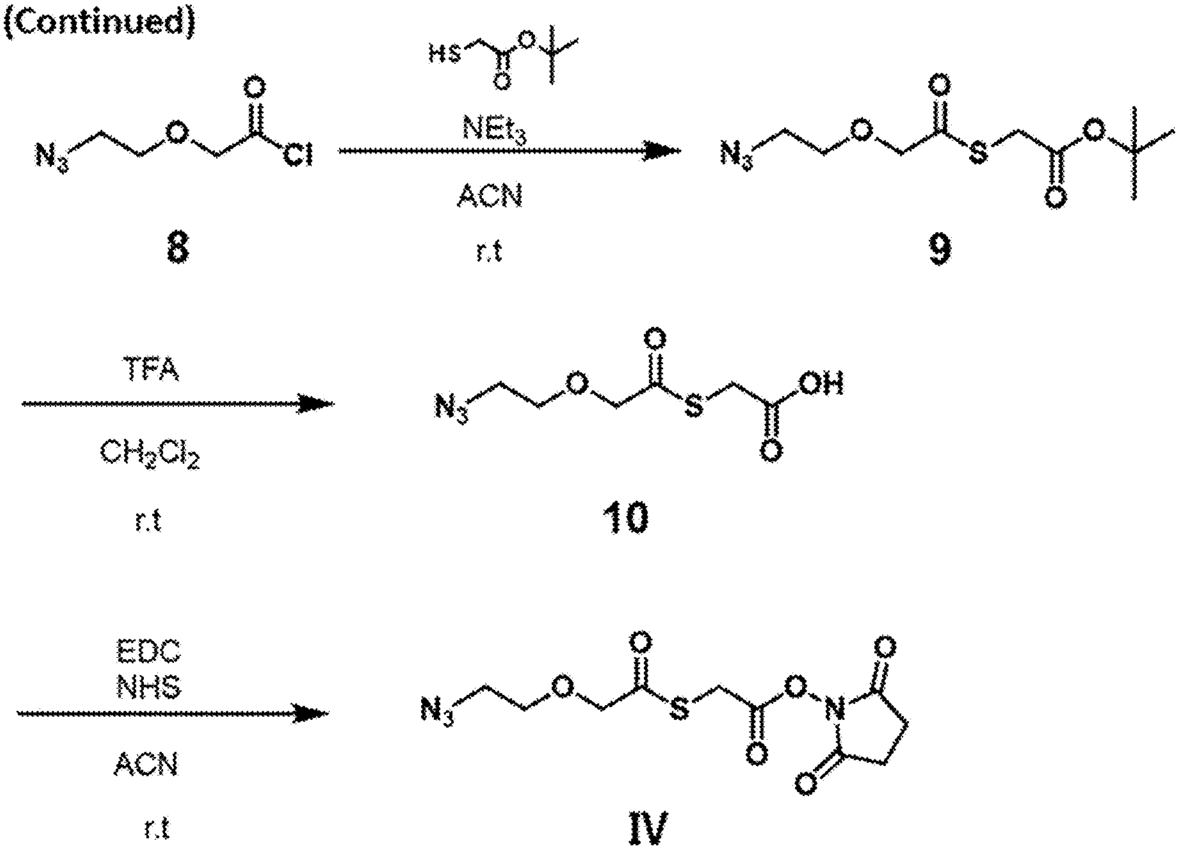

Synthesis of Compound IV (Scheme 9, FIGS. 21 and 22)

Synthesis of Compound 6

2-(2-Chloroethoxy) ethanol (2 mL, 18.94 mmol) was dissolved in distilled water (12 mL), and $NaN_3$ (3.08 g, 47.35 mmol, 2.5 eq.) was added thereto. The resulting mixture was stirred at 80° C. for 16 hours. The reaction mixture was cooled to room temperature, and poured into 5% NaOH (aq.) (20 mL), and then stirred for approximately 10 minutes. The reaction mixture was extracted three times with diethyl ether, and an organic layer was dried over magnesium sulfate, and filtered. The filtrate was concentrated under reduced pressure to obtain 2.47 g (yield: 99%) of a target compound.

Synthesis of Compound 7

2.47 g (18.84 mmol) of Compound 6 was dissolved in acetone (50 mL), and a 1 M Jone's reagent (75.36 mL, 75.36 mmol, 4 eq.) was then slowly added at 0° C. The reaction mixture was stirred at 0° C. for 3 hours, warmed to room temperature, and then stirred for approximately 10 minutes. The reaction mixture was extracted three times with ethyl acetate (EA), and an organic layer was dried over magnesium sulfate, and filtered. The filtrate was concentrated under reduced pressure to obtain 2.69 g (yield: 98%) of a target compound.

Synthesis of Compound 8

2.69 g (18.57 mmol, 1.0 eq.) of Compound 7 was dissolved in 50 mL of DCM, and 0.1 mL (1.29 mmol, 0.07 eq.) of DMF and 2.43 mL (27.86 mmol, 1.5 eq.) of oxalyl chloride were then added dropwise while stirring at room temperature. The reaction solution was stirred for 3 hours, and then concentrated under reduced pressure to obtain 2.42 g (yield: 80%) of a target compound.

Synthesis of Compound 9

0.88 g (5.40 mmol, 1.0 eq.) of Compound 8 was dissolved in 30 mL of DCM, and 0.8 g (5.40 mmol, 1.0 eq.) of tert-butyl 2-mercaptoacetate and 1.41 mL (8.10 mmol, 1.5 eq.) of N,N-diisopropylethylamine were then added dropwise while stirring at room temperature. The reaction mixture was stirred for 2 hours, and then concentrated under reduced pressure. Subsequently, water was added to the reaction solution, and the reaction solution was extracted three times with dichloromethane (DCM). An organic layer was dried over magnesium sulfate, concentrated under reduced pressure, and then purified by column chromatography (Hex:EA=5:1) to obtain 0.73 g (yield: 49%) of a target compound.

Synthesis of Compound 10

0.73 g (2.66 mmol, 1 eq.) of Compound 9 was dissolved in 10 mL of DCM, and 10 mL (129.8 mmol, 48 eq.) of trifluoroacetic acid was then added dropwise while stirring at room temperature. The reaction solution was stirred for 8 hours, and then concentrated under reduced pressure to obtain 0.40 g (yield: 70%) of a target compound.

Synthesis of Compound IV 1.97 g (9.0 mmol, 1.0 eq.) of Compound 10 was dissolved in 25 mL of acetonitrile (ACN), and 2.58 g (13.5 mmol, 1.5 eq.) of 1-ethyl-3-(3-dimethylaminopropyl) carbodiimide (EDCi) and 2.07 g (18.0 mmol, 2.0 eq.) of N-hydroxysuccinimide (NHS) were added while stirring at room temperature. The reaction solution was stirred for 3 hours, and then concentrated under reduced pressure. Subsequently, water was added to the reaction solution, and the reaction solution was extracted three times with EA. An organic layer was recovered, dried over magnesium sulfate, and then concentrated under reduced pressure. Then, the residue was purified on a silica gel column using chromatography (EA:Hex=2:1) to obtain 1.03 g (yield: 36%) of a target compound.

Confirmation of Structure of Compound IV $^1$H NMR (500 MHZ, $CDCl_3$) δ 4.30 (s, 2H), 4.00 (s, 2H), 3.87-3.75 (m, 2H), 3.55-3.47 (m, 2H), 2.86 (s, 4H).

LRMS (ESI): m/z 334.0 [$M+NH_{4+}$]

Figure 23:
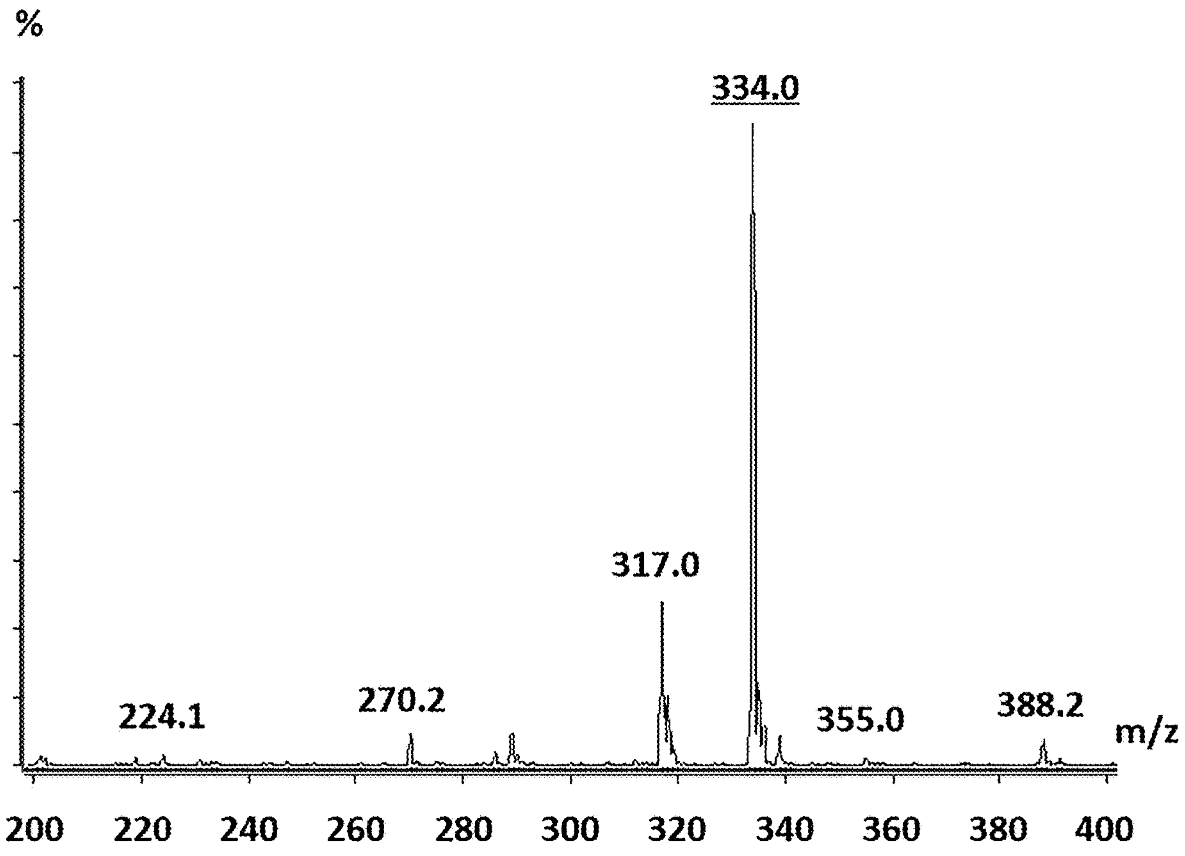
FIG. 23 shows the results of confirming a structure of Compound IV by means of mass spectrometry.

The structure of Compound IV was confirmed by mass spectrometry. The results are shown in FIG. 23.

1.2. Synthesis and Confirmation of Structure of Site-Specific Fc Interactome (SSFI)

1.2.1. Synthesis and Confirmation of Structure of SSFI (where $Xa_1$ is Lysine)

Synthesis of SSFI (6Lys)

A reaction for activating an Fmoc-amino acid to attach the activated residue to a clear amide resin was performed sequentially from the C-terminal amino acid.

Removal of Fmoc was performed in 20% piperidine-containing DMF, and activation and introduction of the FcBP (6Lys)

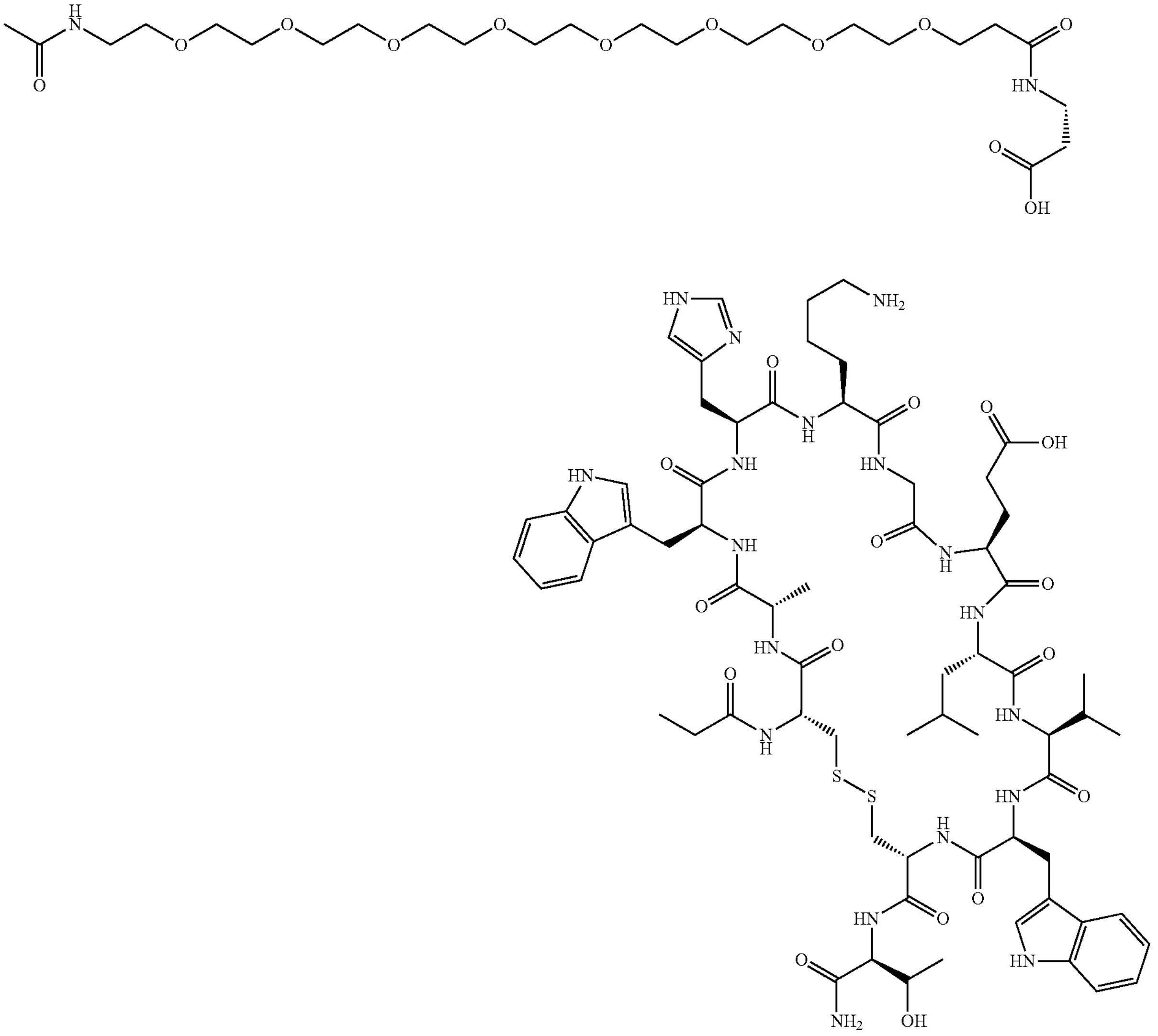

List and Order of Introduction of Fmoc Amino Acids Used

Fmoc-L-Thr (tBu)-OH, Fmoc-Cys (Trt)-OH, Fmoc-L-Trp (Boc)-OH, Fmoc-L-Val-OH, Fmoc-L-Leu-OH, Fmoc-L-Glu (OtBu)-OH, Fmoc-Gly-OH, Fmoc-Lys (Boc)-OH, Fmoc-L-His (Trt)-OH, Fmoc-L-Trp (Boc)-OH, Fmoc-Ala-OH, Fmoc-Cys (Trt)-OH, Fmoc-Asp (tBu)-OH.

Preparation Method (a) Introduction of Amino Acids

Amounts of reagents used in the following process were based on 0.25 mmole. 0.5 g (0.48 mmole/g) of a clear amide resin (Peptide International Inc., USA) was put into a synthesis reactor, and 1 mmole of each Fmoc-amino acid block was weighed to prepare a peptide amino acid sequence from the C-terminus to the N-terminus in the above order.

residue was performed by mixing amino acids prepared to correspond to the sequence with 2 mL of a 0.5 M HOBt-containing DMF solution, 2 mL of a 0.5 M HBTU-containing DMF solution, and 174 μL of DIPEA for 5 minutes, and mixing the resulting mixture for 2 hours in a reactor containing the resin.

Confirmation of an introduction reaction was carried out using a Kaiser test method. When the introduction reaction was confirmed to be incomplete, the introduction reaction was repeated once more, or capping was performed using a 20% $Ac_2O$-containing DMF solution. In each of the introduction reaction and the Fmoc removal, the resin was thoroughly washed with DMF and DCM before moving to the next step. This process was repeatedly performed until the targeted peptide sequence was completed.

(b) Introduction of H-PEG8-OH

To introduce H-PEG8-OH to the N-terminus of the sequence after the introduction of the amino acids was completed, 1 mL of a 0.5 M Fmoc-N-amido-dPEG8-acid-in-DMF solution, 1 mL of a 0.5 M HBTU-containing DMF solution, 1 mL of a 0.5 M HOBt-containing DMF solution, and 87 μL of DIPEA were mixed for 5 minutes, and the resulting mixture was mixed for 2 hours in a reactor containing a reactive resin.

Progression of the reaction was monitored by the Kaiser test method. When the unreacted amine was found to remain, the reaction time was extended for another 1 to 3 hours, or the reaction solution was discarded, and the aforementioned reaction process was repeated again. Removal of the N-terminal Fmoc protective group was performed using 20% piperidine-containing DMF, and the resin to which the peptide was attached was then dried and weighed.

(c) 250 mg of the resin to which the peptide was attached as prepared in the step (b) was stirred with 2 mL of a mixed solution of TFA, TIS, water and EDT (94:1.0:2.5:2.5) at room temperature for 120 minutes to cleave the peptide from the resin. The cleaved mixture was filtered, and the filtrate was concentrated to about half its volume using nitrogen gas. Thereafter, ether was poured into the mixture to precipitate the peptide. The precipitated peptide was washed three times with ether, and dried under nitrogen gas. The dried precipitate was dissolved in 0.1% TFA-30% ACN-containing water, stirred for 6 hours, and then concentrated.

The concentrate was dissolved at a concentration of 0.1 mg/mL in a 5%-DMSO-20%-ACN-containing 0.01 M ammonium acetate buffer (pH 6.5) solution, and then stirred for 3 days while being exposed to air. Progression of a disulfide bond-forming reaction was monitored by HPLC. When the reaction was found not to progress any more, the reaction solution was freeze-dried to obtain a peptide precipitate.

(d) Purification

The peptide precipitate obtained by freeze-drying in the step (c) was separated under the prep-LC primary purification conditions listed in the following Table 4, further purified under the prep-LC secondary purification conditions listed in the following Table 5, and then freeze-dried. The resulting peptide was confirmed to have a purity of 90% or more by analytical HPLC, and the molecular weight of the synthesized peptide was confirmed using an LC/MS mass spectrometer.

H-PEG8-Asp-Cys*-Ala-Trp-His-Lys-Gly-Glu-Leu-Val-Trp-Cys*-Thr-$NH_2$ (Cys*: disulfide bonding sites)

TABLE 4

| Prep-LC primary purification condition | | | |
|---|---|---|---|
| Equipment name | Waters 2525 pump, Waters 2487 UV detector | | |
| Column | Waters, XBridge Prep C18 5 μm OBD 19 × 250 mm | | |
| Mobile phase A/B | 0.1% TFA-20% ACN/0.1% TFA in 80% ACN | | |
| Gradient | 0 min → 30 min: B 0% → B 100% | | |
| Flow rate | 17 mL/min | Detection wavelength | UV 280 nm |

TABLE 5

| Prep-LC secondary purification condition | | | |
|---|---|---|---|
| Equipment name | Waters 2525 pump, Waters 2487 UV detector | | |
| Column | Waters, XBridge Prep C18 5 μm OBD 19 × 250 mm | | |
| Mobile phase A/B | 0.1% TFA-30% ACN/0.1% TFA in 70% ACN | | |
| Gradient | 0 min → 30 min: B 0% → B 100% | | |
| Flow rate | 15 mL/min | Detection wavelength | UV 280 nm |

Confirmation of Structure of SSFI (6Lys)

Synthesis of SSFI (6Lys) was confirmed by molecular weight measurement by matrix-assisted laser desorption/ionization (MALDI) mass spectrometry.

Measuring equipment: Ultraflextreme (Bruker)

Measuring matrix: CHCA (α-Cyano-4-hydroxycinnamic acid) & DHB (2,5-Dihydroxybenzoic acid)

Calculated molecular weight: 2010.29 g/mol

Measured molecular weight $(M+H)^+$: 2011.89 g/mol

Figure 24:
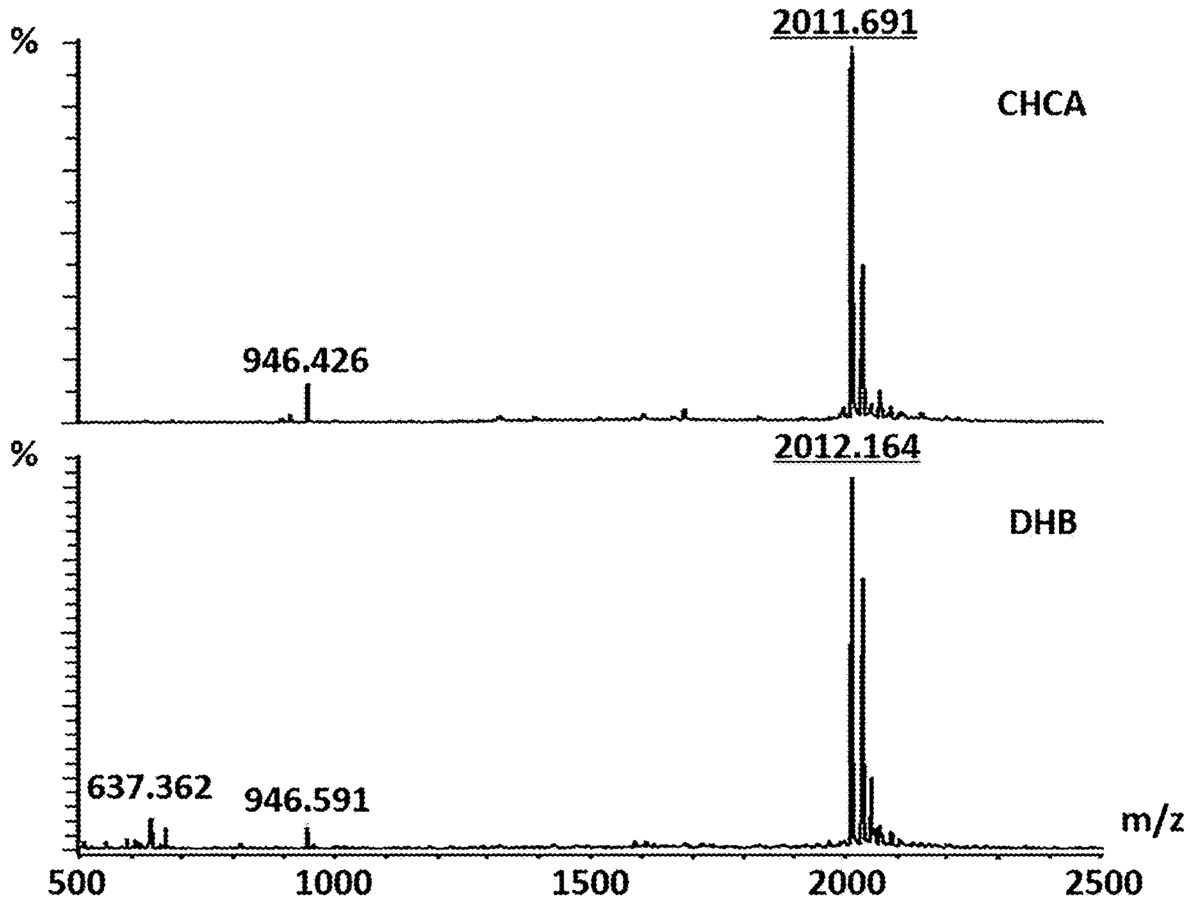
FIG. 24 shows the results of confirming a structure of SSFI (6Lys) by means of mass spectrometry.

The mass spectrometry results of SSFI (6Lys) are shown in FIG. 24.

1.2.2. Synthesis and Confirmation of Structure of SSFI (where $Xa_1$ is Ornithine)

FcBP (6Ornithine)

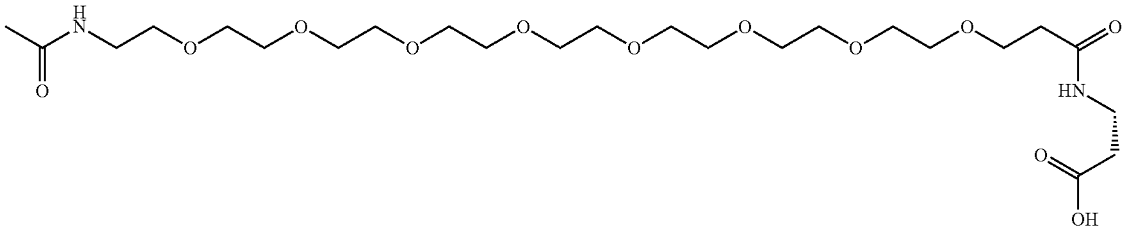

-continued

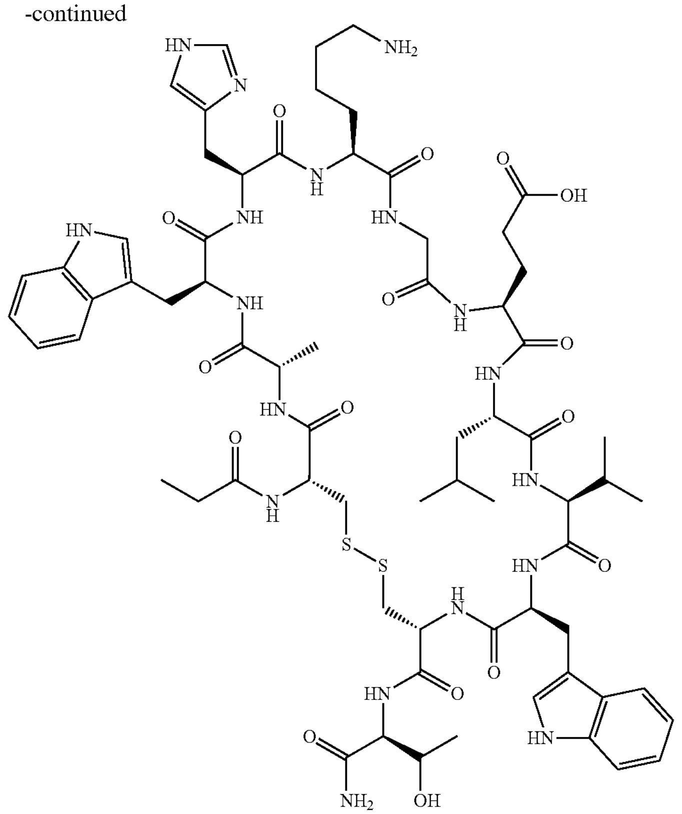

Synthesis of SSFI (6Orn)

List and Order of Introduction of Fmoc Amino Acids Used

Fmoc-L-Thr (tBu)-OH, Fmoc-Cys (Trt)-OH, Fmoc-L-Trp (Boc)-OH, Fmoc-L-Val-OH, Fmoc-L-Leu-OH, Fmoc-L-Glu (OtBu)-OH, Fmoc-Gly-OH, Fmoc-Orn (Boc)-OH, Fmoc-L-His (Trt)-OH, Fmoc-L-Trp (Boc)-OH Fmoc-Ala-OH, Fmoc-Cys (Trt)-OH, Fmoc-Asp (tBu)-OH.

Preparation Method (a) Introduction of Amino Acids

Amounts of reagents used in the following process were based on 0.25 mmole. 0.5 g (0.48 mmole/g) of a clear amide resin (Peptide International Inc., USA) was put into a synthesis reactor, and 1 mmole of each Fmoc-amino acid block was weighed to prepare a peptide amino acid sequence from the C-terminus to the N-terminus in the above.

A reaction for activating an Fmoc-amino acid to attach the activated residue to a clear amide resin was performed sequentially from the C-terminal amino acid.

Removal of Fmoc was performed in 20% piperidine-containing DMF, and activation and introduction of the residue was performed by mixing amino acids prepared to correspond to the sequence with 2 mL of a 0.5 M HOBt-containing DMF solution, 2 mL of a 0.5 M HBTU-containing DMF solution, and 174 μL of DIPEA for 5 minutes, and mixing the resulting mixture for 2 hours in a reactor containing the resin.

Confirmation of an introduction reaction was carried out using a Kaiser test method. When the introduction reaction was confirmed to be incomplete, the introduction reaction was repeated once more, or capping was performed using a 20% $AC_2O$-containing DMF solution. In each of the introduction reaction and the Fmoc removal, the resin was thoroughly washed with DMF and DCM before moving to the next step. This process was repeatedly performed until the targeted peptide sequence was completed.

(b) Introduction of H-PEG8-OH

To introduce H-PEG8-OH to the N-terminus of the sequence after the introduction of the amino acids was completed, 1 mL of a 0.5 M Fmoc-N-amido-dPEG8-acid-in-DMF solution, 1 mL of a 0.5 M HBTU-containing DMF solution, 1 mL of a 0.5 M HOBt-containing DMF solution, and 87 μL of DIPEA were mixed for 5 minutes, and the resulting mixture was mixed for 2 hours in a reactor containing a reactive resin.

Progression of the reaction was monitored by the Kaiser test method. When the unreacted amine was found to remain, the reaction time was extended for another 1 to 3 hours, or the reaction solution was discarded, and the aforementioned reaction process was repeated again. Removal of the N-terminal Fmoc protective group was performed using 20% piperidine-containing DMF, and the resin to which the peptide was attached was then dried and weighed.

(c) 250 mg of the resin to which the peptide was attached as prepared in the step (b) was stirred with 2 mL of a mixed solution of TFA, TIS, water and EDT (94:1.0:2.5:2.5) at room temperature for 120 minutes to cleave the peptide from the resin. The cleaved mixture was filtered, and the filtrate was concentrated to about half its volume using nitrogen gas. Thereafter, ether was poured into the mixture to precipitate the peptide. The precipitated peptide was washed three times with ether, and dried under nitrogen gas. The dried precipitate was dissolved in 0.1% TFA-30% ACN-containing water, stirred for 6 hours, and then concentrated.

The concentrate was dissolved at a concentration of 0.1 mg/mL in a 5%-DMSO-20%-ACN-containing 0.01 M ammonium acetate buffer (pH 6.5) solution, and then stirred for 3 days while being exposed to air. Progression of a disulfide bond-forming reaction was monitored by HPLC. When the reaction was found not to progress any more, the reaction solution was freeze-dried to obtain a peptide precipitate.

(d) Purification

The peptide precipitate obtained by freeze-drying in the step (c) was separated under the prep-LC primary purification conditions listed in the following Table 6, further purified under the prep-LC secondary purification conditions listed in the following Table 7, and then freeze-dried. The resulting peptide was confirmed to have a purity of 90% or more by analytical HPLC, and the molecular weight of the synthesized peptide was confirmed using an LC/MS mass spectrometer.

```
H-PEG8-Asp-Cys*-Ala-Trp-His-Orn-Gly-Glu-Leu-Val-
Trp-Cys*-Thr-NH2 (Cys*: disulfide bonding sites)
```

TABLE 6

| Prep-LC primary purification condition | | | |
|---|---|---|---|
| Equipment name | Waters 2525 pump, Waters 2487 UV detector | | |
| Column | Waters, XBridge Prep C18 5 μm OBD 19 × 250 mm | | |
| Mobile phase A/B | 0.1 % TFA-20% ACN/0.1% TFA in 80% ACN | | |
| Gradient | 0 min → 30 min: B 0% → B 100% | | |
| Flow rate | 17 mL/min | Detection wavelength | UV 280 nm |

TABLE 7

| Prep-LC secondary purification condition | | | |
|---|---|---|---|
| Equipment name | Waters 2525 pump, Waters 2487 UV detector | | |
| Column | Waters, XBridge Prep C18 5 μm OBD 19 × 250 mm | | |
| Mobile phase A/B | 0.1% TFA-30% ACN/0.1% TFA in 70% ACN | | |
| Gradient | 0 min → 30 min: B 0% → B 100% | | |
| Flow rate | 15 ml/min | Detection wavelength | UV 280 nm |

Confirmation of Structure of SSFI (6Orn)

Synthesis of SSFI (6Ornithine) was confirmed by molecular weight measurement by matrix-assisted laser desorption/ionization (MALDI) mass spectrometry.

Measuring equipment: Ultraflextreme (Bruker)

Measuring matrix: CHCA (α-Cyano-4-hydroxycinnamic acid) & DHB (2,5-Dihydroxybenzoic acid)

Calculated molecular weight: 1996.26 g/mol

Measured molecular weight $(M+2H)^{2+}$: 999.13 g/mol

Figure 25:
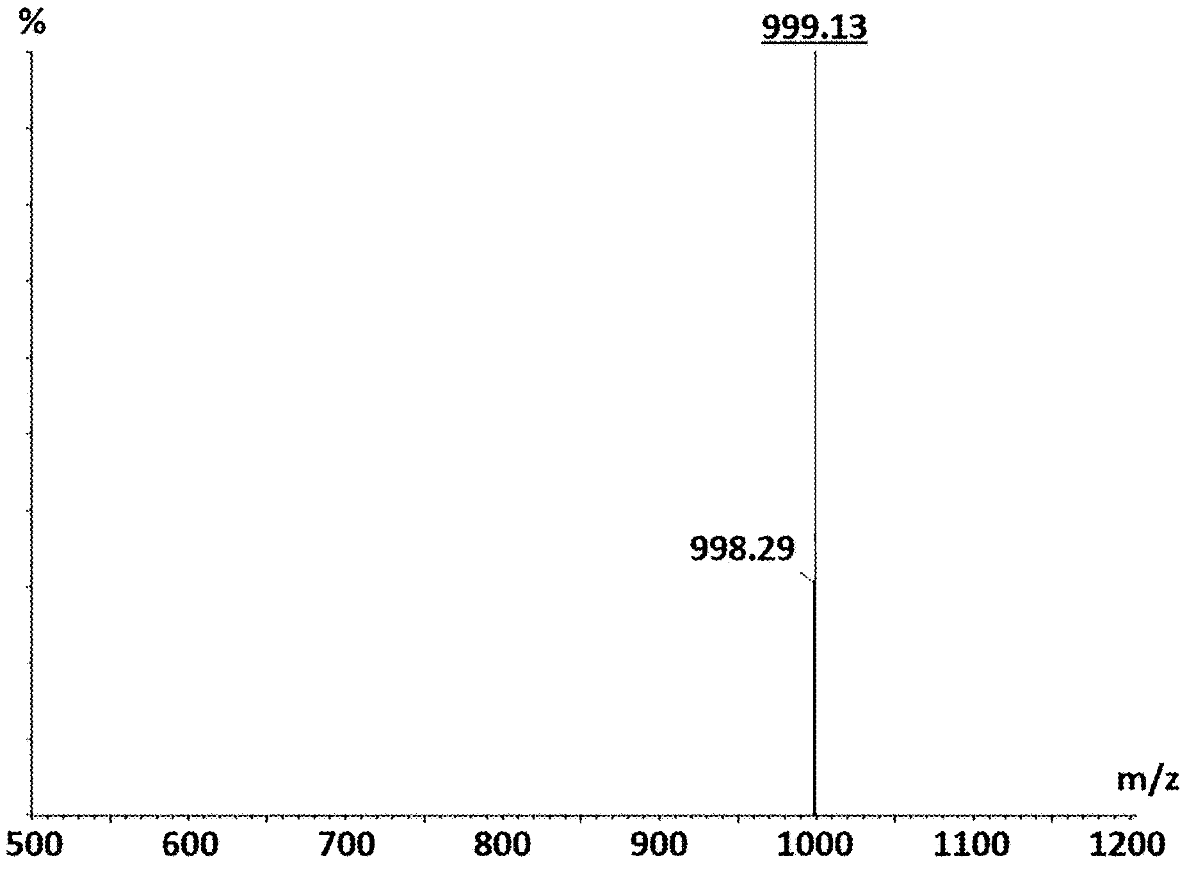
FIG. 25 shows the results of confirming a structure of SSFI (6Orn) by means of mass spectrometry.

The mass spectrometry results of SSFI (6Orn) are shown in FIG. 25.

1.2.3. Synthesis and Confirmation of Structure of SSFI (where $Xa_1$ is Diaminobutyric Acid (Dab))

FcBP(6Dab)
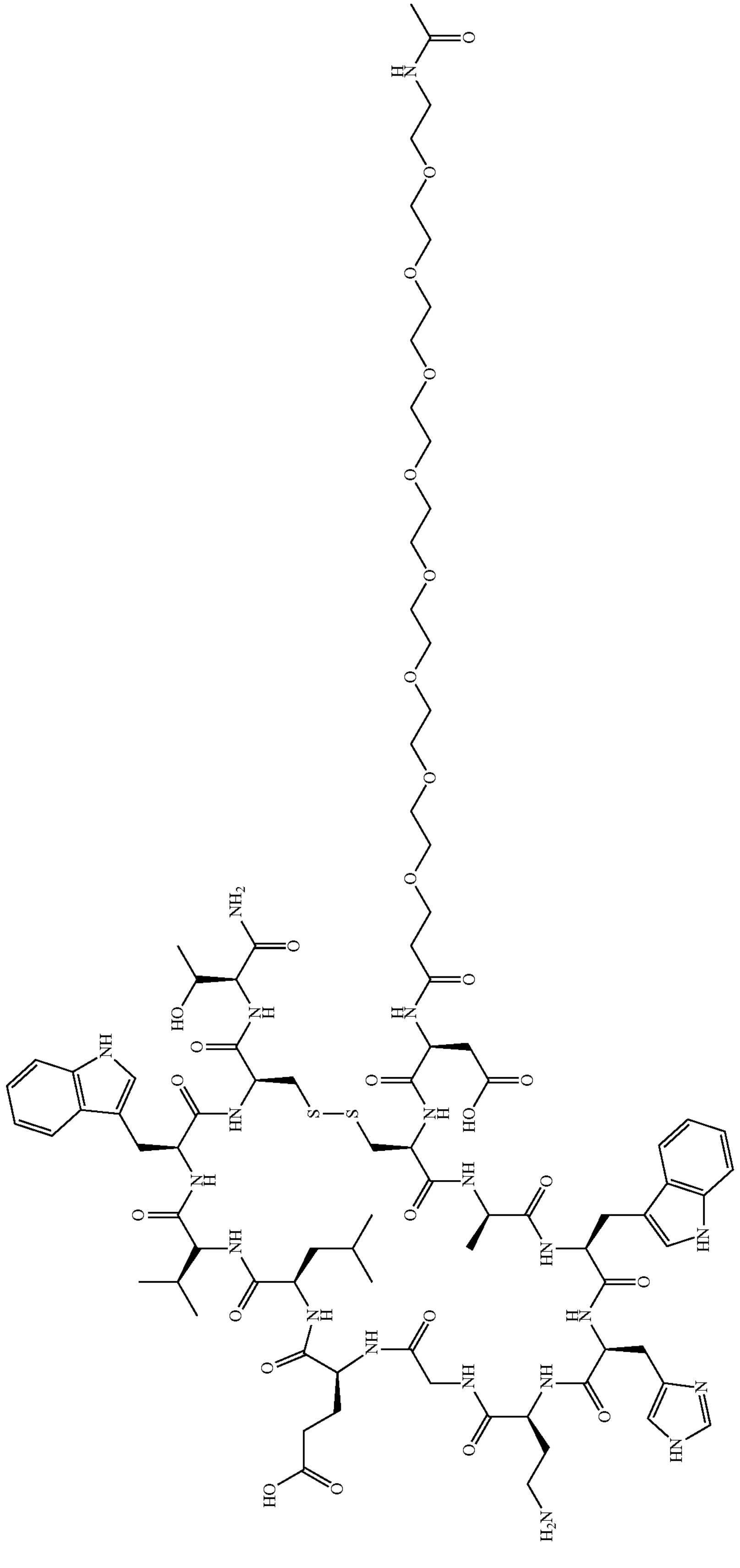

Synthesis of SSFI (6Dab)

List and Order of Introduction of Fmoc Amino Acids Used

Fmoc-L-Thr (tBu)-OH, Fmoc-Cys (Trt)-OH, Fmoc-L-Trp (Boc)-OH, Fmoc-L-Val-OH, Fmoc-L-Leu-OH, Fmoc-L-Glu (OtBu)-OH, Fmoc-Gly-OH, Fmoc-Dab (Boc)-OH, Fmoc-L-His (Trt)-OH, Fmoc-L-Trp (Boc)-OH Fmoc-Ala-OH, Fmoc-Cys (Trt)-OH, Fmoc-Asp (tBu)-OH.

Preparation Method (a) Introduction of Amino Acids

Amounts of reagents used in the following process were based on 0.25 mmole. 0.5 g (0.48 mmole/g) of a clear amide resin (Peptide International Inc., USA) was put into a synthesis reactor, and 1 mmole of each Fmoc-amino acid block was weighed to prepare a peptide amino acid sequence from the C-terminus to the N-terminus in the above order.

A reaction for activating an Fmoc-amino acid to attach the activated residue to a clear amide resin was performed sequentially from the C-terminal amino acid.

Removal of Fmoc was performed in 20% piperidine-containing DMF, and activation and introduction of the residue was performed by mixing amino acids prepared to correspond to the sequence with 2 mL of a 0.5 M HOBt-containing DMF solution, 2 mL of a 0.5 M HBTU-containing DMF solution, and 174 μL of DIPEA for 5 minutes, and mixing the resulting mixture for 2 hours in a reactor containing the resin.

Confirmation of an introduction reaction was carried out using a Kaiser test method. When the introduction reaction was confirmed to be incomplete, the introduction reaction was repeated once more, or capping was performed using a 20% $AC_2O$-containing DMF solution. In each of the introduction reaction and the Fmoc removal, the resin was thoroughly washed with DMF and DCM before moving to the next step. This process was repeatedly performed until the targeted peptide sequence was completed.

(b) Introduction of H-PEG8-OH

To introduce H-PEG8-OH to the N-terminus of the sequence after the introduction of the amino acids was completed, 1 mL of a 0.5 M Fmoc-N-amido-dPEG8-acid-in-DMF solution, 1 mL of a 0.5 M HBTU-containing DMF solution, 1 mL of a 0.5 M HOBt-containing DMF solution, and 87 μL of DIPEA were mixed for 5 minutes, and the resulting mixture was mixed for 2 hours in a reactor containing a reactive resin.

Progression of the reaction was monitored by the Kaiser test method. When the unreacted amine was found to remain, the reaction time was extended for another 1 to 3 hours, or the reaction solution was discarded, and the aforementioned reaction process was repeated again. Removal of the N-terminal Fmoc protective group was performed using 20% piperidine-containing DMF, and the resin to which the peptide was attached was then dried and weighed.

(c) 250 mg of the resin to which the peptide was attached as prepared in the step (b) was stirred with 2 mL of a mixed solution of TFA, TIS, water and EDT (94:1.0:2.5:2.5) at room temperature for 120 minutes to cleave the peptide from the resin. The cleaved mixture was filtered, and the filtrate was concentrated to about half its volume using nitrogen gas. Thereafter, ether was poured into the mixture to precipitate the peptide. The precipitated peptide was washed three times with ether, and dried under nitrogen gas. The dried precipitate was dissolved in 0.1% TFA-30% ACN-containing water, stirred for 6 hours, and then concentrated.

The concentrate was dissolved at a concentration of 0.1 mg/mL in a 5%-DMSO-20%-ACN-containing 0.01 M ammonium acetate buffer (pH 6.5) solution, and then stirred for 3 days while being exposed to air. Progression of a disulfide bond-forming reaction was monitored by HPLC. When the reaction was found not to progress any more, the reaction solution was freeze-dried to obtain a peptide precipitate.

(d) Purification

The peptide precipitate obtained by freeze-drying in the step (c) was separated under the prep-LC primary purification conditions listed in the following Table 8, further purified under the prep-LC secondary purification conditions listed in the following Table 9, and then freeze-dried. The resulting peptide was confirmed to have a purity of 90% or more by analytical HPLC, and the molecular weight of the synthesized peptide was confirmed using an LC/MS mass spectrometer.

```
H-PEG8-Asp-Cys*-Ala-Trp-His-Dab-Gly-Glu-Leu-Val-
Trp-Cys*-Thr-NH2 (Cys*: disulfide bonding sites)
```

TABLE 8

| Prep-LC primary purification condition | | | |
|---|---|---|---|
| Equipment name | Waters 2525 pump, Waters 2487 UV detector | | |
| Column | Waters, XBridge Prep C18 5 μm OBD 19 × 250 mm | | |
| Mobile phase A/B | 0.1% TFA-20% ACN/0.1% TFA in 80% ACN | | |
| Gradient | 0 min → 30 min: B 0% → B 100% | | |
| Flow rate | 17 mL/min | Detection wavelength | UV 280 nm |

TABLE 9

| Prep-LC secondary purification condition | | | |
|---|---|---|---|
| Equipment name | Waters 2525 pump. Waters 2487 UV detector | | |
| Column | Waters, XBridge Prep C18 5 μm OBD 19 × 250 mm | | |
| Mobile phase A/B | 0.1% TFA-30% ACN/0.1% TFA in 70% ACN | | |
| Gradient | 0 min → 30 min: B 0% → B 100% | | |
| Flow rate | 15 mL/min | Detection wavelength | UV 280 nm |

Confirmation of Structure of SSFI (6Dab)

Synthesis of SSFI (6Dab) was confirmed by molecular weight measurement by matrix-assisted laser desorption/ionization (MALDI) mass spectrometry.

Measuring equipment: Ultraflextreme (Bruker)

Measuring matrix: CHCA (α-Cyano-4-hydroxycinnamic acid) & DHB (2,5-Dihydroxybenzoic acid)

Calculated molecular weight: 1982.24 g/mol

Measured molecular weight $(M+2H)^{2+}$: 992.33 g/mol

Figure 26:
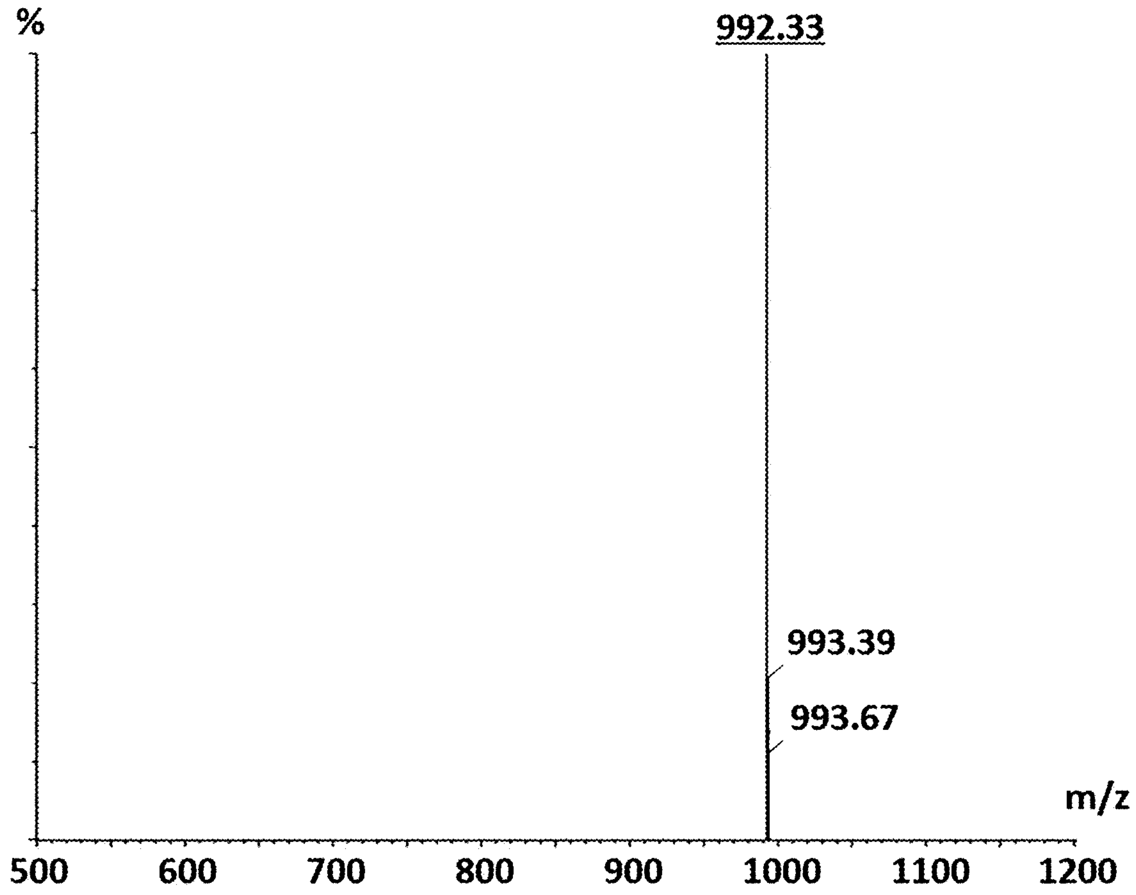
FIG. 26 shows the results of confirming a structure of SSFI (6Dab) by means of mass spectrometry.

The mass spectrometry results of SSFI (6Dab) are shown in FIG. 26.

1.2.4. Synthesis and Confirmation of Structure of SSFI (where $Xa_1$ is Diaminopropionic Acid (Dap))

FcBP(6Dap)
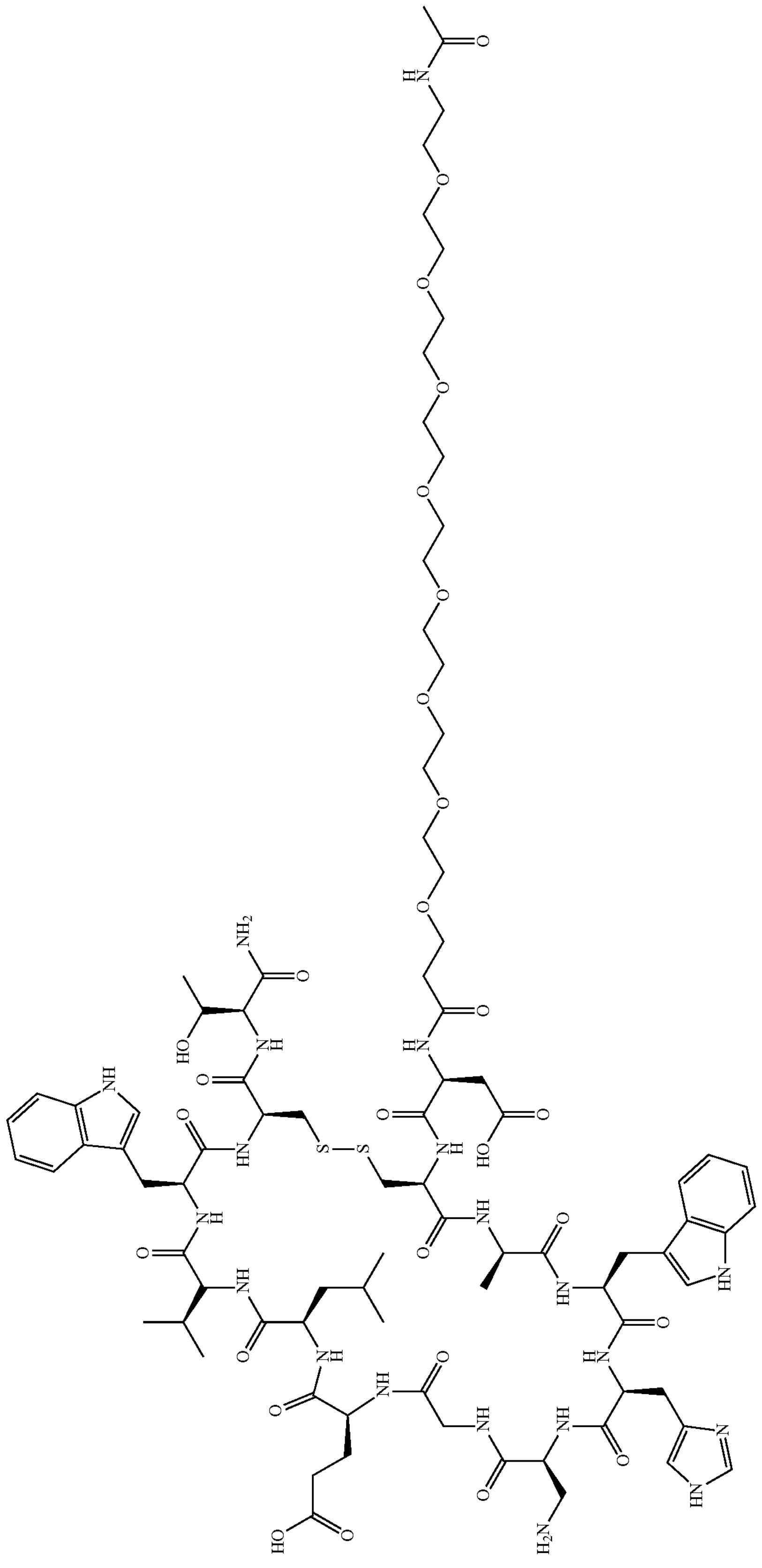

Synthesis of SSFI (6Dap)

Sequence: Nor.-PEG8-DCAWHA(beta amino alanine, Dap)GELVWCT-$CONH_2$

List and Order of Introduction of Fmoc Amino Acids Used

Fmoc-L-Thr (tBu)-OH, Fmoc-Cys (Trt)-OH, Fmoc-L-Trp (Boc)-OH, Fmoc-L-Val-OH, Fmoc-L-Leu-OH, Fmoc-L-Glu (OtBu)-OH, Fmoc-Gly-OH, Fmoc-Dap (Boc)-OH, Fmoc-L-His (Trt)-OH, Fmoc-L-Trp (Boc)-OH Fmoc-Ala-OH, Fmoc-Cys (Trt)-OH, Fmoc-Asp (tBu)-OH.

Preparation Method (a) Introduction of Amino Acids

Amounts of reagents used in the following process were based on 0.25 mmole. 0.5 g (0.48 mmole/g) of a clear amide resin (Peptide International Inc., USA) was put into a synthesis reactor, and 1 mmole of each Fmoc-amino acid block was weighed to prepare a peptide amino acid sequence from the C-terminus to the N-terminus in the above order.

A reaction for activating an Fmoc-amino acid to attach the activated residue to a clear amide resin was performed sequentially from the C-terminal amino acid.

Removal of Fmoc was performed in 20% piperidine-containing DMF, and activation and introduction of the residue was performed by mixing amino acids prepared to correspond to the sequence with 2 mL of a 0.5 M HOBt-containing DMF solution, 2 mL of a 0.5 M HBTU-containing DMF solution, and 174 μL of DIPEA for 5 minutes, and mixing the resulting mixture for 2 hours in a reactor containing the resin.

Confirmation of an introduction reaction was carried out using a Kaiser test method. When the introduction reaction was confirmed to be incomplete, the introduction reaction was repeated once more, or capping was performed using a 20% $AC_2O$-containing DMF solution. In each of the introduction reaction and the Fmoc removal, the resin was thoroughly washed with DMF and DCM before moving to the next step. This process was repeatedly performed until the targeted peptide sequence was completed.

(b) Introduction of H-PEG8-OH

To introduce H-PEG8-OH to the N-terminus of the sequence after the introduction of the amino acids was completed, 1 mL of a 0.5 M Fmoc-N-amido-dPEG8-acid-in-DMF solution, 1 mL of a 0.5 M HBTU-containing DMF solution, 1 mL of a 0.5 M HOBt-containing DMF solution, and 87 μL of DIPEA were mixed for 5 minutes, and the resulting mixture was mixed for 2 hours in a reactor containing a reactive resin.

Progression of the reaction was monitored by the Kaiser test method. When the unreacted amine was found to remain, the reaction time was extended for another 1 to 3 hours, or the reaction solution was discarded, and the aforementioned reaction process was repeated again. Removal of the N-terminal Fmoc protective group was performed using 20% piperidine-containing DMF, and the resin to which the peptide was attached was then dried and weighed.

(c) 250 mg of the resin to which the peptide was attached as prepared in the step (b) was stirred with 2 mL of a mixed solution of TFA, TIS, water and EDT (94:1.0:2.5:2.5) at room temperature for 120 minutes to cleave the peptide from the resin. The cleaved mixture was filtered, and the filtrate was concentrated to about half its volume using nitrogen gas. Thereafter, ether was poured into the mixture to precipitate the peptide. The precipitated peptide was washed three times with ether, and dried under nitrogen gas. The dried precipitate was dissolved in 0.1% TFA-30% ACN-containing water, stirred for 6 hours, and then concentrated.

The concentrate was dissolved at a concentration of 0.1 mg/mL in a 5%-DMSO-20%-ACN-containing 0.01 M ammonium acetate buffer (pH 6.5) solution, and then stirred for 3 days while being exposed to air. Progression of a disulfide bond-forming reaction was monitored by HPLC. When the reaction was found not to progress any more, the reaction solution was freeze-dried to obtain a peptide precipitate.

(d) Purification

The peptide precipitate obtained by freeze-drying in the step (c) was separated under the prep-LC primary purification conditions listed in the following Table 10, further purified under the prep-LC secondary purification conditions listed in the following Table 11, and then freeze-dried. The resulting peptide was confirmed to have a purity of 90% or more by analytical HPLC, and the molecular weight of the synthesized peptide was confirmed using an LC/MS mass spectrometer.

H-PEG8-Asp-Cys*-Ala-Trp-His-Dap-Gly-Glu-Leu-Val-Trp-Cys*-Thr-$NH_2$ (Cys*: disulfide bonding sites)

TABLE 10

| Prep-LC primary purification condition | | | |
|---|---|---|---|
| Equipment name | Waters 2525 pump. Waters 2487 UV detector | | |
| Column | Waters, XBridge Prep C18 5 μm OBD 19 × 250 mm | | |
| Mobile phase A/B | 0.1% TFA-20% ACN/0.1% TFA in 80% ACN | | |
| Gradient | 0 min → 30 min: B 0% → B 100% | | |
| Flow rate | 17 mL/min | Detection wavelength | UV 280 nm |

TABLE 12

| Prep-LC secondary purification condition | |
|---|---|
| Equipment name | Waters 2525 pump, Waters 2487 UV detector |
| Column | Waters, XBridge Prep C18 5 μm OBD 19 × 250 mm |
| Mobile phase A/B | 0.1% TFA-30% ACN/0.1% TFA, in 70% ACN |
| Gradient | 0 min → 30 min: B 0% → B 100% |
| Flow rate | 15mL/min Detection wavelength UV 280 nm |

Confirmation of Structure of SSFI (6Dap)

Measuring equipment: Quattro Premier Xe (Waters)

Calculated molecular weight: 1968.21 g/mol

Measured molecular weight $(M+2H)^{2+}$: 984.71 g/mol

Figure 27:
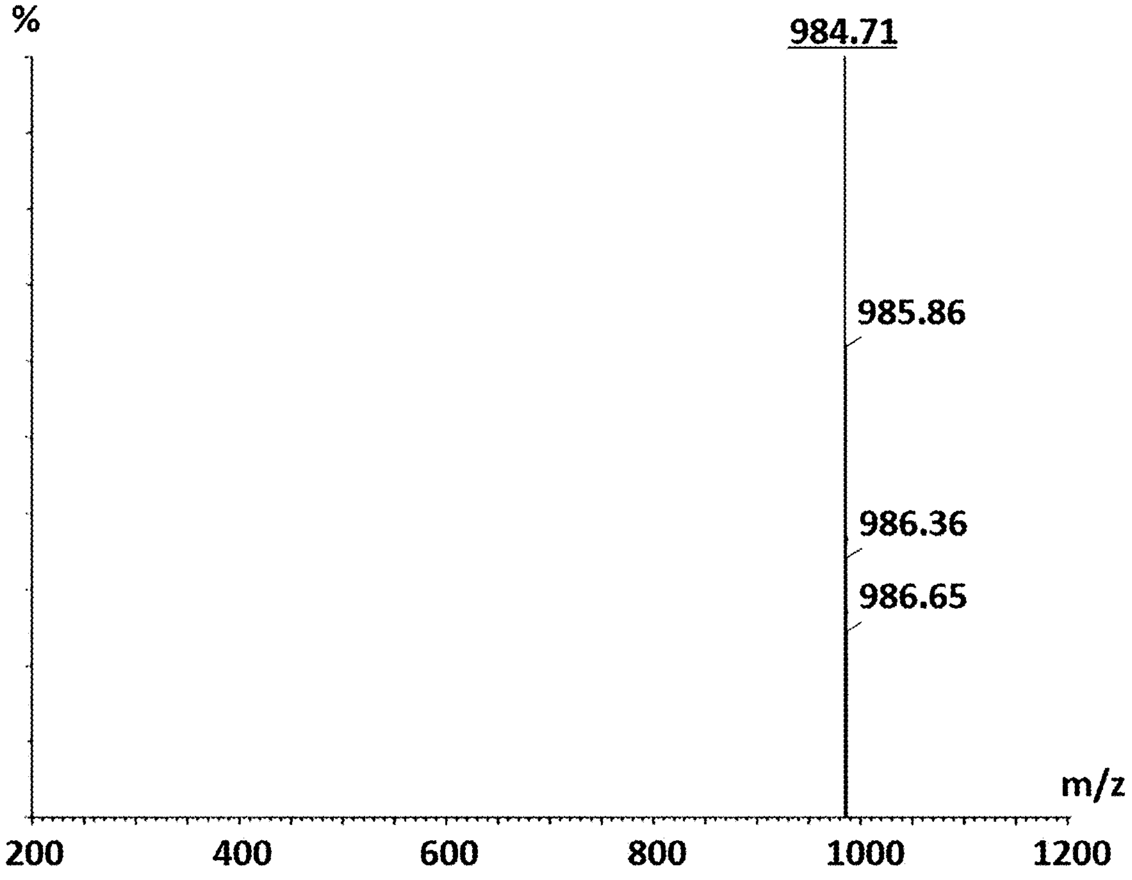
FIG. 27 shows the results of confirming a structure of SSFI (6Dap) by means of mass spectrometry.

The mass spectrometry results of SSFI (6Dap) are shown in FIG. 27.

1.3. Synthesis and Confirmation of Structure of VC Linker
1.3.1. Synthesis and Confirmation of Structure of VC Linker (DD2)
[Scheme 10]
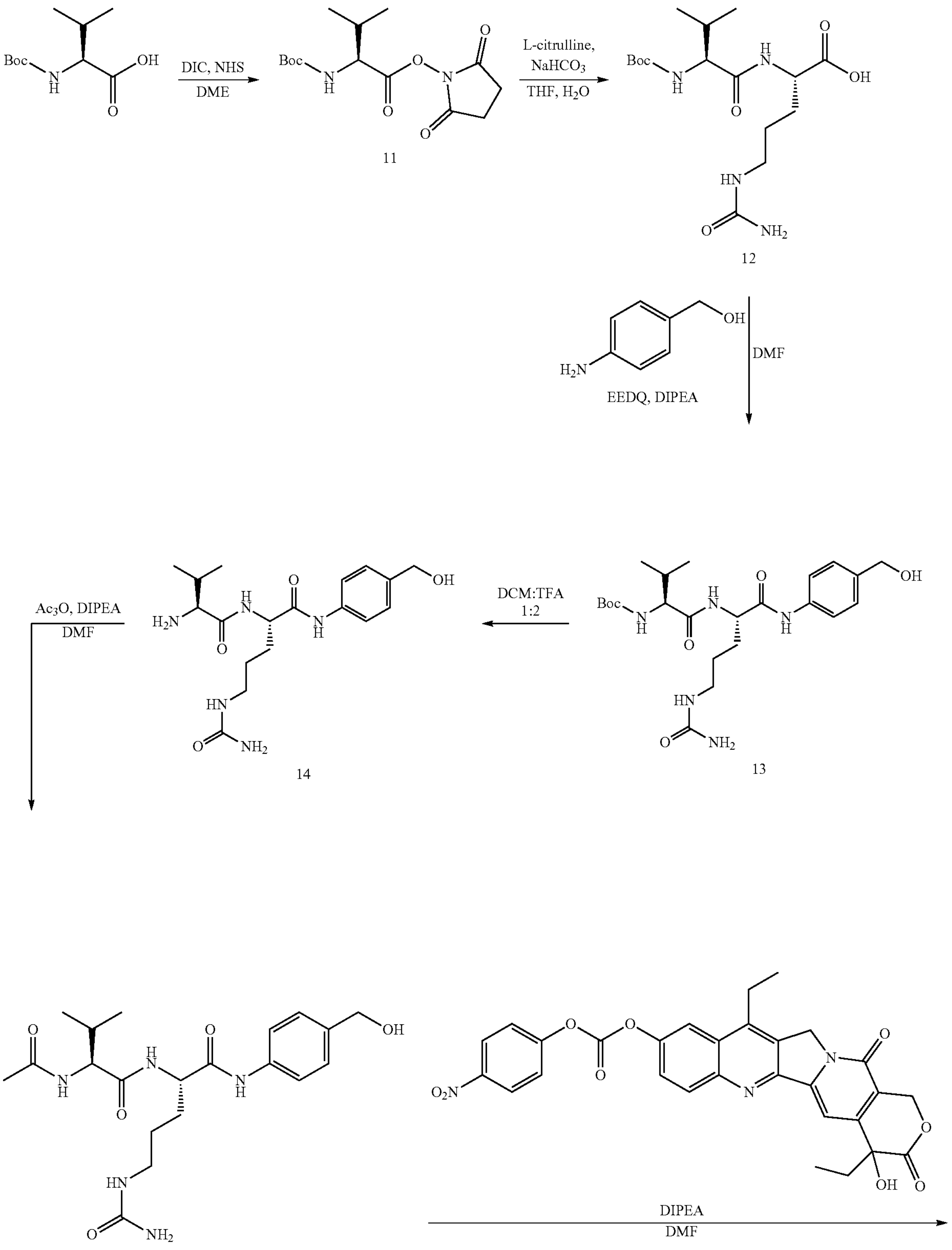
11
12
14
13
15

-continued

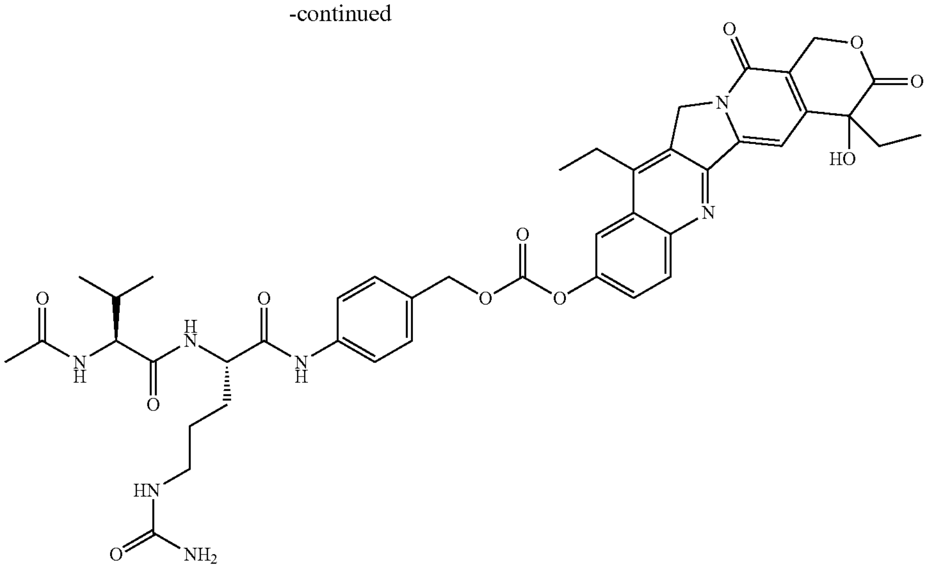

DD2

Synthesis of VC Linker (DD2)

Synthesis of Compound 11

5 g (14.7 mmol, 1.0 eq.) of Fmoc-Val-OH and 1.7 g (14.7 mmol, 1.0 eq.) of N-hydroxysuccinimide (NHS) were dissolved in 140 mL of dimethoxyethane (DME), and stirred. 2.5 mL (16.2 mmol, 1.1 eq.) of N,N'-diisopropylcarbodiimide (DIC) was added dropwise at 0° C., and stirred for 16 hours. The reaction solution was filtered under reduced pressure to remove floating matter, and the filtrate was concentrated under reduced pressure. The residue was dissolved in acetone, and stored at a low temperature for 4 hours in a refrigerator. Thereafter, the resulting solution was filtered under reduced pressure to remove the re-formed floating matter, and used in the next reaction without any purification (crude yield: 5.5 g, 86%). TLC (EA:Hex=1:1); $R_f$=0.5.

Synthesis of Compound 12

2.0 g (11.5 mmol, 1.0 eq.) of L-citrulline was dissolved in 100 ml of a 1:1 mixed solution of tetrahydrofuran (THF) and water, and stirred. 988 mg of sodium hydrogen carbonate was added thereto, and stirred. Thereafter, 5.0 g (11.5 mmol, 1.0 eq.) of Compound 8 was dissolved in 80 mL of acetone, added dropwise to the reaction solution, and then stirred. The resulting mixture was stirred for 21 hours, and then concentrated under reduced pressure to remove the organic solvent. An aqueous layer was washed with ethyl acetate (EA), and then titrated to pH 3 by slow dropwise addition of 2 N HCl. EA was added thereto so that the precipitate in an organic layer was extracted. Then, the organic layer was dried over a saturated saline solution and sodium sulfate, and used in the next reaction without any purification (crude yield: 5.6 g, 98%). TLC (DCM:MeOH=10:1, one drop of formic acid); $R_f$=0.1.

Synthesis of Compound 13

50 mL of 10% piperidine in N, N-dimethylformamide (DMF) was added dropwise to 2.84 g (5.72 mmol, 1.0 eq.) of Compound 12, and stirred. After 4 hours, the resulting mixture was concentrated under reduced pressure to remove a reaction solution, and the residue was dissolved in water, and filtered under reduced pressure to remove the formed floating matter. An aqueous layer was concentrated to obtain a target compound, which was used in the next reaction without any purification. TLC (DCM:MeOH=10:1); $R_f$=0.01.

Synthesis of Compound 14

54 mg (0.22 mmol, 1.0 eq.) of Compound 10 was dissolved in 2 mL of DMF, and 0.05 mL (0.264 mmol, 1.2 eq.) of N,N-diisopropylethylamine (DIPEA) was added dropwise thereto. Compound 13 was completely dissolved by adding 2 ml of water, and 0.05 mL (0.528 mmol, 2.4 eq.) of an acetic anhydride was added dropwise thereto at room temperature. After 3 hours, the resulting mixture was concentrated under reduced pressure to remove a reaction solution, and the concentrate was purified by reversed-phase column chromatography to obtain a target compound. TLC (DCM:MeOH=10:1); $R_f$=0.05.

Synthesis of Compound 15

1 g (3.16 mmol, 1.0 eq.) of Compound 14 was dissolved in 30 mL of a 2:1 mixed solution of DCM and methanol, and 868 mg (3.48 mmol, 1.1 eq.) of N-ethoxycarbonyl-2-ethoxy-1,2-dihydroquinoline (EEDQ) was added thereto, and stirred. 451 mg (3.66 mmol, 1.16 eq.) of 4-aminobenzyl alcohol was added thereto, and stirred for 5 hours. The resulting mixture was concentrated under reduced pressure to remove a reaction solution, and the concentrate was purified by column chromatography (10% MeOH in DCM) to obtain 419 mg of a target compound (yield: 32%). TLC (DCM:MeOH=10:1); $R_f$=0.1.

Synthesis of Compound DD2

109 mg (0.3 mmol, 1.2 eq.) of phenol-activated SN38 and 0.06 mL (0.33 mmol, 1.3 eq.) of DIPEA were added dropwise to a solution obtained by dissolving 105 mg (0.25 mmol, 1.0 eq.) of Compound 15 in 10 mL of DMF. The resulting mixture was stirred for 20 hours, and then concentrated under reduced pressure to remove a reaction solution. The concentrate was purified by column chromatography (10% MeOH in DCM) to obtain a target compound. TLC (DCM:MeOH=10:1); $R_f$=0.2.

Confirmation of Structure of VC Linker (DD2)

LRMS (ESI): m/z 840.4 $[M+H^+]$

Figure 28:
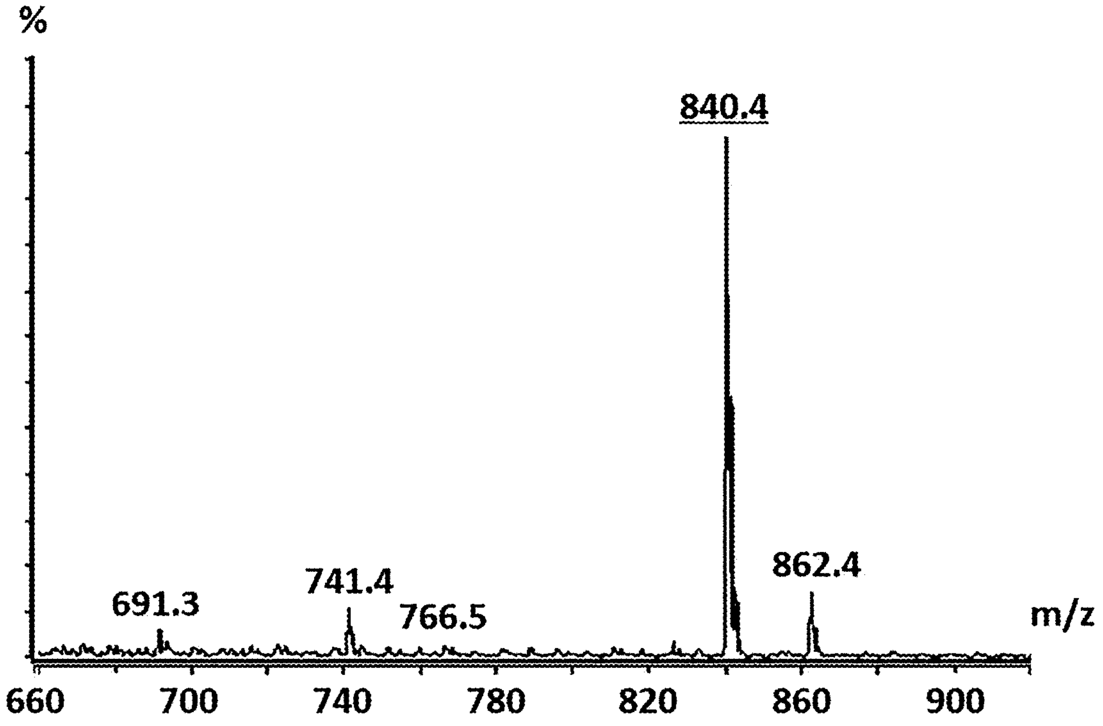
FIG. 28 shows the results of confirming a structure of DD2 by means of mass spectrometry.

The results are shown in FIG. 28.

1.3.2. Synthesis and Confirmation of Structure of VC Linker (DD3)
[Scheme 11]
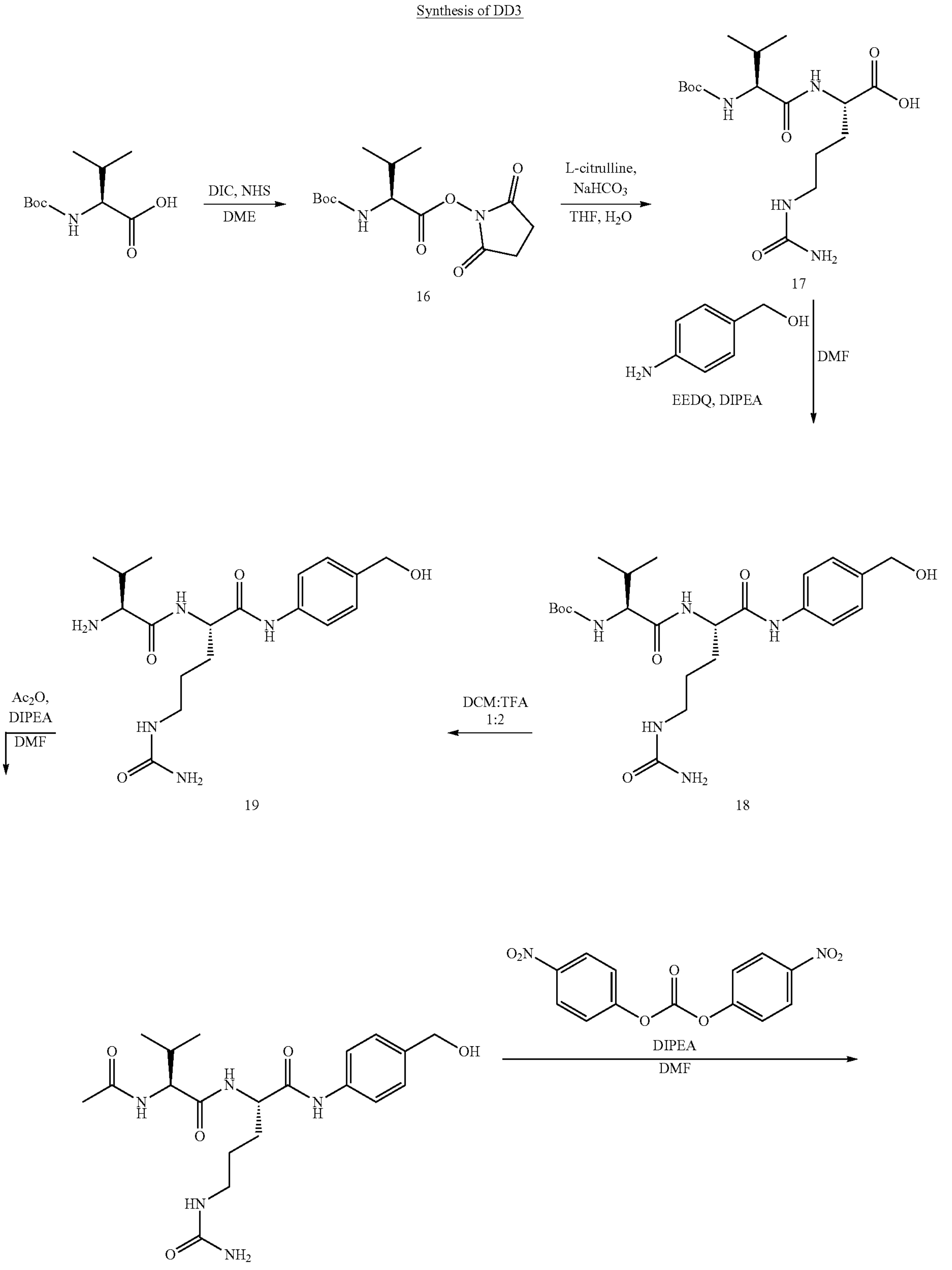
16
17
18
19
20

-continued

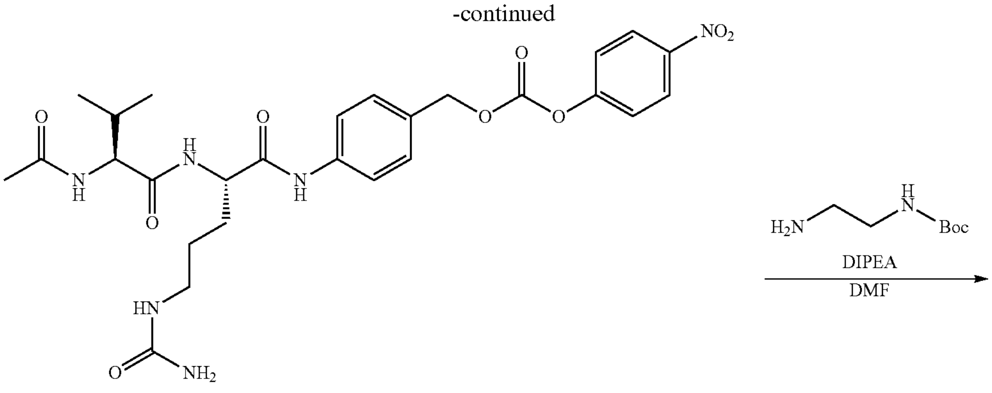

21

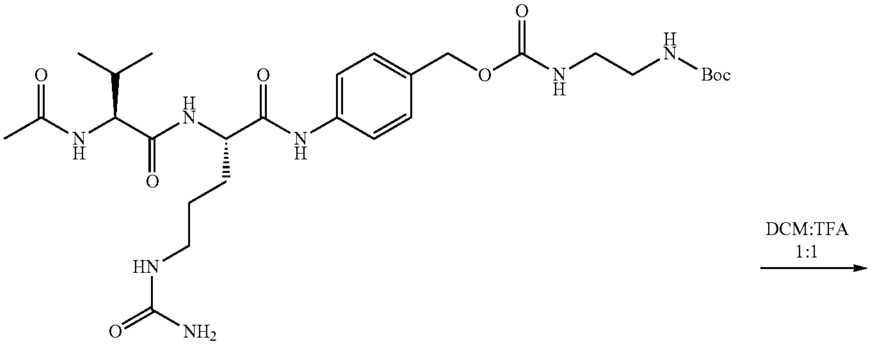

22

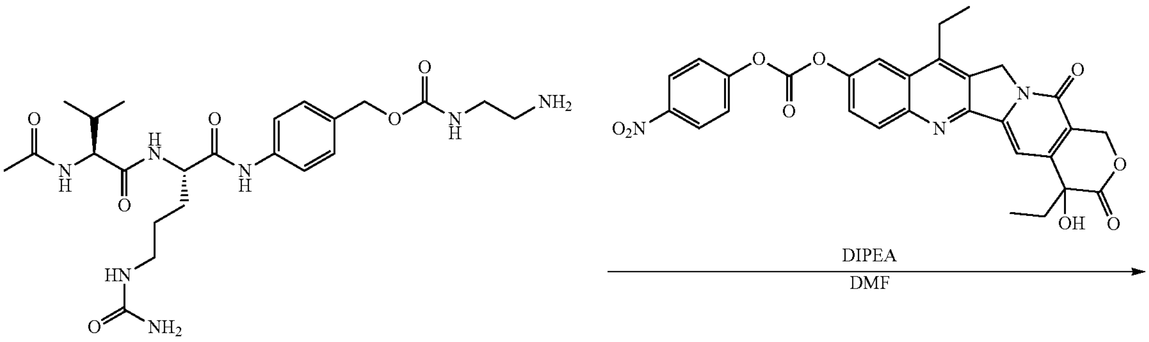

23

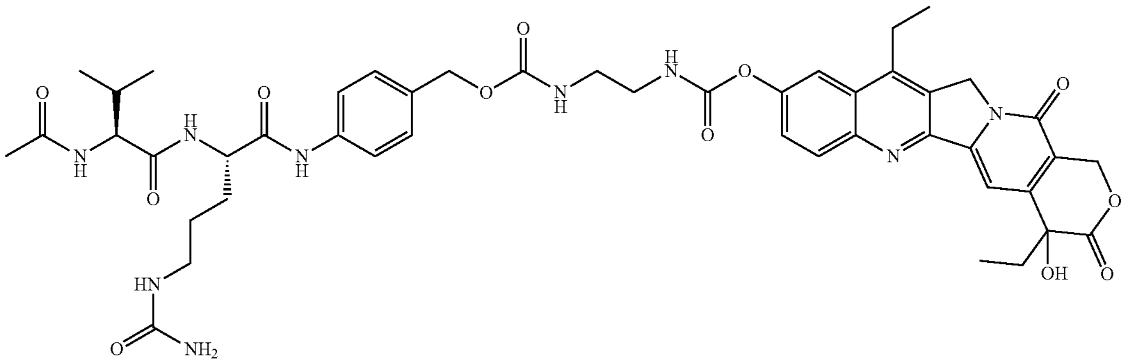

DD3

Synthesis of VC Linker (DD3)

Synthesis of Compound 16

5 g (14.7 mmol, 1.0 eq.) of Fmoc-Val-OH and 1.7 g (14.7 mmol, 1.0 eq.) of N-hydroxysuccinimide (NHS) were dissolved in 140 mL of dimethoxyethane (DME), and stirred. 2.5 mL (16.2 mmol, 1.1 eq.) of N,N'-diisopropylcarbodiimide (DIC) was added dropwise at 0° C., and stirred for 16 hours. The reaction solution was filtered under reduced pressure to remove floating matter, and the filtrate was concentrated under reduced pressure. The residue was dissolved in acetone, and stored at a low temperature for 4 hours in a refrigerator. Thereafter, the resulting solution was filtered under reduced pressure to remove the re-formed floating matter, and used in the next reaction without any purification (crude yield: 5.5 g, 86%). TLC (EA:Hex=1:1); $R_f$=0.5.

Synthesis of Compound 17

2.0 g (11.5 mmol, 1.0 eq.) of L-citrulline was dissolved in 100 mL of a 1:1 mixed solution of tetrahydrofuran (THF) and water, and stirred. 988 mg of sodium hydrogen carbonate was added thereto, and stirred. Thereafter, 5.0 g (11.5 mmol, 1.0 eq.) of Compound 16 was dissolved in 80 mL of acetone, added dropwise to the reaction solution, and then stirred. The resulting mixture was stirred for 21 hours, and then concentrated under reduced pressure to remove the organic solvent. An aqueous layer was washed with ethyl acetate (EA), and then titrated to pH 3 by dropwise addition of 2 N HCl. EA was added thereto so that the precipitate in an organic layer was extracted. Then, the organic layer was dried over a saturated saline solution and sodium sulfate, and used in the next reaction without any purification (crude yield: 5.6 g, 98%). TLC (DCM:MeOH=10:1, one drop of formic acid); $R_f$=0.1.

Synthesis of Compound 18

50 mL of 10% piperidine in N,N-dimethylformamide (DMF) was added dropwise to 2.84 g (5.72 mmol, 1.0 eq.) of Compound 17, and stirred. After 4 hours, the resulting mixture was concentrated under reduced pressure to remove a reaction solution, and the residue was dissolved in water, and filtered under reduced pressure to remove the formed floating matter. An aqueous layer was concentrated to obtain a target compound, which was used in the next reaction without any purification. TLC (DCM:MeOH=10:1); $R_f$=0.01.

Synthesis of Compound 19

54 mg (0.22 mmol, 1.0 eq.) of Compound 18 was dissolved in 2 mL of DMF, and 0.05 mL (0.264 mmol, 1.2 eq.) of N,N-diisopropylethylamine (DIPEA) was added dropwise thereto. Compound 15 was completely dissolved by adding 2 ml of water, and 0.05 mL (0.528 mmol, 2.4 eq.) of an acetic anhydride was added dropwise thereto at room temperature. After 3 hours, the resulting mixture was concentrated under reduced pressure to remove a reaction solution, and the concentrate was purified by reversed-phase column chromatography to obtain a target compound. TLC (DCM:MeOH=10:1); $R_f$=0.05.

Synthesis of Compound 20

1 g (3.16 mmol, 1.0 eq.) of Compound 19 was dissolved in 30 ml of a 2:1 mixed solution of DCM and methanol, and 868 mg (3.48 mmol, 1.1 eq.) of N-ethoxycarbonyl-2-ethoxy-1,2-dihydroquinoline (EEDQ) was added thereto, and stirred. 451 mg (3.66 mmol, 1.16 eq.) of 4-aminobenzyl alcohol was added thereto, and stirred for 5 hours. The resulting mixture was concentrated under reduced pressure to remove a reaction solution, and the concentrate was purified by column chromatography (10% MeOH in DCM) to obtain 419 mg of a target compound (yield: 32%). TLC (DCM:MeOH=10:1); $R_f$=0.1.

Synthesis of Compound 21

240 mg (0.55 mmol, 1.0 eq.) of Compound 20 was dissolved in 10 mL of DMF, and 0.3 mL (1.65 mmol, 3.0 eq.) of DIPEA was added dropwise thereto, and stirred. Thereafter, a reaction was carried out by adding 509 mg (1.65 mmol, 3.0 eq.) of bis-(4-aminophenyl) carbonate. After 3 hours, the resulting mixture was concentrated under reduced pressure to remove a reaction solution, and diethyl ether was added thereto to precipitate a target compound, which was filtered under reduced pressure. The obtained target compound was used in the next reaction without any purification.

Synthesis of Compound 22

33 mg (0.06 mmol, 1.0 eq.) of Compound 21 was dissolved in 5 mL of DMF, and 16 mg (0.08 mmol, 1.3 eq.) of 1-[(tert-butoxycarbonyl)amino]-2-aminoethane and 0.02 mL (0.08 mmol, 1.3 eq.) of DIPEA were added dropwise thereto, and stirred. The resulting mixture was stirred for 7 hours, and then concentrated under reduced pressure to remove a reaction solution, and diethyl ether was added thereto to precipitate a target compound, which was filtered under reduced pressure. The obtained target compound was used in the next reaction without any purification. TLC (DCM:MeOH=10:1); $R_f$=0.1.

Synthesis of Compound 23

17 mg (0.03 mmol, 1.0 eq.) of Compound 22 was dissolved in 1 mL of DCM, and 1 mL of trifluoroacetic acid (TFA) was then added dropwise thereto at 0° C. A reaction was carried out by stirring the resulting mixture at 0° C. for 30 minutes, followed by stirring at room temperature for 30 minutes. Thereafter, the mixture was concentrated under reduced pressure to remove a reaction solution such as DCM, and this concentration was then repeated three times. The concentrated matter was dried under high vacuum, and purified by reversed-phase column chromatography to obtain 13 mg of a target compound. TLC (DCM:MeOH=10:1); $R_f$=0.01.

Synthesis of Compound DD3

0.01 mL (0.04 mmol, 1.5 eq.) of DIPEA was added dropwise to a solution obtained by dissolving 13 mg (0.03 mmol, 1.0 eq.) of Compound 23 in 3 mL of DMF, and 22 mg (0.04 mmol, 1.5 eq.) of phenol-activated SN38 was added thereto. The resulting mixture was stirred for an hour, and then concentrated under reduced pressure to remove a reaction solution. The concentrate was purified by column chromatography (10% MeOH in DCM) to obtain a target compound. TLC (DCM:MeOH=10:1); $R_f$=0.2.

Confirmation of Structure of VC Linker (DD3)

LRMS (ESI): m/z 926.4 [M+H$^+$]

Figure 29:
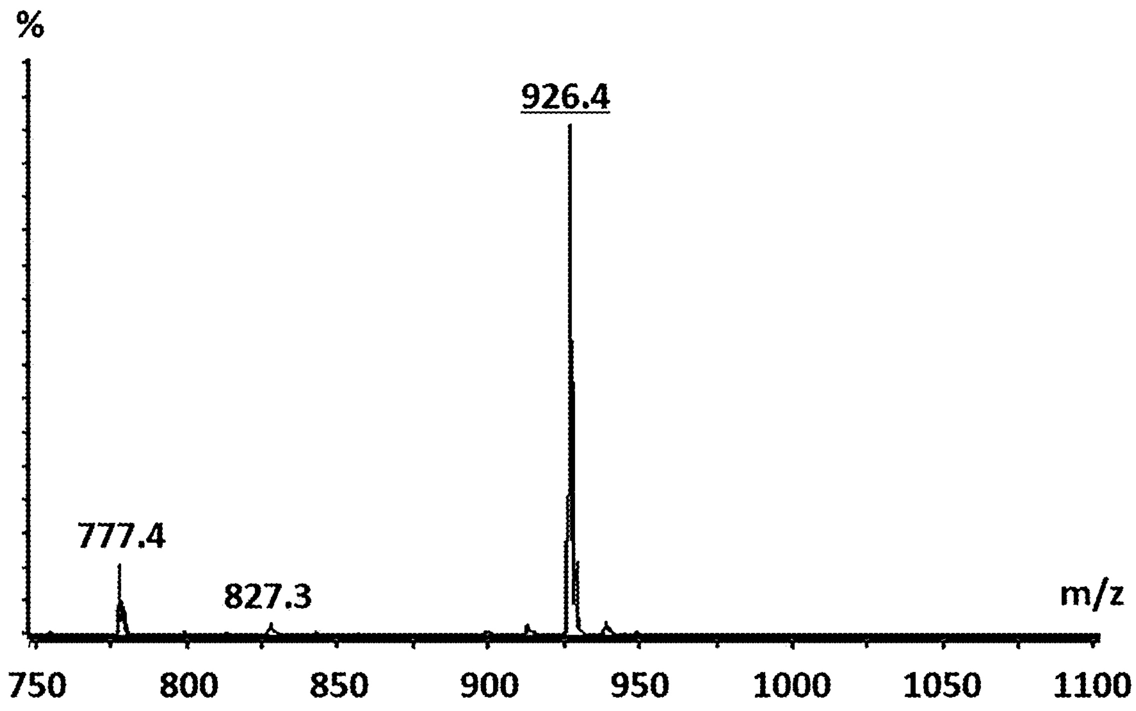
FIG. 29 shows the results of confirming a structure of DD3 by means of mass spectrometry.

The results are shown in FIG. 29.

1.3.3. Synthesis and Confirmation of Structure of VC Linker (DD4)

[Scheme 12] Synthesis of DD4

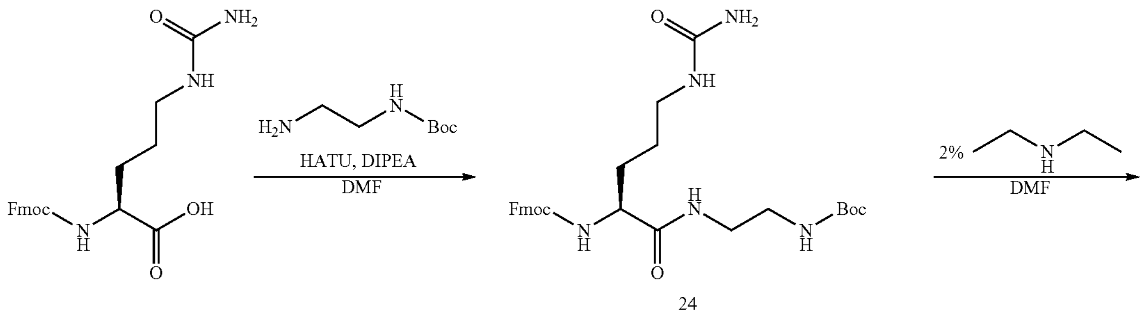

-continued

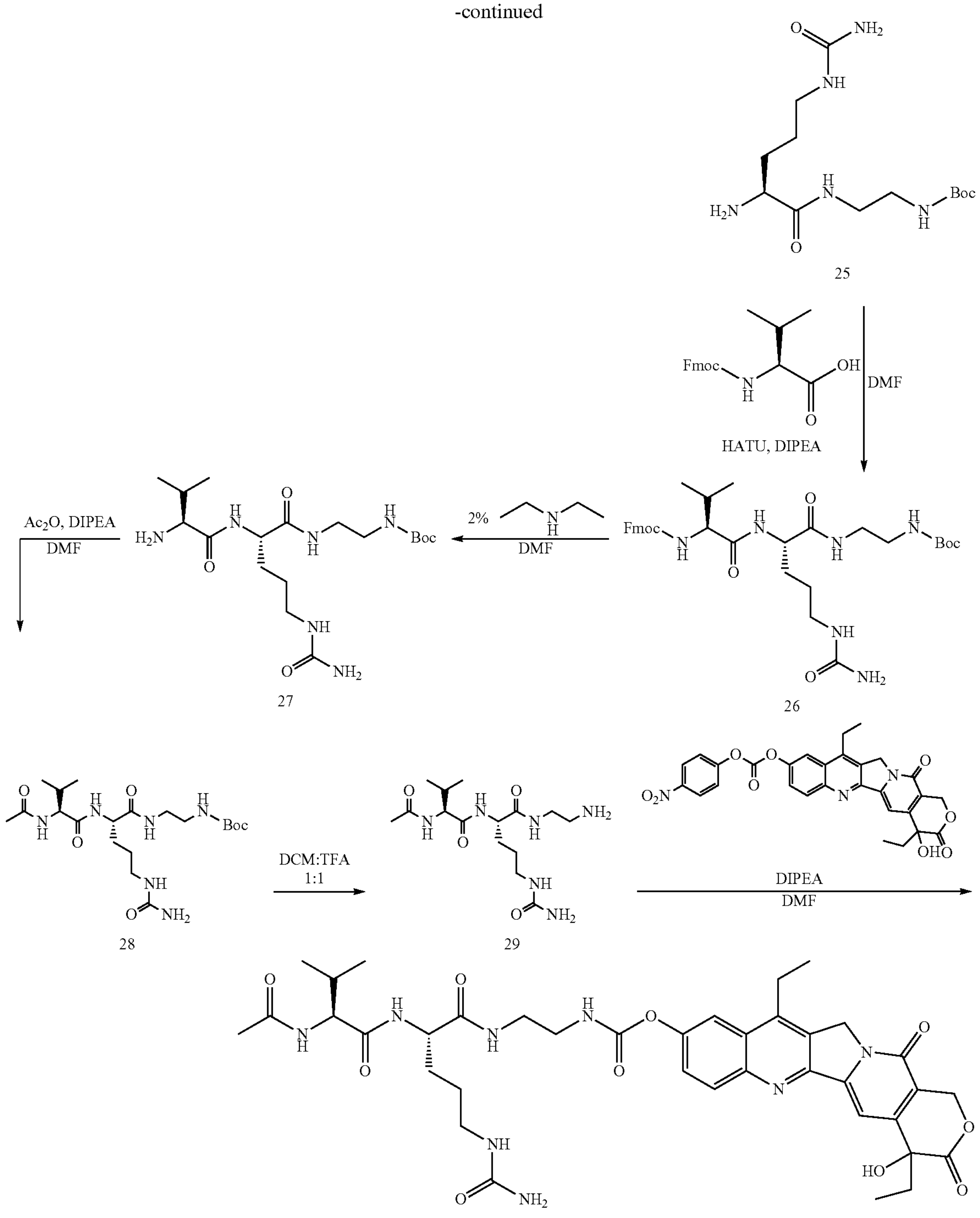

25

26

27

28

29

DD4

Synthesis of VC Linker (DD4)

Synthesis of Compound 24

5 g (14.7 mmol, 1.0 eq.) of Fmoc-Val-OH and 1.7 g (14.7 mmol, 1.0 eq.) of N-hydroxysuccinimide (NHS) were dissolved in 140 ml of dimethoxyethane (DME), and stirred. 2.5 mL (16.2 mmol, 1.1 eq.) of N,N'-diisopropylcarbodiimide (DIC) was added dropwise at 0° C., and stirred for 16 hours. The reaction solution was filtered under reduced pressure to remove floating matter, and the filtrate was concentrated under reduced pressure. The residue was dissolved in acetone, and stored at a low temperature for 4 hours in a refrigerator. Thereafter, the resulting solution was filtered under reduced pressure to remove the re-formed floating matter, and used in the next reaction without any purification (crude yield: 5.5 g, 86%). TLC (EA:Hex=1:1); $R_f$=0.5.

Synthesis of Compound 25

2.0 g (11.5 mmol, 1.0 eq.) of L-citrulline was dissolved in 100 ml of a 1:1 mixed solution of tetrahydrofuran (THF) and water, and stirred. 988 mg of sodium hydrogen carbonate was added thereto, and stirred. Thereafter, 5.0 g of Compound 21 (11.5 mmol, 1.0 eq.) was dissolved in 80 mL of acetone, added dropwise to the reaction solution, and then stirred. The resulting mixture was stirred for 21 hours, and then concentrated under reduced pressure to remove the organic solvent. An aqueous layer was washed with ethyl acetate (EA), and then titrated to pH 3 by slow dropwise addition of 2 N HCl. EA was added thereto so that the precipitate in an organic layer was extracted. Then, the organic layer was dried over a saturated saline solution and sodium sulfate, and used in the next reaction without any purification (crude yield: 5.6 g, 98%). TLC (DCM:MeOH=10:1, one drop of formic acid); $R_f$=0.1.

Synthesis of Compound 26

50 mL of 10% piperidine in N, N-dimethylformamide (DMF) was added dropwise to 2.84 g (5.72 mmol, 1.0 eq.) of Compound 25, and stirred. After 4 hours, the resulting mixture was concentrated under reduced pressure to remove a reaction solution, and the residue was dissolved in water, and filtered under reduced pressure to remove the formed floating matter. An aqueous layer was concentrated to obtain a target compound, which was used in the next reaction without any purification. TLC (DCM:MeOH=10:1); $R_f$=0.01.

Synthesis of Compound 27

54 mg (0.22 mmol, 1.0 eq.) of Compound 26 was dissolved in 2 mL of DMF, and 0.05 mL (0.264 mmol, 1.2 eq.) of N, N-diisopropylethylamine (DIPEA) was added dropwise thereto. Compound 23 was completely dissolved by adding 2 mL of water, and 0.05 mL (0.528 mmol, 2.4 eq.) of an acetic anhydride was added dropwise thereto at room temperature. After 3 hours, the resulting mixture was concentrated under reduced pressure to remove a reaction solution, and the concentrate was purified by reversed-phase column chromatography to obtain a target compound. TLC (DCM:MeOH=10:1); $R_f$=0.05.

Synthesis of Compound 28

300 mg (0.95 mmol, 1.0 eq.) of Compound 27 was dissolved in 6 mL of DMF, and 550 mg (1.43 mmol, 1.5 eq.) of 1-[bis(dimethylamino)methylene]-1H-1,2,3-triazolo[4,5-b]pyridinium 3-oxide hexafluorophosphate (HATU) was then added thereto. Thereafter, 0.25 mL (1.43 mmol, 1.5 eq.) of DIPEA was added dropwise, and 230 mg (1.43 mmol, 1.5 eq.) of 1-[(tert-butoxycarbonyl)amino]-2-aminoethane was dissolved in 3.5 mL of DMF, and added dropwise at room temperature. After 7 hours, the reaction solution was diluted with ethyl acetate (EA), and an organic layer was washed with a saturated sodium hydrogen carbonate solution. Then, the organic layer was dried over a saturated saline solution and sodium sulfate, and filtered to obtain a target compound. The obtained target compound was used in the next reaction without any purification. TLC (DCM:MeOH=10:1); $R_f$=0.5.

Synthesis of Compound 29

Compound 28 was dissolved in a 2:1 mixed solution of DCM and TFA, and a reaction was then carried out at 0° C. Thereafter, the reaction mixture was concentrated under reduced pressure to remove a reaction solution such as DCM, and this concentration was then repeated three times. The residue was dried under high vacuum, and purified by reversed-phase column chromatography to obtain 370 mg of a target compound. TLC (DCM:MeOH=10:1); $R_f$=0.01.

Synthesis of Compound DD4

0.03 mL (0.17 mmol, 1.2 eq.) of DIPEA was added dropwise to a solution obtained by dissolving 50 mg (0.14 mmol, 1.0 eq.) of Compound 26 in 3 mL of DMF, and 107 mg (0.21 mmol, 1.5 eq.) of phenol-activated SN38 was added thereto. The resulting mixture was stirred for an hour, and then concentrated under reduced pressure to remove a reaction solution. The concentrate was purified by column chromatography (10% MeOH in DCM) to obtain a target compound. TLC (DCM:MeOH=10:1); $R_f$=0.1.

Confirmation of Structure of VC Linker (DD4)

LRMS (ESI): m/z 777.3 [M+H$^+$]

Figure 30:
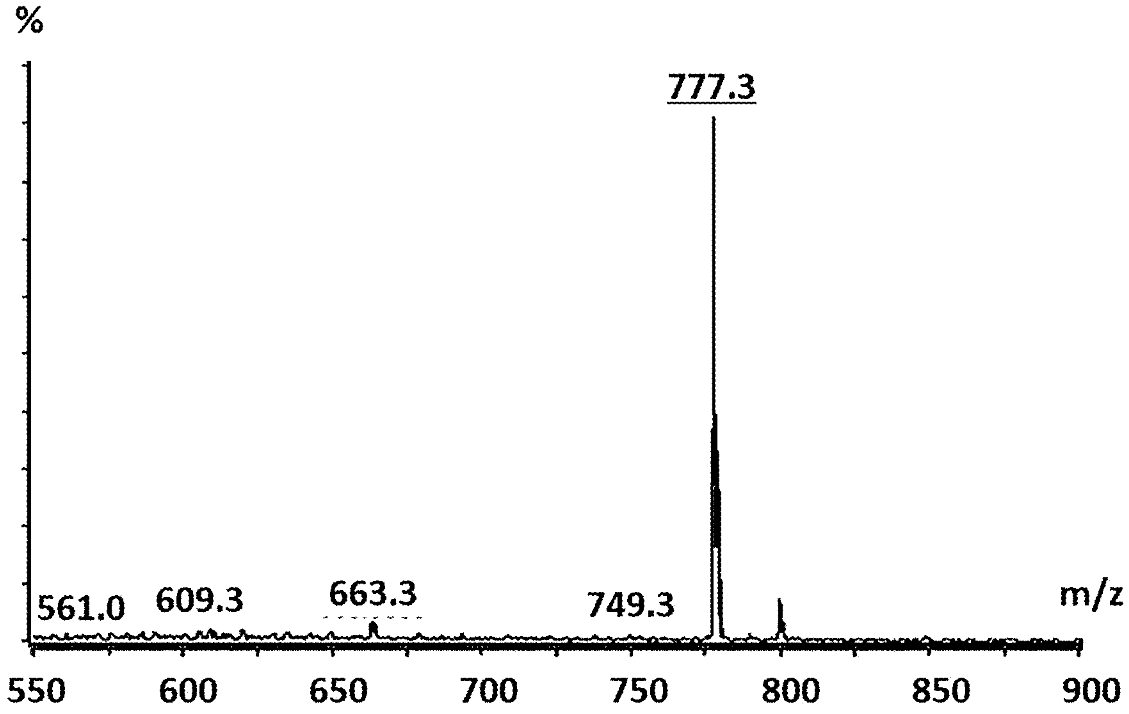
FIG. 30 shows the results of confirming a structure of DD4 by means of mass spectrometry.

The results are shown in FIG. 30.

1.3.4. Synthesis and Confirmation of Structure of VC Linker (DD5)

[Scheme 13] Synthesis of DD5

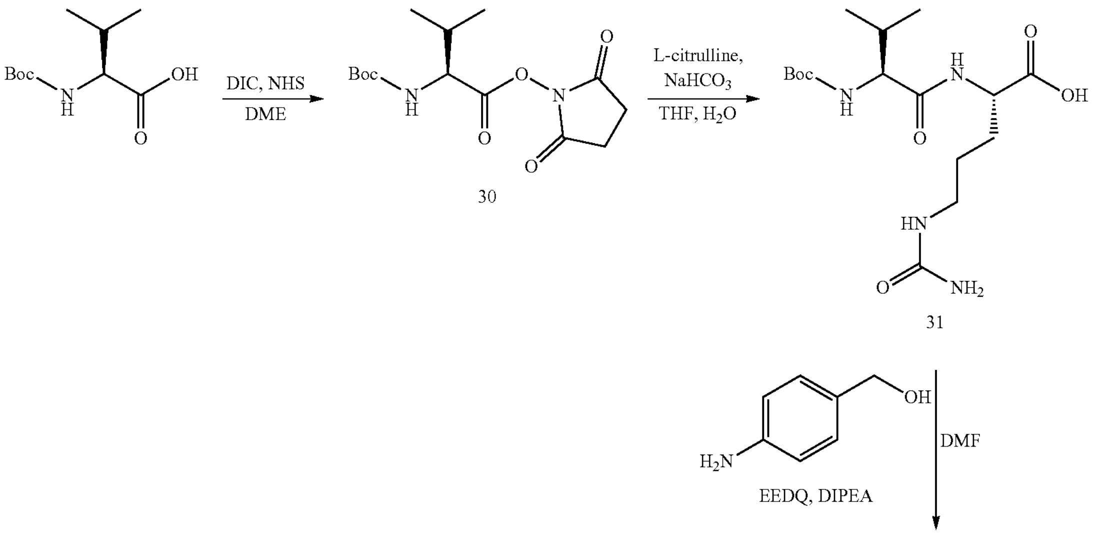

30

31

-continued
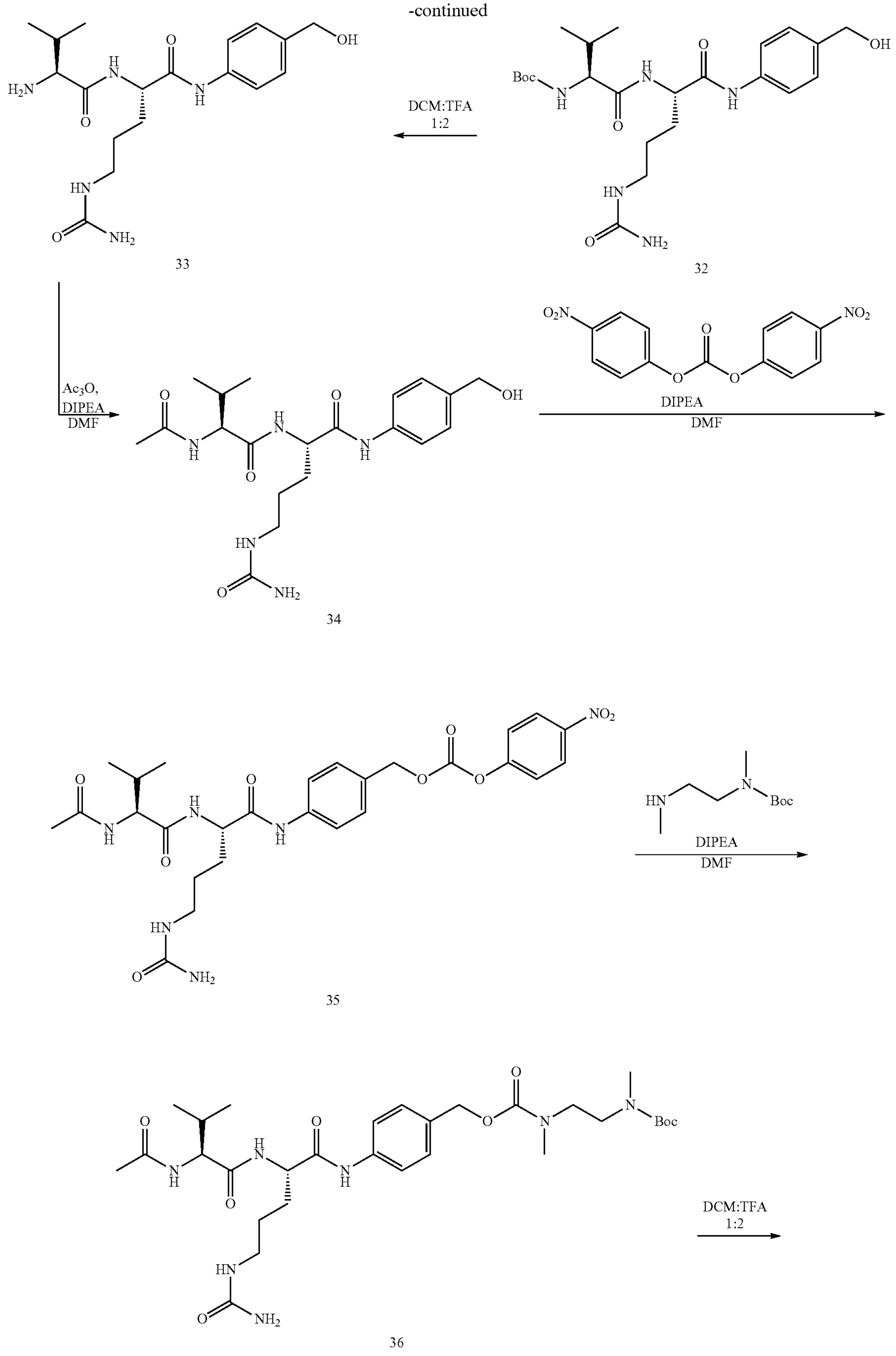

-continued

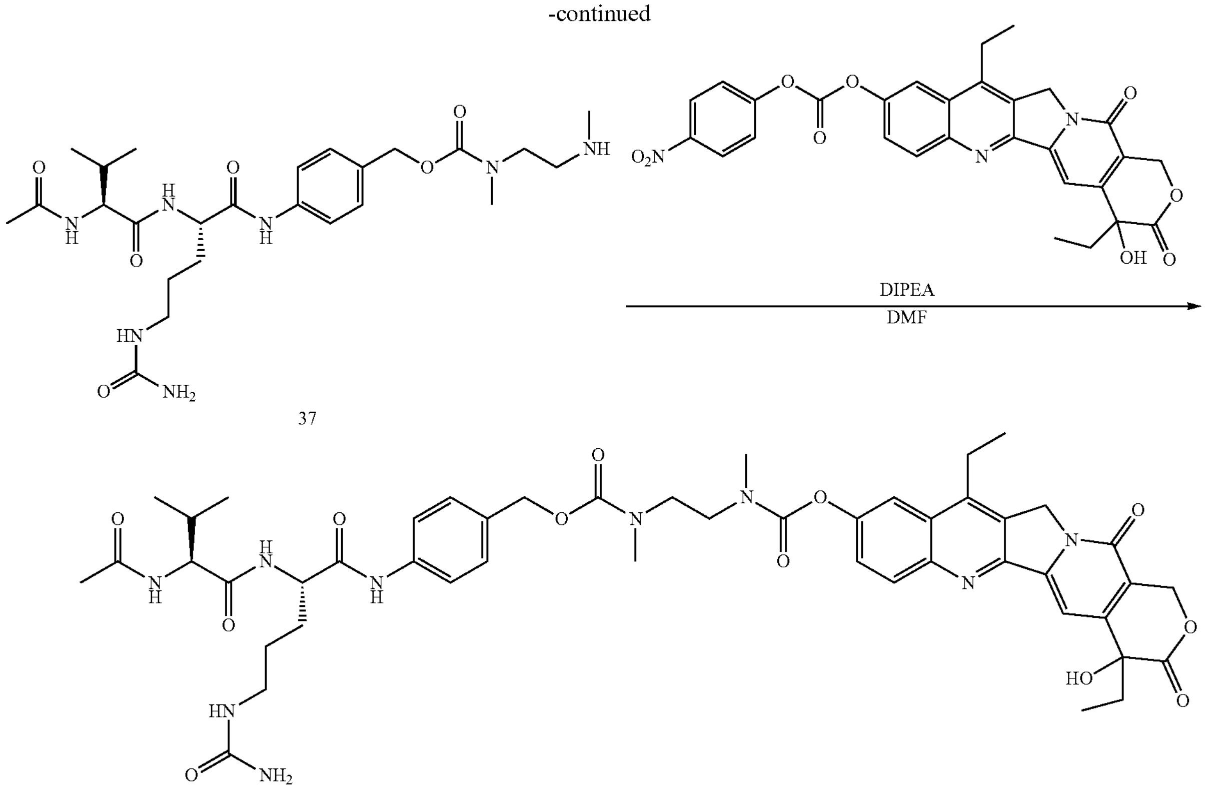

37

DD5

Synthesis of VC Linker (DD5)

Synthesis of Compound 30

5 g (14.7 mmol, 1.0 eq.) of Fmoc-Val-OH and 1.7 g (14.7 mmol, 1.0 eq.) of N-hydroxysuccinimide (NHS) were dissolved in 140 mL of dimethoxyethane (DME), and stirred. 2.5 mL (16.2 mmol, 1.1 eq.) of N,N'-diisopropylcarbodiimide (DIC) was added dropwise at 0° C., and stirred for 16 hours. The reaction solution was filtered under reduced pressure to remove floating matter, and the filtrate was concentrated under reduced pressure. The residue was dissolved in acetone, and stored at a low temperature for 4 hours in a refrigerator. Thereafter, the resulting solution was filtered under reduced pressure to remove the re-formed floating matter, and used in the next reaction without any purification (crude yield: 5.5 g, 86%). TLC (EA:Hex=1:1); $R_f$=0.5.

Synthesis of Compound 31

2.0 g (11.5 mmol, 1.0 eq.) of L-citrulline was dissolved in 100 ml of a 1:1 mixed solution of tetrahydrofuran (THF) and water, and stirred. 988 mg of sodium hydrogen carbonate was added thereto, and stirred. Thereafter, 5.0 g (11.5 mmol, 1.0 eq.) of Compound 30 was dissolved in 80 mL of acetone, added dropwise to the reaction solution, and then stirred. The resulting mixture was stirred for 21 hours, and then concentrated under reduced pressure to remove the organic solvent. An aqueous layer was washed with ethyl acetate (EA), and then titrated to pH 3 by slow dropwise addition of 2 N HCl. EA was added thereto so that the precipitate in an organic layer was extracted. Then, the organic layer was dried over a saturated saline solution and sodium sulfate, and used in the next reaction without any purification (crude yield: 5.6 g, 98%). TLC (DCM:MeOH=10:1, one drop of formic acid); $R_f$=0.1.

Synthesis of Compound 32

50 mL of 10% piperidine in N, N-dimethylformamide (DMF) was added dropwise to 2.84 g (5.72 mmol, 1.0 eq.) of Compound 31, and stirred. After 4 hours, the resulting mixture was concentrated under reduced pressure to remove a reaction solution, and the residue was dissolved in water, and filtered under reduced pressure to remove the formed floating matter. An aqueous layer was concentrated to obtain a target compound, which was used in the next reaction without any purification. TLC (DCM:MeOH=10:1); $R_f$=0.01.

Synthesis of Compound 33

54 mg (0.22 mmol, 1.0 eq.) of Compound 29 was dissolved in 2 mL of DMF, and 0.05 mL (0.264 mmol, 1.2 eq.) of N,N-diisopropylethylamine (DIPEA) was added dropwise thereto. Compound 32 was completely dissolved by adding 2 mL of water, and 0.05 mL (0.528 mmol, 2.4 eq.) of an acetic anhydride was added dropwise thereto at room temperature. After 3 hours, the resulting mixture was concentrated under reduced pressure to remove a reaction solution, and the concentrate was purified by reversed-phase column chromatography to obtain a target compound. TLC (DCM:MeOH=10:1); $R_f$=0.05.

Synthesis of Compound 34

1 g (3.16 mmol, 1.0 eq.) of Compound 33 was dissolved in 30 ml of a 2:1 mixed solution of DCM and methanol, and 868 mg (3.48 mmol, 1.1 eq.) of N-ethoxycarbonyl-2-ethoxy-1,2-dihydroquinoline (EEDQ) was added thereto, and stirred. 451 mg (3.66 mmol, 1.16 eq.) of 4-aminobenzyl alcohol was added thereto, and stirred for 5 hours. The resulting mixture was concentrated under reduced pressure to remove a reaction solution, and the concentrate was purified by column chromatography (10% MeOH in DCM) to obtain 419 mg of a target compound (yield: 32%). TLC (DCM:MeOH=10:1); $R_f$=0.1.

Synthesis of Compound 35

240 mg (0.55 mmol, 1.0 eq.) of Compound 34 was dissolved in 10 mL of DMF, and 0.3 mL (1.65 mmol, 3.0 eq.) of DIPEA was added dropwise thereto, and stirred. Thereafter, a reaction was carried out by adding 509 mg (1.65 mmol, 3.0 eq.) of bis-(4-aminophenyl) carbonate. After 3 hours, the resulting mixture was concentrated under reduced pressure to remove a reaction solution, and diethyl ether was added thereto to precipitate a target compound, which was filtered under reduced pressure. The obtained target compound was used in the next reaction without any purification.

Synthesis of Compound 36

33 mg (0.06 mmol, 1.0 eq.) of Compound 35 was dissolved in 5 mL of DMF, and 16 mg (0.08 mmol, 1.3 eq.) of N-[(tert-butoxy) carbonyl]-N, N'-dimethylethylenediamine and 0.02 mL (0.08 mmol, 1.3 eq.) of DIPEA were added dropwise thereto, and stirred. The resulting mixture was stirred for 7 hours, and then concentrated under reduced pressure to remove a reaction solution, and diethyl ether was added thereto to precipitate a target compound, which was filtered under reduced pressure. The obtained target compound was used in the next reaction without any purification. TLC (DCM:MeOH=10:1); $R_f$=0.1.

Synthesis of Compound 37

17 mg (0.03 mmol, 1.0 eq.) of Compound 36 was dissolved in 1 mL of DCM, and 1 mL of trifluoroacetic acid (TFA) was then added dropwise thereto at 0° C. A reaction was carried out by stirring the resulting mixture at 0° C. for 30 minutes, followed by stirring at room temperature for 30 minutes. Thereafter, the mixture was concentrated under reduced pressure to remove a reaction solution such as DCM, and this concentration was then repeated three times. The concentrated matter was dried under high vacuum, and purified by reversed-phase column chromatography to obtain 13 mg of a target compound. TLC (DCM:MeOH=10:1); $R_f$=0.01.

Synthesis of Compound DD5

0.01 mL (0.04 mmol, 1.5 eq.) of DIPEA was added dropwise to a solution obtained by dissolving 13 mg (0.03 mmol, 1.0 eq.) of Compound 37 in 3 mL of DMF, and 22 mg (0.04 mmol, 1.5 eq.) of phenol-activated SN38 was added thereto. The resulting mixture was stirred for an hour, and then concentrated under reduced pressure to remove a reaction solution. The concentrate was purified by column chromatography (10% MeOH in DCM) to obtain a target compound. TLC (DCM:MeOH=10:1); $R_f$=0.2.

3-4-2: Confirmation of Structure of VC Linker (DD5)

LRMS (ESI): m/z 954.4 [M+H$^+$]

Figure 31:
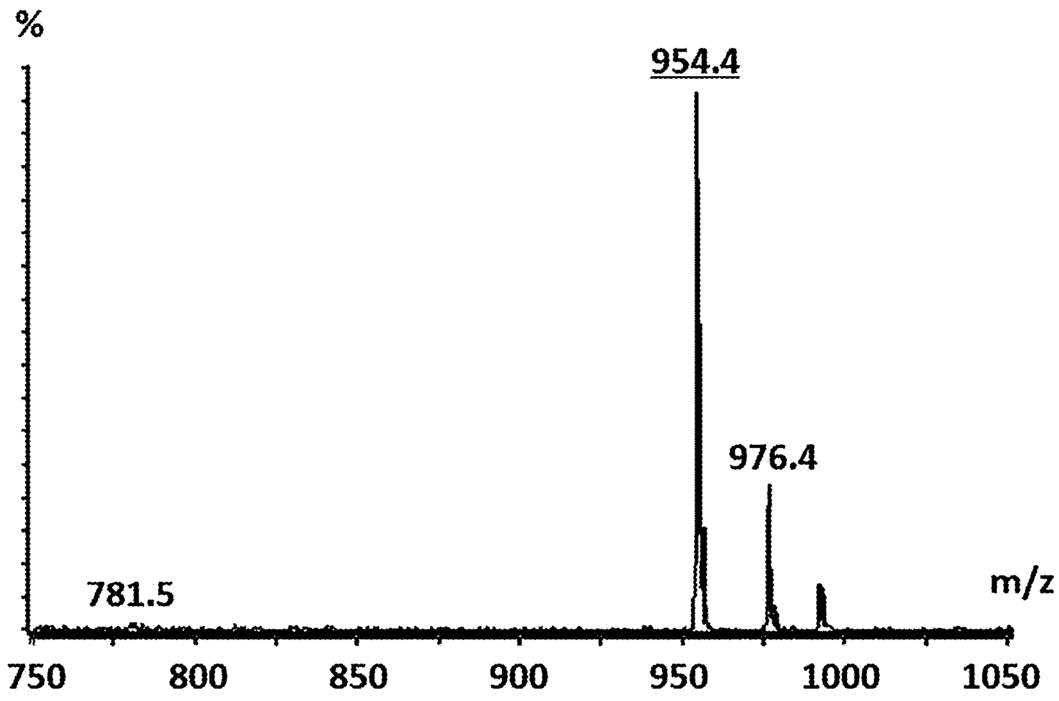
FIG. 31 shows the results of confirming a structure of DD5 by means of mass spectrometry.

The results are shown in FIG. 31.

1.3.5. Synthesis and Confirmation of Structure of VC Linker (DD6)

[Scheme 14]

Synthesis of DD6

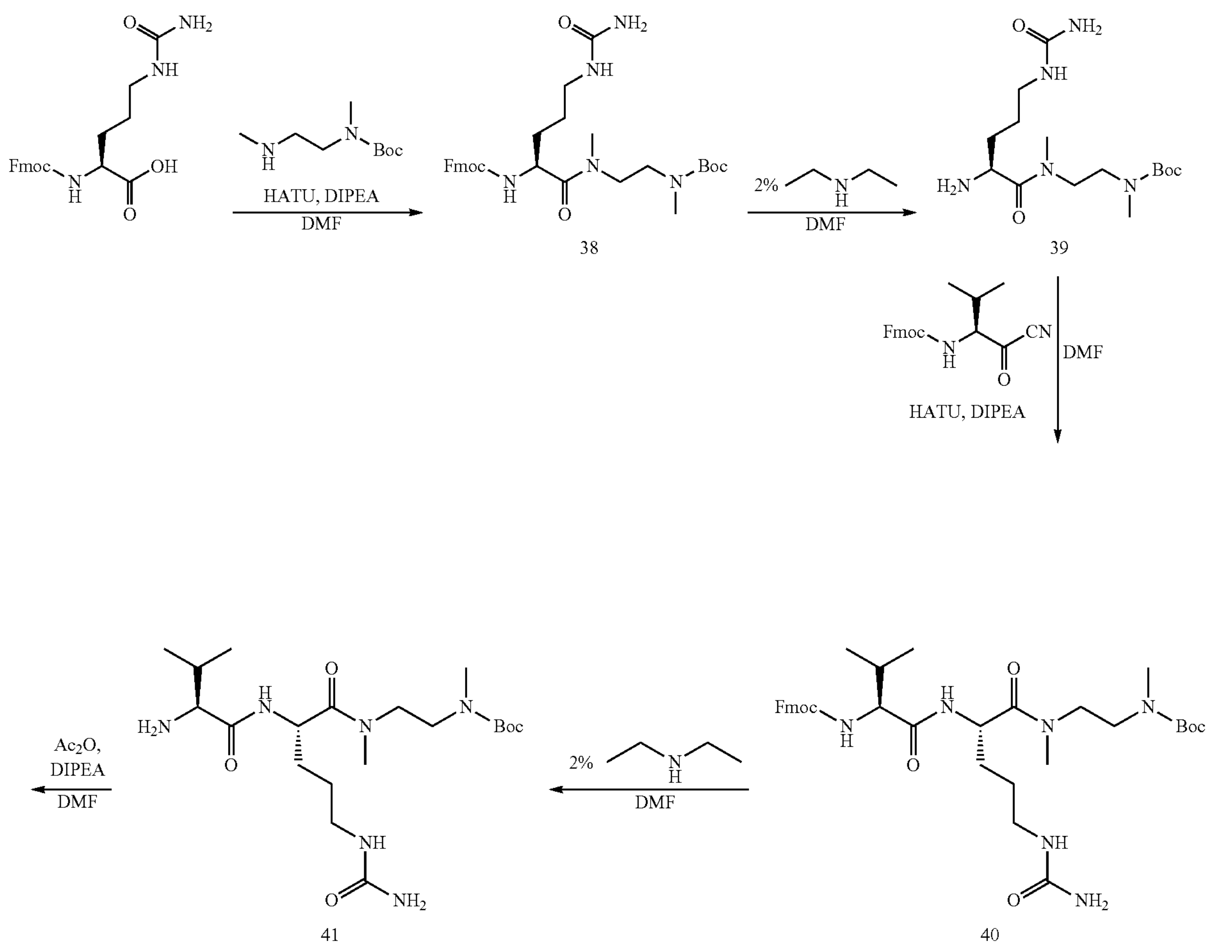

-continued

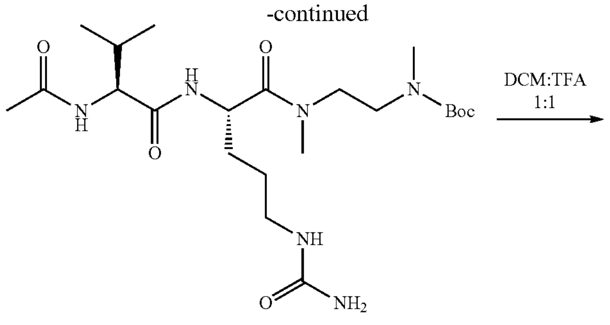

42

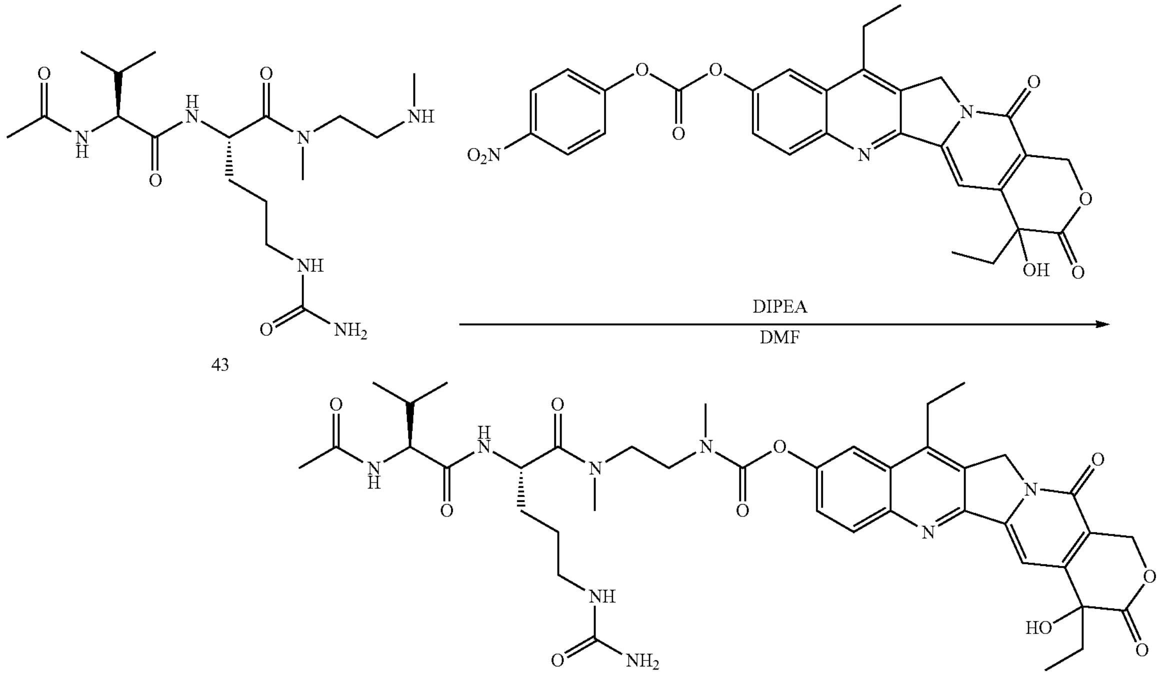

43

DD6

Synthesis of VC Linker (DD6)

Synthesis of Compound 38

5 g (14.7 mmol, 1.0 eq.) of Fmoc-Val-OH and 1.7 g (14.7 mmol, 1.0 eq.) of N-hydroxysuccinimide (NHS) were dissolved in 140 mL of dimethoxyethane (DME), and stirred. 2.5 mL (16.2 mmol, 1.1 eq.) of N,N'-diisopropylcarbodiimide (DIC) was added dropwise at 0° C., and stirred for 16 hours. The reaction solution was filtered under reduced pressure to remove floating matter, and the filtrate was concentrated under reduced pressure. The residue was dissolved in acetone, and stored at a low temperature for 4 hours in a refrigerator. Thereafter, the resulting solution was filtered under reduced pressure to remove the re-formed floating matter, and used in the next reaction without any purification (crude yield: 5.5 g, 86%). TLC (EA:Hex=1:1); $R_f$=0.5.

Synthesis of Compound 39

2.0 g (11.5 mmol, 1.0 eq.) of L-citrulline was dissolved in 100 ml of a 1:1 mixed solution of tetrahydrofuran (THF) and water, and stirred. 988 mg of sodium hydrogen carbonate was added thereto, and stirred. Thereafter, 5.0 g (11.5 mmol, 1.0 eq.) of Compound 38 was dissolved in 80 mL of acetone, added dropwise to the reaction solution, and then stirred. The resulting mixture was stirred for 21 hours, and then concentrated under reduced pressure to remove the organic solvent. An aqueous layer was washed with ethyl acetate (EA), and then titrated to pH 3 by slow dropwise addition of 2 N HCl. EA was added thereto so that the precipitate in an organic layer was extracted. Then, the organic layer was dried over a saturated saline solution and sodium sulfate, and used in the next reaction without any purification (crude yield: 5.6 g, 98%). TLC (DCM:MeOH=10:1, one drop of formic acid); Rt=0.1.

Synthesis of Compound 40

50 mL of 10% piperidine in N,N-dimethylformamide (DMF) was added dropwise to 2.84 g (5.72 mmol, 1.0 eq.) of Compound 39, and stirred. After 4 hours, the resulting mixture was concentrated under reduced pressure to remove a reaction solution, and the residue was dissolved in water, and filtered under reduced pressure to remove the formed floating matter. An aqueous layer was concentrated to obtain a target compound, which was used in the next reaction without any purification. TLC (DCM:MeOH=10:1); $R_f$=0.01.

Synthesis of Compound 41

54 mg (0.22 mmol, 1.0 eq.) of Compound 40 was dissolved in 2 mL of DMF, and 0.05 mL (0.264 mmol, 1.2 eq.) of N,N-diisopropylethylamine (DIPEA) was added dropwise thereto. Compound 37 was completely dissolved by adding 2 ml of water, and 0.05 mL (0.528 mmol, 2.4 eq.) of an acetic anhydride was added dropwise thereto at room temperature. After 3 hours, the resulting mixture was concentrated under reduced pressure to remove a reaction solution, and the concentrate was purified by reversed-phase column chromatography to obtain a target compound. TLC (DCM:MeOH=10:1); $R_f$=0.05.

Synthesis of Compound 42

300 mg (0.95 mmol, 1.0 eq.) of Compound 41 was dissolved in 6 mL of DMF, and 550 mg (1.43 mmol, 1.5 eq.) of 1-[bis(dimethylamino)methylene]-1H-1,2,3-triazolo[4,5-b]pyridinium 3-oxide hexafluorophosphate (HATU) was then added thereto. Thereafter, 0.25 mL (1.43 mmol, 1.5 eq.) of DIPEA was added dropwise, and 230 mg (1.43 mmol, 1.5 eq.) of N-[(tert-butoxy) carbonyl]-N, N'-dimethylethylenediamine was dissolved in 3.5 mL of DMF, and added dropwise at room temperature. After 7 hours, the reaction solution was diluted with ethyl acetate (EA), and an organic layer was washed with a saturated sodium hydrogen carbonate solution. Then, the organic layer was dried over a saturated saline solution and sodium sulfate, and filtered to obtain a target compound. The obtained target compound was used in the next reaction without any purification. TLC (DCM:MeOH=10:1); $R_f$=0.5.

Synthesis of Compound 43

Compound 42 was dissolved in a 2:1 mixed solution of DCM and TFA, and a reaction was then carried out at 0° C. Thereafter, the reaction mixture was concentrated under reduced pressure to remove a reaction solution such as DCM, and this concentration was then repeated three times. The residue was dried under high vacuum, and purified by reversed-phase column chromatography to obtain 370 mg of a target compound. TLC (DCM:MeOH=10:1); $R_f$=0.01.

Synthesis of Compound DD6

0.03 mL (0.17 mmol, 1.2 eq.) of DIPEA was added dropwise to a solution obtained by dissolving 50 mg (0.14 mmol, 1.0 eq.) of Compound 43 in 3 mL of DMF, and 107 mg (0.21 mmol, 1.5 eq.) of phenol-activated SN38 was added thereto. The resulting mixture was stirred for an hour, and then concentrated under reduced pressure to remove a reaction solution. The concentrate was purified by column chromatography (10% MeOH in DCM) to obtain a target compound. TLC (DCM:MeOH=10:1); $R_f$=0.1.

Confirmation of Structure of VC Linker (DD6)

LRMS (ESI): m/z 805.5 $[M+H^+]$

Figure 32:
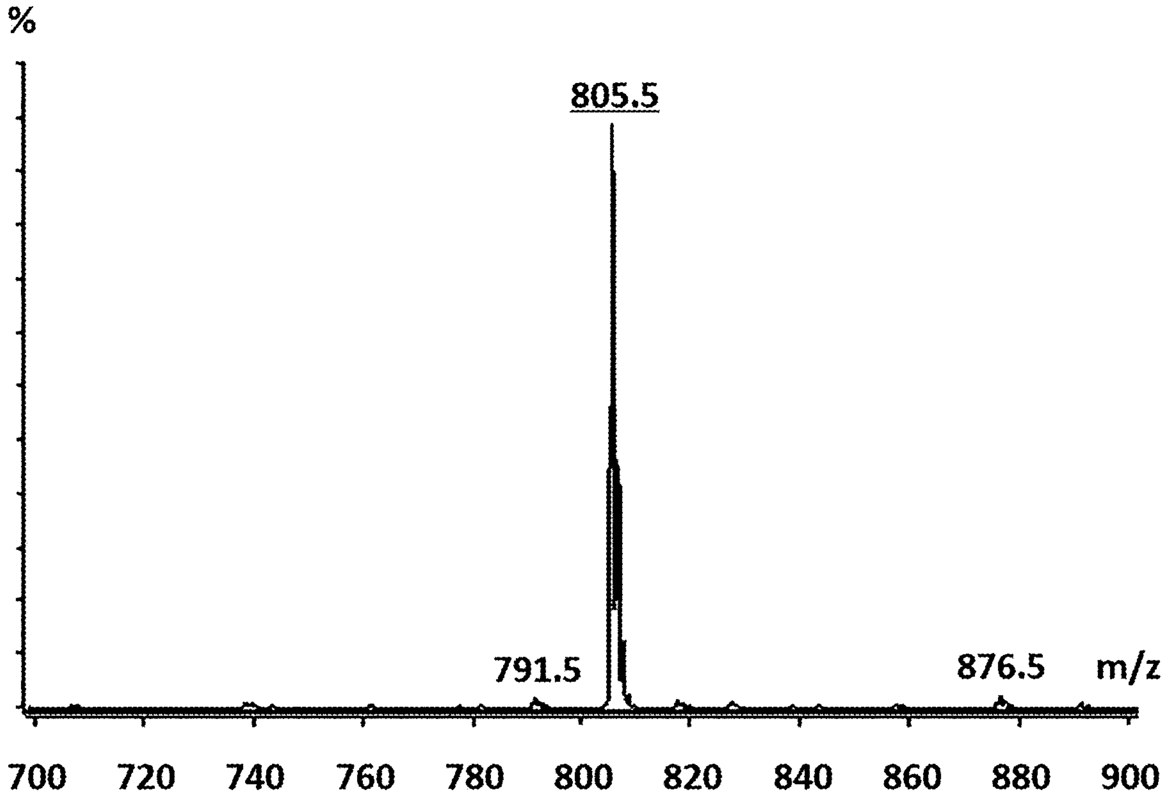
FIG. 32 shows the results of confirming a structure of DD6 by means of mass spectrometry.

The results are shown in FIG. 32.

2. Preparation of Agent for Transferring Site-Specific First Click-Chemistry Functional Group to Antibody ($H_1$-$L_2$-SSFI)

2.1. Synthesis and Confirmation of Structure of Compound I-SSFI (where $Xa_1$ is Lysine)

I-FcBP(6Lys)
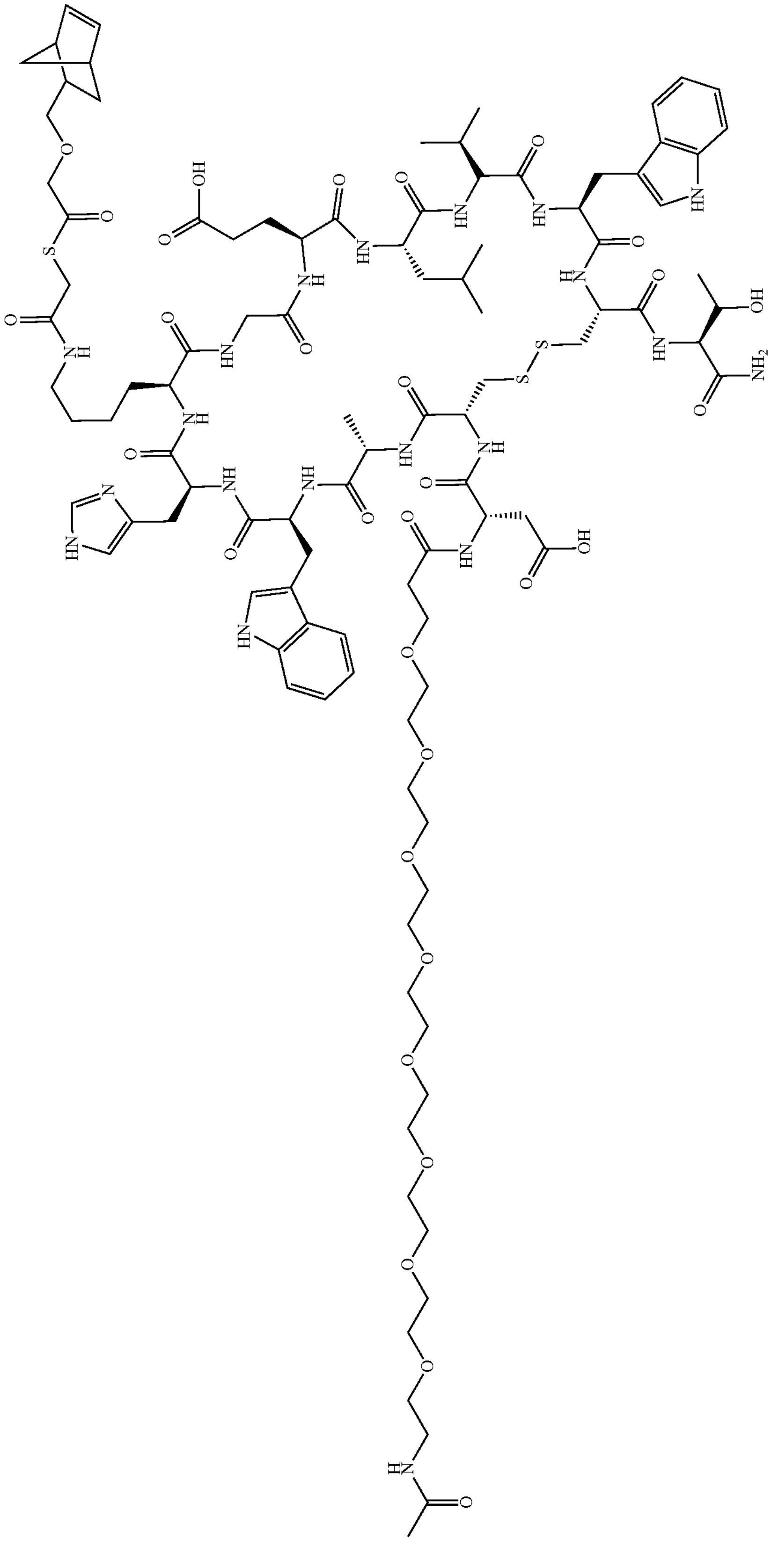
Exact Mass: 2264.99

Synthesis Method of Compound I-SSFI (Lys)

Synthesis of Compound I-SSFI was carried out in DMF, and 3 equivalents of DIPEA and 8.4 μmol of Compound I were dissolved in 7.3 μmol of SSFI, and stirred to introduce Compound I into SSFI.

After the termination of the reaction was confirmed, the reaction solution was concentrated, and purification of Compound I-SSFI by preparative-HPLC was attempted. After the purification, the Compound I-SSFI was freeze-dried to obtain a target compound, the amount of which was confirmed to be 12 mg (purity: >95% up (HPLC), and yield: 71%).

Confirmation of Structure of Compound I-SSFI

Measuring equipment: Waters Quattro Premier Xe

Calculated molecular weight: 2246.99 g/mol

Measured molecular weight $(M/2+H)^{2+}$: 1124.90 g/mol

Figure 33:
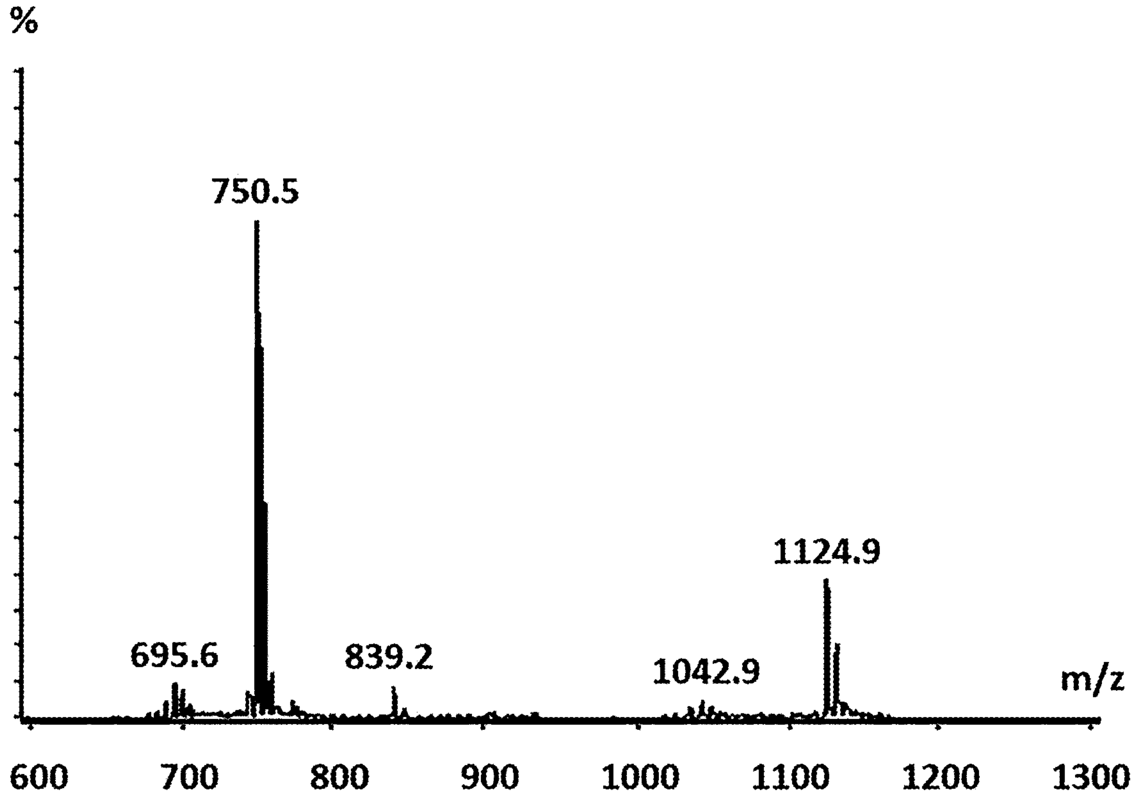
FIG. 33 shows the results of confirming a structure of Compound I-SSFI (6Lys) by means of mass spectrometry.

The results are shown in FIG. 33.

2.2. Synthesis and Confirmation of Structure of Compound II-SSFI (Wherein $Xa_1$ is Lysine)

II-FcBP(6Lys)
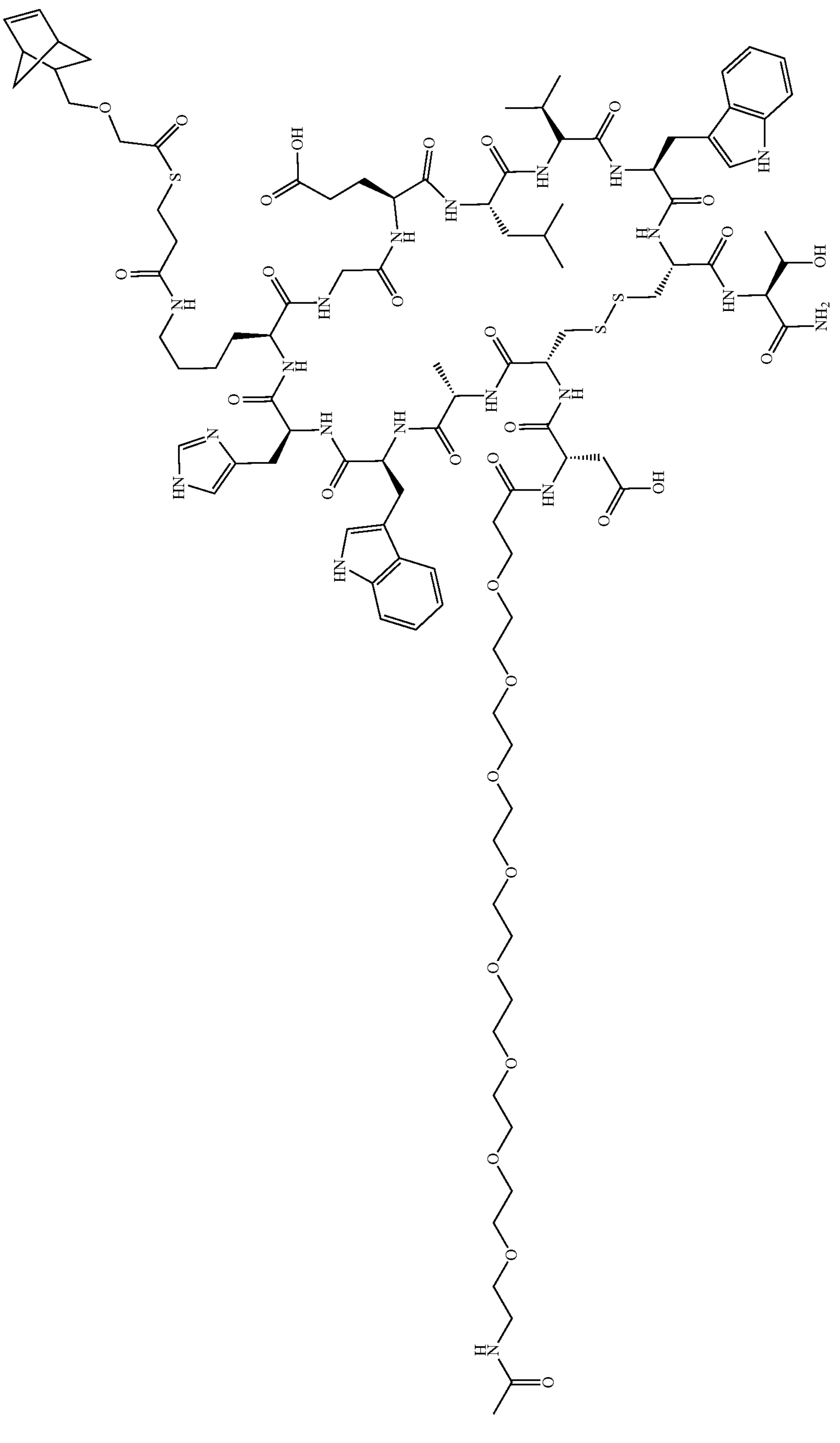
Exact Mass: 2261.01

Synthesis Method of Compound II-SSFI (Lys)

Synthesis of Compound II-SSFI was carried out in DMF, and 3 equivalents of DIPEA and 8.4 μmol of Compound II were dissolved in 7.3 μmol of SSFI, and stirred to introduce Compound II into SSFI.

After the termination of the reaction was confirmed, the reaction solution was concentrated, and purification of Compound II-SSFI by preparative-HPLC was attempted. After the purification, the Compound II-SSFI was freeze-dried to obtain a target compound, the amount of which was confirmed to be 13 mg (purity: >95% up (HPLC), and yield: 78%).

Confirmation of Structure of Compound II-SSFI (Lys)

Measuring equipment: Ultraflextreme (Bruker)

Measuring matrix: CHCA (α-Cyano-4-hydroxycinnamic acid) & DHB (2,5-Dihydroxybenzoic acid)

Calculated molecular weight: 2261.01 g/mol

Measured molecular weight $(M/2+H)^{2+}$: 2263.26 g/mol

Figure 34:
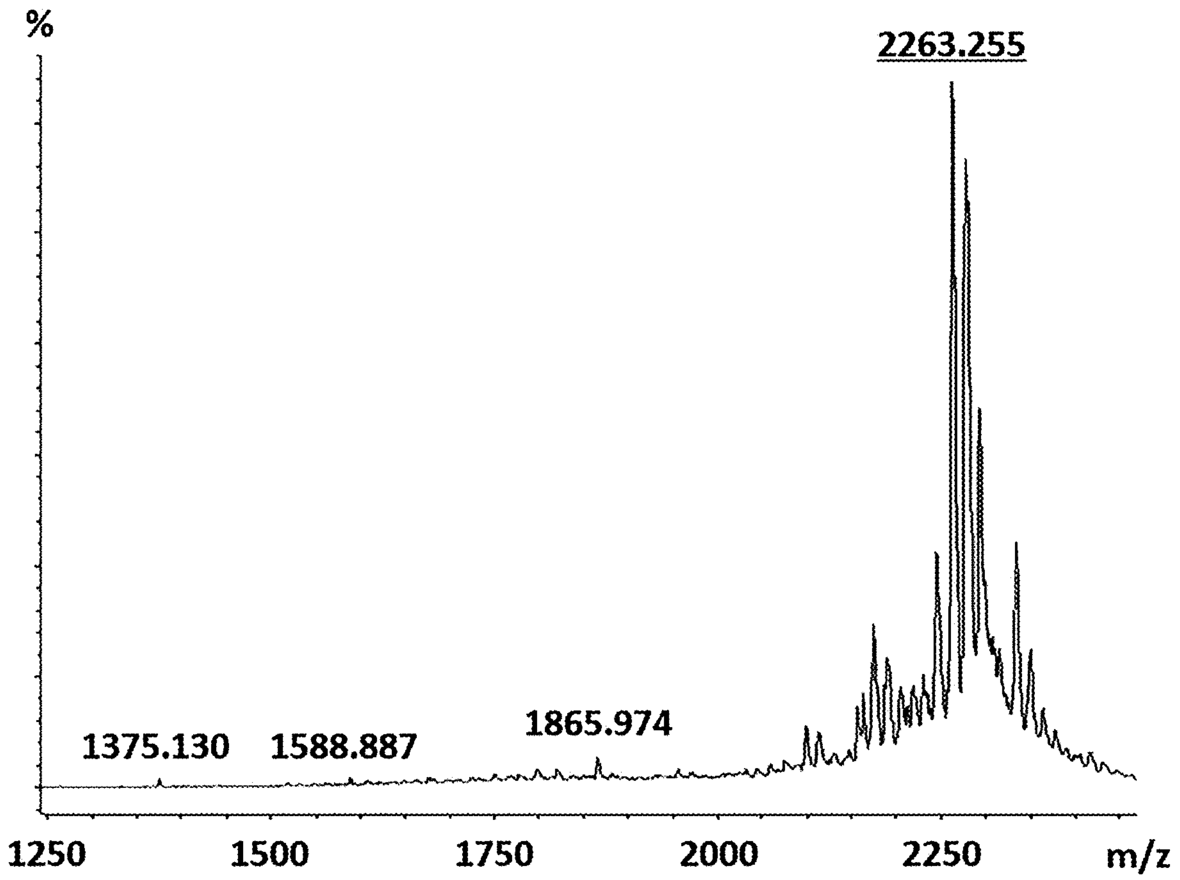
FIG. 34 shows the results of confirming a structure of Compound II-SSFI (6Lys) by means of mass spectrometry.

The results are shown in FIG. 34.

2.3. Synthesis and Confirmation of Structure of Compound III-SSFI (Wherein $Xa_1$ is Lysine)

III-FcBP(6Lys)
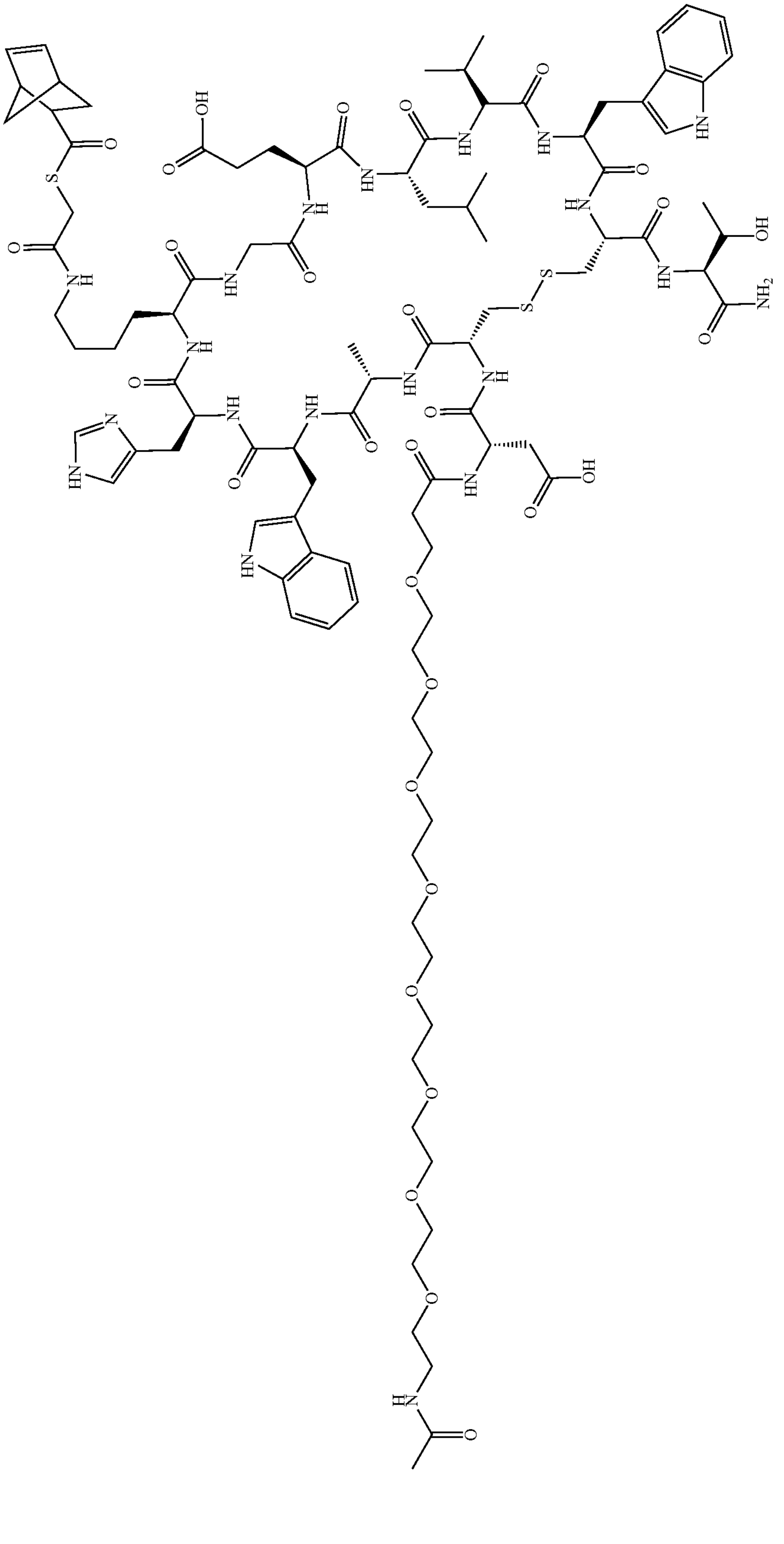
Exact Mass: 2202.97

Synthesis Method of Compound III-SSFI (Lys)

Synthesis of Compound III-SSFI was carried out in DMF, and 3 equivalents of DIPEA and 8.4 μmol of Compound Ill were dissolved in 7.3 μmol of SSFI, and stirred to introduce Compound III into SSFI.

After the termination of the reaction was confirmed, the reaction solution was concentrated, and purification of Compound III-SSFI by preparative-HPLC was attempted. After the purification, the Compound III-SSFI was freeze-dried to obtain a target compound, the amount of which was confirmed to be 12 mg (purity: >95% up (HPLC), and yield: 75%).

Confirmation of Structure of Compound III-SSFI (Lys)

Measuring equipment: Waters Quattro Premier Xe

Calculated molecular weight: 2202.97 g/mol

Measured molecular weight $(M/2+H)^{2+}$: 1103.64 g/mol

Figure 35:
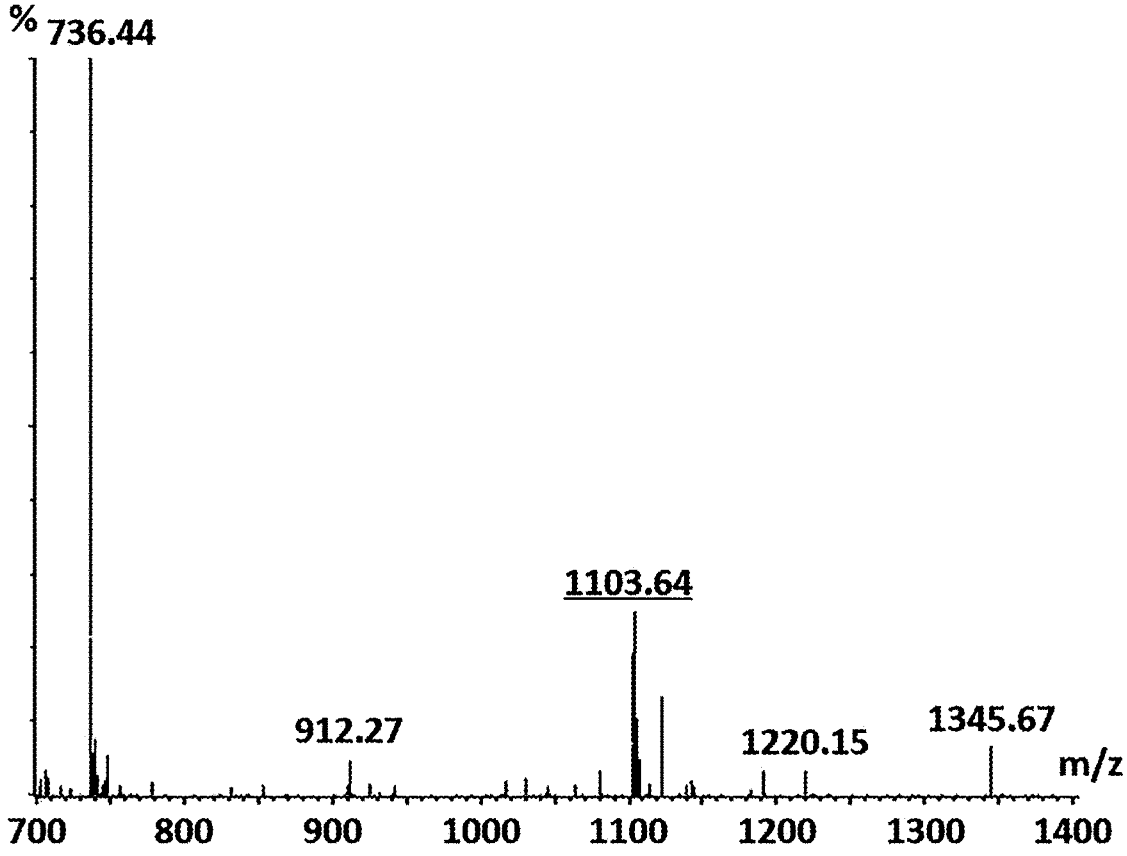
FIG. 35 shows the results of confirming a structure of Compound III-SSFI (6Lys) by means of mass spectrometry.

The results are shown in FIG. 35.

2.4. Synthesis and Confirmation of Structure of Compound III-SSFI (Wherein $Xa_1$ is Ornithine)

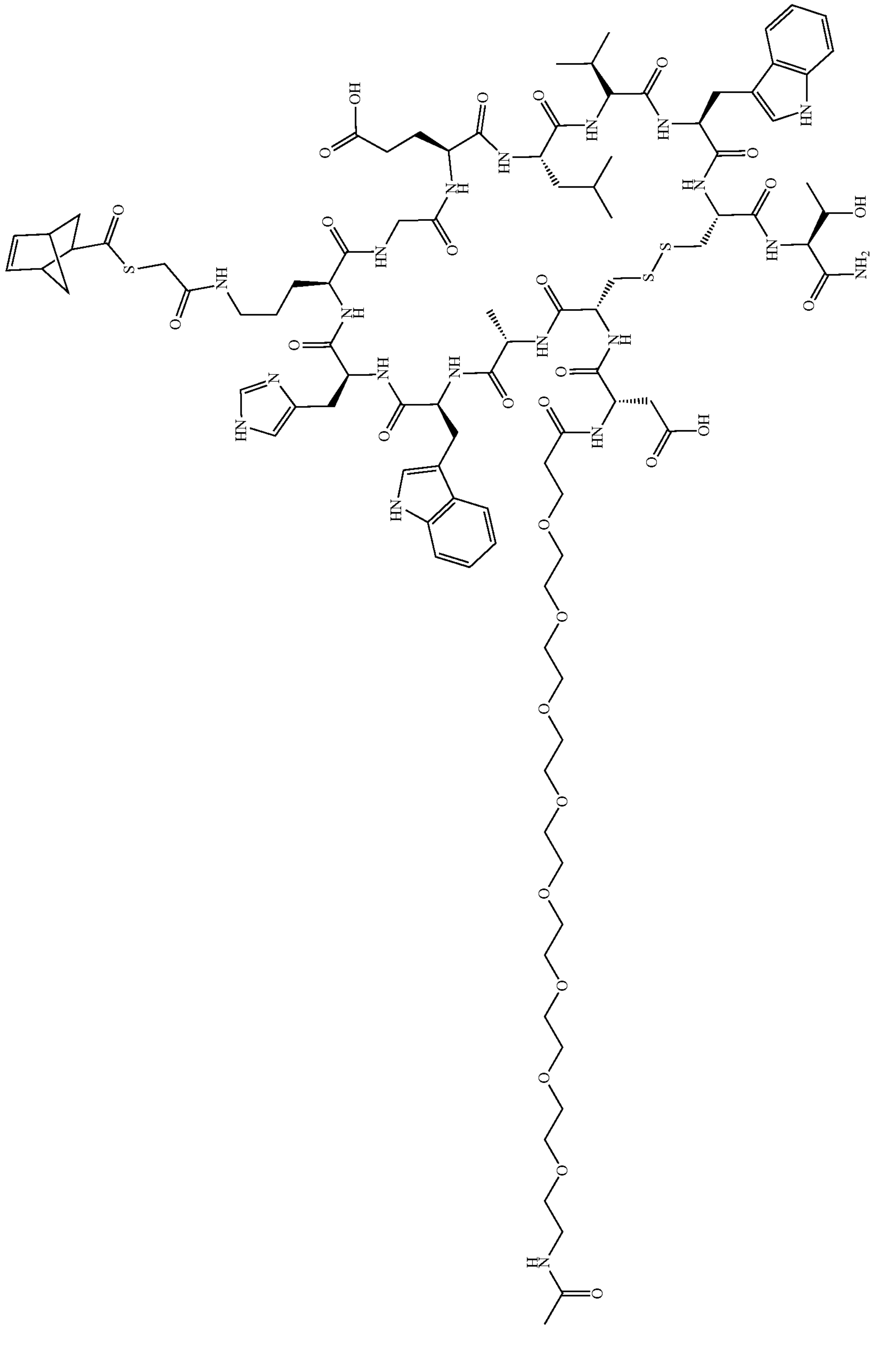
Exact Mass: 2188.95

Synthesis Method of Compound III-SSFI (Orn)

Synthesis of Compound III-SSFI was carried out in DMF, and 3 equivalents of DIPEA and 8.4 μmol of Compound Ill were dissolved in 7.3 μmol of SSFI, and stirred to introduce Compound III into SSFI.

After the termination of the reaction was confirmed, the reaction solution was concentrated, and purification of Compound III-SSFI by preparative-HPLC was attempted. After the purification, the Compound III-SSFI was freeze-dried to obtain a target compound, the amount of which was confirmed to be 14 mg (purity: >95% up (HPLC), and yield: 87%).

Confirmation of Structure of Compound III-SSFI (Orn)

Measuring equipment: Waters Quattro Premier Xe

Calculated molecular weight: 2188.97 g/mol

Measured molecular weight $(M/2+H)^{2+}$: 1096.64 g/mol

Figure 36:
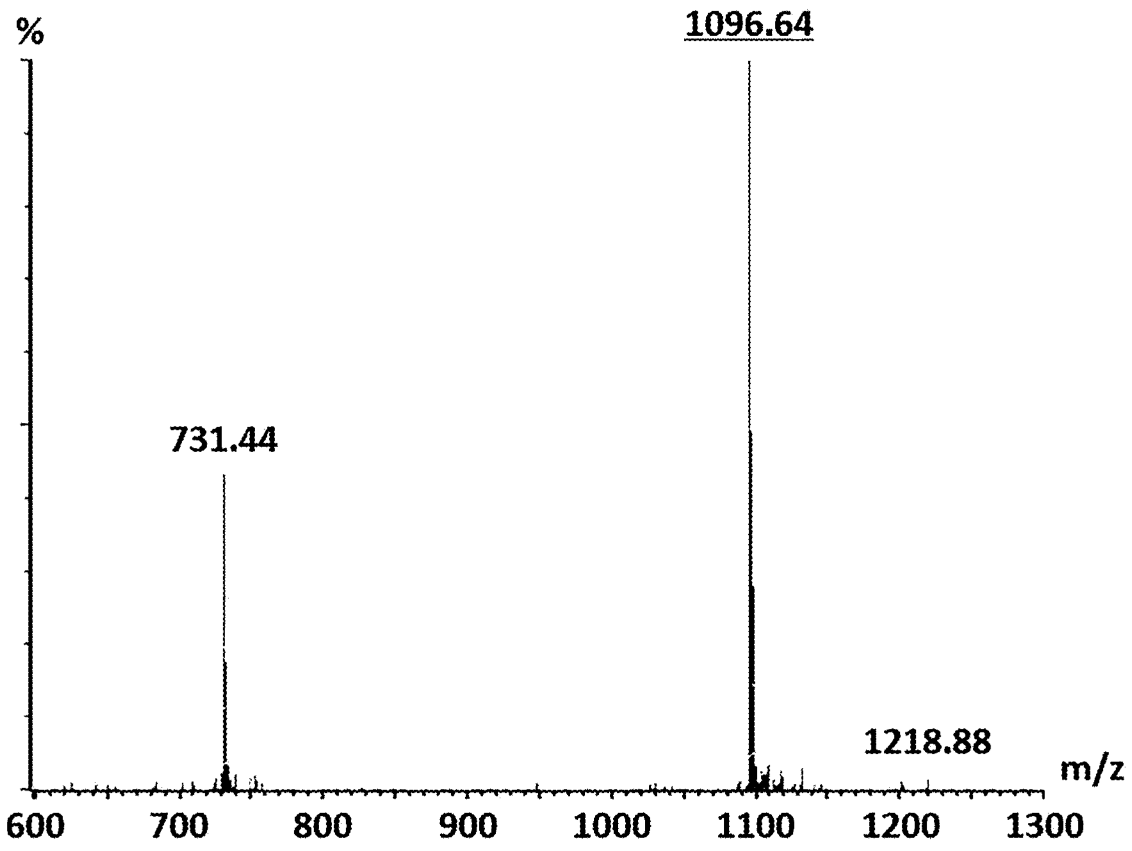
FIG. 36 shows the results of confirming a structure of Compound III-SSFI (6Orn) by means of mass spectrometry.

The results are shown in FIG. 36.

2.5. Synthesis and Confirmation of Structure of Compound III-SSFI (Wherein $Xa_1$ is 2,4-diaminobutanoic Acid (Dab))

III-FcBP(6Dab)
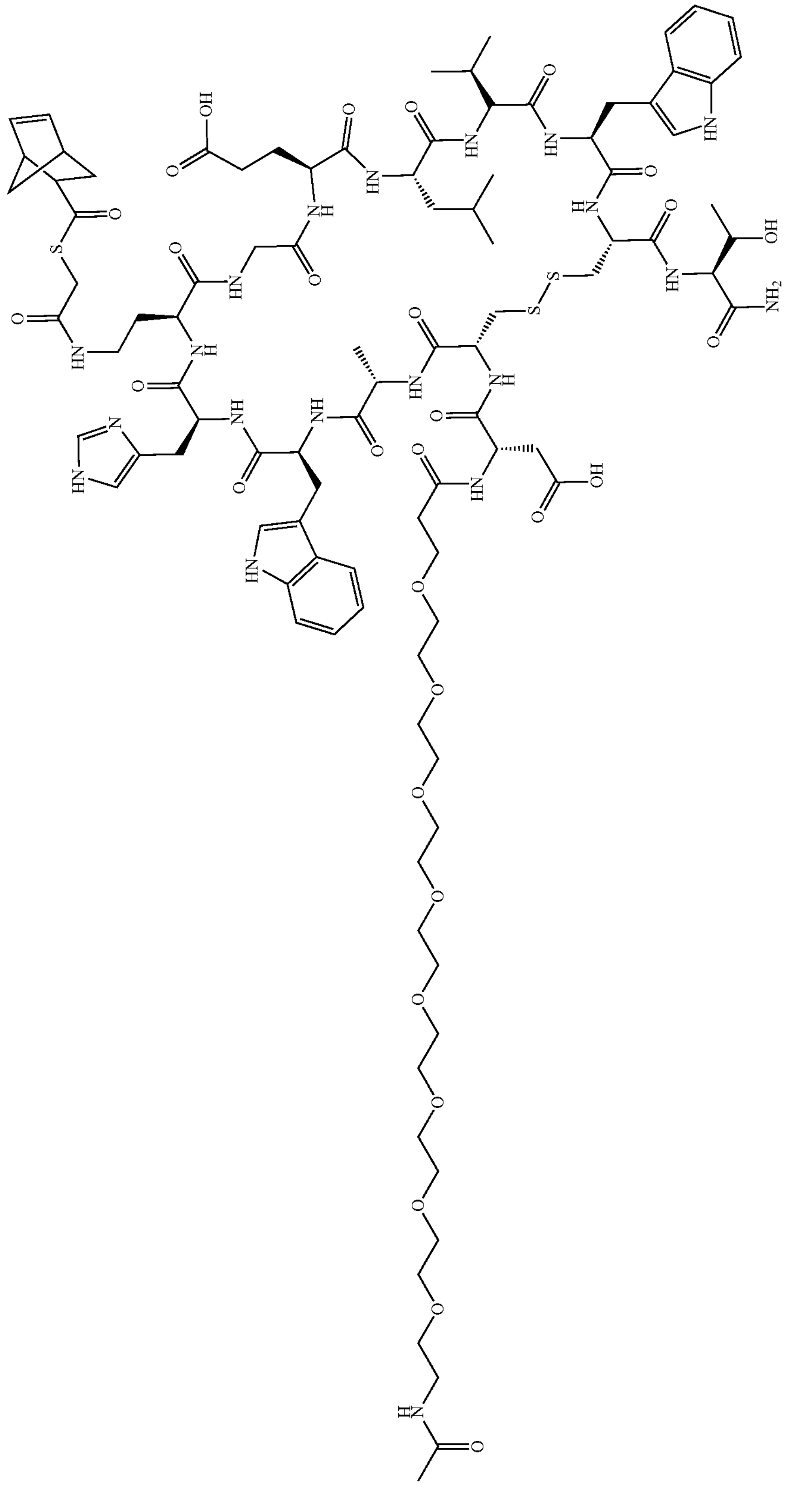
Exact Mass: 2174.94

Synthesis Method of Compound III-SSFI (Dab)

Synthesis of Compound III-SSFI was carried out in DMF, and 3 equivalents of DIPEA and 8.4 μmol of Compound III were dissolved in 7.3 μmol of SSFI, and stirred to introduce Compound III into SSFI.

After the termination of the reaction was confirmed, the reaction solution was concentrated, and purification of Compound III-SSFI by preparative-HPLC was attempted. After the purification, the Compound III-SSFI was freeze-dried to obtain a target compound, the amount of which was confirmed to be 12 mg (purity: >95% up (HPLC), and yield: 75%).

Confirmation of Structure of Compound III-SSFI (Dab)

Measuring equipment: Waters Quattro Premier Xe

Calculated molecular weight: 2174.94 g/mol

Measured molecular weight $(M/2+H)^{2+}$: 1089.94 g/mol

Figure 37:
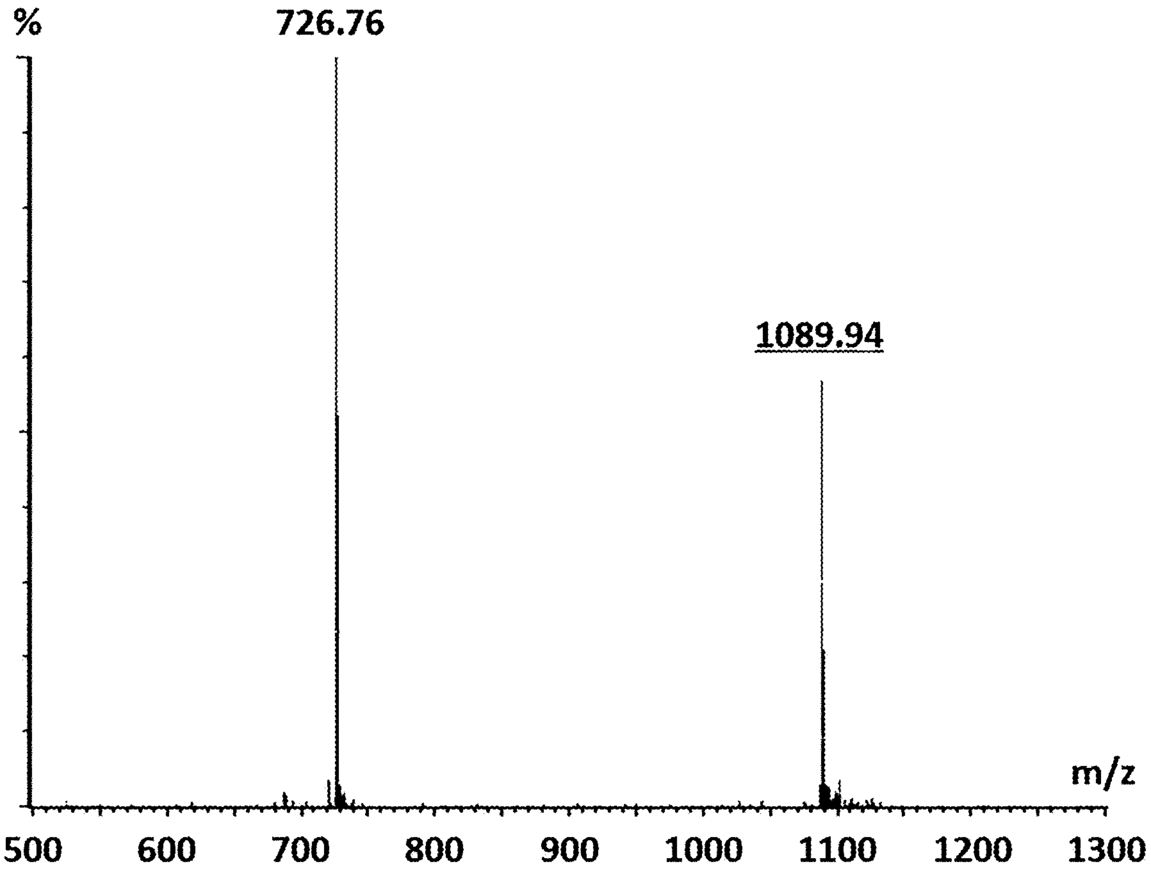
FIG. 37 shows the results of confirming a structure of Compound III-SSFI (6Dab) by means of mass spectrometry.

The results are shown in FIG. 37.

2.6. Synthesis and Confirmation of Structure of Compound III-SSFI (Wherein $Xa_1$ is 2,3-diaminopropionic acid (Dap))

III-FcBP(6Dap)
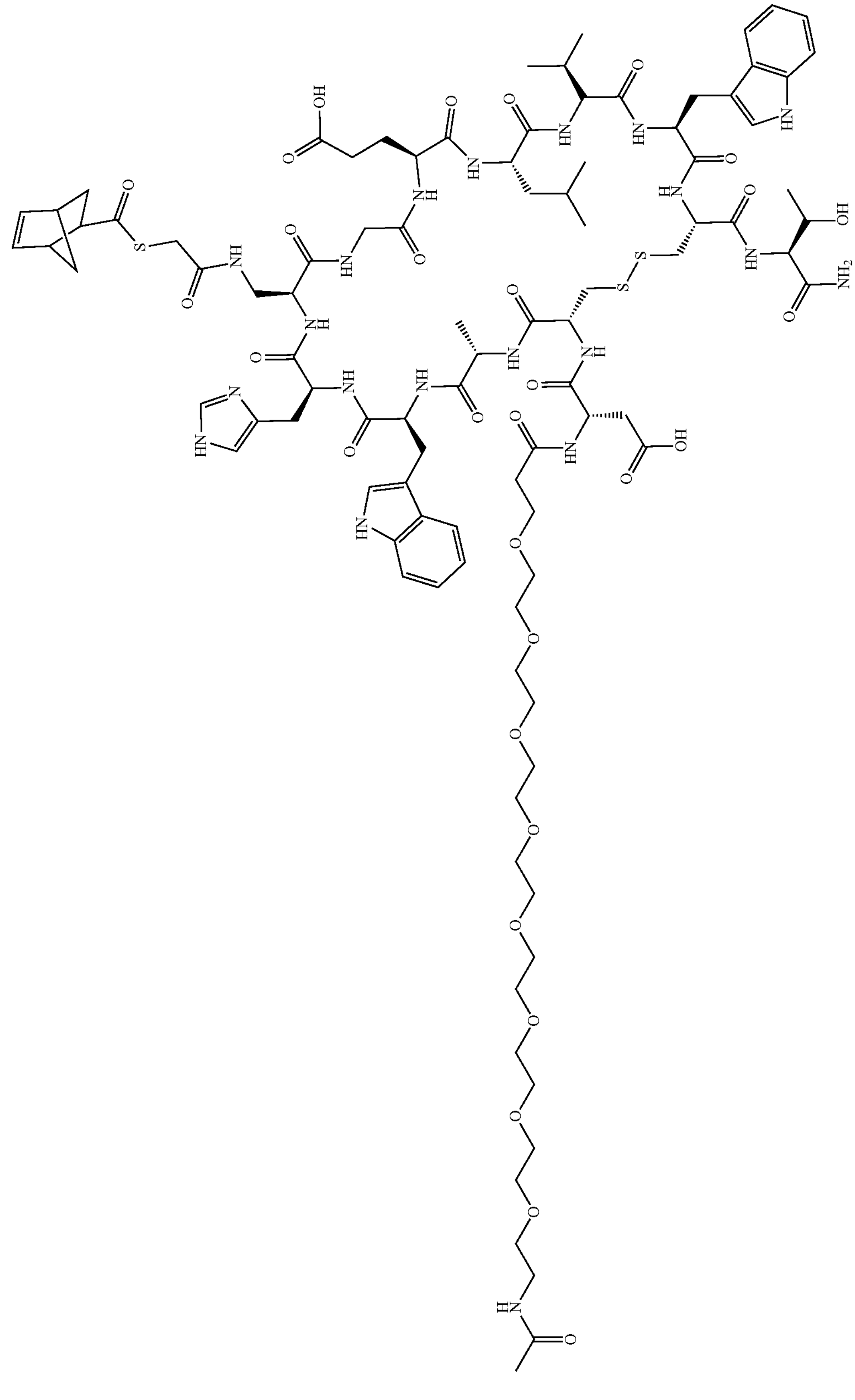
Exact Mass: 2160.92

Synthesis Method of Compound III-SSFI (Dap)

Synthesis of Compound III-SSFI was carried out in DMF, and 3 equivalents of DIPEA and 8.4 μmol of Compound III were dissolved in 7.3 μmol of SSFI, and stirred to introduce Compound III into SSFI.

After the termination of the reaction was confirmed, the reaction solution was concentrated, and purification of Compound III-SSFI by preparative-HPLC was attempted. After the purification, the Compound III-SSFI was freeze-dried to obtain a target compound, the amount of which was confirmed to be 12 mg (purity: >95% up (HPLC), and yield: 75%).

Confirmation of Structure of Compound III-SSFI (Dap)

Measuring equipment: Waters Quattro Premier Xe

Calculated molecular weight: 2160.92 g/mol

Measured molecular weight $(M/2+H)^{2+}$: 1082.34 g/mol

Figure 38:
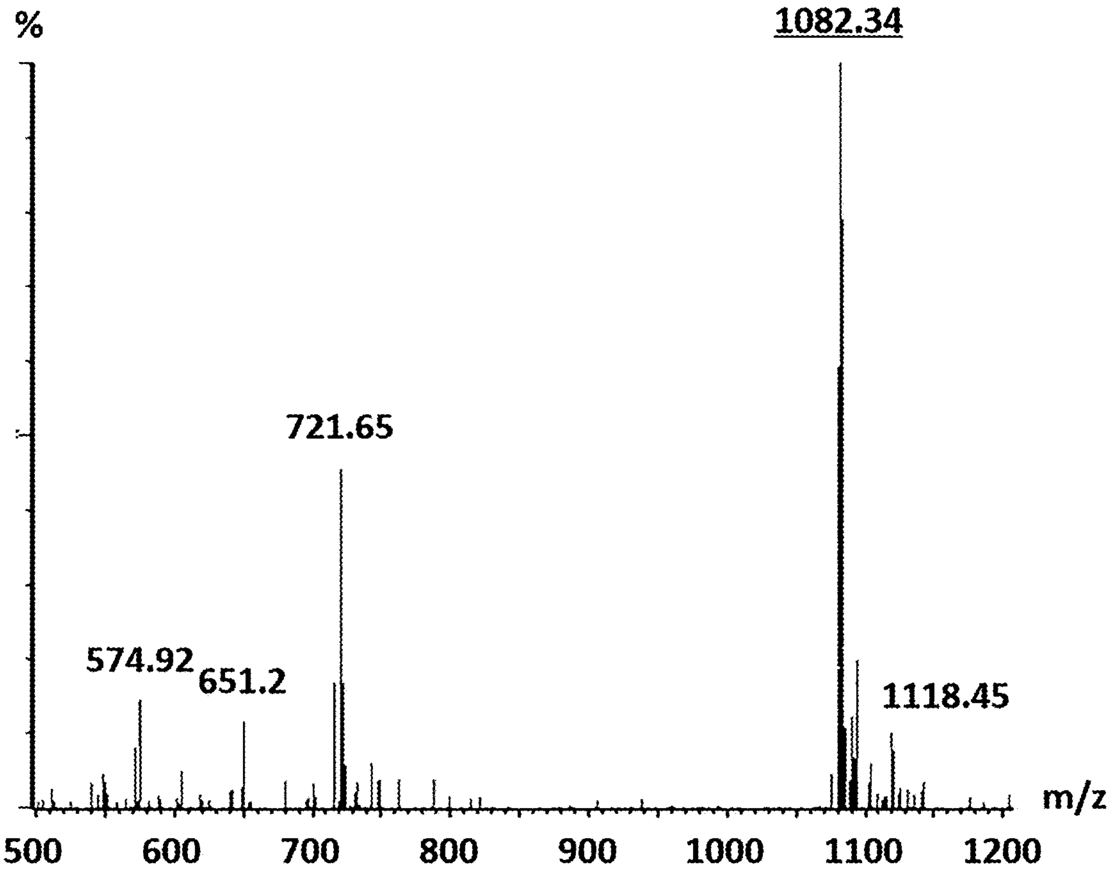
FIG. 38 shows the results of confirming a structure of Compound III-SSFI (6Dap) by means of mass spectrometry.

The results are shown in FIG. 38.

2.7. Synthesis and Confirmation of Structure of Compound IV-SSFI (Wherein $Xa_1$ is Dap)

III-FcBP(6Dap)
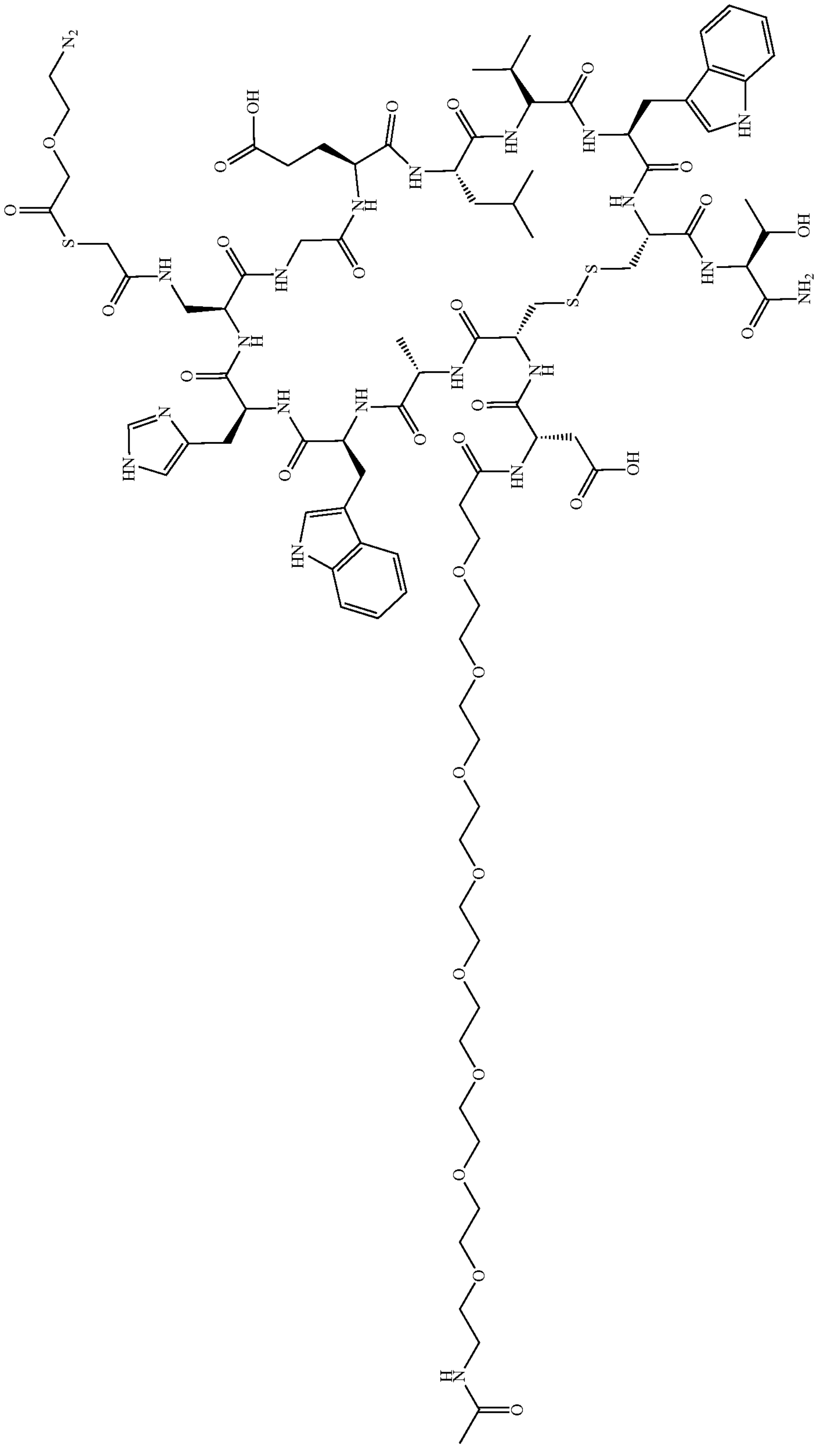
Exact Mass: 2167.90

Synthesis Method of Compound IV-SSFI (Dap)

Synthesis of Compound IV-SSFI was carried out in DMF, and 3 equivalents of DIPEA and 8.4 μmol of Compound IV were dissolved in 7.3 μmol of SSFI, and stirred to introduce Compound IV into SSFI.

After the termination of the reaction was confirmed, the reaction solution was concentrated, and purification of Compound IV-SSFI by preparative-HPLC was attempted. After the purification, the Compound IV-SSFI was freeze-dried to obtain a target compound, the amount of which was confirmed to be 12 mg (purity: >95% up (HPLC), and yield: 76%).

Confirmation of Structure of Compound IV-SSFI (Dap)

Measuring equipment: Waters Quattro Premier Xe

Calculated molecular weight: 2167.90 g/mol

Measured molecular weight $(M/2+H)^{2+}$: 1085.60 g/mol

Figure 39:
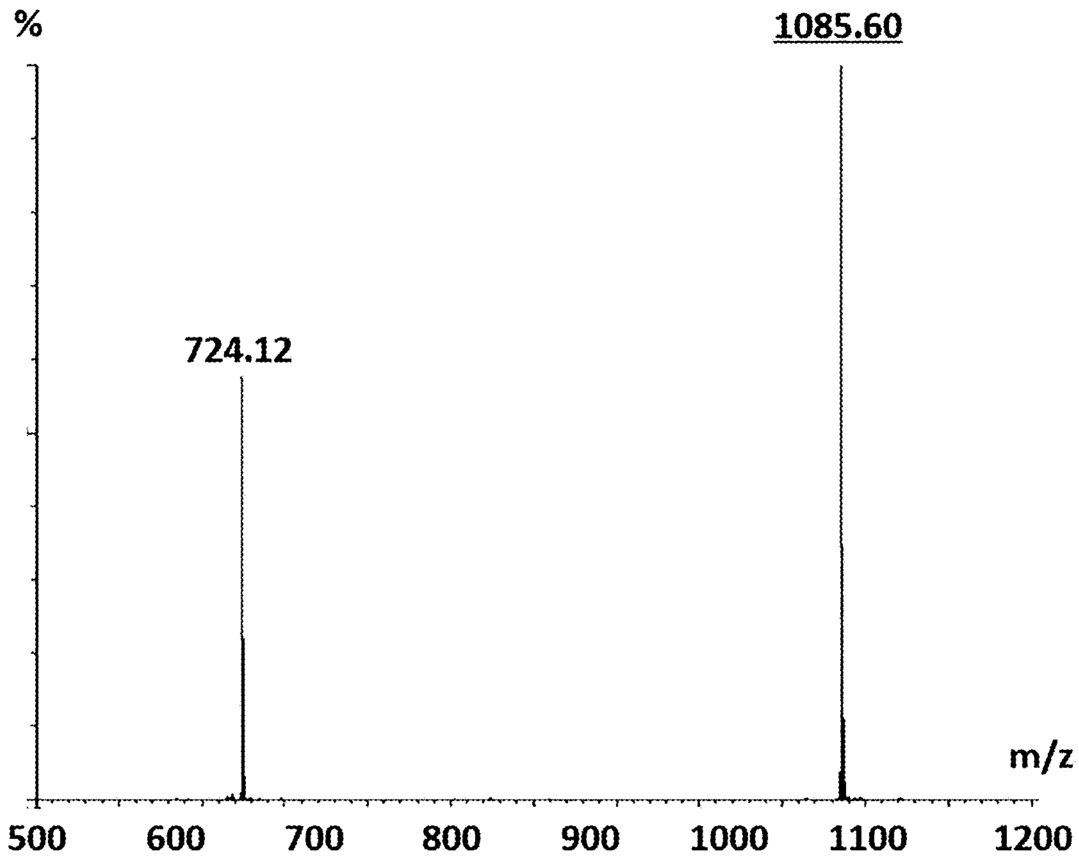
FIG. 39 shows the results of confirming a structure of Compound IV-SSFI (6Dap) by means of mass spectrometry.

The results are shown in FIG. 39.

3. Synthesis and Confirmation of Structure of Antibody Containing First Click-Chemistry Functional Group in Site-Specific Manner 3.1. Synthesis of Antibody-Norbornene Synthesis Method of Trastuzumab-Norbornene (1)

Introduction Reaction Using Compound I-SSFI (Lys)

Synthesis of Ab (246/248 Lys)-norbornene was carried out in a buffer using Compound I-SSFI (Lys). A 1×PBS buffer (0.01% Tween 20, pH 7.4) was used as the reaction buffer. To introduce norbornene at a certain site of an antibody (trastzumab, 4 mg/mL), 8 equivalents of Compound I-SSFI (Lys) was added per one antibody, and reacted at room temperature for 72 hours, and the reaction monitoring and termination were confirmed by HIC-HPLC. As the binding of norbornene to the antibody proceeds, the peaks on the chromatogram were observed to shift from 4 minutes to 4.5 minutes and 5 minutes, thereby confirming a degree of progression of the reaction. The Ab-norbornene conjugate was dialyzed three times using a 1×PBS buffer (pH 7.4), and purified using a size exclusion chromatography technique.

Figure 40:
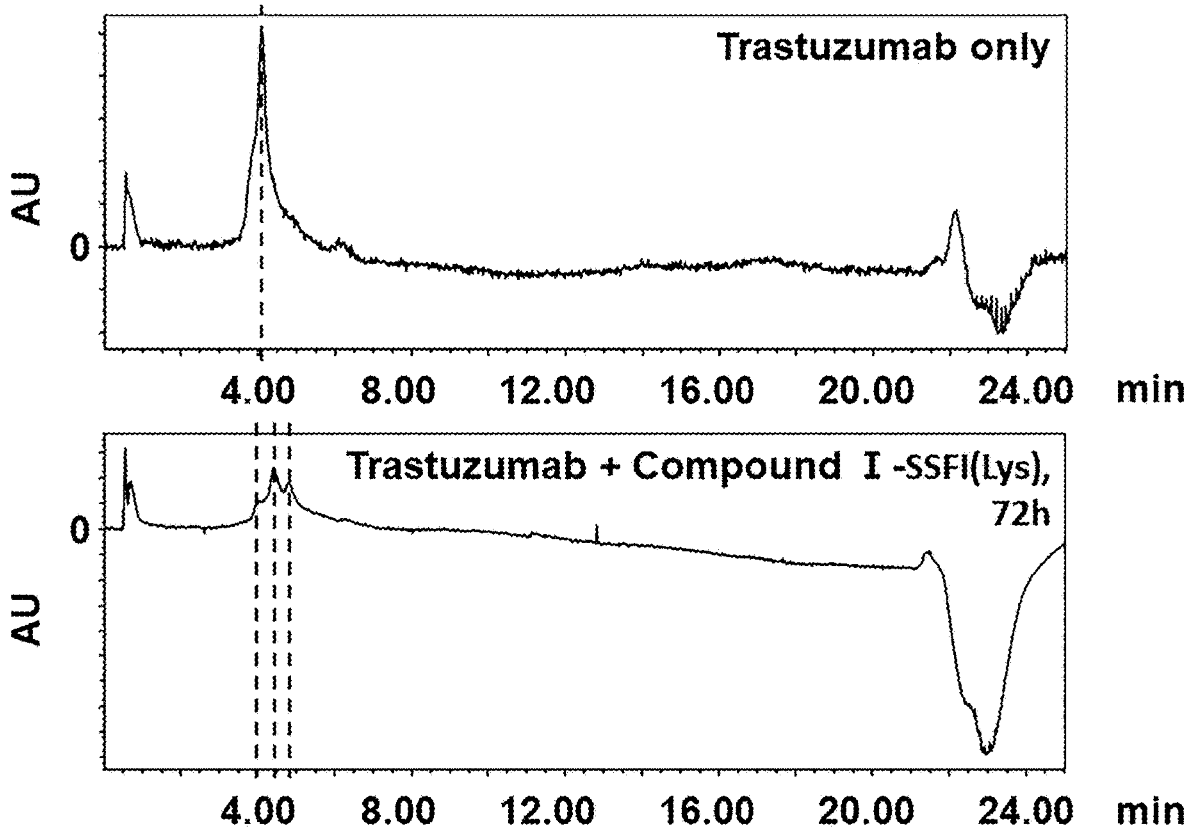
FIG. 40 shows the results of observing a binding reaction using trastuzumab and Compound I-SSFI (6Lys) by means of HIC-HPLC.

Observation of the binding reaction between trastuzumab and Compound I-SSFI (Lys) according to reaction time is shown in FIG. 40.

Synthesis Method of Trastuzumab-Norbornene (2)

Introduction Reaction Using Compound II-SSFI (Lys)

Synthesis of Ab (246/248 Lys)-norbornene was carried out in a buffer using Compound II-SSFI (Lys). A 1×PBS buffer (0.01% Tween 20, pH 7.4) was used as the reaction buffer. To introduce norbornene at a certain site of an antibody (trastzumab, 4 mg/mL), 8 equivalents of Compound II-SSFI (Lys) was added per one antibody, and reacted at room temperature for 72 hours, and the reaction monitoring and termination were confirmed by HIC-HPLC. As the binding of norbornene to the antibody proceeds, the peaks on the chromatogram were observed to shift from 4 minutes to 4.5 minutes, thereby confirming a degree of progression of the reaction. The Ab-norbornene conjugate was dialyzed three times using a 1×PBS buffer (pH 7.4), and purified using a size exclusion chromatography technique.

Figure 41:
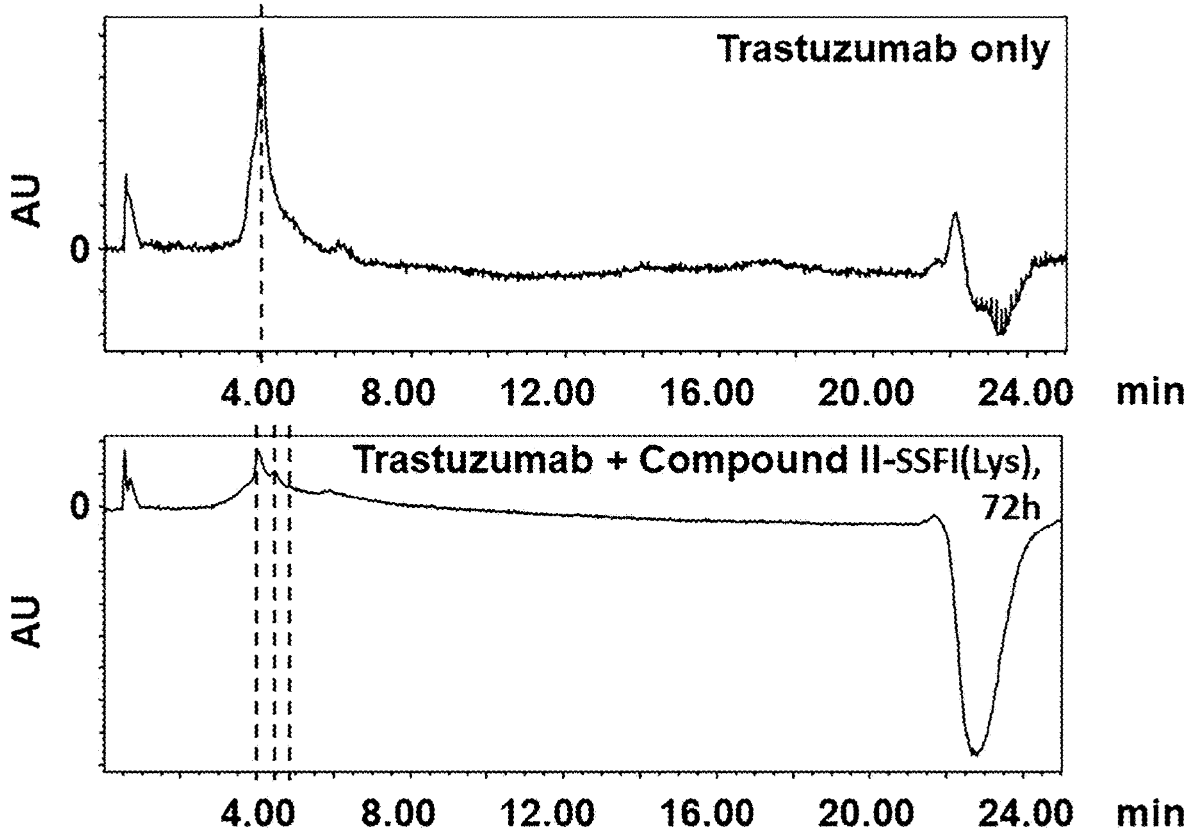
FIG. 41 shows the results of observing a binding reaction using trastuzumab and Compound II-SSFI (6Lys) by means of HIC-HPLC.

Observation of the binding reaction between trastuzumab and Compound II-SSFI (Lys) according to reaction time is shown in FIG. 41.

Synthesis Method of Trastuzumab-Norbornene (3)

Introduction Reaction Using Compound III-SSFI (Dap, Dab, Orn, or Lys)

Synthesis of Ab (246/248 Lys)-norbornene was carried out in a buffer using Compound III-SSFI (Lys). A 1×PBS buffer (0.01% Tween 20, pH 7.4) was used as the reaction buffer. To introduce norbornene at a certain site of an antibody (Herceptin or trastzumab, 4 mg/mL), 10 equivalents of Compound III-SSFI (Dap, Dab, Orn, or Lys) was added per one antibody, and reacted at room temperature for 28 hours, and the reaction monitoring and termination were confirmed by HIC-HPLC. As the binding of norbornene to the antibody proceeds, the peaks on the chromatogram were observed to shift from 6.2 minutes to 6.4 to 6.7 minutes, thereby confirming a degree of progression of the reaction. The Ab-norbornene conjugate was dialyzed using a 1×PBS buffer (pH 7.4), and purified using a size exclusion chromatography technique.

Figure 42:
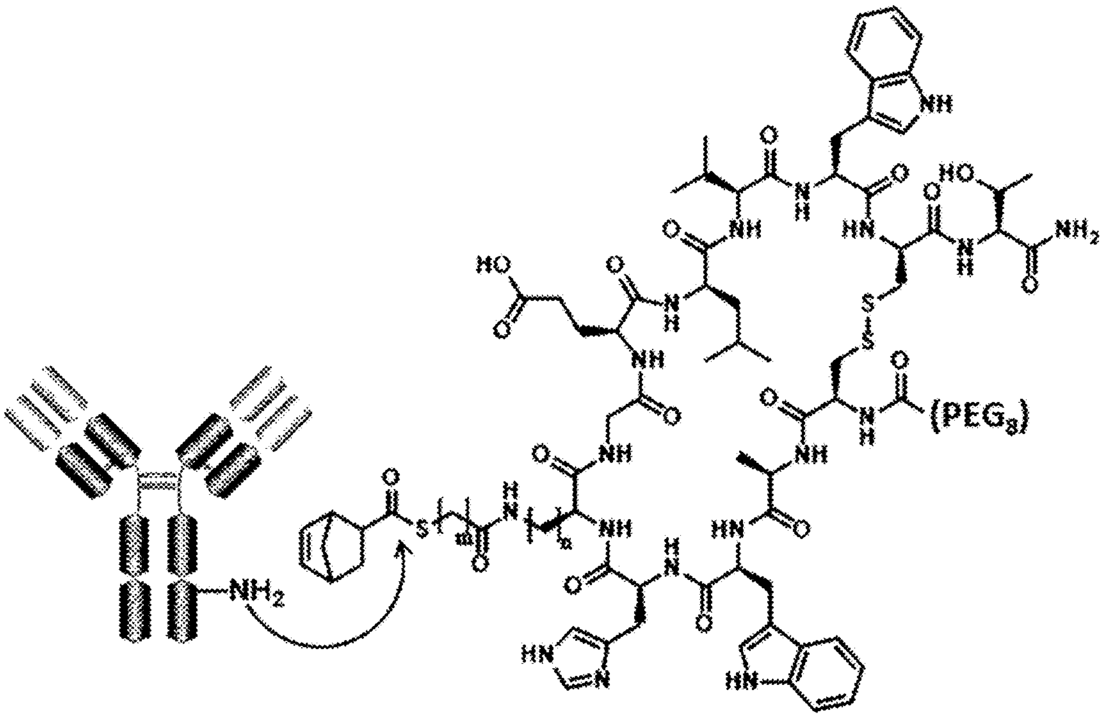
FIG. 42 shows a reaction of an antibody with Compound III-SSFI (6Dap, Dab, Orn, or Lys).
Figure 43:
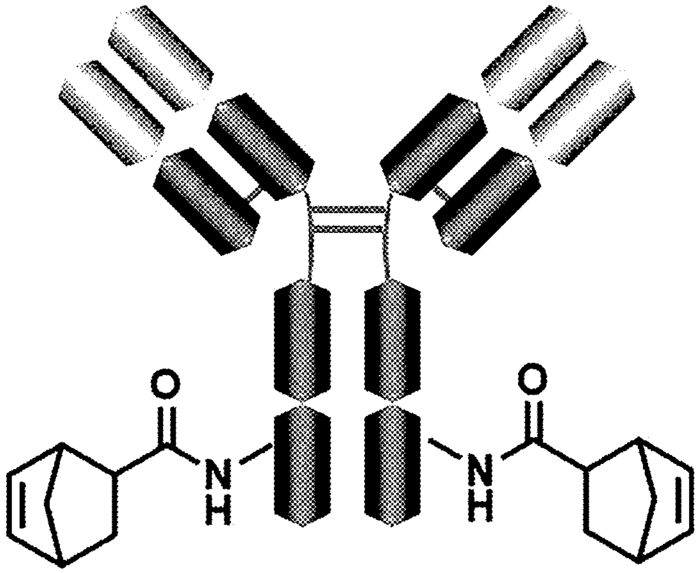
FIG. 43 shows a structure of Ab (246/248)-Norbornene as the final product.

The reaction between Compound III-SSFI (Dap, Dab, Orn, or Lys) and the antibody is shown in FIG. 42, and the structure of the final product (i.e., Ab (246/248)-Norbornene) is shown in FIG. 43.

Figure 44:
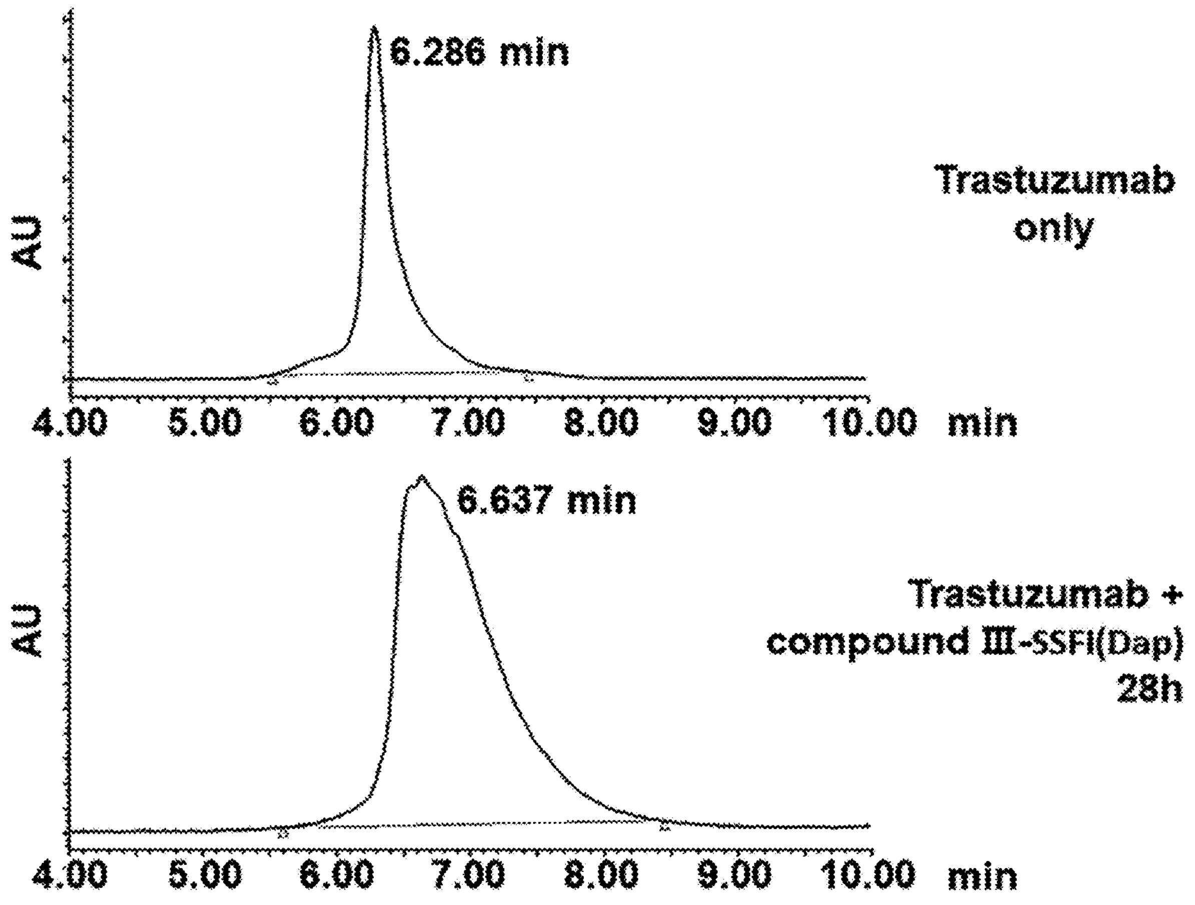
FIG. 44 shows the results of observing a binding reaction using trastuzumab and Compound III-SSFI (6Dap) by means of HIC-HPLC.

Observation of the binding reaction between trastuzumab and Compound III-SSFI (Dap) according to reaction time is shown in FIG. 44.

Figure 45:
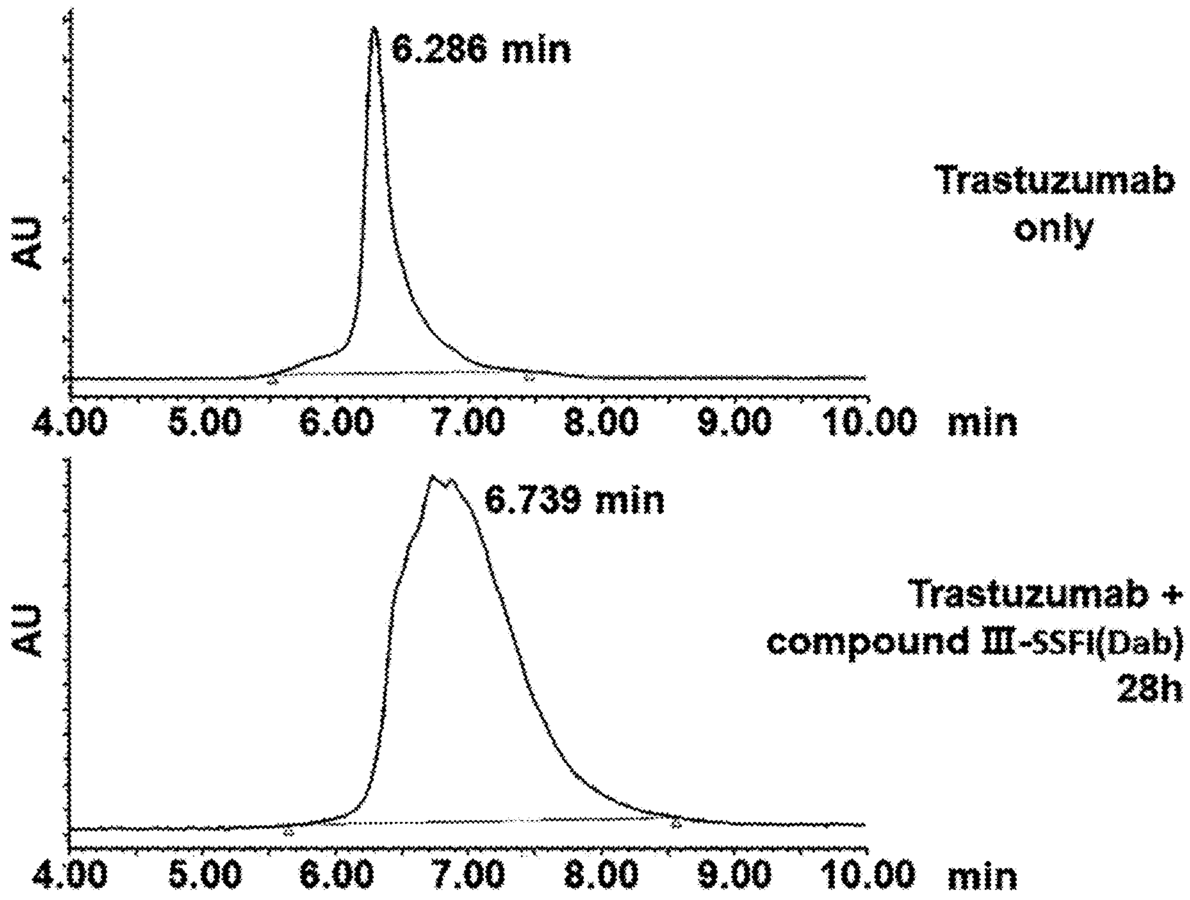
FIG. 45 shows the results of observing a binding reaction using trastuzumab and Compound III-SSFI (6Dab) by means of HIC-HPLC.

Observation of the binding reaction between trastuzumab and Compound III-SSFI (Dab) according to reaction time is shown in FIG. 45.

Figure 46:
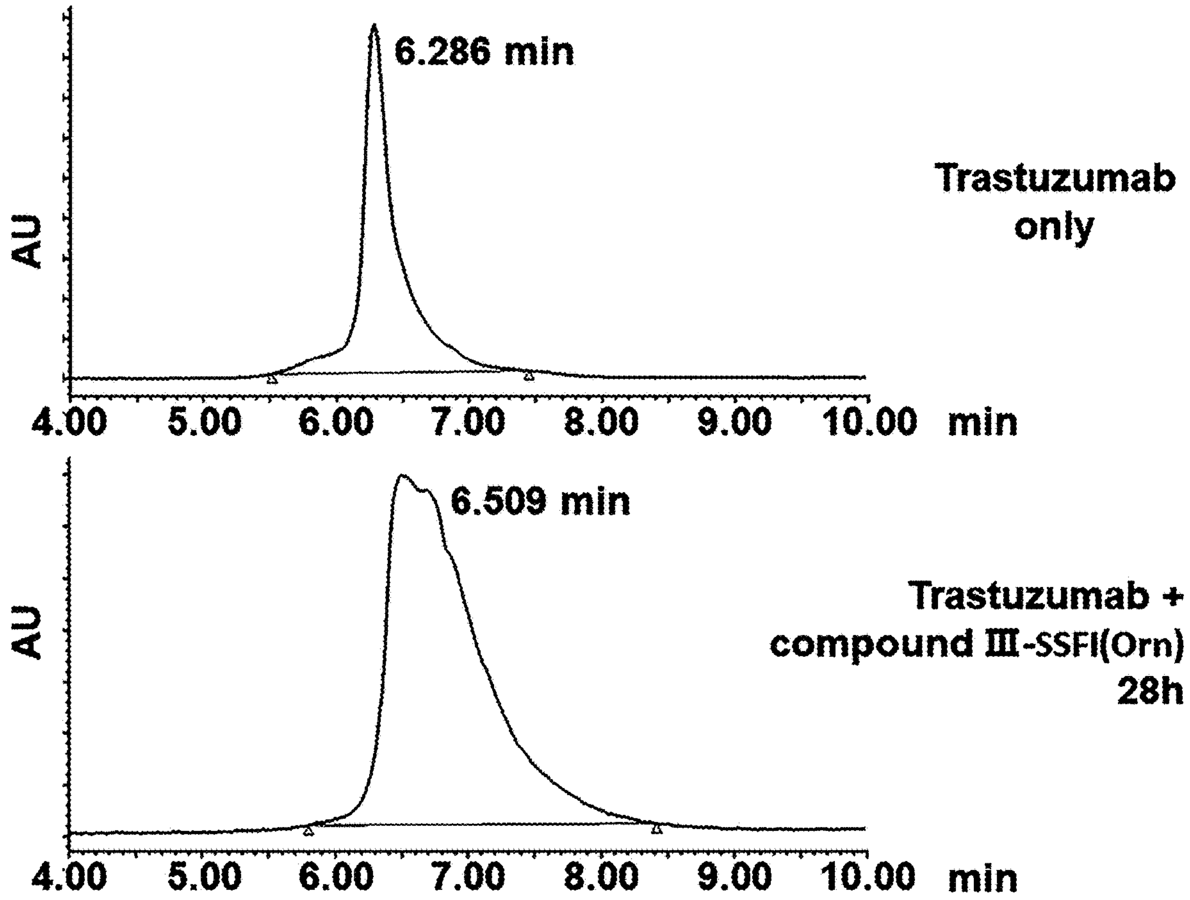
FIG. 46 shows the results of observing a binding reaction using trastuzumab and Compound III-SSFI (6Orn) by means of HIC-HPLC.

Observation of the binding reaction between trastuzumab and Compound III-SSFI (Orn) according to reaction time is shown in FIG. 46.

Figure 47:
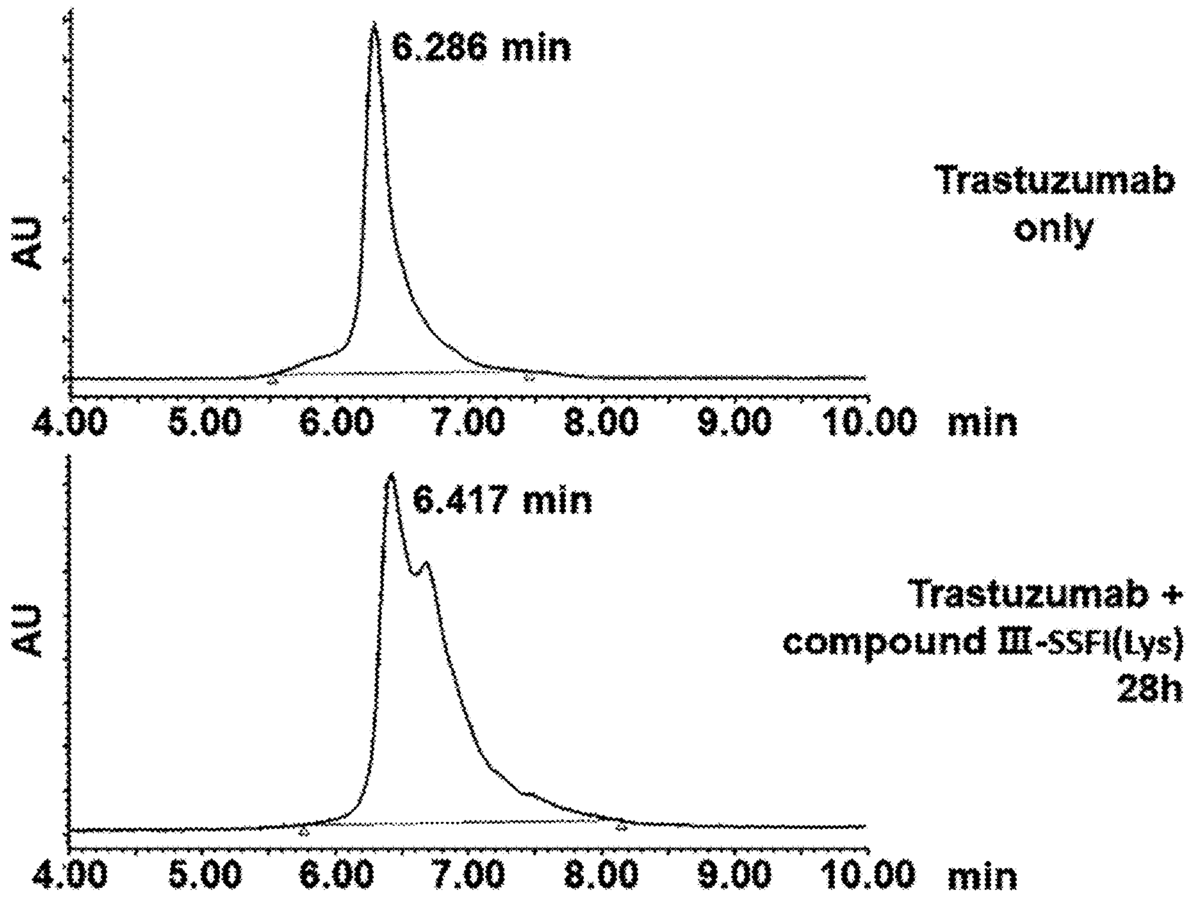
FIG. 47 shows the results of observing a binding reaction using trastuzumab and Compound III-SSFI (6Lys) by means of HIC-HPLC.

Observation of the binding reaction between trastuzumab and Compound III-SSFI (Lys) according to reaction time is shown in FIG. 47.

3.2. Synthesis of Antibody-Azide

Synthesis Method of Trastuzumab-Azide (4)

Introduction Reaction Using Compound IV-SSFI (Dap)

Synthesis of Ab (246/248 Lys)-azide was carried out in a buffer using Compound IV-SSFI (Dap). A 1×PBS buffer (0.01% Tween 20, pH 7.4) was used as the reaction buffer. To introduce an azide at a certain site of an antibody (trastzumab, 4 mg/mL), 10 equivalents of Compound IV-SSFI (Dap) was added per one antibody, and reacted at room temperature for 24 hours, and the reaction monitoring and termination were confirmed by HIC-HPLC. As the binding of norbornene to the antibody proceeds, the peaks on the chromatogram were observed to shift from 6 minutes to 6.3 minutes, thereby confirming a degree of progression of the reaction. The Ab-norbornene conjugate was dialyzed three times using a 1×PBS buffer (pH 7.4), and purified using a size exclusion chromatography technique.

Figure 48:
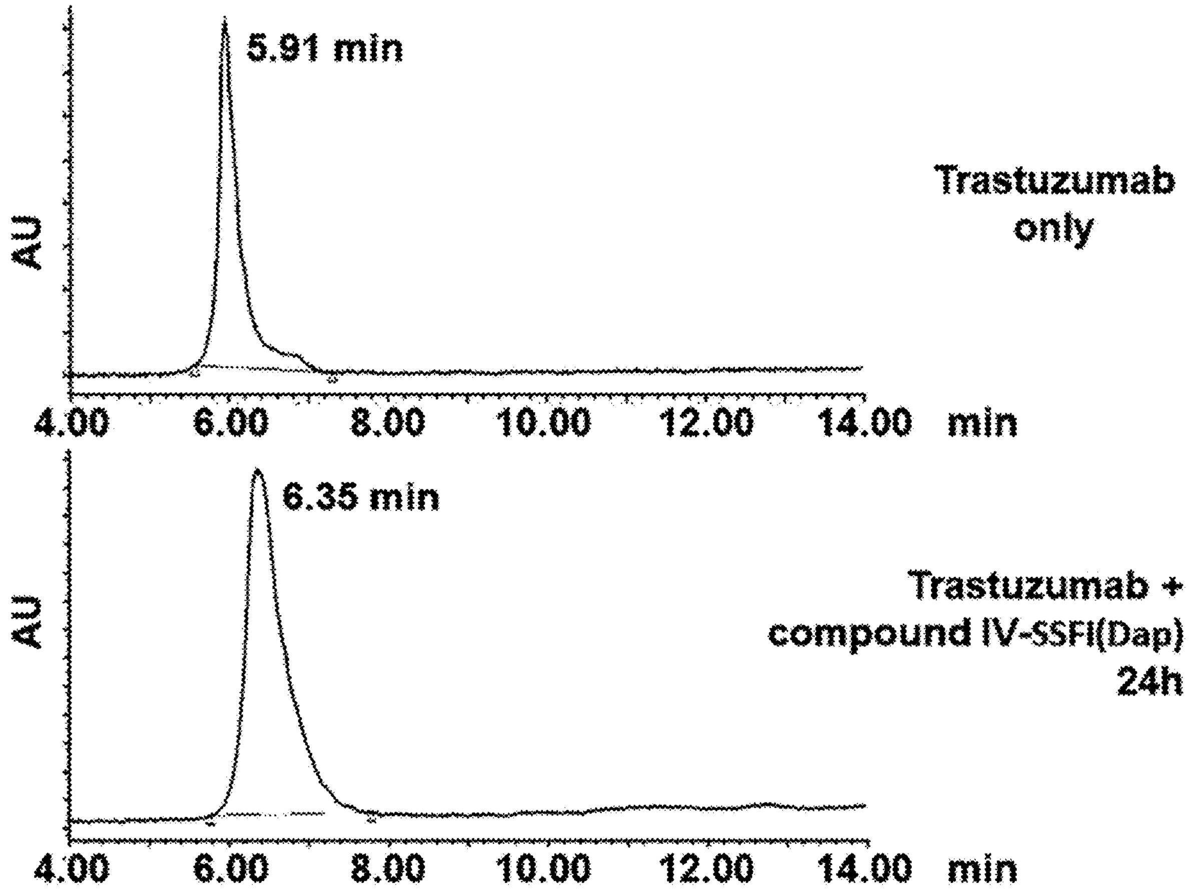
FIG. 48 shows the results of observing a binding reaction using trastuzumab and Compound IV-SSFI (6Dap) by means of HIC-HPLC.

Observation of the binding reaction between trastuzumab and Compound IV-SSFI (Dap) according to reaction time is shown in FIG. 48.

3.3. Confirmation of Structure and Site-Specific Binding of Trastuzumab-Norbornene Conjugate An antibody-norbornene complex in which a norbornene linker was bound to an antibody via Compound III-SSFI (Dap) was confirmed by mass spectrometry. It was determined to which site of the antibody the norbornene was bound via F(ab')2 and Fc/2 after the antibody-norbornene complex was treated with an IdeS enzyme. It was confirmed that the Ides Fc/2-norbornene complex was found to have an "Obs-Theo" value of 2991.68, a value which is an exact match in consideration of the combined value of the mass value of N-glycan, the value of a loss of one lysine residue, and the value of one norbornene molecule, which corresponded to the molecular weight of 120 Da, (a value of −0.10 was considered to be a system error in the high-mass molecular weight analysis). The observed mass spectrum of the Ides_F(ab')2 was detected, but the mass value of one charge was not shifted due to the complexity of the respective mass spectra, thereby making impossible to obtain the corresponding mass value.

Figure 49:
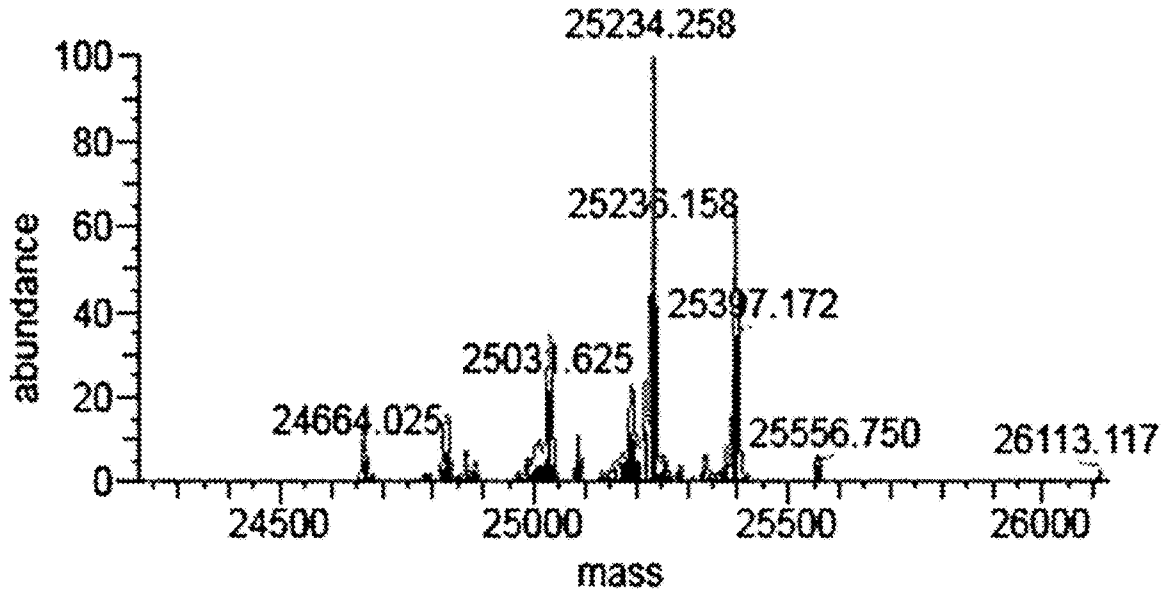
FIG. 49 and FIG. 50 show an increase of molecular weight spectra by antibody-norbornene binding.
Figure 50:
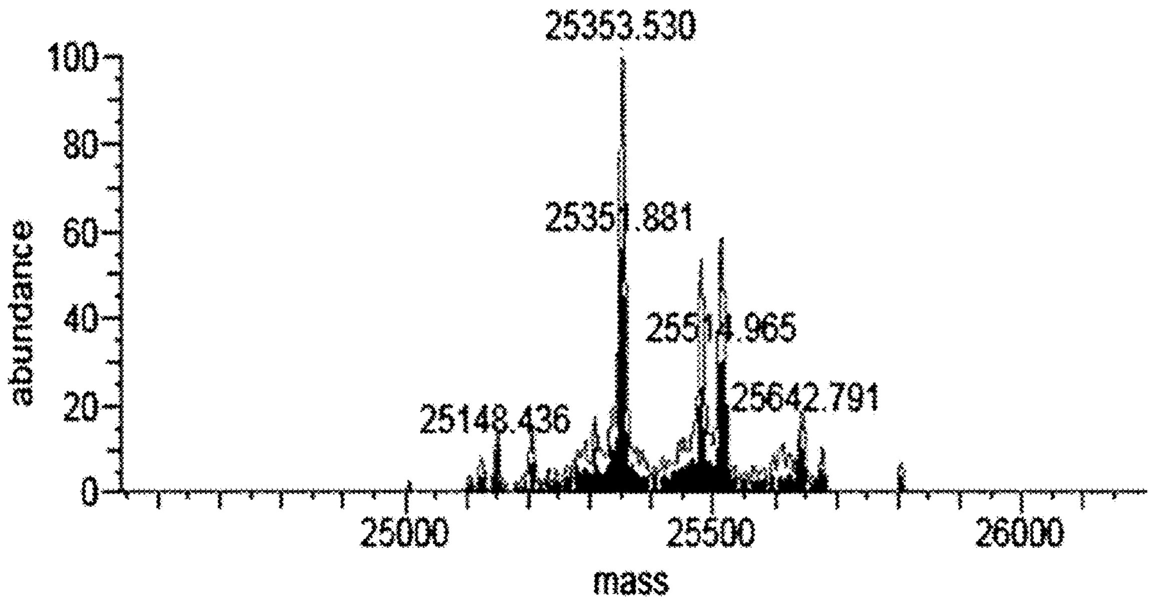
Figure 51:
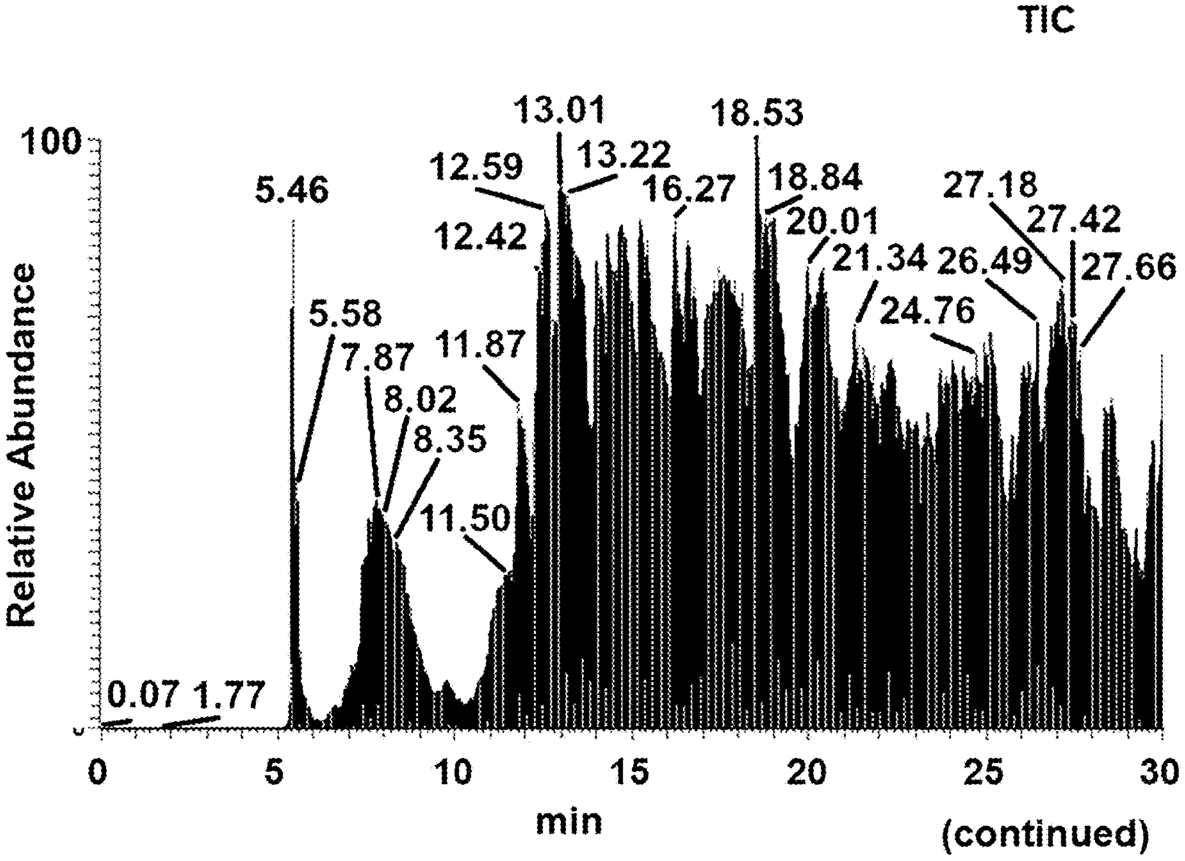
FIG. 51, FIG. 52, FIG. 53 and FIG. 54 show the MS/MS chromatogram results of trastuzumab and antibody-norbornene complexes.
Figure 52:
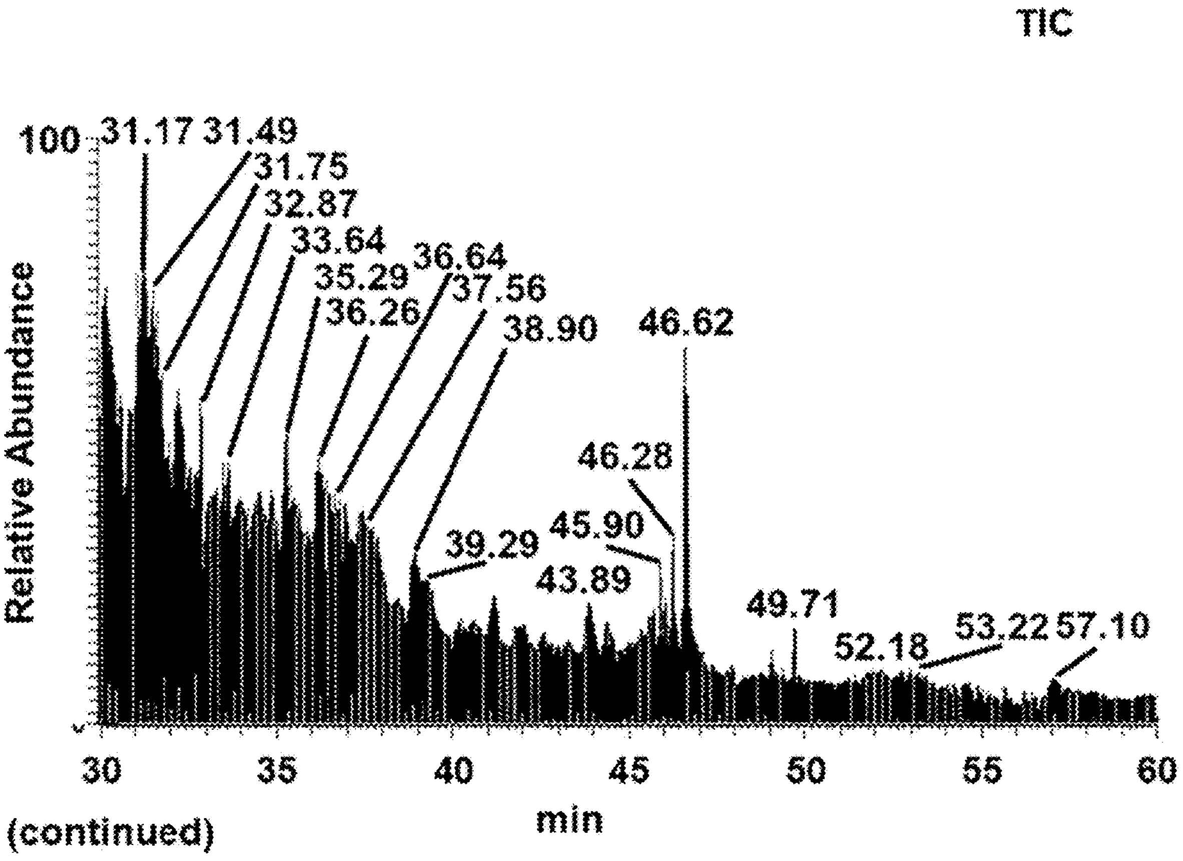
Figure 53:
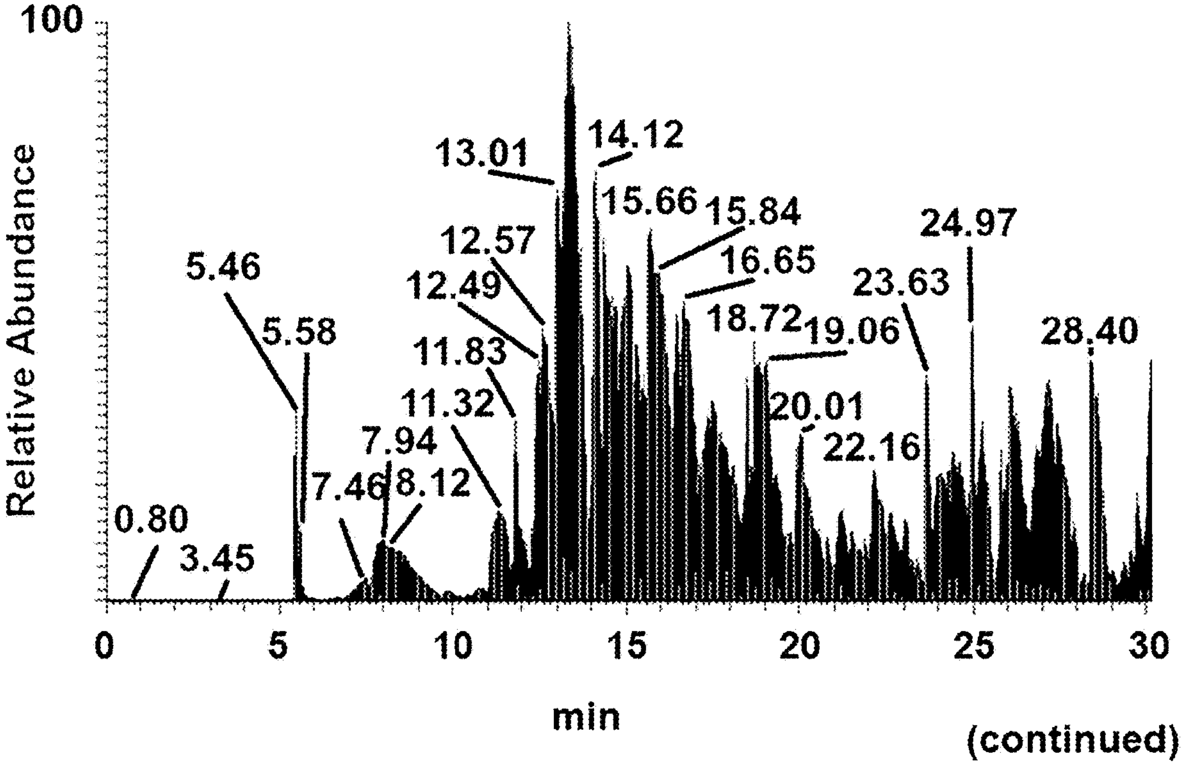
Figure 54:
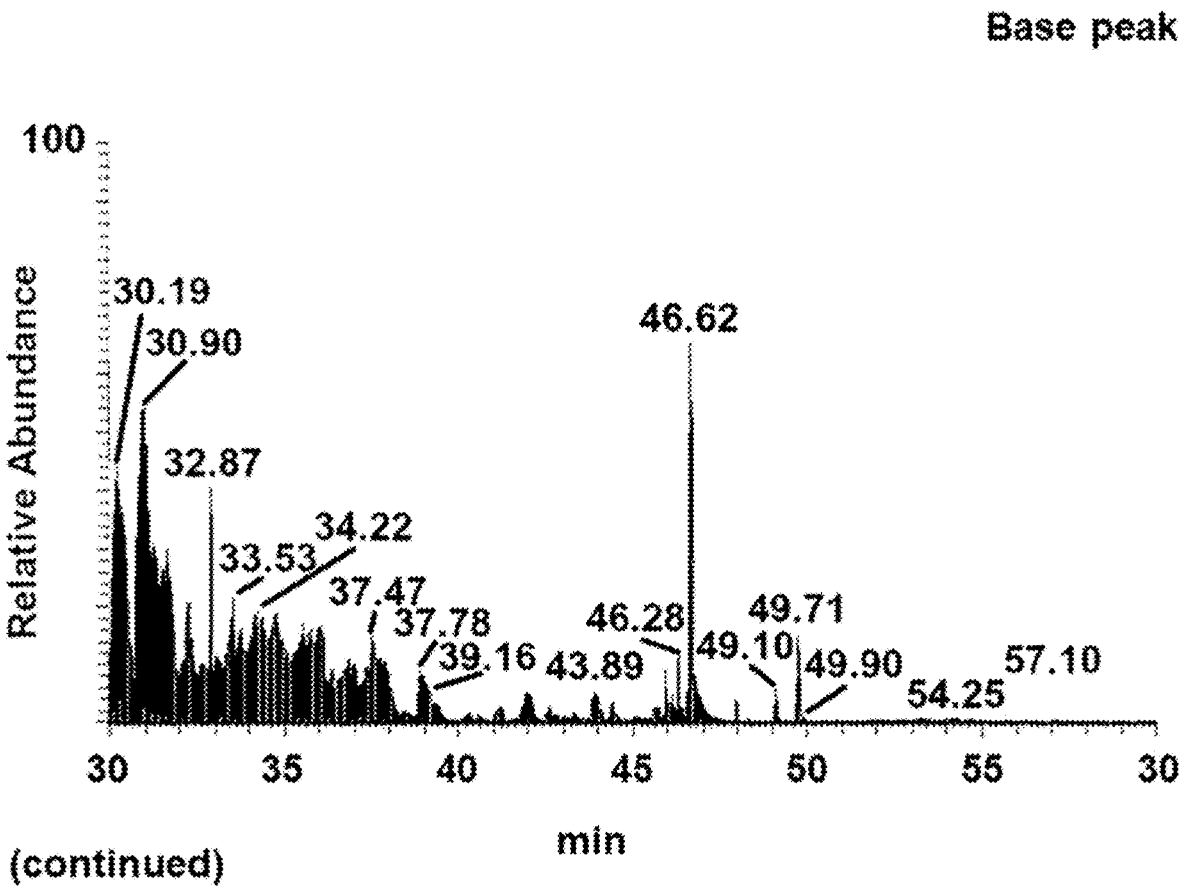

The spectra of the complex having an increased molecular weight due to the antibody-norbornene binding are shown in FIGS. 49 and 50, and changes in molecular weights due to the norbornene conjugation are as listed in Table 12.

TABLE 12

Changes in molecular weights of antibody-norbornene conjugates

| Sample | | Theoretical mass (peptide full seq.) | Observed mass | Δ mass (Obs-Theo) (continued-) |
|---|---|---|---|---|
| Trastuzumab | Ides Fc/2 | 23916.08 | 25231.10 | 1315.02 |
| Trastuzumab-norbornene conjugate | Ides Fc/2 | 23916.08 | 25353.53 | 1437.45 |

| (continued-) N-glcan (G0F/G0F) | C-term (−2K) | Norbornene conjugate | Δ mass | |
|---|---|---|---|---|
| 1445.00 | 128 | ND | −1.98 | (G0F/−K) |
| 1445.00 | 128 | 122 | −1.55 | (G0F/−K) |

Figure 55:
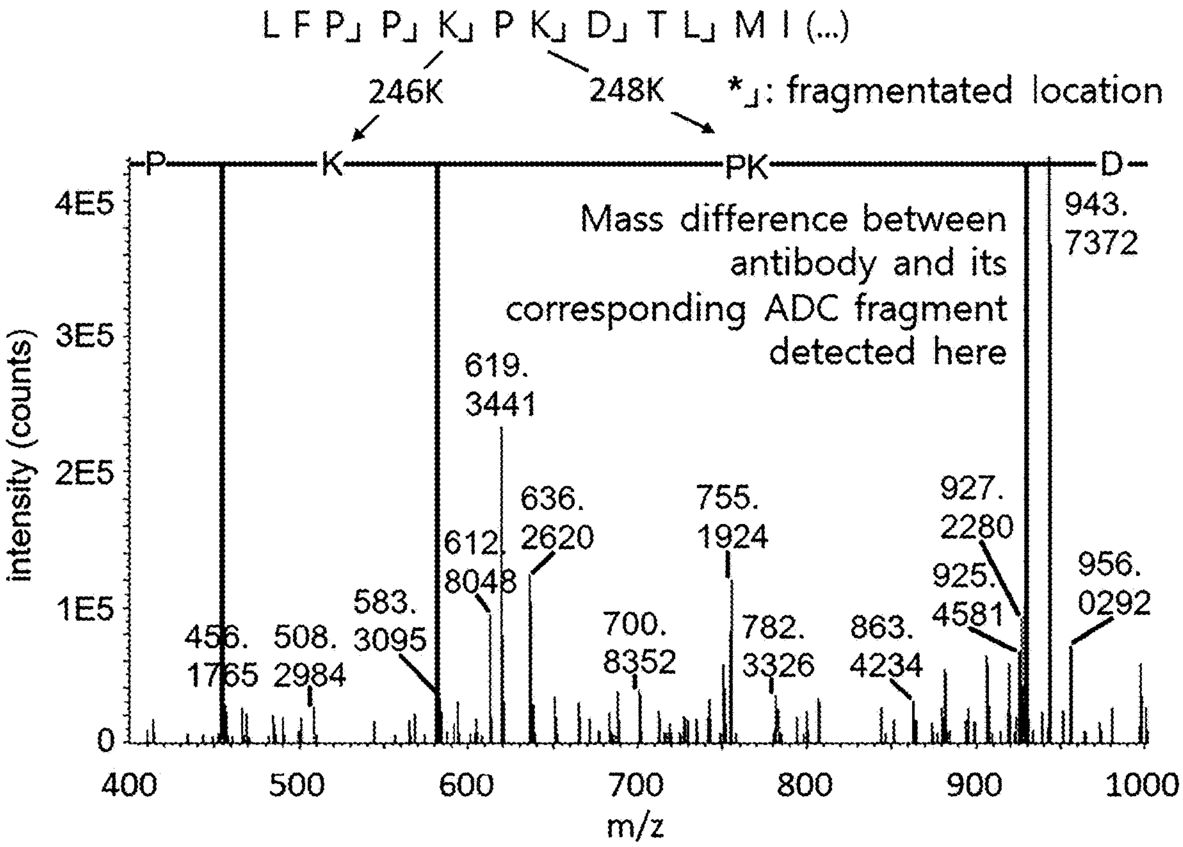
FIG. 55 shows the sequence matching results by means of the MS/MS spectrum.

Also, the norbornene binding site of the antibody-norbornene complex was confirmed through comparison of the MS/MS spectrum with trastuzumab. As a result, it was confirmed that the norbornene molecule was bound to a K248 site of the sequence LFPPKPKDTLMISRTPEVTCVVVDVSHEDPEVKF. The MS/MS chromatograms are shown FIGS. 51 to 54, and the sequence matching results based on the MS/MS spectra are shown in FIG. 55.

The conditions for the analysis are as follows:

UPLC Conditions

Measuring equipment: Acquity UPLC I-Class system

1. Column: Thermo MAbPac™ RP (2.1 mm×5 mm)
2. Column Temp.: 60° C.
3. Mobile phase A. 0.1% Formic acid in water B. 0.1% Formic acid in acetonitrile Mass Spectroscopy Conditions Measuring equipment: LTQ Elite (Thermo)

Source type: HESI

Capillary Temp.: 320° C.

Source heater temp.: 300° C.

Sheath gas flow: 40.00

Aux gas flow: 20.00

Sweep gas flow: 5.00

Source voltage (KV): 4.00

FTMS resolution: 120,000

FTMS mass range: 400 to 4,000

3.4. Confirmation of Structure of Trastuzumab-Azide

Figure 56:
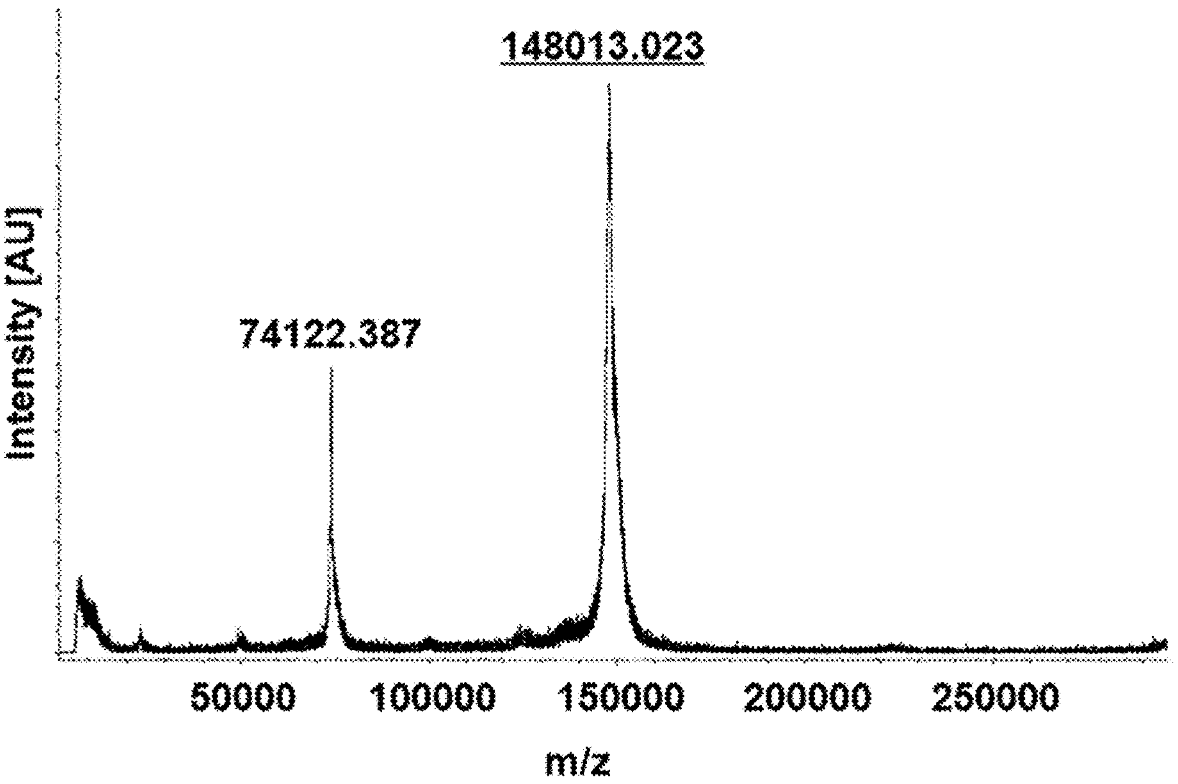
FIG. 56 shows the mass spectrum of trastuzumab measured to confirm a trastuzumab-azide structure.
Figure 57:
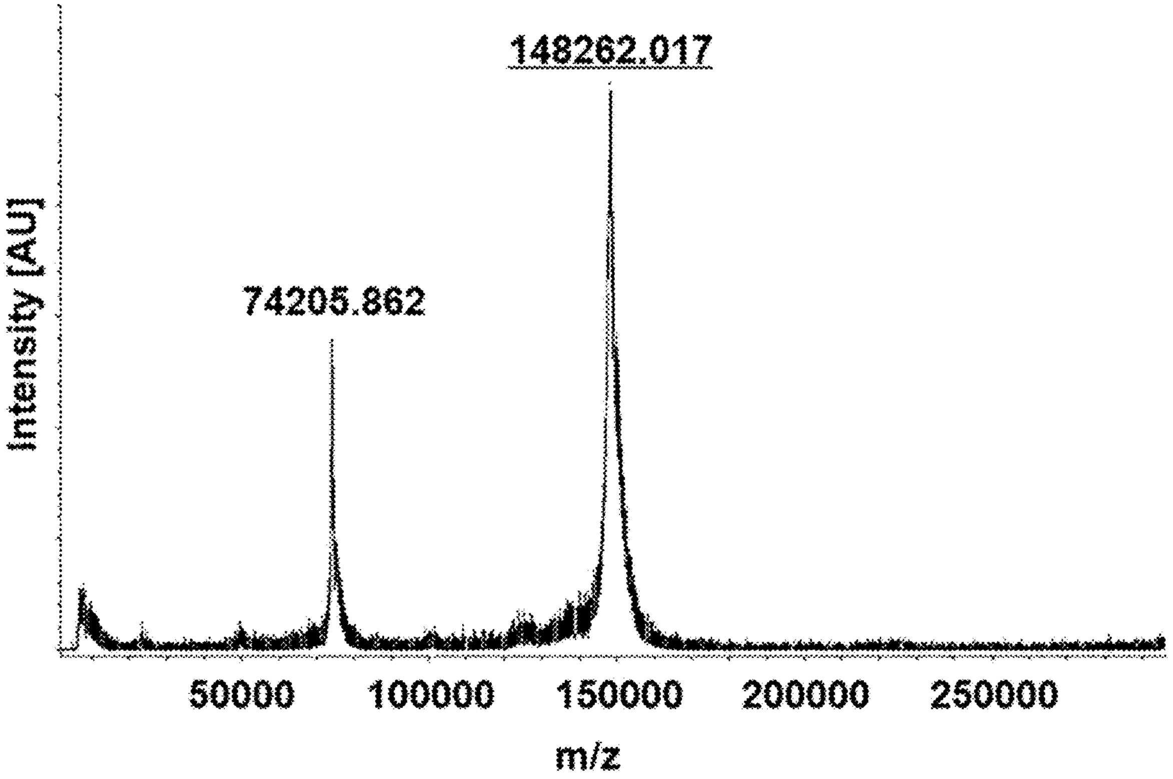
FIG. 57 shows the mass spectrum of a trastuzumab-azide complex measured to confirm the trastuzumab-azide structure.

The antibody-azide complex in which an azide linker was bound to an antibody via Compound IV-SSFI (Dap) was confirmed using mass spectrometry. A molecular weight increase of 249 Da was confirmed when two molecules of an azide compound were bound to trastuzumab. The measured mass spectrum of trastuzumab is shown in FIG. 56, and the mass spectrum of the antibody-azide complex to which two azide molecules were bound is shown in FIG. 57.

Measuring equipment: Ultraflex III (TOF/TOF)

Analysis mode: Linear mode

Polarity: Positive

Detection: m/z 2,000 to 300,000

Laser repetition rate: 100 Hz

Number of shots: 1,000 shots

Deflection: On, 5,000 Da

Voltage: Ion Source kV, Ion Source II 23.00 kV, Lens 9.00 kV

Calculated molecular weight: 148,271 g/mol

Measured molecular weight: 148,262 g/mol

4. Synthesis and Confirmation of Structure of Antibody-Payload Conjugate 4.1. Synthesis Method and Confirmation of Structure of Payload

[Scheme 15] Synthesis of Tetrazine-DM1
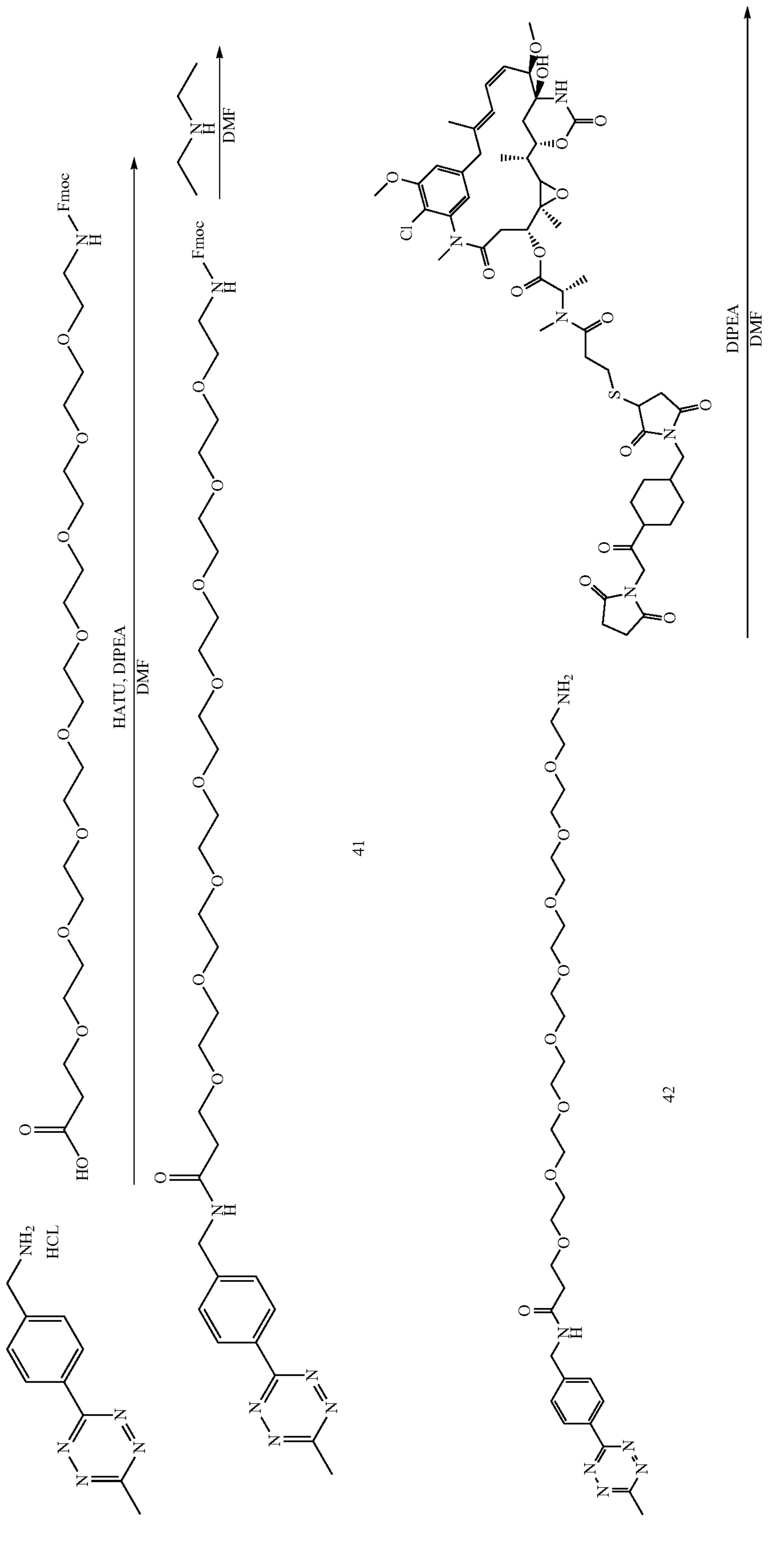
41
42

-continued
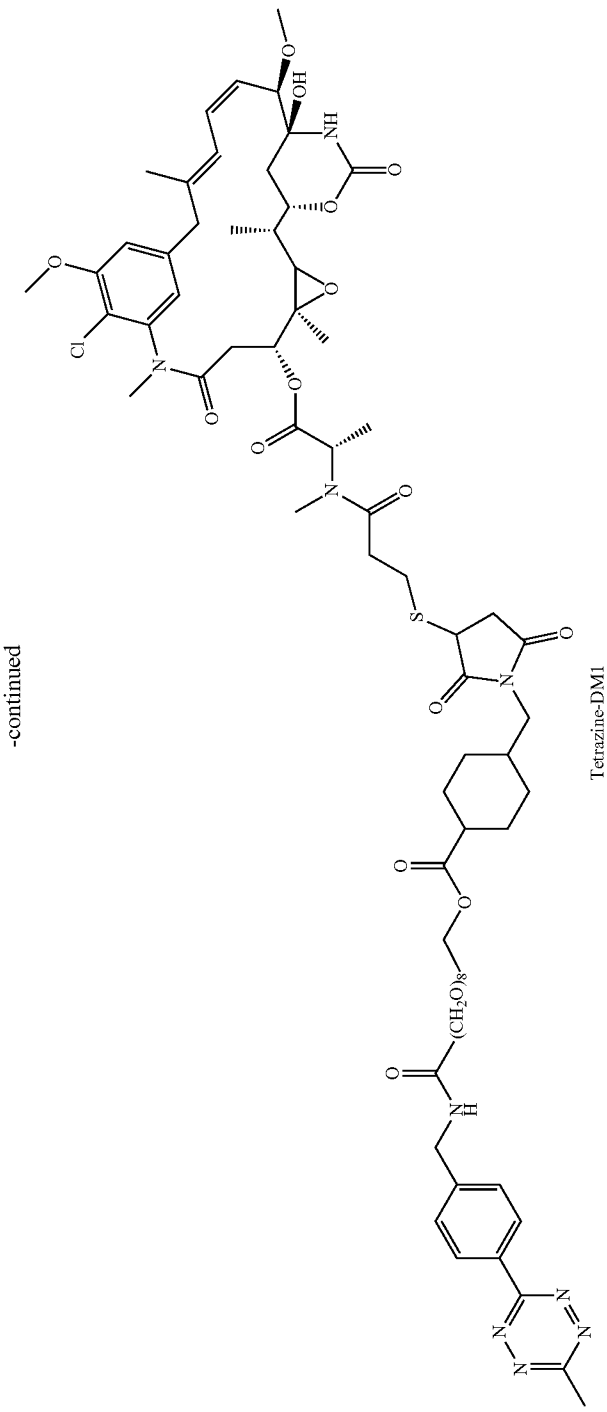
Tetrazine-DM1

Synthesis Method of Tetrazine-DM1

Synthesis of Compound 41

0.53 g (0.8 mmol, 1.0 eq.) of Fmoc-PEG8-OH was dissolved in 7 mL of DMF, and then stirred. Thereafter, 0.38 g (1.0 mmol, 1.25 eq.) of HATU and 0.3 mL (1.7 mmol, 2.1 eq.) of DIPEA were added dropwise thereto. 0.205 g (0.86 mmol, 1.1 eq.) of methyltetrazine-amine. HCl was added dropwise, and 0.3 mL (1.7 mmol, 2.1 eq.) of DIPEA was added dropwise thereto. The resulting mixture was stirred for 4 hours, and then concentrated under reduced pressure to remove the solvent. The mixture was purified by column chromatography (5% MeOH in DCM) to obtain a target compound. TLC (DCM:MeOH=20:1); $R_f$=0.3.

Synthesis of Compound 42

0.527 g (0.62 mmol, 1.0 eq.) of Compound 41 was dissolved in 6 mL of DMF, and 0.3 mL of diethylamine was added dropwise thereto. The resulting mixture was stirred for 2.5 hours, and then concentrated under reduced pressure to remove the solvent. The mixture was purified by column chromatography (DCM:MeOH:$NH_4OH$=80:25:2.5) to obtain a target compound, the amount of which was confirmed to be 0.273 g (yield: 70%). TLC (DCM:MeOH:$NH_4OH$=80:25:2.5); $R_f$=0.1.

Synthesis of Tetrazine-DM1

0.355 g (0.57 mmol, 1.5 eq.) of Compound 42 was dissolved in 25 mL of DMF, and then stirred. 0.405 g (0.38 mmol, 1.0 eq.) of DM1-SMCC-NHS was added thereto, and DIPEA was added dropwise until the pH of the mixture reached pH 9.0. Thereafter, the mixture was stirred for 2 hours. The reaction solution was concentrated under reduced pressure, and then purified by column chromatography (10% MeOH in DCM) to obtain a target compound, the amount of which was confirmed to be 0.434 g (yield: 73%). TLC (DCM:MeOH=10:1); $R_f$=0.5.

Confirmation of Structure of Tetrazine-DM1

LRMS (ESI): m/z 782.6 [$M+2H^+$]

Figure 58:
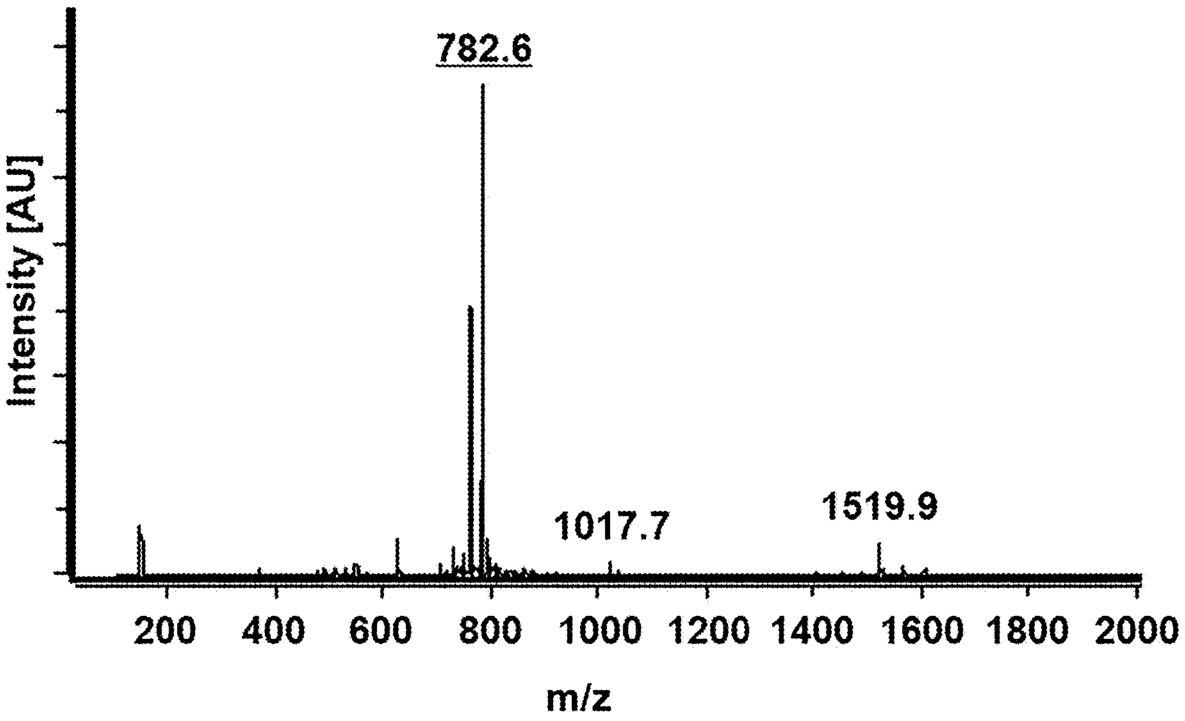
FIG. 58 shows the results of confirming a structure of tetrazine-DM1 by means of mass spectrometry.

The results are shown in FIG. 58.

4.2. Synthesis and Confirmation of Structure of Antibody-Payload Conjugate 4.2.1. Antibody-Norbornene-Tetrazine-DM1

Synthesis Method of Trastuzumab-Norbornene-Tetrazine-DM1 (1)

Introduction Reaction of Tetrazine-DM1 into Trastuzumab-Norbornene Using Compound III-SSFI (Dap)

An antibody-payload conjugate was constructed using trastuzumab into which two norbornene molecules were introduced via Compound III-SSFI (Dap). A reaction was carried out using 25 mL of the antibody-payload conjugate at a concentration of 4.5 mg/mL, and conjugation of a tetrazine-PEG8-DM1 drug was attempted for a biorthogonal reaction (i.e., biorthogonal chemistry) with norbornene conjugated to the antibody. 40 Equivalents of the drug was used per one antibody, and the conjugation reaction was performed at room temperature for 24 hours in a 20 mM histidine acetate solution (pH 5.5). The conjugation reaction was monitored by HIC-HPLC, and it was observed that the peaks appearing at 7.7 minutes after only a norbornene molecule was bound to trastuzumab were shifted to 8.7 minutes (DAR 1) and 10.5 minutes (DAR 2) as the tetrazine-PEG8-DM1 drug reacted with the antibody-norbornene linker. As a result, formation of the antibody-payload conjugate was observed.

Figure 59:
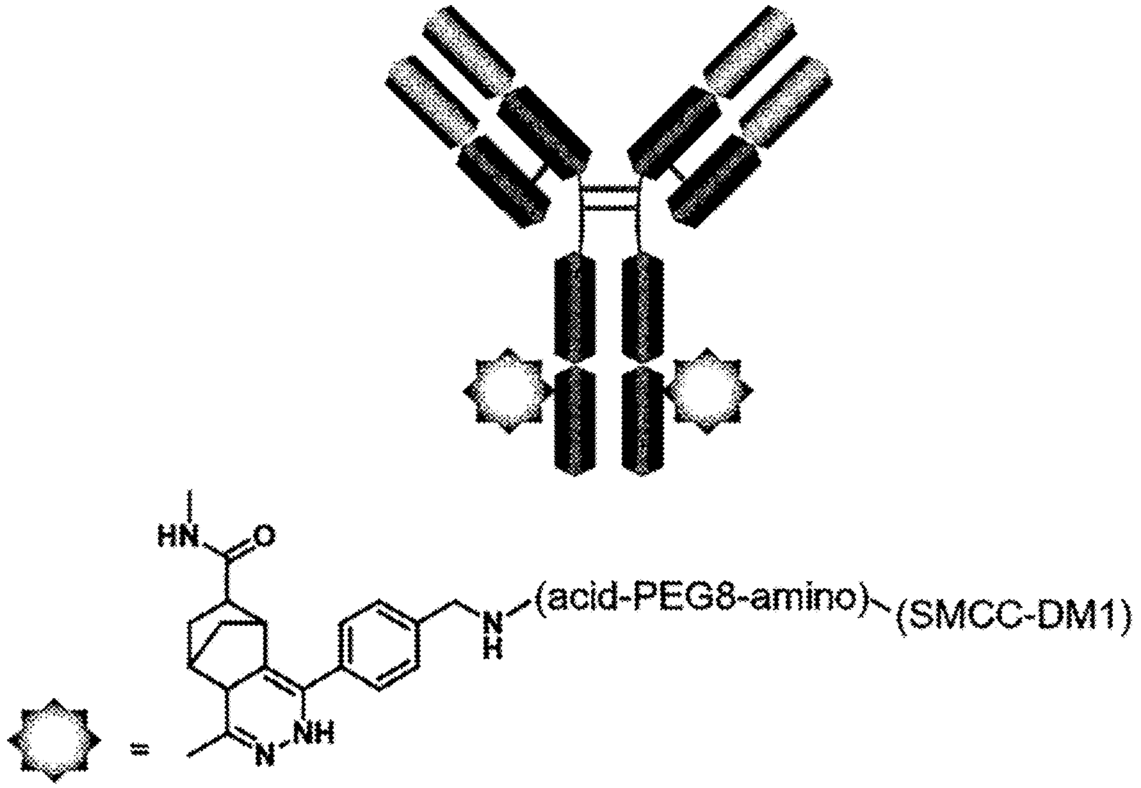
FIG. 59 shows a structure of a Compound III-SSFI (6Dap)-based trastuzumab-DM1 conjugate.
Figure 60:
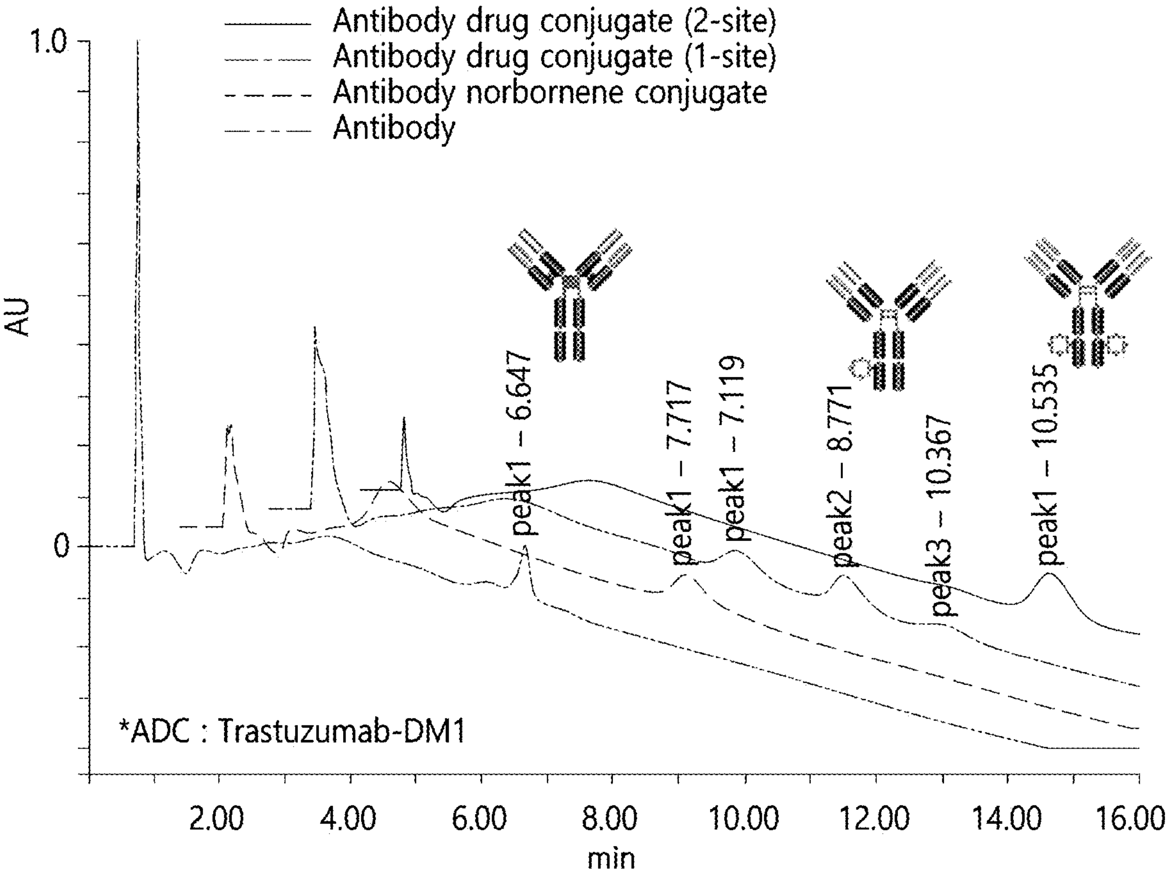
FIG. 60 shows the results of observing a formation reaction of a trastuzumab-DM1 conjugate by means of HIC-HPLC.

The structure of the product 'antibody-payload conjugate' is shown in FIG. 59, and the reaction monitoring by HIC-HPLC is shown in FIG. 60 (Table 13).

TABLE 13

Reaction monitoring by HIC-HPLC for formation of antibody-payload conjugate

| Retention time | Composition |
|---|---|
| 6.6 min | Trastuzumab |
| 7.7 min | Trastuzumab-norborene conjugate |
| 8.7 min | Trastuzumab-DM1 conjugate (1 site, DAR1) |
| 10.5 min | Trastuzumab-DM1 conjugate (2 site, DAR2) |

Confirmation of Trastuzumab-Norbornene-Tetrazine-DM1 Structure (2)

An antibody-drug conjugate in which tetrazine-DM1 was bound to Trastuzumab-Norbornene was confirmed by mass spectrometry. It was determined to which site of the antibody the tetrazine-DM1 was bound via $F(ab')_2$ and Fc/2 after the antibody-drug conjugate was treated with an IdeS enzyme. It was confirmed that the Ides Fc/2-DM1 complex was found to have an "Obs-Theo" value of 1673.5, indicating that the drug was bound to the conjugate in consideration of the combined value of one tetrazine-DM1 molecule, which corresponded to the molecular weight of 1,688.80 Da (a dehydration reaction was observed in the molecular weight analysis of the DM1-series drug). The observed mass spectrum of the Ides_$F(ab')_2$ was detected, but the mass value of one charge was not shifted due to the complexity of the respective mass spectra, thereby making impossible to obtain the corresponding mass value.

Figure 61:
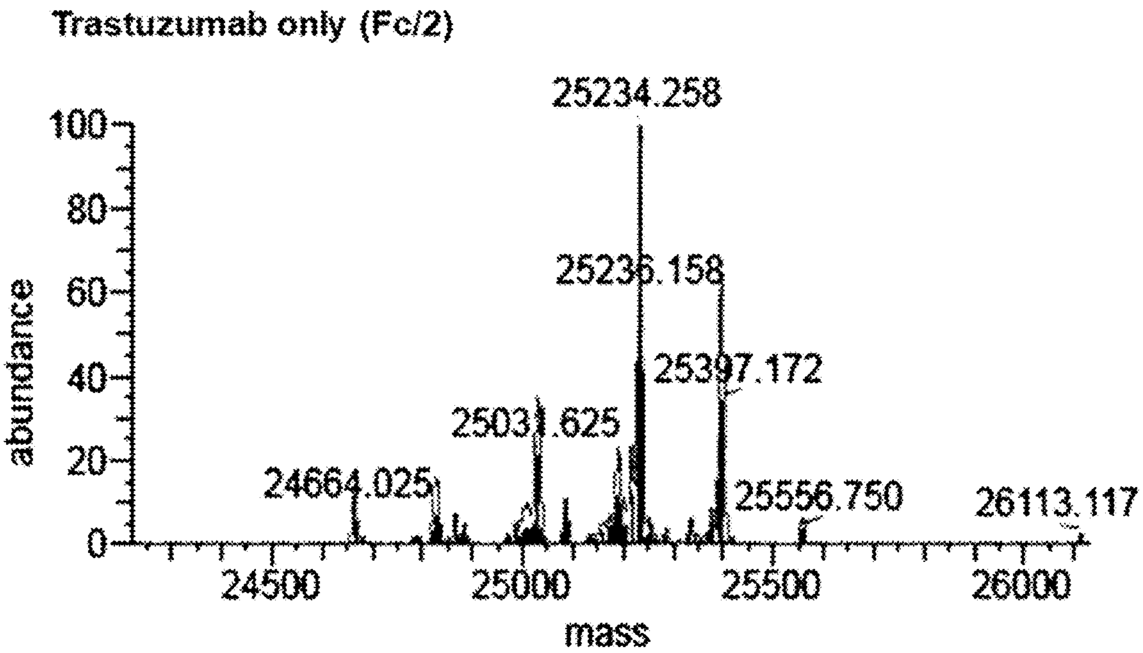
FIG. 61 and FIG. 62 show an increase of molecular weight spectra by norbornene-tetrazine-DM1 binding.
Figure 62:
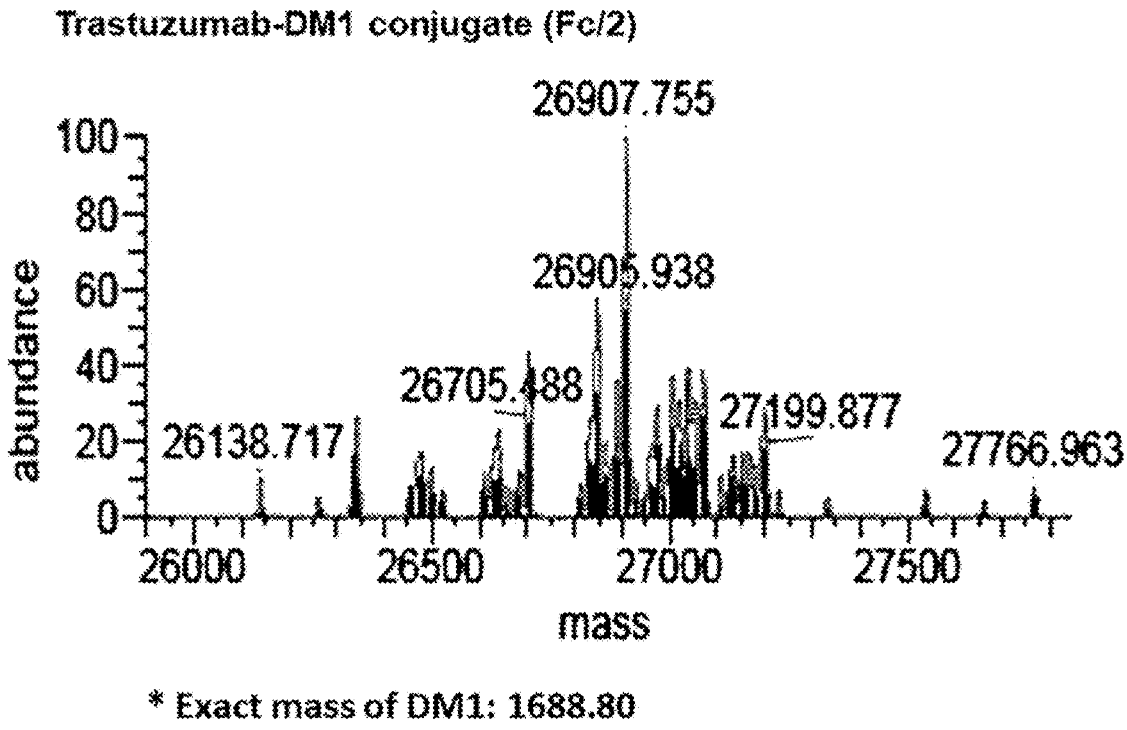

The spectra of the complex having an increased molecular weight due to the trastuzumab-norbornene-tetrazine-DM1 binding are shown in FIGS. 61 and 62.

UPLC Conditions

Measuring equipment: Acquity UPLC I-Class system

1. Column: Thermo MAbPac™ RP (2.1 mm×5 mm)
2. Column Temp: 60° C.
3. Mobile phase A. 0.1% Formic acid in water B. 0.1% Formic acid in acetonitrile Mass Spectroscopy Conditions Measuring equipment: LTQ Elite (Thermo)

Source type: HESI

Capillary Temp.: 320° C.

Source heater temp.: 300° C.

Sheath gas flow: 40.00

Aux gas flow: 20.00

Sweep gas flow: 5.00

Source voltage (KV): 4.00

FTMS resolution: 120,000

FTMS mass range: 400 to 4,000

5. FcRn Binding Analysis of Antibody-Drug Conjugate

The antibody-drug conjugate constructed in this patent was named 'AbClick®Pro.'

To check whether or not the antibody-drug conjugate (see FIG. 59; AbClick®Pro (NC, DM1)) had an antibody recycling function, the binding affinity of the conjugate for a neonatal Fc receptor (FcRn), which is closely associated with the in vivo antibody recycling, was analyzed. As one of the biomolecular interaction systems, Octet (model: Octet QK384) was used to determine the reaction affinity of FcRn for the constructed ADC. As a difference in reflection of light caused by a surface change, which occurs according to a degree of reaction between molecules attached to a surface of a sensor and molecules in a sample, was recognized as being free of a label, kinetic analysis was performed. Trastuzumab, Kadcyla, and AbClick®Pro (NC, DM1) were used as the samples to measure binding affinities for FcRn under a condition of pH 6.0. As a result, it was confirmed that the measured KD values were $1.12\times10^{-7}$ M, $1.12\times10^{-7}$ M, and $8.84\times10^{-8}$ M, respectively, indicating that AbClick®Pro had a similar or superior binding affinity, compared to Kadcyla (Table 14).

TABLE 14

FcRn binding analysis of antibody-drug conjugate

| | FcRn binding | | |
|---|---|---|---|
| pH 6.0 | KD_Kinetics (M) | Ka (1/Ms) | Kd (1/S) |
| Trastuzumab | 1.12E−7 | 3.31E+05 | 3.69E−02 |
| Kadcyla | 1.12E−7 | 2.10E+05 | 2.37E−02 |
| *AbClick ® Pro | 8.84E−8 | 2.26E+05 | 1.99E−02 |

6. Antigen Binding Analysis of Antibody-Drug Conjugate

Figure 63:
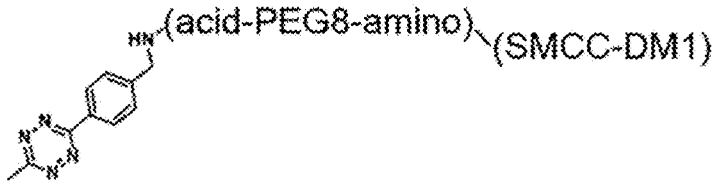
FIG. 63 shows structures of three designs of payloads bound to an antibody labeled with norbornene.
Figure 63:
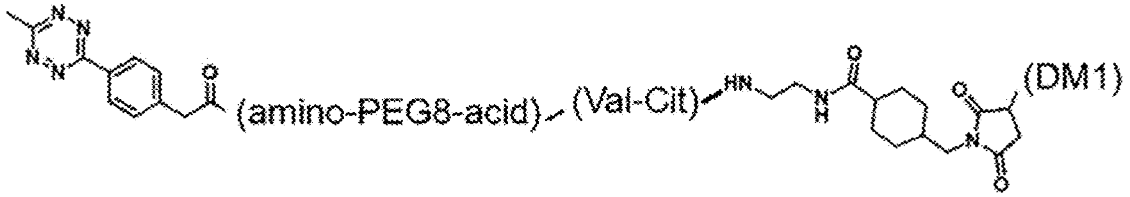
Figure 63:

It was determined through enzyme-linked immunosorbent assay (ELISA) analysis whether or not a Her2 protein was bound to the antibody-drug conjugate. The antibody-norbornene complex constructed using trastuzumab and Compound III-SSFI (Dap) was used as the antibody-drug conjugate for measurement of antigen binding affinity. Structures of three drugs to be bound to the antibody-norbornene complex are shown in FIG. 63.

The dissociation constants (Kd) of Herceptin (trastuzumab), Kadcyla, AbClick®Pro (NC, DM1), AbClick®Pro (VC, DM1), and AbClick®Pro (VC, MMAE) from the antigen were confirmed to be approximately 98.6 pM, approximately 94.8 pM, approximately 121.4 pM, approximately 137.0 pM, and approximately 117.3 pM, respectively. Based on the results, it was confirmed that the binding site of the drug did not affect the binding affinity of the constructed ADC for the antigen.

Figure 64:
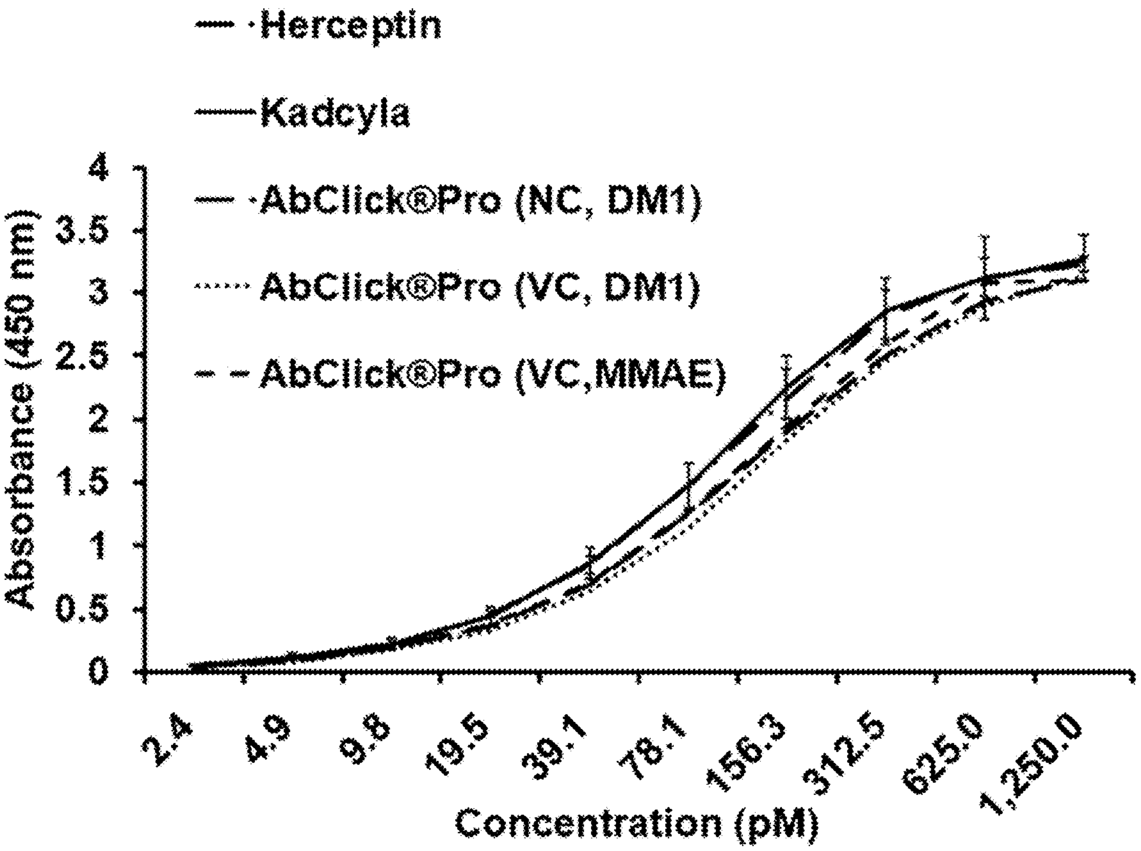
FIG. 64 shows the results of analyzing antigen binding affinity of an antibody-drug conjugate.

A graph of measuring the antigen binding affinities of the antibody-drug conjugates is shown in FIG. 64 (Table 15).

TABLE 15

Antigen binding analysis of antibody-drug conjugate

| Antibody | $K_D$ Value (binding affinity, pM) |
|---|---|
| Herceptin | 98.6 |
| Kadcyla | 947 |
| AbClick ®Pro (NC,DM1) | 121.4 |
| AbClick ®Pro (VC, DM1) | 137.0 |
| AbCHck ®Pro (VC,MMAE) | 117.3 |

7. Confirmation of Serum Stability of Antibody-Drug Conjugate

It was determined through enzyme-linked immunosorbent assay (ELISA) analysis whether or not the antibody-drug conjugate was stable in serum. The stabilities of the antibody-drug conjugates in rat, rabbit and human sera were tested at room temperature. It was confirmed that a pattern of an intact ADC (i.e., drug-bound ADC) residual level of the self-constructed ADC "AbClick®Pro (NC, DM1)" over time was consistent with that of the Kadcyla® group.

Figure 65:
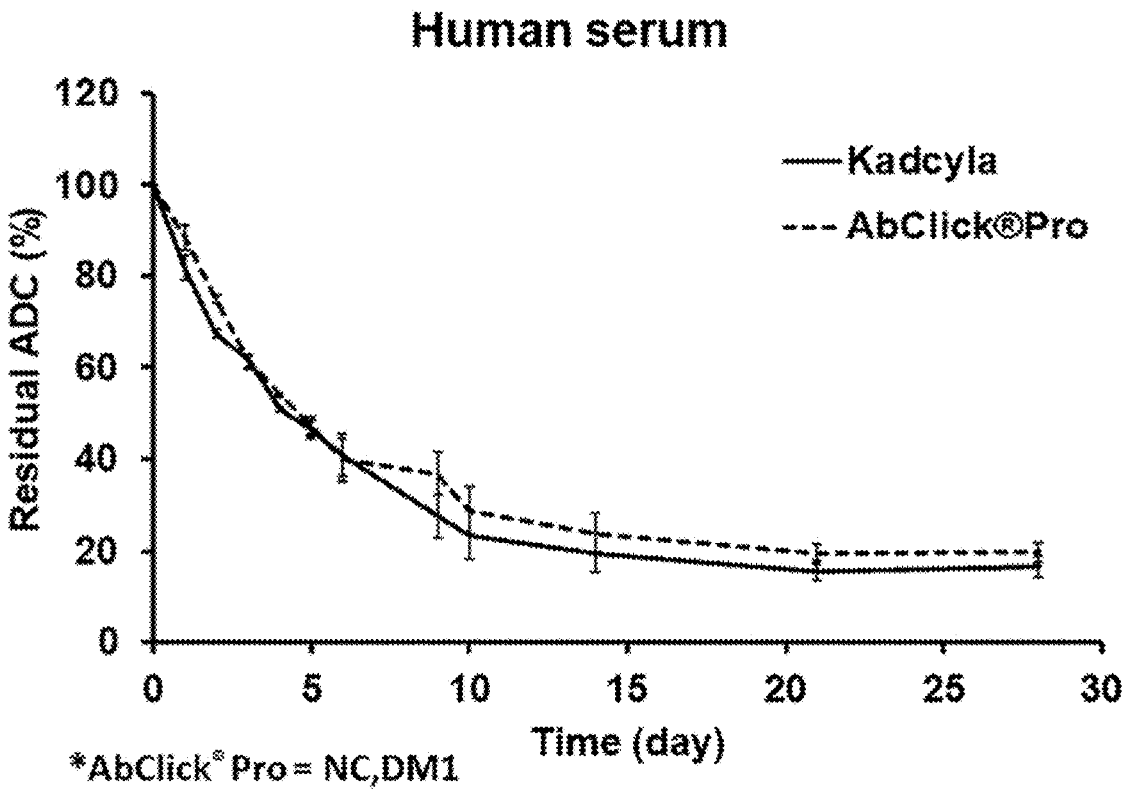
FIG. 65, FIG. 66 and FIG. 67 show the results of analyzing serum stability of the antibody-drug conjugate.
Figure 66:
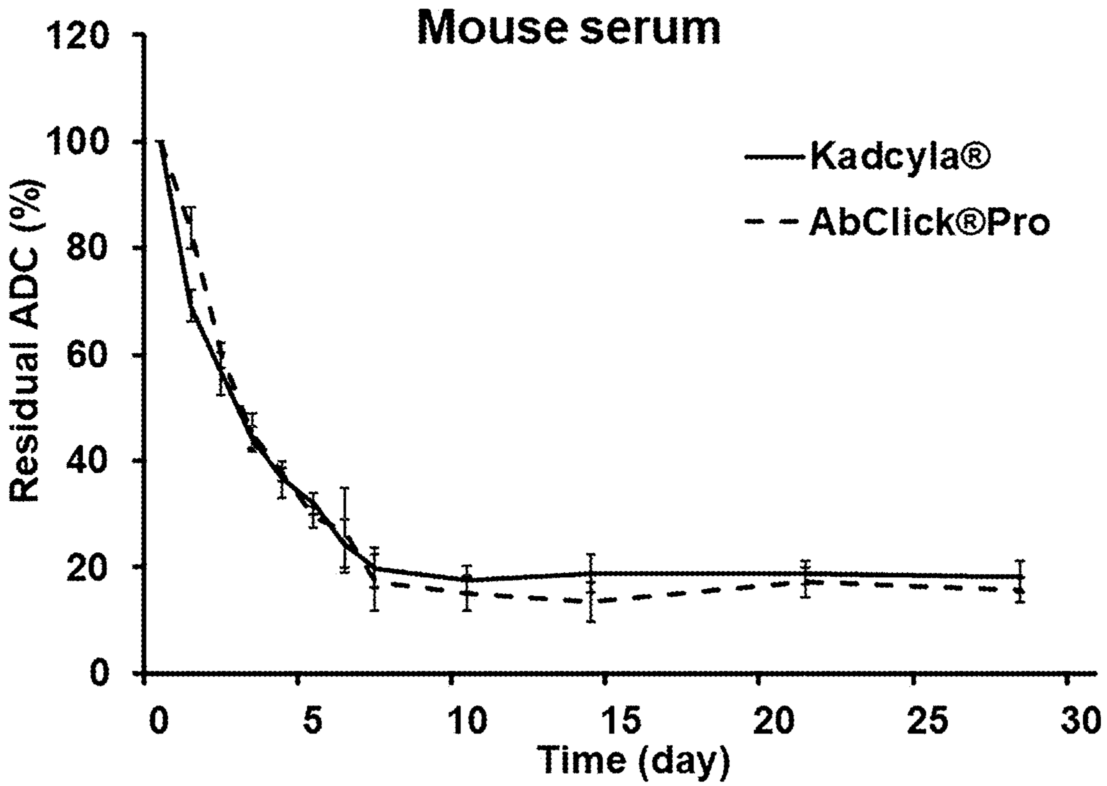
Figure 67:
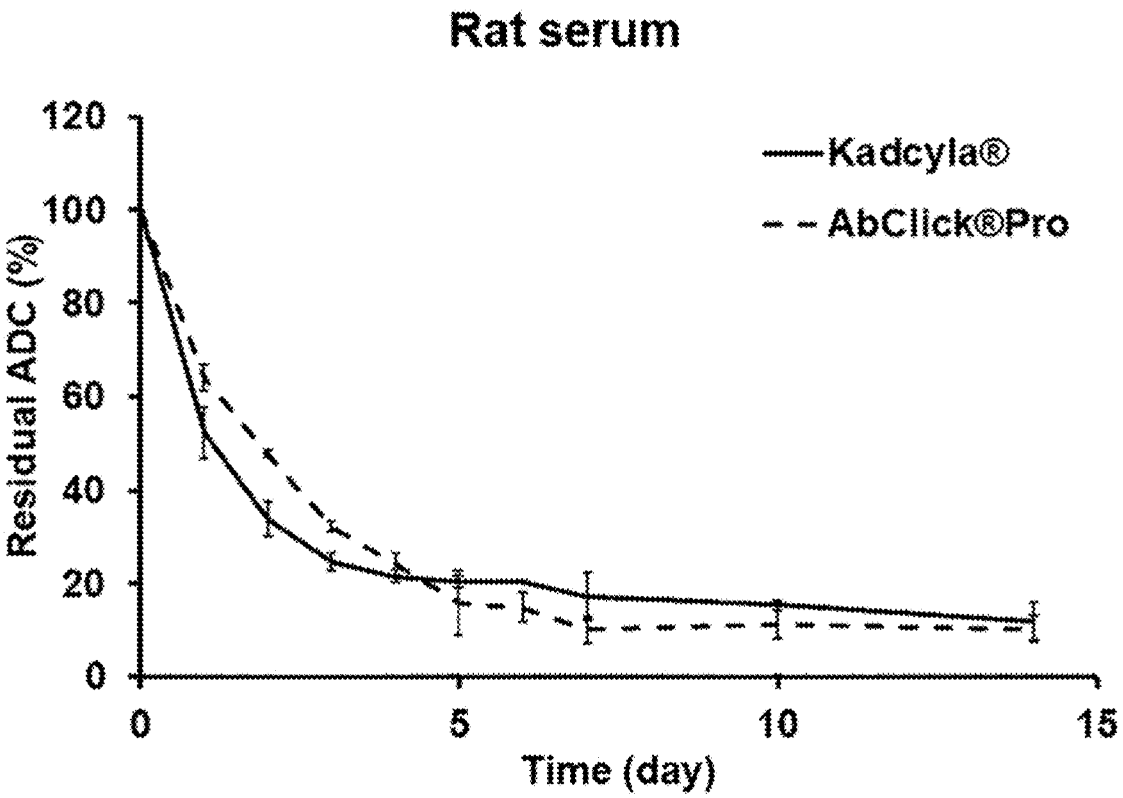

The results of serum stability analysis of the antibody-drug conjugate are shown in FIGS. 65 to 67.

8. Evaluation of Medicinal Effect of Antibody-Drug Conjugate (AbClick®Pro) at Cellular Level (In Vitro Cytotoxicity Test)

Medicinal effects of the three antibody-drug conjugates (ADC, AbClick®Pro series) using trastuzumab were evaluated according to a level of a target marker in cancer cells, and a cytotoxicity test was performed using NCI-N87 and MDA-MB-468 as a positive cell line expressing the target antigen (Her2) 'cell line' and a negative cell line expressing BT474, respectively. The three antibody-drug conjugates (AbClick®Pro (NC, DM1), AbClick®Pro (VC, DM1), and AbClick®Pro (VC, MMAE)) constructed in the Her2-overexpressing cells NCI-N87 were observed after the cells were treated with different concentrations of the antibody-drug conjugates. As a result, it was confirmed that the antibody-drug conjugates had IC50 values of 207.7 ng/ml, 93.9 ng/ml, and 57.7 ng/ml, indicating that the antibody-drug conjugates had an excellent anti-cancer effect. The three antibody-drug conjugates (AbClick®Pro (NC, DM1), AbClick®Pro (VC, DM1), and AbClick®Pro (VC, MMAE)) constructed in another Her2-overexpressing cell line BT474 were observed after the cells were treated with different concentrations of the antibody-drug conjugates. As a result, it was confirmed that the antibody-drug conjugates had IC50 values of 47.7 ng/ml, 44.6 ng/ml, and 1.09 ng/ml, indicating that the antibody-drug conjugates had an excellent anti-cancer effect. The utility of the AbClick®Pro (VC, MMAE) as the novel ADC was confirmed because the AbClick®Pro (VC, MMAE) was observed to have an equal or superior apoptotic effect, compared to Kadcyla as the commercially available Herceptin ADC.

Figure 68:
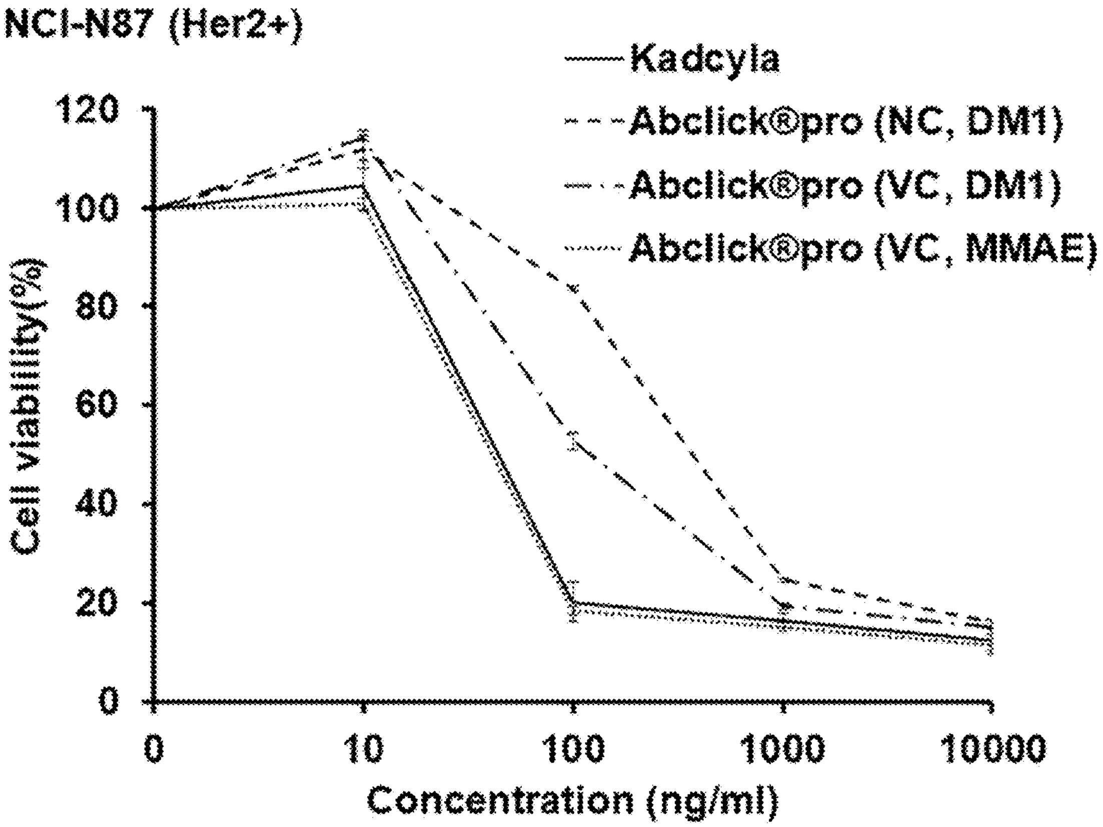
FIG. 68, FIG. 69 and FIG. 70 show the results of evaluating a medicinal effect of the antibody-drug conjugate at a cellular level.
Figure 69:
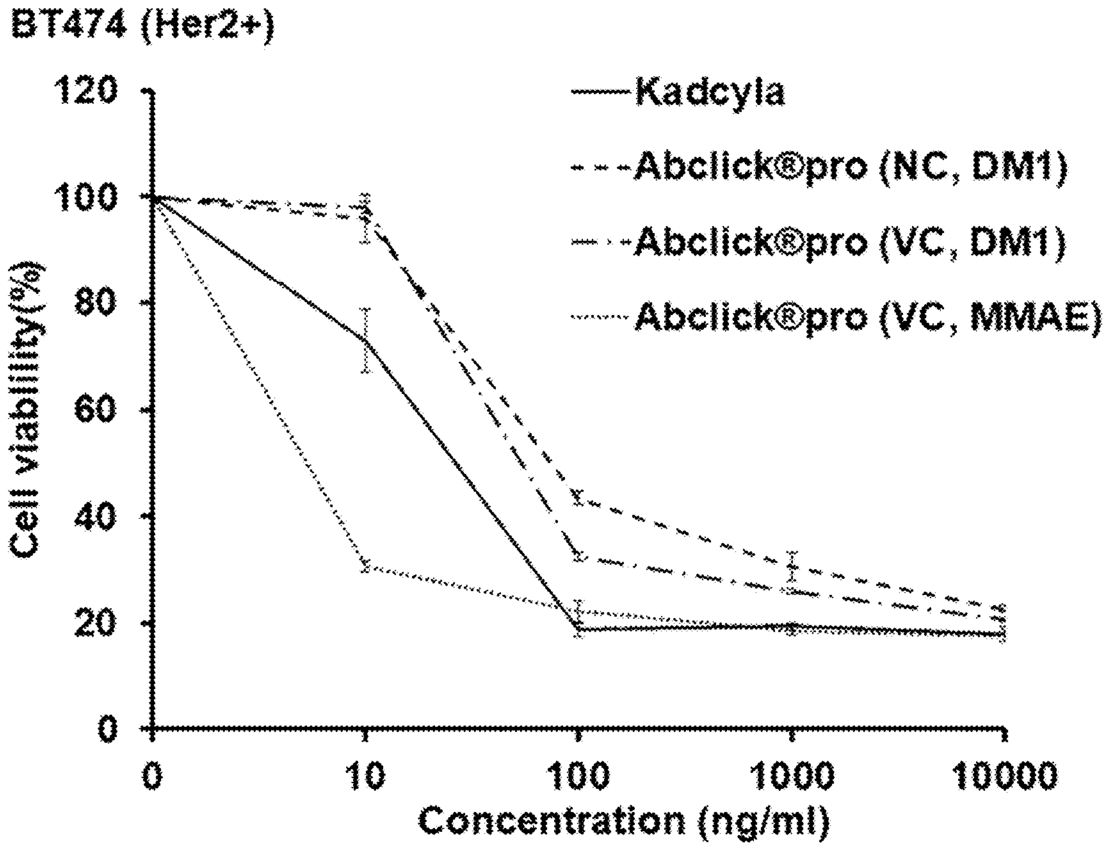
Figure 70:
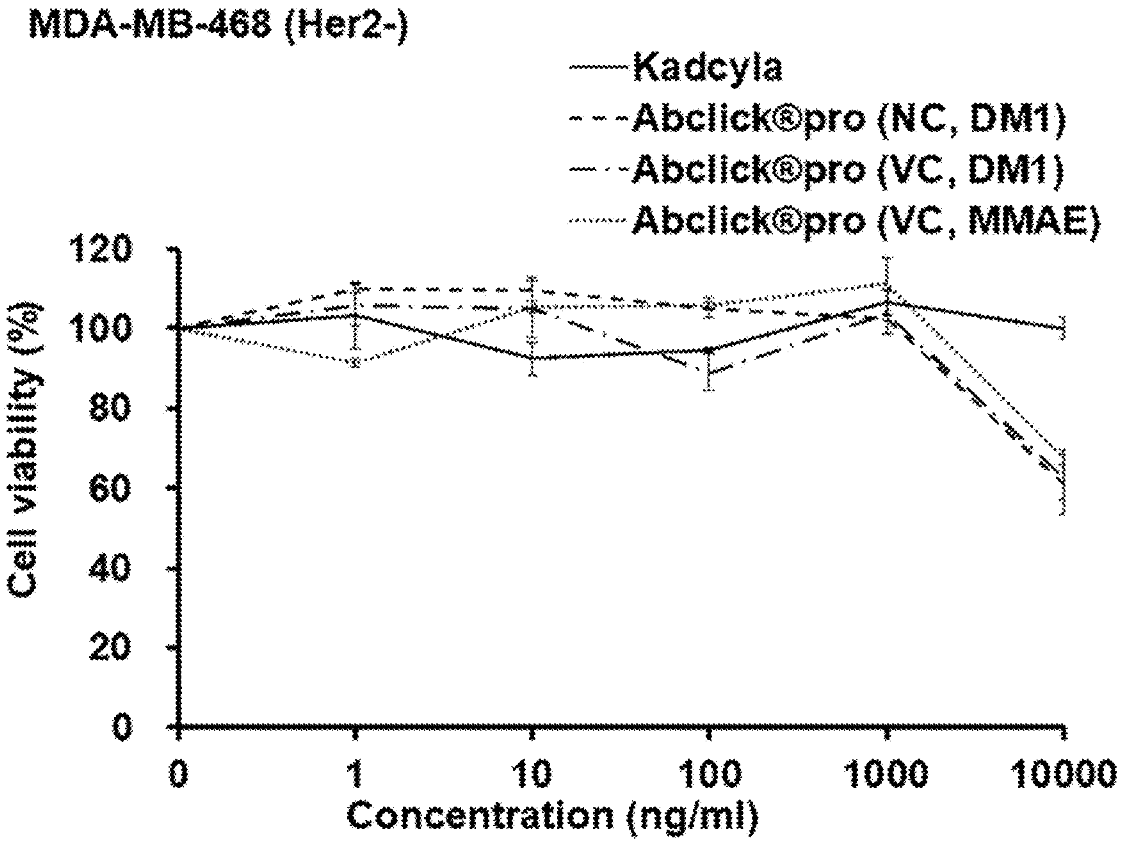

The test results are shown in FIGS. 68 to 70.

9. Evaluation of Medicinal Effect of Antibody-Drug Conjugate (AbClick®Pro) at Animal Level (In Vitro Cytotoxicity Test)

A target antigen-overexpressing NCI-N87 gastric cancer cell line was subcutaneously transplanted into mice to establish a xenograft model, and the mice were divided into 4 groups to perform an anti-cancer efficacy test on the materials administered. Because the BALB/c nude mice used in this test were deficient in T cells, cancer cells were easily transplanted into the BALB/c nude mice. Therefore, the BALB/c nude mice were used as a model suitable for an anti-cancer efficacy test using a rodent.

(a) Preparation of Cell Line

One vial of a human tumor cell line (NCI-N87 cell line) was put into a cell culture flask containing an RPMI1640 medium (Gibco, 22400-089) supplemented with heat-inactivated 10% fetal bovine serum (FBS; Gibco, 10082-742), and cultured at 37° C. in a 5% $CO_2$ incubator. The cell culture medium was washed with PBS, and diluted 10-fold with 2.5% trypsin-EDTA (Gibco, 15090). Thereafter, the diluted cell culture medium was added to separate the cells, and the cells were centrifuged (at 1,000 rpm for 5 minutes) to discard a supernatant. A fresh medium was added to the cell pellets to obtain a cell suspension. The viability of the cells was confirmed using a microscope, and the cells were diluted to a concentration of $1.25\times10^7$ cells/mL with a solution obtained by mixing a medium and Matrigel at a mixing ratio of 1:1 to prepare a cell line.

(b) Transplantation of Cell Line

A cell line was prepared using a method described in the section "4.3) (4) Preparation of cell line." The cells were re-suspended and homogenized to prepare a cell line, and the prepared cell line was immediately administered to animals. For transplantation of the cell line, the back region of the animal was sterilized with 70% alcohol, the dorsal skin was pulled with the thumb and forefinger to form a space between the skin and muscles. Thereafter, a syringe with a 26 gauge needle was stuck in a subcutaneous pocket between the thumb and forefinger, and the cell line was then subcutaneously administered at a dose of $2.5\times10^6$ cells/0.2 mL/head from the front of the animal. During an acclimation period, healthy animals were selected, and subjected to cell line inoculation. When the size of a tumor in the cell line-transplanted site reached approximately 100 to 150 $mm^3$, the mice were divided according to the size of a ranked tumor so that the tumor sizes in each group were distributed as uniformly as possible.

(c) Configuration of Experimental Groups and Determination of Dose and Administration Method Cell line=NCI-N87

Mouse type=BALB/c nude (CAnN.Cg-Foxn1nu/CrljOri)

Number per group=5

Administration method=Intravenous injection (using a 26-gauge needle syringe)

Dose=5 mg/kg

Number of administration=Once/3 day, administered three times

Observation period=5 weeks

Group 1: PBS; Group 2: Herceptin (trastuzumab); Group 3: Kadcyla; Group 4: AbClick®Pro (NC, DM1); Group 5: AbClick®Pro (VC, DM1); and Group 6: AbClick®Pro (VC, MMAE)

(d) Observation and Inspection Items

General Symptoms

During the administration and observation periods, the type of general symptoms (including death), the symptom onset date, and the severity of symptoms were observed once a day, and recorded for each individual. The individuals whose general symptoms worsened were quarantined.

Body Weight

The body weight was measured on the grouping date or the start date for administration of the test substance, and then measured twice a week.

Measurement of Tumor Size

The tumor size was measured twice a week for 5 weeks from the start date for administration of the test substance. The major- and minor-axis lengths of a tumor were measured using calipers, and the tumor size was calculated according to the following equation.

Tumor size=$ab^2/2$ ($a$: a major-axis length; and $b$: a minor-axis length)

(e) Results

The mice in the groups into which phosphate buffered saline (PBS) and Herceptin (trastuzumab) were injected did not show a tendency to suppress the growth of tumor for an observation period of 5 weeks. It was confirmed that the AbClick®Pro-series antibody-drug conjugates constructed according to the present invention has a superior ability to suppress the growth of tumor compared to Herceptin, indicating that the antibody-drug conjugates according to the present invention successfully function as the ADC.

Figure 71:
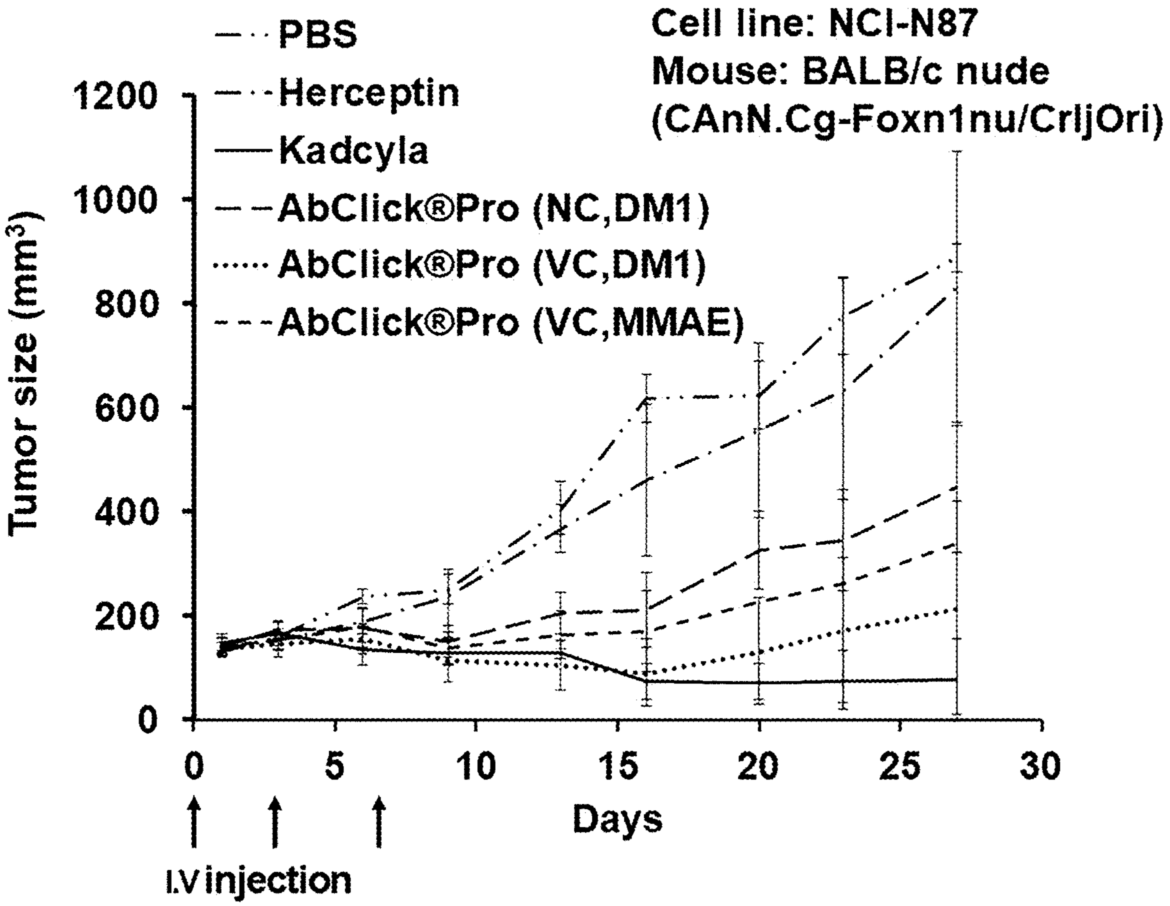
FIG. 71 and FIG. 72 show the results of evaluating a medicinal effect of the antibody-drug conjugate at an animal level.
Figure 72:
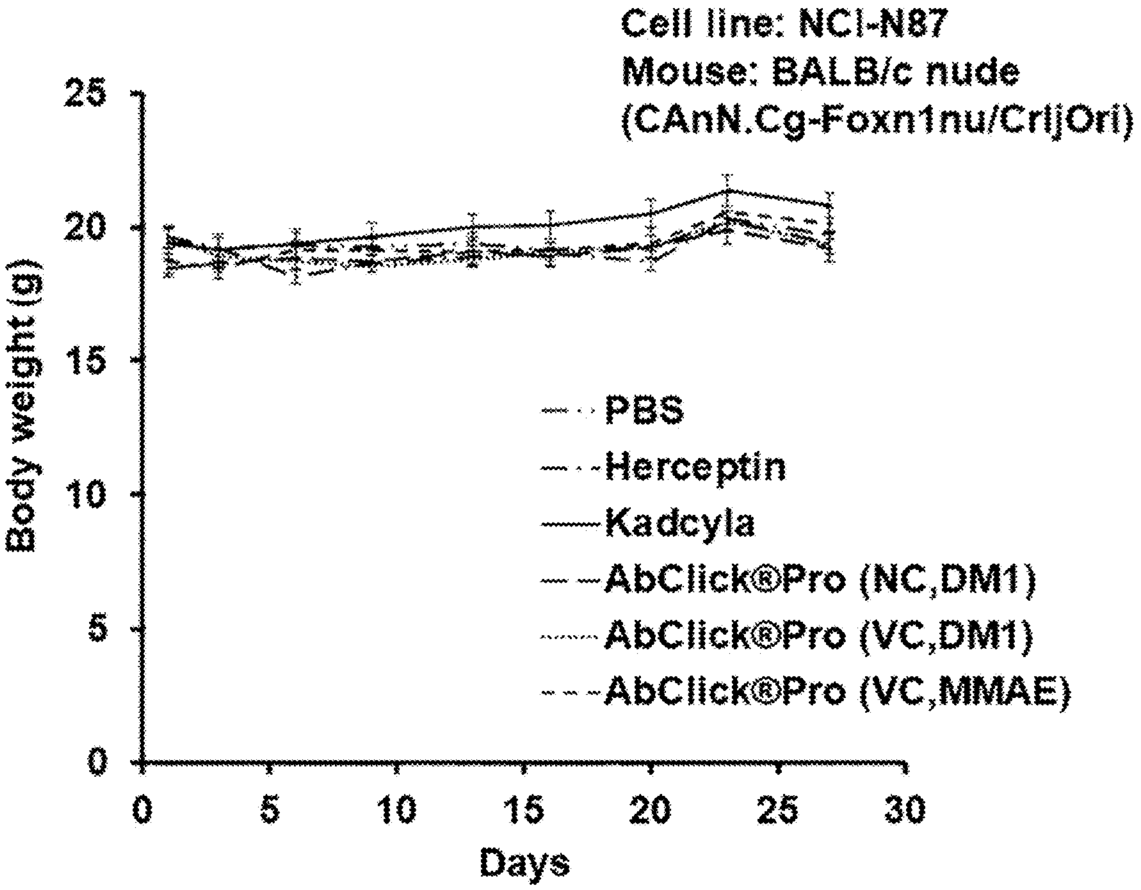

The related results are shown in FIGS. 71 and 72.

10. Pharmacokinetics (PK) Test of Antibody-Drug Conjugate

To analyze the pharmacokinetic characteristics of the antibody-drug conjugate (ADC) manufactured using the AbClick®Pro, an enzyme-linked immunosorbent assay (ELISA) was performed to confirm the pharmacokinetics of the antibody-drug conjugate. The manufactured ADC had an AbClick®Pro (NC, DM1) structure as shown in FIG. 59, and comparative validation with Kadcyla was carried out. Rats (n=3) were used for an animal model. In this case, the rats were intravenously injected with 5 mg/kg of ADC, and then monitored over time. It was confirmed that the intact ADC form (an intact ADC to which a drug was bound) of the administered AbClick®Pro (NC, DM1) was reduced over time. It was judged that the intact ADC had similar or improved drug characteristics, compared to Kadcyla.

Figure 73:
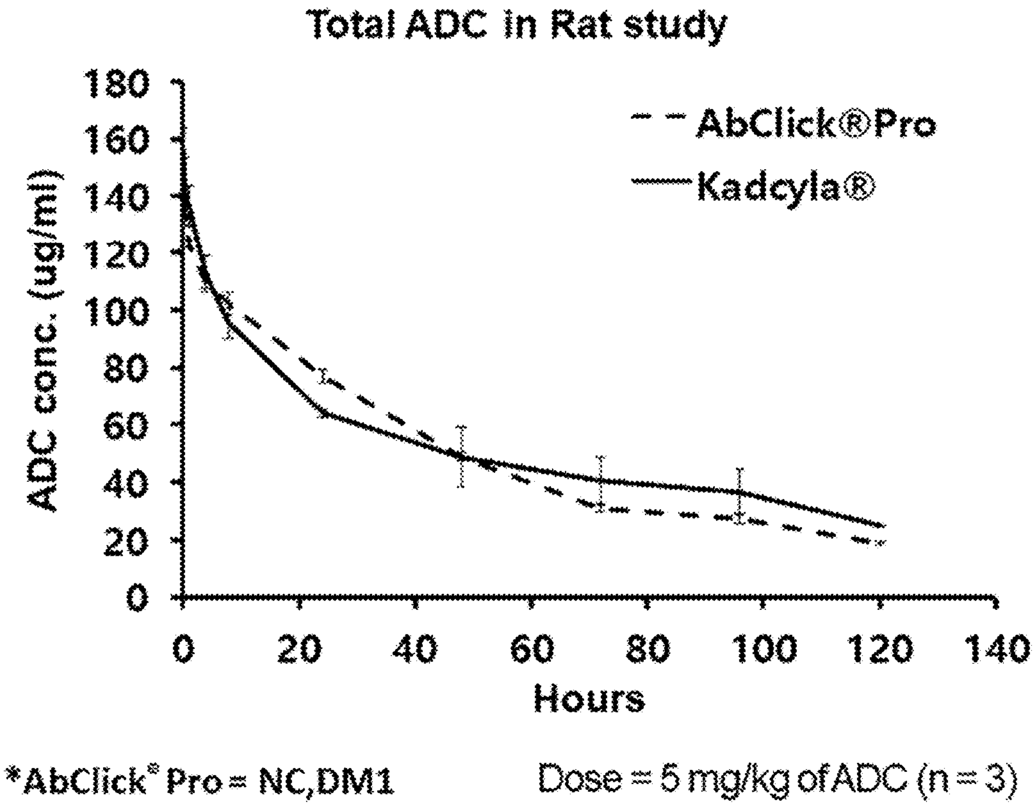
FIG. 73 shows the results of a pharmacokinetics test on the antibody-drug conjugate.

The results are shown in FIG. 73.

What is claimed is:

1. A peptide-compound conjugate having a structure of formula 6-3:

D-C-A-W-H-$(Xa_1)'$-G-E-L-V—W-C-T (SEQ ID NO: 16), [formula 6-3]

wherein,

D is an aspartic acid residue, C is a cysteine residue, A is an alanine residue, W is a tryptophan residue, H is a histidine residue, G is a glycine residue, E is a glutamic acid residue, L is a leucine residue, V is a valine residue, and T is a threonine residue, and $(Xa_1)'$ is

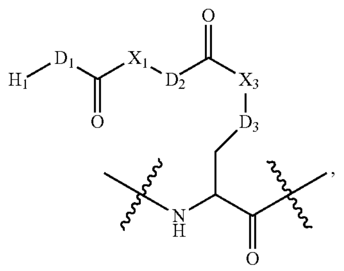

wherein $H_1$ is a click chemistry functional group selected from the group consisting of a terminal alkyne, an azide, a strained alkyne, a diene, a dienophile, a dibenzocyclooctyne-amine, a trans-cyclooctene, a norbornene, an alkene, a thiol, and a tetrazine, $D_1$ is selected from a covalent bond, $C_{1-4}$alkylene or heteroalkylene, $C_{2-4}$alkenylene, $C_{2-4}$alkynylene, and $C_{3-8}$cycloalkylene, $X_1$ is S, $D_2$ is selected from $C_{1-7}$alkylene, $C_{2-7}$alkenylene, $C_{2-7}$alkynylene, and $C_{3-8}$cycloalkylene, $D_3$ is a covalent bond, or $C_{1-3}$alkylene, and $X_3$ is NH, wherein the peptide exhibits the activity of binding to human immunoglobulin G (IgG), and wherein the cysteine residue adjacent to the N-terminus of formula 6-3 and the cysteine residue adjacent to the C-terminus of formula 6-3 are optionally linked.

2. The peptide-compound conjugate according to claim 1, wherein $D_1$ is a covalent bond and $D_2$ is methylene.

3. The peptide-compound conjugate according to claim 1, wherein $D_1$ is selected from a covalent bond and $-(CH_2)_{1-4}-$.

4. The peptide-compound conjugate according to claim 1, wherein $D_1$ comprises at least one heteroatom.

5. The peptide-compound conjugate according to claim 1, wherein $D_2$ is $-CH_2-$.

6. The peptide-compound conjugate according to claim 1, wherein $D_3$ is selected from a covalent bond and $-(CH_2)_{1-3}-$.

7. The peptide-compound conjugate according to claim 1, wherein $D_1$ is $-CH_2OCH_2-$.

8. The peptide-compound conjugate according to claim 1, wherein $D_1$ is $-CH_2CH_2OCH_2-$.

9. The peptide-compound conjugate according to claim 1, wherein a moiety comprising polyethylene glycol (PEG) is linked to a N-terminal amine group of the aspartic acid residue.

10. The peptide-compound conjugate according to claim 1, wherein a moiety represented by the following structure is linked to a N-terminal amine group of the aspartic acid residue:

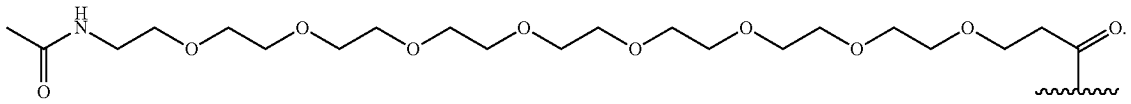 [SMILES: *C(=O)CCOCCOCCOCCOCCOCCOCCOCCOCCNC(C)=O]

11. The peptide-compound conjugate of claim 1, wherein the peptide-compound conjugate is represented by any one selected from the following structures:

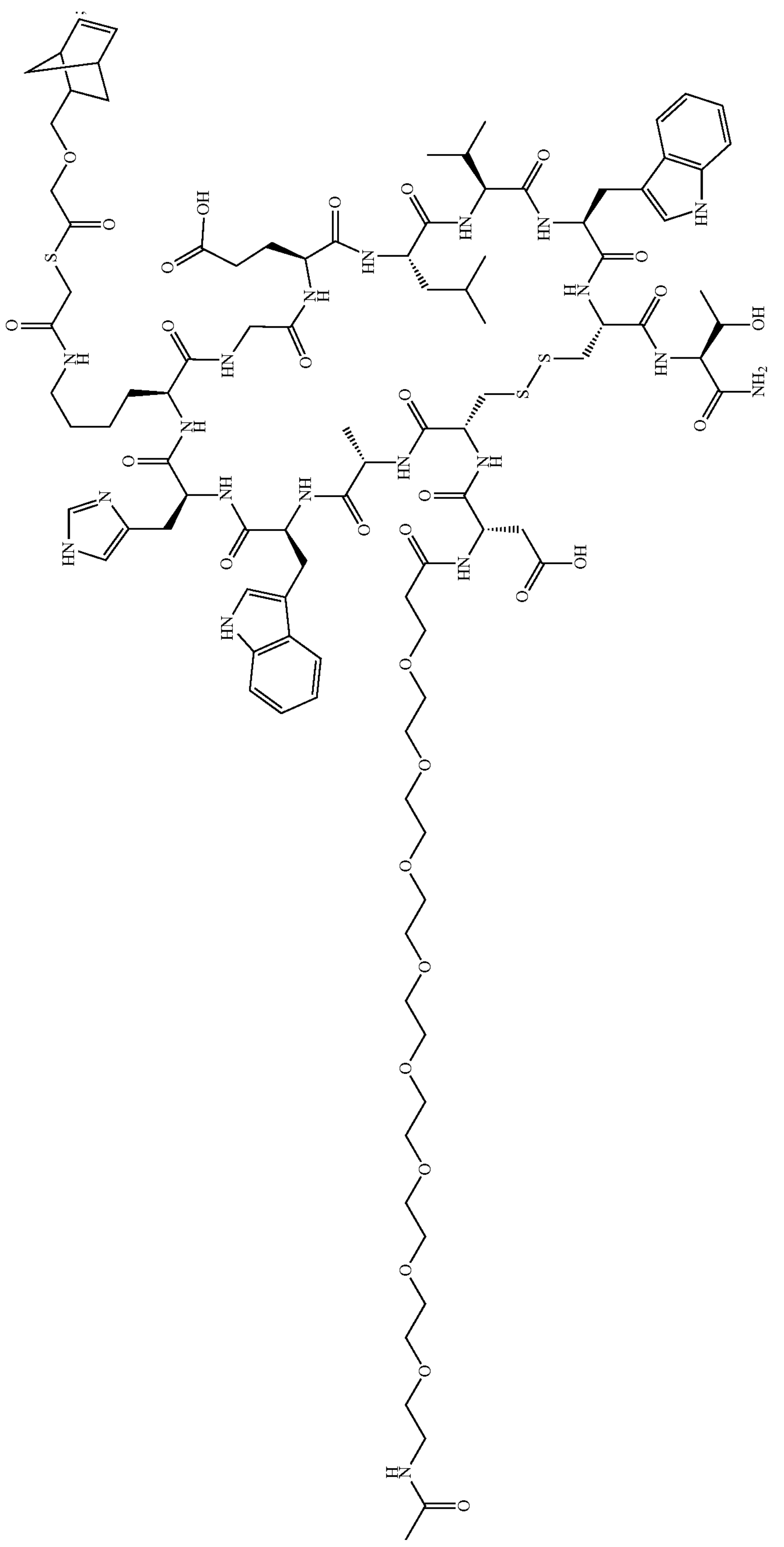

-continued
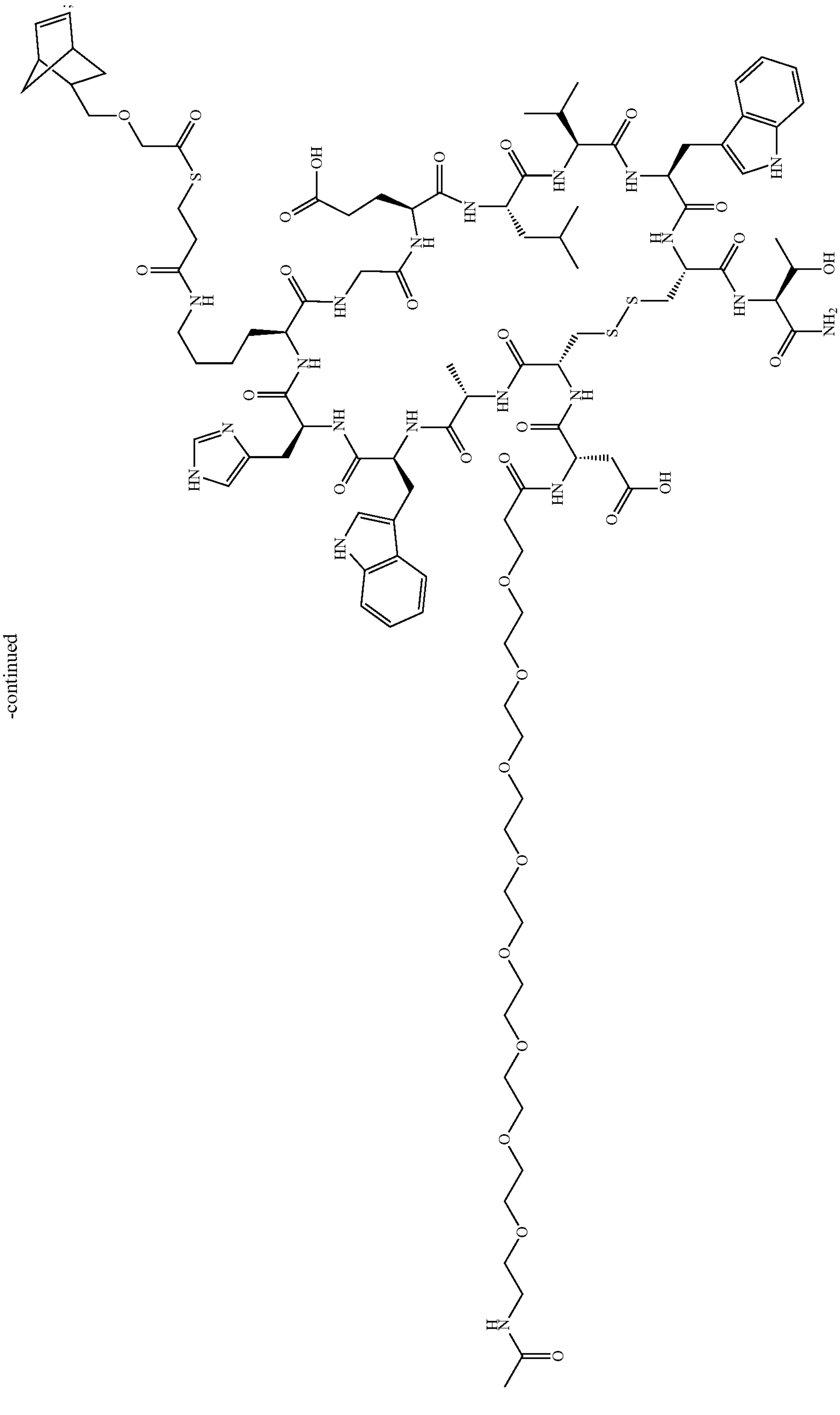

-continued
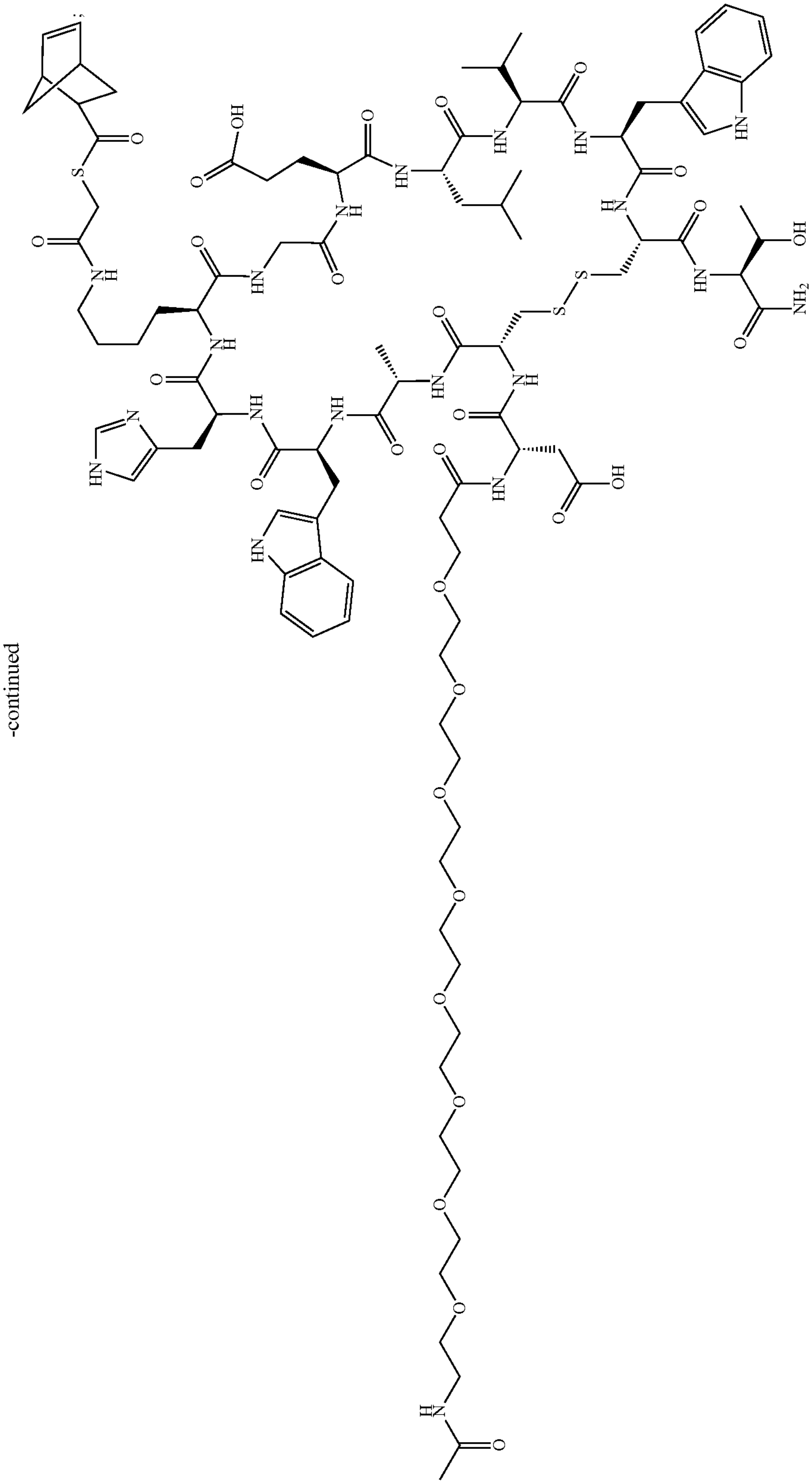

-continued
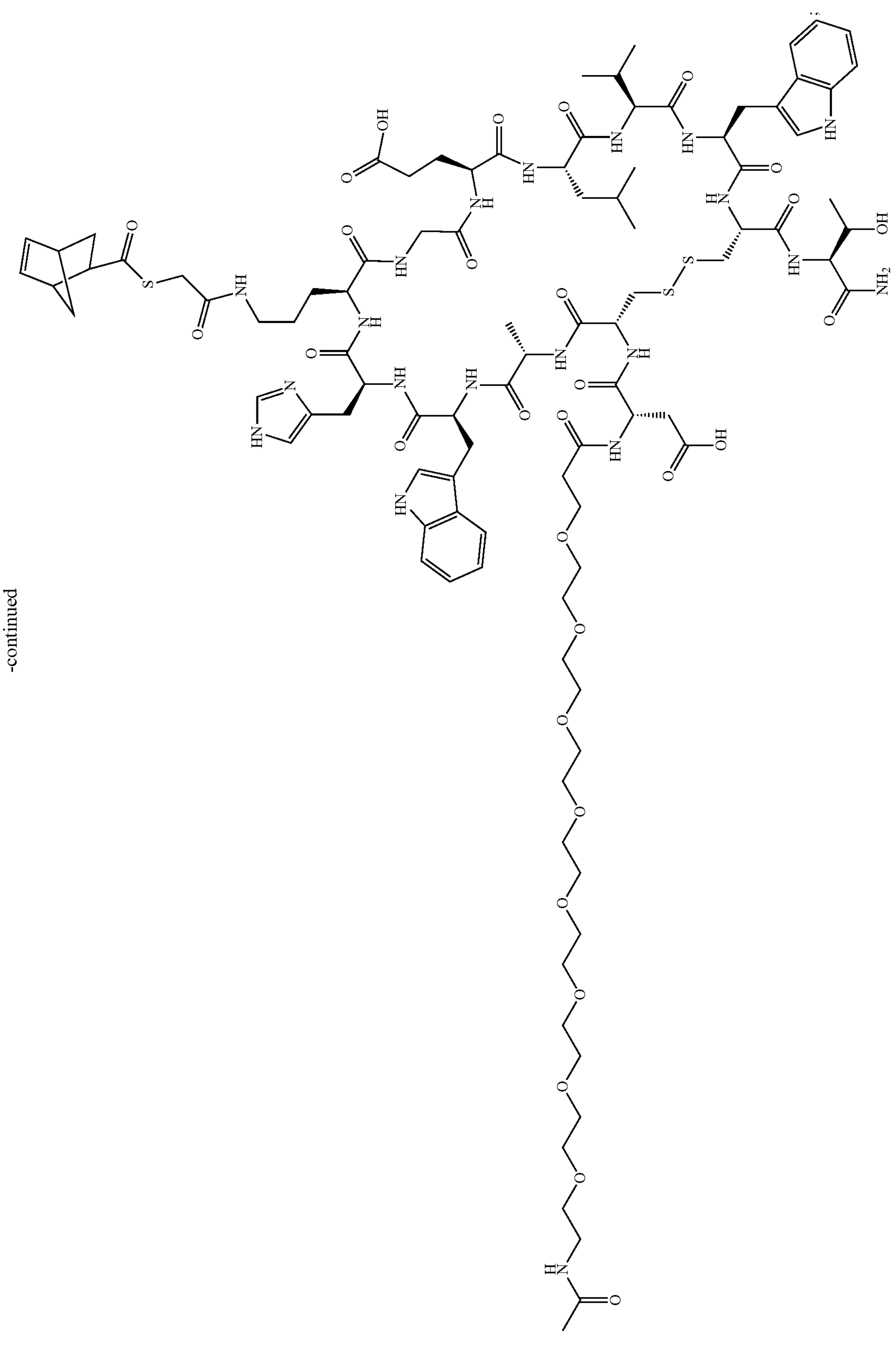

-continued
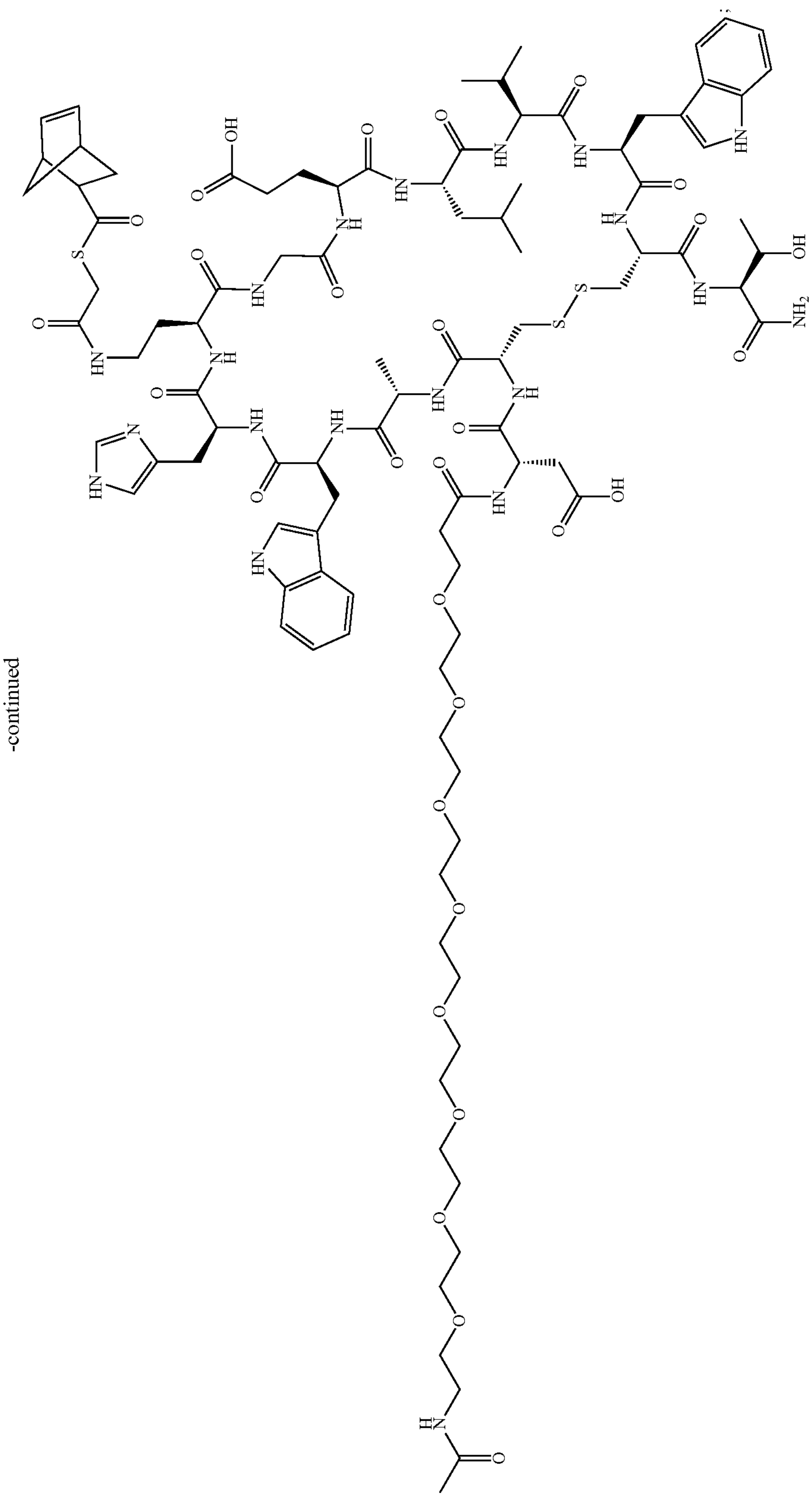

-continued
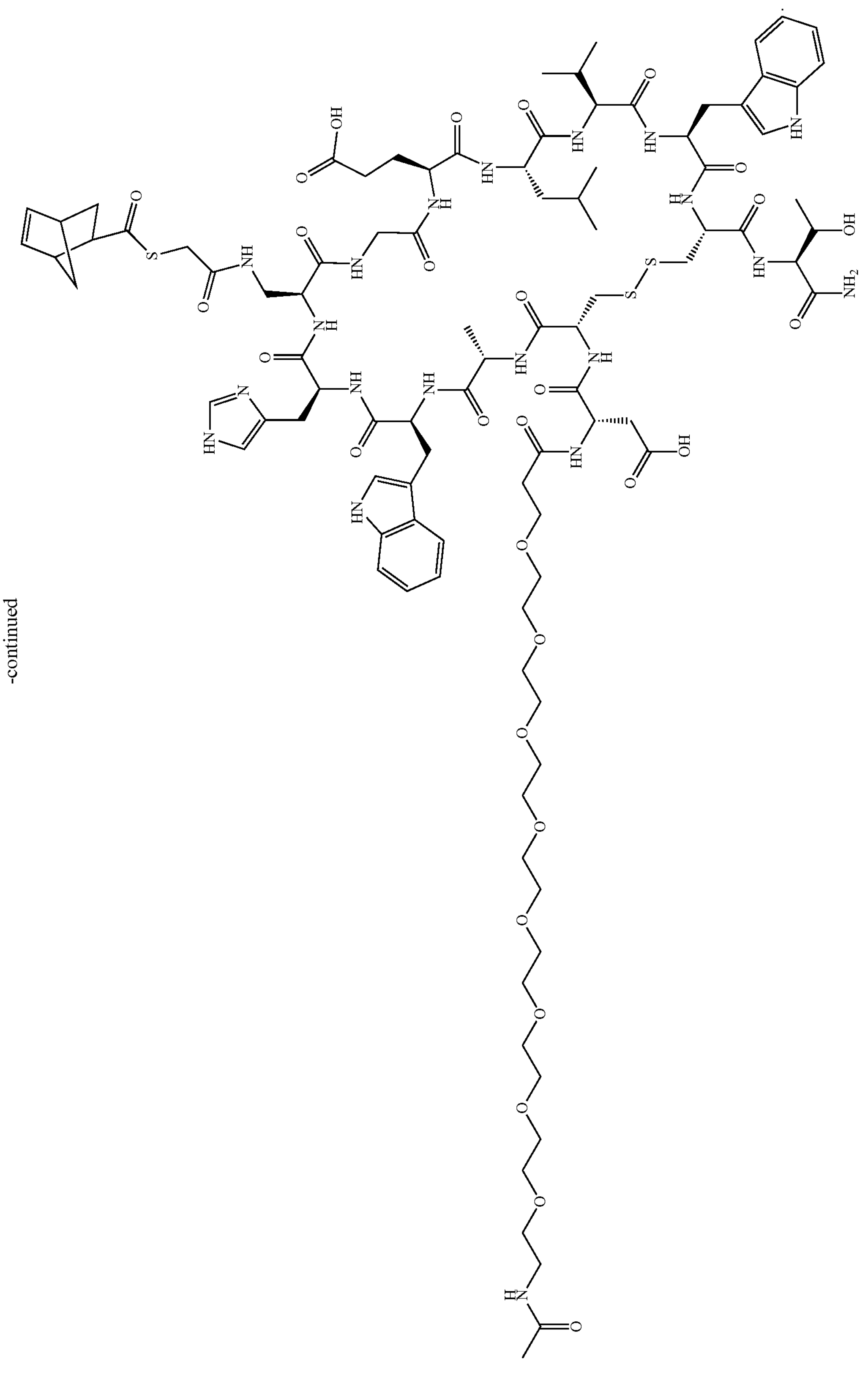

12. The peptide-compound conjugate of claim 1, wherein the peptide-compound conjugate is represented by the following structure:
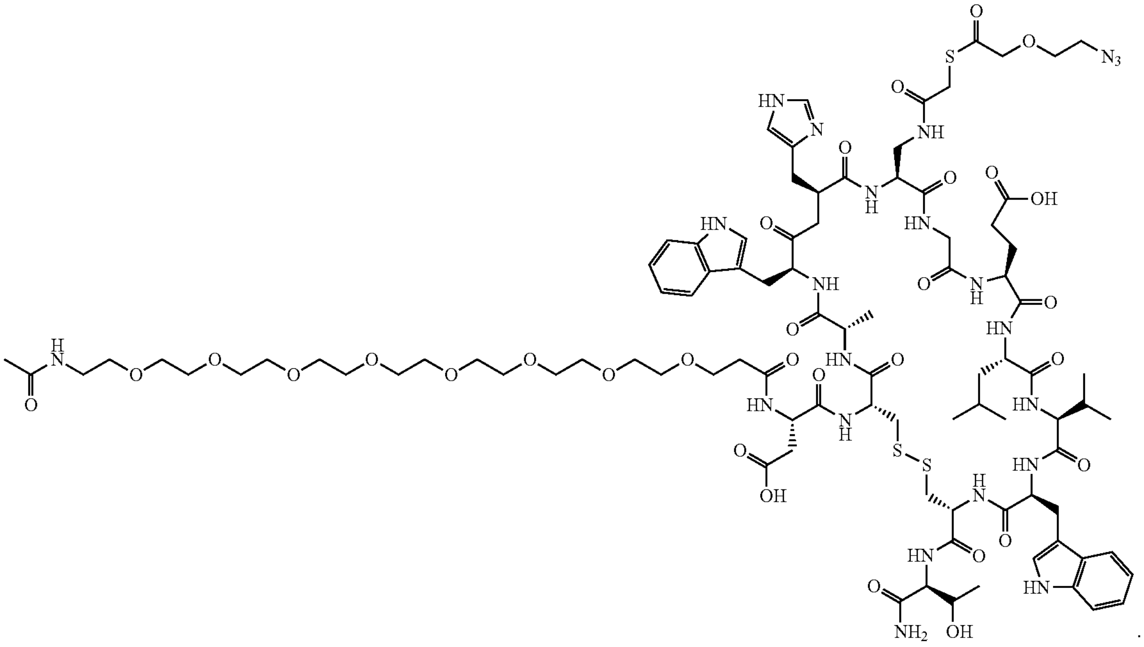 [SMILES: CC(=O)NCCOCCOCCOCCOCCOCCOCCOCCOCCC(=O)N[C@@H](CC(=O)O)C(=O)N[C@H]1CSSC[C@@H](C(=O)N[C@H](C(N)=O)C(C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CNC(=O)CSC(=O)COCCN=[N+]=[N-])NC(=O)[C@H](Cc2c[nH]cn2)CC(=O)[C@H](Cc2c[nH]c3ccccc23)NC(=O)[C@H](C)NC1=O]
.
* * * * *